(12) United States Patent
Ofir et al.

(10) Patent No.: US 10,351,910 B2
(45) Date of Patent: Jul. 16, 2019

(54) GENE AND PROTEIN EXPRESSION PROPERTIES OF ADHERENT STROMAL CELLS CULTURED IN 3D

(71) Applicant: Pluristem Ltd., Haifa (IL)

(72) Inventors: Rachel Ofir, Mitzpe Adi (IL); Eytan Abraham, Frederick, MD (US)

(73) Assignee: PLURISTEM LTD, Haifa (IL)

( * ) Notice: Subject to any disclaimer, the term of this patent is extended or adjusted under 35 U.S.C. 154(b) by 526 days.

(21) Appl. No.: 14/432,402

(22) PCT Filed: Feb. 20, 2014

(86) PCT No.: PCT/IB2014/059114
§ 371 (c)(1),
(2) Date: Mar. 30, 2015

(87) PCT Pub. No.: WO2014/128634
PCT Pub. Date: Aug. 28, 2014

(65) Prior Publication Data
US 2016/0186259 A1    Jun. 30, 2016

Related U.S. Application Data

(60) Provisional application No. 61/766,717, filed on Feb. 20, 2013.

(51) Int. Cl.
| | | |
|---|---|---|
| C12Q 1/68 | (2018.01) | |
| C12Q 1/6881 | (2018.01) | |
| C12N 5/0775 | (2010.01) | |
| C12N 5/077 | (2010.01) | |
| G01N 33/68 | (2006.01) | |
| A61K 35/00 | (2006.01) | |

(52) U.S. Cl.
CPC ......... *C12Q 1/6881* (2013.01); *C12N 5/0652* (2013.01); *C12N 5/0668* (2013.01); *G01N 33/6803* (2013.01); *A61K 35/00* (2013.01); *C12N 2513/00* (2013.01); *C12Q 2600/158* (2013.01); *G01N 2333/475* (2013.01); *G01N 2333/5412* (2013.01); *G01N 2333/5415* (2013.01); *G01N 2333/56* (2013.01); *G01N 2333/78* (2013.01); *G01N 2333/96494* (2013.01)

(58) Field of Classification Search
None
See application file for complete search history.

(56) References Cited

FOREIGN PATENT DOCUMENTS

| | | |
|---|---|---|
| WO | WO 2007/108003 A2 | 9/2007 |
| WO | WO 2010/026574 A1 | 3/2010 |
| WO | WO 2010/026575 A2 | 3/2010 |

OTHER PUBLICATIONS

Handbook of Chemistry and Physics, 49th Edition, 1968, Weast (ed.), The Chemical Rubber Co., Cleveland, Ohio, p. A-245.*
Human Gene Nomenclature Committee entry for Gene Family: VEGF family, https://www.genenames.org/cgi-bin/genefamilies/set/1267, accessed Feb. 23, 2018).*
Hwang et al., The implications of the response of human mesenchymal stromal cells in three-dimensional culture to electrical stimulation for tissue regeneration. Tissue Eng Part A. Feb. 2012;18(3-4):432-45. doi: 10.1089/ten.TEA.2010.0752. Epub Dec. 2, 2011.
Prather et al., Placental-derived and expanded mesenchymal stromal cells (PLX-I) to enhance the engraftment of hematopoietic stem cells derived from umbilical cord blood. Expert Opin Biol Ther. Aug. 2008;8(8):1241-50. doi: 10.1517/14712598.8.8.1241.

* cited by examiner

*Primary Examiner* — James Martinell

(57) ABSTRACT

Adherent stromal cells cultured under three dimensional conditions are provided, characterized, and distinguished from adherent stromal cells cultured under two dimensional conditions.

15 Claims, 2 Drawing Sheets

GENE AND PROTEIN EXPRESSION PROPERTIES OF ADHERENT STROMAL CELLS CULTURED IN 3D

This Application claims the benefit of U.S. Provisional Application No. 61/766,717, filed on Feb. 20, 2013, which is incorporated herein by reference in its entireity.

INTRODUCTION

In recent years, considerable activity has focused on the therapeutic potential of mesenchymal stromal cells for various medical applications including tissue repair of damaged organs such as the brain, heart, bone and liver and in support of bone marrow transplantations. Mesenchymal stromal cells are a heterogeneous population of adherent cells obtained from e.g. bone marrow, adipose tissue, placenta, and blood, that are capable of differentiating into different types of mesenchymal mature cells (e.g. reticular endothelial cells, fibroblasts, adipocytes, osteogenic precursor cells) depending upon influences from various bioactive factors. They have been widely studied in regenerative medicine as the foundation to build new tissues such as bone, cartilage and fat for the repair of injury or replacement of pathologic tissues and as treatment for genetic and acquired diseases [Fibbe and Noort, Ann N Y Acad Sci (2003) 996: 235-44; Horwitz et al., Cytotherapy (2005) 7(5): 393-5; Zimmet and Hare, Basic Res Cardiol (2005) 100(6): 471-81

Mesenchymal stromal cells are adherent stromal cells ("ASC"). That is, they require contact with a substrate for in vitro culture. Cell-substratum interactions play a pivotal role in the biology of adherent cells. Significant differences exist between cells grown on 2-dimensional ("2D") and three-dimensional ("3D") substrates, including differences in gene regulation, protein production, protein secretion, and differentiation. These changes in cell biology in 3D versus 2D culture conditions are mediated by alteration of cell cytoskeleton, cell adhesion, cell-cell integration, and extracellular matrix ("ECM"). (Fu et al.; Kumar et al.; Maloney et al.; Nerurkar et al.; Penolazzi et al.; Birgersdotter et al. 2005; Ghoshi et al. 2005; Engler et al. 2006; Vogel and Sheetz 2006; Lee et al. 2007; Heckmann et al. 2008; Methe et al. 2008; Uccelli et al. 2008.) 3D environments may result in biological alteration of ASC when compared with ASC cultured on 2D surfaces. Different types of 3D scaffolds may include, for example, non-woven fibers, woven fibers, porous sponge-like, and sintered matrices.The altered cell biology in 3D versus 2D culture can have a major impact on the cells' ability to exert a clinically relevant impact on its surroundings.

Culturing conditions suitable for expansion of ASCs have been previously described (e.g., WO 2007/108003, WO 2009/037690). ASC have been shown to exert beneficial therapeutic effects via the secretion of cytokines and chemokines,i.e., action by paracrine or endocrine modes. In this paradigm the cells do not differentiate and integrate into the tissue, but rather secrete proteins that in turn cause the tissue to self-repair by promoting processes such as angiogenesis, reduction of inflammation and, anti-apoptosis, subsequently the injected cells are cleared. (Li, N., et al., *Prosaposin in the secretome of marrow stroma-derived neural progenitor cells protects neural cells from apoptotic death*. J Neurochem, 2010. 112(6): p. 1527-38; van Koppen, A., et al., *Human embryonic mesenchymal stem cell-derived conditioned medium rescues kidney function in rats with established chronic kidney disease*. PLoS One, 2012. 7(6): p. e38746.)

Placental-derived ASCs exhibit many markers common to mesenchymal stromal cells isolated from other tissues. For example, by flow cytometry they express CD105, CD73, CD90 and CD29, and they lack of expression of hematopoietic, endothelial, and trophoblastic-specific cell markers. Adipogenic, osteogenic, and neurogenic differentiation have been achieved after culturing placental derived-mesenchymal stromal cells under appropriate conditions [Yen et al., Stem Cells (2005) 23(1): 3-9].

ASC produced in 2D culture, while also therapeutically valuable, have biological attributes that are distinct from ASC produced in 3D culture. These distinct attributes may give ASC produced in 3D culture a greater therapeutic capacity in certain clinical indications compared to ASC grown in 2D culture. Accordingly, it is important to provide methods of distinguishing ASC produced in 3D culture from those produced in 2D culture. Further, these biological attributes provide a basis for identifying cell populations that have a high therapeutic capacity, irrespective of the method of production of the cells. What is needed are methods of distinguishing cells grown in 3D culture as compared to cells grown in 2D culture.

SUMMARY OF THE INVENTION

In one aspect, the invention provides methods of determing whether an adherent stromal cell was produced by three dimensional culture, comprising:
 (a) detecting or measuring in a sample of adherent stromal cells the expression of one or more biomarkers chosen from CXCL2, CXCL3, CXCL5, CXCL6, CCL11, CSF3, IL8, PRL, CXCL11, CCL7, CCL8, CCL2, IL1A, IL1B, IL36G, IL17C, CCL20, CCR4, CXCL14, IL9R, MCP-3, uPAR, SPP1, CCL5, VEGFA, HGF, SERPINF1, IFNB1, TIMP1, CXCL12, FIGF, PDGFB, KITLG, TNF, TIMP3, FST, NPPB, CXCL10, LIF, COL7A1, IL6, MMP10, MMP9, MMP11, FN1, COL15A1, TNC, or IFNA1 and
 (b) comparing the detected or measured levels to levels of the same biomarker detected or measured in a sample of adherent stromal cells produced by two dimensional culturing ("2D control");
 wherein a modulation of at least two-fold of any one or more of CXCL2, CXCL3, CXCL5, CXCL6, CCL11, CSF3, IL8, PRL, CXCL11, CCL7, CCL8, CCL2, IL1A, IL1B, IL36G, IL17C, CCL20, CCR4, CXCL14, IL9R, MCP-3, uPAR, SPP1, CCL5, VEGFA, HGF, SERPINF1, IFNB1, TIMP1, CXCL12, FIGF, PDGFB, KITLG, TNF, TIMP3, FST, NPPB, CXCL10, LIF, COL7A1, IL6, MMP10, MMP9, MMP11, FN1, COL15A1, TNC, or IFNA1 relative to the 2D control indicates the cell is an adherent stromal cell produced by three dimensional culturing.

In certain embodiments, the expression is measured by gene array.

In some embodiments, each of VEGFA, IL6, and IFNA1 is detected or measured. In other embodiments, each of VEGFA, LIF, COL7A1, IL6, MMP10, MMP9, MMP11, FN1, COL15A1, TNC, and IFNA1 is detected or measured. In still further embodiments, any subcombination of CXCL2, CXCL3, CXCL5, CXCL6, CCL11, CSF3, IL8, PRL, CXCL11, CCL7, CCL8, CCL2, IL1A, IL1B, IL36G, IL17C, CCL20, CCR4, CXCL14, IL9R, MCP-3, uPAR, SPP1, CCL5, VEGFA, HGF, SERPINF1, IFNB1, TIMP1, CXCL12, FIGF, PDGFB, KITLG, TNF, TIMP3, FST, NPPB, CXCL10, LIF, COL7A1, IL6, MMP10, MMP9, MMP11, FN1, COL15A1, TNC, or IFNA1 is detected or measured. In other embodiments, VEGFA and one, two, three, four, or more of LIF, COL7A1, IL6, MMP10, MMP9, MMP11, FN1, COL15A1, TNC, or IFNA1 is detected or measured.

Still other embodiments include a population of cells determined to be produced by three dimensional culturing.

Another embodiment includes a method of determining whether an adherent stromal cell was produced by three dimensional culture, comprising:
  (a) detecting or measuring in a culture medium produced from a sample of adherent stromal cells the expression of either or both of biomarkers VEGFA or IL6, and
  (b) comparing the detected or measured levels to levels of the same biomarker detected or measured in a sample of culture medium produced from adherent stromal cells grown in two dimensional culturing ("2D medium control");
  wherein an modulation (such as, for example, an increase or decrease) of at least two-fold relative to the 2D medium control of either or both of VEGFA or IL6 indicates the cell is an adherent stromal cell produced by three dimensional culturing.

In one embodiment expression is measured by ELISA or using antibody array. In another embodiment, each of VEGFA and IL6 is detected or measured.

In another embodiment, there is provided a method of determing whether an adherent stromal cell was produced by three dimensional culture, comprising:
  (a) detecting or measuring in a sample of adherent stromal cells the expression of at least one biomarker gene chosen from AGN, AGNPT1, VEGFA, LIF, COL7A1, IL6, MMP10, MMP9, MMP11, FN1, COL15A1, TNC, or IFN CXCL2, CXCL3, CXCL5, CXCL6, CCL11, CSF3, IL8, PRL, CXCL11, CCL7, CCL8, CCL2, IL1A, IL1B, IL36G, IL17C, CCL20, CCR4, CXCL14, IL9R, MCP-3, uPAR, SPP1, CCL5, VEGFA, HGF, SERPINF1, IFNB1, TIMP1, TIMP2, CXCL12, FIGF, PDGFB, KITLG, TNF, TIMP3, FST, NPPB, CXCL10, LIF, COL7A1, IL6, MMP10, MMP9, MMP11, FN1, COL15A1, TNC, or IFNA 1; and/or
  (b) detecting or measuring in a sample of culture medium or cellular lysate from the same adherent stromal cells as in (a) the expression of at least one biomarker protein chosen from VEGFA or IL6; and
  (c) comparing the detected or measured levels to levels of the same biomarker detected or measured in the same type of sample of adherent stromal cells produced by two dimensional culturing ("2D control");
  wherein a modulation of at least two-fold relative to the 2D control of any one or more of AGN, AGNPT1, VEGFA, LIF, COL7A1, IL6, MMP10, MMP9, MMP11, FN1, COL15A1, TNC, or IFN CXCL2, CXCL3, CXCL5, CXCL6, CCL11, CSF3, IL8, PRL, CXCL11, CCL7, CCL8, CCL2, IL1A, IL1B, IL36G, IL17C, CCL20, CCR4, CXCL14, IL9R, MCP-3, uPAR, SPP1, CCL5, VEGFA, HGF, SERPINF1, IFNB1, TIMP1, TIMP2, CXCL12, FIGF, PDGFB, KITLG, TNF, TIMP3, FST, NPPB, CXCL10, LIF, COL7A1, IL6, MMP10, MMP9, MMP11, FN1, COL15A1, TNC, or IFNA1 indicates the cell is an adherent stromal cell produced by three dimensional culturing.

In another embodiment, gene expression is detected or measured by gene array and wherein protein expression is detected or measured either using an antibody array or ELISA.

It is to be understood that both the foregoing general description and the following detailed description are exemplary and explanatory only and are not restrictive of the invention, as claimed.

DETAILED DESCRIPTION

Figure 1:
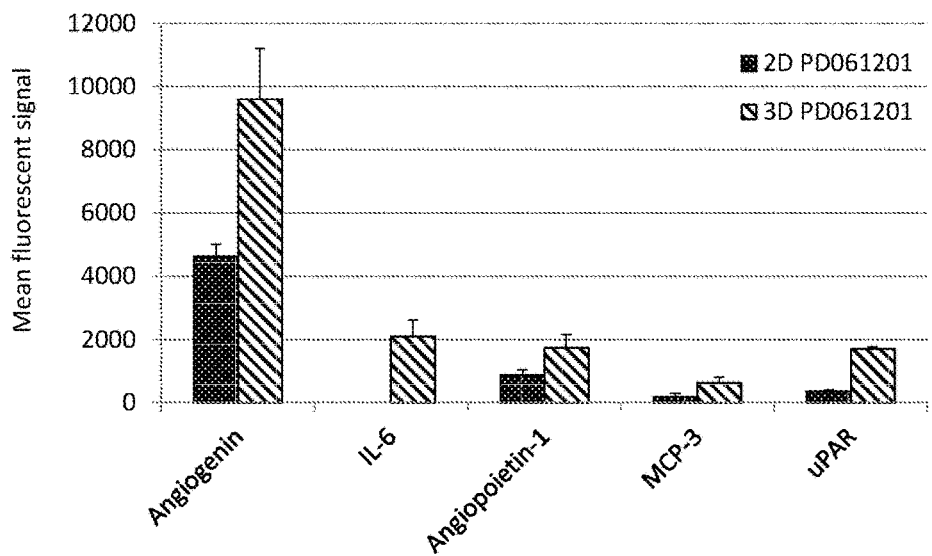
FIG. 1 is a bar graph presenting levels of secreted proteins that are upregulated in 3D (fibracel) vs. 2D (flask) growth: angiogenin, IL-6, angiopoietin-1 MCP-3 and uPAR.

Adherent stromal cells ("ASC") grown in 3D culture show differences in the expression of multiple genes as well as in the production (cell lysate) and secretion (conditioned media) of proteins compared to ASC grown in 2D culture conditions.

As used herein the phrase "adherent cells" refers to a homogeneous or heterogeneous population of cells which are anchorage dependent, i.e., which require attachment to a substrate in order to grow in vitro.

Adherent stromal cells ("ASC") are cells obtained from a tissue, including but not limited to placenta and adipose tissue, that are adherent when cultured in vitro, typically express one or more, two or more, three or more, or all four of CD105, CD73, CD90 and CD29 and lack detectable expression of at least one, two , three, four, five, six, seven, eight, nine, or all ten of CD3, CD4, CD45, CD80, HLA-DR, CD11b, CD14, CD19, CD34 and CD79 by flow cytometry compared to an isotype control.

The term "placenta" refers to any portion of the mammalian female organ which lines the uterine wall and during pregnancy envelopes the fetus, to which it is attached by the umbilical cord. Following birth, the placenta is expelled (and is referred to as a post-partum placenta). In some embodiments, "placenta" refers to whole placenta.

In those aspects and embodiments involving placental-derived adherent stromal cells, the placental-derived ASCs may be obtained from both fetal (i.e., amnion or inner parts of the placenta) and maternal (i.e., decidua basalis, and decidua parietalis) parts of the placenta unless the context otherwise makes clear that only fetal or maternal parts are meant.

Adherent stromal cells can be propagated using two dimensional ("2D") or three dimensional ("3D") culturing conditions. Nonlimiting examples of such culture conditions are provided in the Detailed Description and in the Examples.

"Two-dimensional" or "2D" refers to a culture in which the cells are grown on a flat tissue culture plate surface (e.g. "TCPS").

As used herein the phrase "three dimensional" or "3D" is defined as culture on any surface that has a third dimensionality component. 3D surfaces include but are not limited to porous materials, woven fibers, non-woven fibers, hollow fibers, surfaces with nano or micron scale roughness, sponges, and microcarriers. Other examples of 3D surfaces are given in the examples. It will be appreciated that the conditions of the three-dimensional culture are such that they enable expansion of the adherent cells.

As used herein, "ASC-2D" means a culture of adherent stromal cells from any tissue source that have been grown in 2D culture conditions without a period of 3D culture.

As used herein, "ASC-3D" means a culture of adherent stromal cells from any tissue source that have been grown in 3D-culture conditions. This term encompasses cells that are grown initially in 2D culture then moved to a 3D culture.

"Placental ASC-2D" as used herein is a general term for any culture of placental-derived adherent stromal cells produced using a 2D culture system.

"Placental ASC-3D" as used herein is a general term for any culture of placental-derived adherent stromal cells produced using a 3D culture system.

A "biomarker" as used herein is any gene, secreted protein, surface protein, or intracellular protein that can be used to distinguish an ASC-3D from an ASC-2D. In general, there is at least two fold difference in expression of a biomarker (either positive or negative) between ASC-3D and ASC-2D, however, in some embodiments, biomarkers for which there is less than two fold difference in expression between ASC-3D and ASC-2D are used.

As used herein the terms "expanding" and "expansion" refer to an increase of a cell population (e.g., at least 2 fold), optionally without differentiation accompanying such increase.

It is understood and herein contemplated that the expression of biomarkers on the surface of a cell or secreted by a cell or inside a cell can altered by the culture conditions a cell is subjected to. Culture of cells on various 3D scaffolds, which have differing architecture, stiffness, or coatings, can result in changes to the cultured cell's gene expression and/or protein production and/or secretome. Herein it is proposed that when culturing ASC on a wide range of 3D scaffolds, scaffolds with different architecture, different stiffness and different chemical composition results in the directional up or down regulation of various genes and proteins, and that therefore these genes and proteins can be used as universal markers to identify ASCs cultured on many types of 3D scaffolds as opposed to 2D culture in a flat tissue culture plate surface.

Therefore, in one aspect, disclosed herein are methods of determining whether an adherent stromal cell was produced by three dimensional (3D) culture comprising: (a) detecting or measuring in a sample of adherent stromal cells the expression of one or more biomarkers; and (b) comparing the detected or measured levels to levels of the same biomarker detected or measured in a sample of adherent stromal cells produced by two dimensional culturing ("2D control") wherein differential regulation or modulation of one or more of the biomarkers in the stromal cell culture relative to the 2D control indicates that the stromal cells were produced by 3D culture. It is understood and herein contemplated that the adherent stromal cells can be obtained from a cellular culture, frozen culture, or bioreactor. Thus, in one aspect, disclosed herein are methods of determining whether an adherent stromal cell was produced by three dimensional (3D) culture comprising: (a) detecting or measuring in a sample of adherent stromal cells the expression of one or more biomarkers; and (b) comparing the detected or measured levels to levels of the same biomarker detected or measured in a sample of adherent stromal cells produced by two dimensional culturing ("2D control") wherein differential regulation or modulation of one or more of the biomarkers in the stromal cell culture relative to the 2D control indicates that the stromal cells were produced by 3D culture; and wherein the adherent stromal cells are obtained from an active cell culture, frozen culture, or bioreactor.

It is understood and herein contemplated that the biomarkers used in the disclosed methods can be any gene or protein that is differentially expressed when a cell is grown in a 3D culture compared to a 2D culture. In one aspect, the biomarker of the disclosed methods can comprise 1, 2, 3, 4, 5, 6, 7, 8, 9, 10, 11, 12 13, 14, 15, 20, 25, 30, 35, 40, 45, 50, 100, 200, 300, 400, 500, or a thousand biomarkers. For example, the biomarker can be any one or more of the biomarkers listed in Tables 1-15 or any combination or subcombination thereof. For example, the biomarker can be comprise one or more of ANG, ANGPT1, CXCL3, CXCL5, CXCL6, CSF3, IL8, PRL, CCL2, CXCL11, CCL7, CCL8, CCL2, IL1A, IL1B, IL36G, IL17C, CCL20, CCR4, CXCL14, IL9R, MCP-3, uPAR, SPP1, CCL5, VEGFA, HGF, SERPINF1, IFNA1, TIMP1, TIMP2, CXCL12, FIGF, PDGFB, ANGPT2, KITLG, TNF, TIMP3, FST, NPPB, CXCL10, LIF, COL7A1, IL6, MMP10, MMP9, MMP11, FN1, COL15A1, TNC, or IFNA1 or any combination thereof. Thus, in one aspect, disclosed herein are methods of determining whether an adherent stromal cell was producing by three dimensional culture, comprising: (a) detecting or measuring in a sample of adherent stromal cells the expression of one or more biomarkers comprising ANG, ANGPT1, CXCL3, CXCL5, CXCL6, CSF3, IL8, PRL, CCL2, CXCL11, CCL7, CCL8, CCL2, IL1A, IL1B, IL36G, IL17C, CCL20, CCR4, CXCL14, IL9R, MCP-3, uPAR, SPP1, CCL5, VEGFA, HGF, SERPINF1, IFNA1, TIMP1, TIMP2, CXCL12, FIGF, PDGFB, ANGPT2, KITLG, TNF, TIMP3, FST, NPPB, CXCL10, LIF, COL7A1, IL6, MMP10, MMP9, MMP11, FN1, COL15A1, TNC, or IFNA1; and (b) comparing the detected or measured levels to levels of the same biomarker detected or measured in a sample of adherent stromal cells produced by two dimensional culturing ("2D control") wherein differential regulation or modulation of one or more of the biomarkers in the stromal cell culture relative to the 2D control indicates that the stromal cells were produced by 3D culture. In another aspect disclosed herein are methods of As disclosed herein, any one or more of the biomarkers listed in Tables 1-15 or 18-23 can be used in the disclosed methods. Additionally, any combination or subcombination of the biomarkers in Tables 1-15 or 18-23 can be used. For example, in one aspect disclosed herein are methods of determining whether an adherent stromal cell was produced by three dimensional culture wherein the biomarker comprises one, two, three, four, five, six, seven, eight, nine, ten or more of CXCL2, CXCL3, CXCL5, CXCL6, CCL11, CSF3, IL8, PRL, CCL7, CCL8, CCL2, IL1A, IL1B, IL36G, IL17C, CCL20, MCP-3, uPAR, VEGFA, HGF, SERPINF1, TIMP1, LIF, COL7A1, IL6, MMP10, MMP9, MMP11, FN1, COL15A1, TNC, or IFNA1 is detected or measured. For example, the biomarkers can comprise VEGFA, IL6, IFNA1, VEGFA and IL6, VEGFA and IFNA1, IL6 and IFNA1, or VEGFA, IL6, and IFNA1. In one aspect, disclosed herein are methods of determining whether an adherent stromal cell was produced by three dimensional culture comprising detecting or measuring the biomarkers comprising VEGFA, LIF, COL7A1, IL6, MMP10, MMP11, FN1, COL15A1, TNC, and IFNA1 or a combination or subcombination of one, two, three, four, five, six, seven, eight, nine, or ten of VEGFA, LIF, COL7A1, IL6, MMP10, MMP11, FN1, COL15A1, TNC, and IFNA1. Also disclosed are methods of determining whether an adherent stromal cell was produced by three dimensional culture comprising detecting or measuring the biomarkers comprising VEGFA and one, two, three, four, five, six, seven, eight, nine, ten or more of LIF, COL7A1, IL6, MMP10, MMP11, FN1, COL15A1, TNC, and IFNA1. Additionally, disclosed herein are methods of determining whether an adherent stromal cell was produced by three dimensional culture comprising detecting or measuring the biomarkers comprising IL6 and one, two, three, four, five, six or more of LIF, COL7A1, VEGFA, MMP10, MMP11, FN1, COL15A1, TNC, and IFNA1. Also disclosed are methods of determining whether an adherent stromal cell was produced by three dimensional culture comprising detecting or measuring the biomarkers comprising IFNA1 and one, two, three, four, five, six, seven, eight, nine, ten or more of LIF, COL7A1, IL6, MMP10, MMP11, FN1, COL15A1, TNC, and VEGFA. Thus, for example, disclosed herein are methods of determining whether an adherent stromal cell was produced by three dimensional culture, comprising: (a) detecting or measuring in a culture medium produced from a sample of adherent stromal cells the expression of either or both of biomarkers VEGFA or IL6, and (b) comparing the detected or measured levels to levels of the same biomarker detected or measured in a sample of culture medium produced from adherent stromal cells grown in two dimensional culturing ("2D medium control"); wherein detection or measuring of modulation (such as, for example, an increase or decrease) of at least two-fold relative to the 2D medium control of either or both of VEGFA, IL6, or VEGFA and IL6 indicates the cell is an adherent stromal cell produced by three dimensional culturing.

Also disclosed are methods of determining whether an adherent stromal cell was produced by three dimensional culture, comprising: (a) detecting or measuring in a sample of adherent stromal cells the expression of at least one biomarker gene chosen from VEGFA, LIF, COL7A1, IL6, MMP10, MMP9, MMP11, FN1, COL15A1, TNC, or IFNA1; and/or (b) detecting or measuring in a sample of culture medium or cellular lysate from the same adherent stromal cells as in (a) the expression of at least one biomarker protein chosen from VEGFA or IL6 and a further biomarker comprising CXCL2, CXCL3, CXCL5, CXCL6, CCL11, CSF3, IL8, PRL, CXCL11, CCL7, CCL8, CCL2, IL1A, IL1B, IL36G, IL17C, CCL20, CCR4, CXCL14, IL9R, MCP-3, uPAR, SPP1, CCL5, HGF, SERPINF1, IFNB1, TIMP1, CXCL12, FIGF, PDGFB, KITLG, TNF, TIMP3, FST, NPPB, CXCL10, LIF, COL7A1, MMP10, MMP9, MMP11, FN1, COL15A1, TNC, or IFNA1; and (c) comparing the detected or measured levels to levels of the same biomarker detected or measured in the same type of sample of adherent stromal cells produced by two dimensional culturing ("2D control"); wherein an increase of at least two-fold relative to the 2D control of any one or more of VEGFA, IL6, CXCL2, CXCL3, CXCL5, CXCL6, CCL11, CSF3, IL8, PRL, CXCL11, CCL7, CCL8, CCL2, IL1A, IL1B, IL36G, IL17C, CCL20, CCR4, CXCL14, IL9R, MCP-3, uPAR, SPP1, CCL5, HGF, SERPINF1, IFNB1, TIMP1, CXCL12, FIGF, PDGFB, KITLG, TNF, TIMP3, FST, NPPB, CXCL10, LIF, COL7A1, MMP10, MMP9, MMP11, FN1, COL15A1, TNC, or IFNA1 indicates the cell is an adherent stromal cell produced by three dimensional culturing.

In yet another aspect disclosed herein are methods of determining whether an adherent stromal cell was produced by three dimensional culture wherein the biomarker comprises one, two, three, four, five, six, seven, eight, nine, ten or more of CXCL11, CCR4, CXCL14, IL9R, SPP1, CCL5, IFNB1, CXCL12, FIGF, PDGFB, KITLG, TNF, TIMP3, FST, NPPB, or CXCL10.

It is understood and herein contemplated that genes or proteins expression can fluctuate between any two identical cells grown in the same fashion. Accordingly, the skilled artisan can appreciate that a threshold level of differential expression is preferred to insure that the differences observed between 3D and 2D culture are due to the culturing conditions and not merely variation between cells. In one aspect, the determination that a stromal cell was grown in 3D culture can be made amount of differential regulation or modulation observed in the stromal cell culture being measured and the 2D control is 2, 3, 4, 5, 6, 7, 8, 9, 10, 11, 12, 13, 14, 15, 16, 17, 18, 19, 20, 25, 30, 35, 40, 45, 50-fold or more. Thus, in one aspect, disclosed herein are methods of determining whether an adherent stromal cell was produced by three dimensional (3D) culture. It is understood and herein contemplated that the expression of biomarkers on the surface of a cell or secreted by a cell or inside a cell can altered by the culture conditions a cell is subjected to. Accordingly, in one aspect, disclosed herein are methods of determining whether an adherent stromal cell was producing by three dimensional culture, comprising: (a) detecting or measuring in a sample of adherent stromal cells the expression of one or more biomarkers comprising ANG, ANGPT1, CXCL3, CXCL5, CXCL6, CSF3, IL8, PRL, CCL2, CXCL11, CCL7, CCL8, CCL2, IL1A, IL1B, IL36G, IL17C, CCL20, CCR4, CXCL14, IL9R, MCP-3, uPAR, SPP1, CCL5, VEGFA, HGF, SERPINF1, IFNA1, TIMP1, TIMP2, CXCL12, FIGF, PDGFB, ANGPT2, KITLG, TNF, TIMP3, FST, NPPB, CXCL10, LIF, COL7A1, IL6, MMP10, MMP9, MMP11, FN1, COL15A1, TNC, or IFNA1; and (b) comparing the detected or measured levels to levels of the same biomarker detected or measured in a sample of adherent stromal cells produced by two dimensional culturing ("2D control") wherein an at least two-fold differential regulation or modulation of any one or more of ANG, ANGPT1, CXCL2, CXCL3, CXCL5, CXCL6, CCL11, CSF3, IL8, PRL, CXCL11, CCL7, CCL8, CCL2, IL1A, IL1B, IL36G, IL17C, CCL20, CCR4, CXCL14, IL9R, MCP-3, uPAR, SPP1, CCL5, VEGFA, HGF, SERPINF1, IFNB1, TIMP1, TIMP2, CXCL12, FIGF, PDGFB, KITLG, TNF, TIMP3, FST, NPPB, CXCL10, LIF, COL7A1, IL6, MMP10, MMP9, MMP11, FN1, COL15A1, TNC, or IFNA1 relative to the 2D control indicates the cell is an adherent stromal cell produced by three dimensional culturing.

As used herein, "modulation" refers to any increase or decrease in the expression level of one or more of the proteins measured in the methods. For example, the disclosed methods of determining whether an adherent stromal cell was produced by 3D culture can comprise detecting or measuring in a sample of adherent stromal cells the expression of one or more biomarkers; comparing the detected or measured levels to the levels of the same biomarker detected or measured in 2D control, wherein an increase in the level of the one or more biomarkers relative to the control indicates that the adherent stromal cell was produced by 3D culturing. Similarly, the disclosed methods of determining whether an adherent stromal cell was produced by 3D culture can comprise detecting or measuring in a sample of adherent stromal cells the expression of one or more biomarkers; comparing the detected or measured levels to the levels of the same biomarker detected or measured in 2D control, wherein a decrease in the level of the one or more biomarkers relative to the control indicates that the adherent stromal cell was produced by 3D culturing. It is understood that the amount of increase or decrease of a biomarker can comprise a 2, 3, 4, 5, 6, 7, 8, 9, 10, 11, 12, 13, 14,15, 20, 25, 30, 35, 40, 45, 50-fold or more.

In one aspect, disclosed herein are methods of determining whether an adherent stromal cell was producing by three dimensional culture, comprising: (a) detecting or measuring in a sample of adherent stromal cells the expression of one or more biomarkers; and (b) comparing the detected or measured levels to levels of the same biomarker detected or measured in a sample of adherent stromal cells produced by two dimensional culturing ("2D control") wherein an increase of one or more of the biomarkers in the stromal cell culture relative to the 2D control indicates that the stromal cells were produced by 3D culture. For example, in one aspect, disclosed herein are methods of determining whether an adherent stromal cell was producing by three dimensional culture, comprising: (a) detecting or measuring in a sample of adherent stromal cells the expression of one or more biomarkers comprising ANG, ANGPT1, CXCL2, CXCL3, CXCL5, CXCL6, CCL11, CSF3, IL8, PRL, CCL7, CCL8, CCL2, IL1A, IL1B, IL36G, IL17C, CCL20, MCP-3, uPAR, VEGFA, HGF, SERPINF1, TIMP1, LIF, COL7A1, IL6, MMP10, MMP9, MMP11, FN1, COL15A1, TNC, or IFNA1; and (b) comparing the detected or measured levels to levels of the same biomarker detected or measured in a sample of adherent stromal cells produced by two dimensional culturing ("2D control") wherein an increase of one or more of ANG, ANGPT1, CXCL2, CXCL3, CXCL5, CXCL6, CCL11, CSF3, IL8, PRL, CCL7, CCL8, CCL2, IL1A, IL1B, IL36G, IL17C, CCL20, MCP-3, uPAR, VEGFA, HGF, SERPINF1, TIMP1, LIF, COL7A1, IL6, MMP10, MMP9, MMP11, FN1, COL15A1, TNC, or IFNA1 in the stromal cell culture relative to the 2D control indicates that the stromal cells were produced by 3D culture. In another aspect, the biomarkers comprise VEGFA, LIF, COL7A1, IL6, MMP10, MMP11, FN1, COL15A1, TNC, and/or IFNA1. For example, the biomarkers can comprise VEGFA, IL6, IFNA1, VEGFA and IL6, VEGFA and IFNA1, IL6 and IFNA1, or VEGFA, IL6, and IFNA1. In one aspect, disclosed herein are methods of determining whether an adherent stromal cell was produced by three dimensional culture comprising detecting or measuring the biomarkers comprising VEGFA, LIF, COL7A1, IL6, MMP10, MMP11, FN1, COL15A1, TNC, and IFNA1 or a combination of one, two, three, four, five, six, seven, eight, nine, or ten of VEGFA, LIF, COL7A1, IL6, MMP10, MMP11, FN1, COL15A1, TNC, and IFNA1 wherein an increase of one or more of VEGFA, LIF, COL7A1, IL6, MMP10, MMP11, FN1, COL15A1, TNC, and IFNA1 or a combination of one, two, three, four, five, six, seven, eight, nine, or ten of VEGFA, LIF, COL7A1, IL6, MMP10, MMP11, FN1, COL15A1, TNC, and IFNA1 indicates that the cell was produced by a three dimensional culture. Also disclosed are methods of determining whether an adherent stromal cell was produced by three dimensional culture comprising detecting or measuring an increase in the biomarkers comprising VEGFA and one, two, three, four, five, six, seven, eight, nine, ten or more of LIF, COL7A1, IL6, MMP10, MMP11, FN1, COL15A1, TNC, and IFNA1. Additionally, disclosed herein are methods of determining whether an adherent stromal cell was produced by three dimensional culture comprising detecting or measuring an increase in the biomarkers comprising IL6 and one, two, three, four, five, six or more of LIF, COL7A1, VEGFA, MMP10, MMP11, FN1, COL15A1, TNC, and IFNA1. Also disclosed are methods of determining whether an adherent stromal cell was produced by three dimensional culture comprising detecting or measuring an increase in the biomarkers comprising IFNA1 and one, two, three, four, five, six, seven, eight, nine, ten or more of LIF, COL7A1, IL6, MMP10, MMP11, FN1, COL15A1, TNC, and VEGFA.

Also disclosed are methods of determining whether an adherent stromal cell was producing by three dimensional culture, comprising: (a) detecting or measuring in a sample of adherent stromal cells the expression of one or more biomarkers; and (b) comparing the detected or measured levels to levels of the same biomarker detected or measured in a sample of adherent stromal cells produced by two dimensional culturing ("2D control") wherein a decrease of one or more of the biomarkers in the stromal cell culture relative to the 2D control indicates that the stromal cells were produced by 3D culture. In one aspect, disclosed herein are methods of determining whether an adherent stromal cell was producing by three dimensional culture, comprising: (a) detecting or measuring in a sample of adherent stromal cells the expression of one or more biomarkers comprising CXCL11, CCR4, CXCL14, IL9R, SPP1, CCL5, IFNB1, CXCL12, FIGF, PDGFB, KITLG, TNF, TIMP3, FST, NPPB, or CXCL10.; and (b) comparing the detected or measured levels to levels of the same biomarker detected or measured in a sample of adherent stromal cells produced by two dimensional culturing ("2D control") wherein a decrease of one or more of CXCL11, CCR4, CXCL14, IL9R, SPP1, CCL5, IFNB1, CXCL12, FIGF, PDGFB, KITLG, TNF, TIMP3, FST, NPPB, or CXCL10. in the stromal cell culture relative to the 2D control indicates that the stromal cells were produced by 3D culture.

The skilled artisan will appreciate that adherent stromal cells grown in 3D culture can be used to treat diseases. Thus, in one aspect, disclosed herein are methods of determining whether an adherent stromal cell was produced by a three dimensional culture further comprising administering the cell to a subject in need thereof. Also disclosed are methods of determining whether an adherent stromal cell was produced by a three dimensional culture further comprising further maintaining the cells for later use in medical treatments.

It is understood and herein contemplated that biomarker expression can be detected or measured by any technique known in the art suitable for such purpose. For example, the detection and/or measuring of biomarkers can be performed using next generation sequencing techniques, gene array, protein array, quantitative PCR, real-time PCR, reverse transcriptase (RT) PCR, real-time RT-PCR, Fluorescence In-situ Hybridization (FISH), Flow Cytometry, ELISA, ELISpot, or using antibody array.

Next Generation Sequencing for Genetic Testing

From a technical perspective High-throughput or Next Generation Sequencing (NGS) represents an attractive option for detecting the somatic mutations within a gene. Unlike PCR, microarrays, high-resolution melting and mass spectrometry, which all indirectly infer sequence content, NGS directly ascertains the identity of each base and the order in which they fall within a gene. The newest platforms on the market have the capacity to cover an exonic region 10,000 times over, meaning the content of each base position in the sequence is measured thousands of different times. This high level of coverage ensures that the consensus sequence is extremely accurate and enables the detection of rare variants within a heterogeneous sample. For example, in a sample extracted from FFPE tissue, relevant mutations are only present at a frequency of 1% with the wild-type allele comprising the remainder. When this sample is sequenced at 10,000×coverage, then even the rare allele, comprising only 1% of the sample, is uniquely measured 100 times over. Thus, NGS can provide reliably accurate results with very high sensitivity, making it ideal for clinical diagnostic testing of FFPEs and other mixed samples.

Examples of Next Generation Sequencing techniques include, but are not limited to Massively Parallel Signature Sequencing (MPSS), Polony sequencing, pyrosequencing, Reversible dye-terminator sequencing, SOLiD sequencing, Ion semiconductor sequencing, DNA nanoball sequencing, Helioscope single molecule sequencing, Single molecule real time (SMRT) sequencing, Single molecule real time (RNAP) sequencing, and Nanopore DNA sequencing.

MPSS was a bead-based method that used a complex approach of adapter ligation followed by adapter decoding, reading the sequence in increments of four nucleotides; this method made it susceptible to sequence-specific bias or loss of specific sequences.

Polony sequencing, combined an in vitro paired-tag library with emulsion PCR, an automated microscope, and ligation-based sequencing chemistry to sequence an *E. coli* genome at an accuracy of >99.9999% and a cost approximately 1/10 that of Sanger sequencing.

A parallelized version of pyrosequencing, the method amplifies DNA inside water droplets in an oil solution (emulsion PCR), with each droplet containing a single DNA template attached to a single primer-coated bead that then forms a clonal colony. The sequencing machine contains many picolitre-volume wells each containing a single bead and sequencing enzymes. Pyrosequencing uses luciferase to generate light for detection of the individual nucleotides added to the nascent DNA, and the combined data are used to generate sequence read-outs. This technology provides intermediate read length and price per base compared to Sanger sequencing on one end and Solexa and SOLiD on the other.

A sequencing technology based on reversible dye-terminators. DNA molecules are first attached to primers on a slide and amplified so that local clonal colonies are formed. Four types of reversible terminator bases (RT-bases) are added, and non-incorporated nucleotides are washed away. Unlike pyrosequencing, the DNA can only be extended one nucleotide at a time. A camera takes images of the fluorescently labeled nucleotides, then the dye along with the terminal 3' blocker is chemically removed from the DNA, allowing the next cycle.

SOLiD technology employs sequencing by ligation. Here, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting bead, each containing only copies of the same DNA molecule, are deposited on a glass slide. The result is sequences of quantities and lengths comparable to Illumina sequencing.

Ion semiconductor sequencing is based on using standard sequencing chemistry, but with a novel, semiconductor based detection system. This method of sequencing is based on the detection of hydrogen ions that are released during the polymerization of DNA, as opposed to the optical methods used in other sequencing systems. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogens and a proportionally higher electronic signal.

DNA nanoball sequencing is a type of high throughput sequencing technology used to determine the entire genomic sequence of an organism. The method uses rolling circle replication to amplify small fragments of genomic DNA into DNA nanoballs. Unchained sequencing by ligation is then used to determine the nucleotide sequence. This method of DNA sequencing allows large numbers of DNA nanoballs to be sequenced per run.

Helicos's single-molecule sequencing uses DNA fragments with added polyA tail adapters, which are attached to the flow cell surface. The next steps involve extension-based sequencing with cyclic washes of the flow cell with fluorescently labeled nucleotides (one nucleotide type at a time, as with the Sanger method). The reads are performed by the Helioscope sequencer.

SMRT sequencing is based on the sequencing by synthesis approach. The DNA is synthesized in zero-mode waveguides (ZMWs)—small well-like containers with the capturing tools located at the bottom of the well. The sequencing is performed with use of unmodified polymerase (attached to the ZMW bottom) and fluorescently labeled nucleotides flowing freely in the solution. The wells are constructed in a way that only the fluorescence occurring by the bottom of the well is detected. The fluorescent label is detached from the nucleotide at its incorporation into the DNA strand, leaving an unmodified DNA strand.

Single molecule real time sequencing based on RNA polymerase (RNAP), which is attached to a polystyrene bead, with distal end of sequenced DNA is attached to another bead, with both beads being placed in optical traps. RNAP motion during transcription brings the beads in closer and their relative distance changes, which can then be recorded at a single nucleotide resolution. The sequence is deduced based on the four readouts with lowered concentrations of each of the four nucleotide types (similarly to S angers method).

Nanopore sequencing is based on the readout of electrical signal occurring at nucleotides passing by alpha-hemolysin pores covalently bound with cyclodextrin. The DNA passing through the nanopore changes its ion current. This change is dependent on the shape, size and length of the DNA sequence. Each type of the nucleotide blocks the ion flow through the pore for a different period of time.

VisiGen Biotechnologies uses a specially engineered DNA polymerase. This polymerase acts as a sensor—having incorporated a donor fluorescent dye by its active centre. This donor dye acts by FRET (fluorescent resonant energy transfer), inducing fluorescence of differently labeled nucleotides. This approach allows reads performed at the speed at which polymerase incorporates nucleotides into the sequence (several hundred per second). The nucleotide fluorochrome is released after the incorporation into the DNA strand.

Sequencing by hybridization is a non-enzymatic method that uses a DNA microarray. A single pool of DNA whose sequence is to be determined is fluorescently labeled and hybridized to an array containing known sequences. Strong hybridization signals from a given spot on the array identify its sequence in the DNA being sequenced. Mass spectrometry may be used to determine mass differences between DNA fragments produced in chain-termination reactions.

Another NGS approach is sequencing by synthesis (SBS) technology which is capable of overcoming the limitations of existing pyrosequencing based NGS platforms. Such technologies rely on complex enzymatic cascades for read out, are unreliable for the accurate determination of the number of nucleotides in homopolymeric regions and require excessive amounts of time to run individual nucleotides across growing DNA strands. The SBS NGS platform uses a direct sequencing approach to produce a sequencing strategy with very a high precision, rapid pace and low cost.

SBS sequencing is initialized by fragmenting of the template DNA into fragments, amplification, annealing of DNA sequencing primers, and finally affixing as a high-density array of spots onto a glass chip. The array of DNA fragments are sequenced by extending each fragment with modified nucleotides containing cleavable chemical moieties linked to fluorescent dyes capable of discriminating all four possible nucleotides. The array is scanned continuously by a high-resolution electronic camera (Measure) to determine the fluorescent intensity of each base (A, C, G or T) that was newly incorporated into the extended DNA fragment. After the incorporation of each modified base the array is exposed to cleavage chemistry to break off the fluorescent dye and end cap allowing additional bases to be added. The process is then repeated until the fragment is completely sequenced or maximal read length has been achieved.

mRNA Detection and Quantification

A number of widely used procedures exist for detecting and determining the abundance of a particular mRNA in a total or poly(A) RNA sample. For example, specific mRNAs can be detected using Northern blot analysis, nuclease protection assays (NPA), in situ hybridization (e.g., fluorescence in situ hybridization (FISH)), or reverse transcription-polymerase chain reaction (RT-PCR), and microarray.

In theory, each of these techniques can be used to detect specific RNAs and to precisely determine their expression level. In general, Northern analysis is the only method that provides information about transcript size, whereas NPAs are the easiest way to simultaneously examine multiple messages. In situ hybridization is used to localize expression of a particular gene within a tissue or cell type, and RT-PCR is the most sensitive method for detecting and quantitating gene expression.

RT-PCR allows for the detection of the RNA transcript of any gene, regardless of the scarcity of the starting material or relative abundance of the specific mRNA. In RT-PCR, an RNA template is copied into a complementary DNA (cDNA) using a retroviral reverse transcriptase. The cDNA is then amplified exponentially by PCR using a DNA polymerase. The reverse transcription and PCR reactions can occur in the same or difference tubes. RT-PCR is somewhat tolerant of degraded RNA. As long as the RNA is intact within the region spanned by the primers, the target will be amplified.

Relative quantitative RT-PCR involves amplifying an internal control simultaneously with the gene of interest. The internal control is used to normalize the samples. Once normalized, direct comparisons of relative abundance of a specific mRNA can be made across the samples. It is crucial to choose an internal control with a constant level of expression across all experimental samples (i.e., not affected by experimental treatment). Commonly used internal controls (e.g., GAPDH, β-actin, cyclophilin) often vary in expression and, therefore, may not be appropriate internal controls. Additionally, most common internal controls are expressed at much higher levels than the mRNA being studied. For relative RT-PCR results to be meaningful, all products of the PCR reaction must be analyzed in the linear range of amplification. This becomes difficult for transcripts of widely different levels of abundance.

Competitive RT-PCR is used for absolute quantitation. This technique involves designing, synthesizing, and accurately quantitating a competitor RNA that can be distinguished from the endogenous target by a small difference in size or sequence. Known amounts of the competitor RNA are added to experimental samples and RT-PCR is performed. Signals from the endogenous target are compared with signals from the competitor to determine the amount of target present in the sample.

Northern analysis is the easiest method for determining transcript size, and for identifying alternatively spliced transcripts and multigene family members. It can also be used to directly compare the relative abundance of a given message between all the samples on a blot. The Northern blotting procedure is straightforward and provides opportunities to evaluate progress at various points (e.g., intactness of the RNA sample and how efficiently it has transferred to the membrane). RNA samples are first separated by size via electrophoresis in an agarose gel under denaturing conditions. The RNA is then transferred to a membrane, cross-linked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

The Nuclease Protection Assay (NPA) (including both ribonuclease protection assays and S1 nuclease assays) is a sensitive method for the detection and quantitation of specific mRNAs. The basis of the NPA is solution hybridization of an antisense probe (radiolabeled or nonisotopic) to an RNA sample. After hybridization, single-stranded, unhybridized probe and RNA are degraded by nucleases. The remaining protected fragments are separated on an acrylamide gel. Solution hybridization is typically more efficient than membrane-based hybridization, and it can accommodate up to 100 µg of sample RNA, compared with the 20-30 µg maximum of blot hybridizations. NPAs are also less sensitive to RNA sample degradation than Northern analysis since cleavage is only detected in the region of overlap with the probe (probes are usually about 100-400 bases in length).

NPAs are the method of choice for the simultaneous detection of several RNA species. During solution hybridization and subsequent analysis, individual probe/target interactions are completely independent of one another. Thus, several RNA targets and appropriate controls can be assayed simultaneously (up to twelve have been used in the same reaction), provided that the individual probes are of different lengths. NPAs are also commonly used to precisely map mRNA termini and intron/exon junctions.

In situ hybridization (ISH) is a powerful and versatile tool for the localization of specific mRNAs in cells or tissues. Unlike Northern analysis and nuclease protection assays, ISH does not require the isolation or electrophoretic separation of RNA. Hybridization of the probe takes place within the cell or tissue. Since cellular structure is maintained throughout the procedure, ISH provides information about the location of mRNA within the tissue sample.

The procedure begins by fixing samples in neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while non-isotopically labeled probes are conveniently detected with colorimetric or fluorescent reagents.

DNA Detection and Quantification

A number of widely used procedures exist for detecting and determining the abundance of a particular DNA in a sample. For example, the technology of PCR permits amplification and subsequent detection of minute quantities of a target nucleic acid. Details of PCR are well described in the art, including, for example, U.S. Pat. Nos. 4,683,195 to Mullis et al., 4,683,202 to Mullis and 4,965,188 to Mullis et al. Generally, oligonucleotide primers are annealed to the denatured strands of a target nucleic acid, and primer extension products are formed by the polymerization of deoxynucleoside triphosphates by a polymerase. A typical PCR method involves repetitive cycles of template nucleic acid denaturation, primer annealing and extension of the annealed primers by the action of a thermostable polymerase. The process results in exponential amplification of the target nucleic acid, and thus allows the detection of targets existing in very low concentrations in a sample. It is understood and herein contemplated that there are variant PCR methods known in the art that may also be utilized in the disclosed methods, for example, Quantitative PCR (QPCR); microarrays, real-time PCR; hot start PCR; nested PCR; allele-specific PCR; and Touchdown PCR.

Microarrays

An array is an orderly arrangement of samples, providing a medium for matching known and unknown DNA samples based on base-pairing rules and automating the process of identifying the unknowns. An array experiment can make use of common assay systems such as microplates or standard blotting membranes, and can be created by hand or make use of robotics to deposit the sample. In general, arrays are described as macroarrays or microarrays, the difference being the size of the sample spots. Macroarrays contain sample spot sizes of about 300 microns or larger and can be easily imaged by existing gel and blot scanners. The sample spot sizes in microarray can be 300 microns or less, but typically less than 200 microns in diameter and these arrays usually contains\ thousands of spots. Microarrays require specialized robotics and/or imaging equipment that generally are not commercially available as a complete system. Terminologies that have been used in the literature to describe this technology include, but not limited to: biochip, DNA chip, DNA microarray, GENECHIP® (Affymetrix, Inc which refers to its high density, oligonucleotide-based DNA arrays), and gene array.

DNA microarrays or DNA chips are fabricated by high-speed robotics, generally on glass or nylon substrates, for which probes with known identity are used to determine complementary binding, thus allowing massively parallel gene expression and gene discovery studies. An experiment with a single DNA chip can provide information on thousands of genes simultaneously. It is herein contemplated that the disclosed microarrays can be used to monitor gene expression, disease diagnosis, gene discovery, drug discovery (pharmacogenomics), and toxicological research or toxicogenomics.

There are two variants of the DNA microarray technology, in terms of the property of arrayed DNA sequence with known identity. Type I microarrays comprise a probe cDNA (500~5,000 bases long) that is immobilized to a solid surface such as glass using robot spotting and exposed to a set of targets either separately or in a mixture. This method is traditionally referred to as DNA microarray. With Type I microarrays, localized multiple copies of one or more polynucleotide sequences, preferably copies of a single polynucleotide sequence are immobilized on a plurality of defined regions of the substrate's surface. A polynucleotide refers to a chain of nucleotides ranging from 5 to 10,000 nucleotides. These immobilized copies of a polynucleotide sequence are suitable for use as probes in hybridization experiments.

To prepare beads coated with immobilized probes, beads are immersed in a solution containing the desired probe sequence and then immobilized on the beads by covalent or non-covalent means. Alternatively, when the probes are immobilized on rods, a given probe can be spotted at defined regions of the rod. Typical dispensers include a micropipette delivering solution to the substrate with a robotic system to control the position of the micropipette with respect to the substrate. There can be a multiplicity of dispensers so that reagents can be delivered to the reaction regions simultaneously. In one embodiment, a microarray is formed by using ink-jet technology based on the piezoelectric effect, whereby a narrow tube containing a liquid of interest, such as oligonucleotide synthesis reagents, is encircled by an adapter. An electric charge sent across the adapter causes the adapter to expand at a different rate than the tube and forces a small drop of liquid onto a substrate.

Samples may be any sample containing polynucleotides (polynucleotide targets) of interest and obtained from any bodily fluid (blood, urine, saliva, phlegm, gastric juices, etc.), cultured cells, biopsies, or other tissue preparations. DNA or RNA can be isolated from the sample according to any of a number of methods well known to those of skill in the art. In one embodiment, total RNA is isolated using the TRIzol total RNA isolation reagent (Life Technologies, Inc., Rockville, Md.) and RNA is isolated using oligo d(T) column chromatography or glass beads. After hybridization and processing, the hybridization signals obtained should reflect accurately the amounts of control target polynucleotide added to the sample.

The plurality of defined regions on the substrate can be arranged in a variety of formats. For example, the regions may be arranged perpendicular or in parallel to the length of the casing. Furthermore, the targets do not have to be directly bound to the substrate, but rather can be bound to the substrate through a linker group. The linker groups may typically vary from about 6 to 50 atoms long. Linker groups include ethylene glycol oligomers, diamines, diacids and the like. Reactive groups on the substrate surface react with one of the terminal portions of the linker to bind the linker to the substrate. The other terminal portion of the linker is then functionalized for binding the probes.

Sample polynucleotides may be labeled with one or more labeling moieties to allow for detection of hybridized probe/target polynucleotide complexes. The labeling moieties can include compositions that can be detected by spectroscopic, photochemical, biochemical, bioelectronic, immunochemical, electrical, optical or chemical means. The labeling moieties include radioisotopes, such as $^{32}P$, $^{33}P$ or $^{35}S$, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, biotin, and the like.

Labeling can be carried out during an amplification reaction, such as polymerase chain reaction and in vitro or in vivo transcription reactions. Alternatively, the labeling moiety can be incorporated after hybridization once a probe-target complex his formed. In one embodiment, biotin is first incorporated during an amplification step as described above. After the hybridization reaction, unbound nucleic acids are rinsed away so that the only biotin remaining bound to the substrate is that attached to target polynucleotides that are hybridized to the polynucleotide probes. Then, an avidin-conjugated fluorophore, such as avidin-phycoerythrin, that binds with high affinity to biotin is added.

Hybridization causes a polynucleotide probe and a complementary target to form a stable duplex through base pairing. Hybridization methods are well known to those skilled in the art. Stringent conditions for hybridization can be defined by salt concentration, temperature, and other chemicals and conditions. Varying additional parameters, such as hybridization time, the concentration of detergent (sodium dodecyl sulfate, SDS) or solvent (formamide), and the inclusion or exclusion of carrier DNA, are well known to those skilled in the art. Additional variations on these conditions will be readily apparent to those skilled in the art.

Methods for detecting complex formation are well known to those skilled in the art. In one embodiment, the polynucleotide probes are labeled with a fluorescent label and measurement of levels and patterns of complex formation is accomplished by fluorescence microscopy, preferably confocal fluorescence microscopy. An argon ion laser excites the fluorescent label, emissions are directed to a photomultiplier and the amount of emitted light detected and quantitated. The detected signal should be proportional to the amount of probe/target polynucleotide complex at each position of the microarray. The fluorescence microscope can be associated with a computer-driven scanner device to generate a quantitative two-dimensional image of hybridization intensities. The scanned image is examined to determine the abundance/expression level of each hybridized target polynucleotide.

In a differential hybridization experiment, polynucleotide targets from two or more different biological samples are labeled with two or more different fluorescent labels with different emission wavelengths. Fluorescent signals are detected separately with different photomultipliers set to detect specific wavelengths. The relative abundances/expression levels of the target polynucleotides in two or more samples are obtained. Typically, microarray fluorescence intensities can be normalized to take into account variations in hybridization intensities when more than one microarray is used under similar test conditions. In one embodiment, individual polynucleotide probe/target complex hybridization intensities are normalized using the intensities derived from internal normalization controls contained on each microarray.

Type II microarrays comprise an array of oligonucleotides (20~80-mer oligos) or peptide nucleic acid (PNA) probes that is synthesized either in situ (on-chip) or by conventional synthesis followed by on-chip immobilization. The array is exposed to labeled sample DNA, hybridized, and the identity/abundance of complementary sequences are determined. This method, "historically" called DNA chips, was developed at Affymetrix, Inc., which sells its photolithographically fabricated products under the GENECHIP® trademark.

The basic concept behind the use of Type II arrays for gene expression is simple: labeled cDNA or cRNA targets derived from the mRNA of an experimental sample are hybridized to nucleic acid probes attached to the solid support. By monitoring the amount of label associated with each DNA location, it is possible to infer the abundance of each mRNA species represented. Although hybridization has been used for decades to detect and quantify nucleic acids, the combination of the miniaturization of the technology and the large and growing amounts of sequence information, have enormously expanded the scale at which gene expression can be studied.

Microarray manufacturing can begin with a 5-inch square quartz wafer. Initially the quartz is washed to ensure uniform hydroxylation across its surface. Because quartz is naturally hydroxylated, it provides an excellent substrate for the attachment of chemicals, such as linker molecules, that are later used to position the probes on the arrays.

The wafer is placed in a bath of silane, which reacts with the hydroxyl groups of the quartz, and forms a matrix of covalently linked molecules. The distance between these silane molecules determines the probes' packing density, allowing arrays to hold over 500,000 probe locations, or features, within a mere 1.28 square centimeters. Each of these features harbors millions of identical DNA molecules. The silane film provides a uniform hydroxyl density to initiate probe assembly. Linker molecules, attached to the silane matrix, provide a surface that may be spatially activated by light.

Probe synthesis occurs in parallel, resulting in the addition of an A, C, T, or G nucleotide to multiple growing chains simultaneously. To define which oligonucleotide chains will receive a nucleotide in each step, photolithographic masks, carrying 18 to 20 square micron windows that correspond to the dimensions of individual features, are placed over the coated wafer. The windows are distributed over the mask based on the desired sequence of each probe. When ultraviolet light is shone over the mask in the first step of synthesis, the exposed linkers become deprotected and are available for nucleotide coupling.

Once the desired features have been activated, a solution containing a single type of deoxynucleotide with a removable protection group is flushed over the wafer's surface. The nucleotide attaches to the activated linkers, initiating the synthesis process.

Although each position in the sequence of an oligonucleotide can be occupied by 1 of 4nucleotides, resulting in an apparent need for 25×4, or 100, different masks per wafer, the synthesis process can be designed to significantly reduce this requirement. Algorithms that help minimize mask usage calculate how to best coordinate probe growth by adjusting synthesis rates of individual probes and identifying situations when the same mask can be used multiple times.

Some of the key elements of selection and design are common to the production of all microarrays, regardless of their intended application. Strategies to optimize probe hybridization, for example, are invariably included in the process of probe selection. Hybridization under particular pH, salt, and temperature conditions can be optimized by taking into account melting temperatures and using empirical rules that correlate with desired hybridization behaviors.

To obtain a complete picture of a gene's activity, some probes are selected from regions shared by multiple splice or polyadenylation variants. In other cases, unique probes that distinguish between variants are favored. Inter-probe distance is also factored into the selection process.

A different set of strategies is used to select probes for genotyping arrays that rely on multiple probes to interrogate individual nucleotides in a sequence. The identity of a target base can be deduced using four identical probes that vary only in the target position, each containing one of the four possible bases.

Alternatively, the presence of a consensus sequence can be tested using one or two probes representing specific alleles. To genotype heterozygous or genetically mixed samples, arrays with many probes can be created to provide redundant information, resulting in unequivocal genotyping. In addition, generic probes can be used in some applications to maximize flexibility. Some probe arrays, for example, allow the separation and analysis of individual reaction products from complex mixtures, such as those used in some protocols to identify single nucleotide polymorphisms (SNPs).

Real-time PCR

Real-time PCR monitors the fluorescence emitted during the reaction as an indicator of amplicon production during each PCR cycle (i.e., in real time) as opposed to the endpoint detection. The real-time progress of the reaction can be viewed in some systems. Real-time PCR does not detect the size of the amplicon and thus does not allow the differentiation between DNA and cDNA amplification, however, it is not influenced by non-specific amplification unless SYBR Green is used. Real-time PCR quantitation eliminates post-PCR processing of PCR products. This helps to increase throughput and reduce the chances of carryover contamination. Real-time PCR also offers a wide dynamic range of up to $10^7$-fold. Dynamic range of any assay determines how much target concentration can vary and still be quantified. A wide dynamic range means that a wide range of ratios of target and normaliser can be assayed with equal sensitivity and specificity. It follows that the broader the dynamic range, the more accurate the quantitation. When combined with RT-PCR, a real-time RT-PCR reaction reduces the time needed for measuring the amount of amplicon by providing for the visualization of the amplicon as the amplification process is progressing.

The real-time PCR system is based on the detection and quantitation of a fluorescent reporter. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed. A significant increase in fluorescence above the baseline value measured during the 3-15 cycles can indicate the detection of accumulated PCR product.

A fixed fluorescence threshold is set significantly above the baseline that can be altered by the operator. The parameter CT (threshold cycle) is defined as the cycle number at which the fluorescence emission exceeds the fixed threshold.

There are three main fluorescence-monitoring systems for DNA amplification: (1) hydrolysis probes; (2) hybridising probes; and (3) DNA-binding agents. Hydrolysis probes include TaqMan probes, molecular beacons and scorpions. They use the fluorogenic 5' exonuclease activity of Taq polymerase to measure the amount of target sequences in cDNA samples.

TaqMan probes are oligonucleotides longer than the primers (20-30 bases long with a Tm value of 10° C. higher) that contain a fluorescent dye usually on the 5' base, and a quenching dye (usually TAMRA) typically on the 3' base. When irradiated, the excited fluorescent dye transfers energy to the nearby quenching dye molecule rather than fluorescing (this is called FRET=Förster or fluorescence resonance energy transfer). Thus, the close proximity of the reporter and quencher prevents emission of any fluorescence while the probe is intact. TaqMan probes are designed to anneal to an internal region of a PCR product. When the polymerase replicates a template on which a TaqMan probe is bound, its 5' exonuclease activity cleaves the probe. This ends the activity of quencher (no FRET) and the reporter dye starts to emit fluorescence which increases in each cycle proportional to the rate of probe cleavage. Accumulation of PCR products is detected by monitoring the increase in fluorescence of the reporter dye (note that primers are not labelled). TaqMan assay uses universal thermal cycling parameters and PCR reaction conditions. Because the cleavage occurs only if the probe hybridises to the target, the origin of the detected fluorescence is specific amplification. The process of hybridisation and cleavage does not interfere with the exponential accumulation of the product. One specific requirement for fluorogenic probes is that there be no G at the 5' end. A 'G' adjacent to the reporter dye can quench reporter fluorescence even after cleavage.

Molecular beacons also contain fluorescent (FAM, TAMRA, TET, ROX) and quenching dyes (typically DAB-CYL) at either end but they are designed to adopt a hairpin structure while free in solution to bring the fluorescent dye and the quencher in close proximity for FRET to occur. They have two arms with complementary sequences that form a very stable hybrid or stem. The close proximity of the reporter and the quencher in this hairpin configuration suppresses reporter fluorescence. When the beacon hybridises to the target during the annealing step, the reporter dye is separated from the quencher and the reporter fluoresces (FRET does not occur). Molecular beacons remain intact during PCR and must rebind to target every cycle for fluorescence emission. This will correlate to the amount of PCR product available. All real-time PCR chemistries allow detection of multiple DNA species (multiplexing) by designing each probe/beacon with a spectrally unique fluor/quench pair as long as the platform is suitable for melting curve analysis if SYBR green is used. By multiplexing, the target(s) and endogenous control can be amplified in single tube.

With Scorpion probes, sequence-specific priming and PCR product detection is achieved using a single oligonucleotide. The Scorpion probe maintains a stem-loop configuration in the unhybridised state. The fluorophore is attached to the 5' end and is quenched by a moiety coupled to the 3' end. The 3' portion of the stem also contains sequence that is complementary to the extension product of the primer. This sequence is linked to the 5' end of a specific primer via a non-amplifiable monomer. After extension of the Scorpion primer, the specific probe sequence is able to bind to its complement within the extended amplicon thus opening up the hairpin loop. This prevents the fluorescence from being quenched and a signal is observed.

Another alternative is the double-stranded DNA binding dye chemistry, which quantitates the amplicon production (including non-specific amplification and primer-dimer complex) by the use of a non-sequence specific fluorescent intercalating agent (SYBR-green I or ethidium bromide). It does not bind to ssDNA. SYBR green is a fluorogenic minor groove binding dye that exhibits little fluorescence when in solution but emits a strong fluorescent signal upon binding to double-stranded DNA. Disadvantages of SYBR green-based real-time PCR include the requirement for extensive optimisation. Furthermore, non-specific amplifications require follow-up assays (melting point curve or dissociation analysis) for amplicon identification. The method has been used in HFE-C282Y genotyping. Another controllable problem is that longer amplicons create a stronger signal (if combined with other factors, this may cause CDC camera saturation, see below). Normally SYBR green is used in singleplex reactions, however when coupled with melting point analysis, it can be used for multiplex reactions.

The threshold cycle or the CT value is the cycle at which a significant increase in ΔRn is first detected (for definition of ΔRn, see below). The threshold cycle is when the system begins to detect the increase in the signal associated with an exponential growth of PCR product during the log-linear phase. This phase provides the most useful information about the reaction (certainly more important than the endpoint). The slope of the log-linear phase is a reflection of the amplification efficiency. The efficiency (Eff) of the reaction can be calculated by the formula: $\text{Eff}=10^{(-1/slope)}-1$. The efficiency of the PCR should be 90-100% (3.6>slope >3.1). A number of variables can affect the efficiency of the PCR. These factors include length of the amplicon, secondary structure and primer quality. Although valid data can be obtained that fall outside of the efficiency range, the qRT-PCR should be further optimised or alternative amplicons designed. For the slope to be an indicator of real amplification (rather than signal drift), there has to be an inflection point. This is the point on the growth curve when the log-linear phase begins. It also represents the greatest rate of change along the growth curve. (Signal drift is characterised by gradual increase or decrease in fluorescence without amplification of the product.) The important parameter for quantitation is the $C_T$. The higher the initial amount of genomic DNA, the sooner accumulated product is detected in the PCR process, and the lower the $C_T$ value. The threshold should be placed above any baseline activity and within the exponential increase phase (which looks linear in the log transformation). Some software allows determination of the cycle threshold ($C_T$) by a mathematical analysis of the growth curve. This provides better run-to-run reproducibility. A $C_T$ value of 40 means no amplification and this value cannot be included in the calculations. Besides being used for quantitation, the $C_T$ value can be used for qualitative analysis as a pass/fail measure.

Multiplex TaqMan assays can be performed using multiple dyes with distinct emission wavelengths. Available dyes for this purpose are FAM, TET, VIC and JOE (the most expensive). TAMRA is reserved as the quencher on the probe and ROX as the passive reference. For best results, the combination of FAM (target) and VIC (endogenous control) is recommended (they have the largest difference in emission maximum) whereas JOE and VIC should not be combined. It is important that if the dye layer has not been chosen correctly, the machine will still read the other dye's spectrum. For example, both VIC and FAM emit fluorescence in a similar range to each other and when doing a single dye, the wells should be labelled correctly. In the case of multiplexing, the spectral compensation for the post run analysis should be turned on (on ABI 7700: Instrument/Diagnostics/Advanced Options/Miscellaneous). Activating spectral compensation improves dye spectral resolution.

Nested PCR

The disclosed methods can further utilize nested PCR. Nested PCR increases the specificity of DNA amplification, by reducing background due to non-specific amplification of DNA. Two sets of primers are being used in two successive PCRs. In the first reaction, one pair of primers is used to generate DNA products, which besides the intended target, may still consist of non-specifically amplified DNA fragments. The product(s) are then used in a second PCR with a set of primers whose binding sites are completely or partially different from and located 3' of each of the primers used in the first reaction. Nested PCR is often more successful in specifically amplifying long DNA fragments than conventional PCR, but it requires more detailed knowledge of the target sequences.

Primers and Probes

The disclosed methods and assays can use primers and probes. As used herein, "primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

As used herein, "probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are disclosed. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids. As an example of the use of primers, one or more primers can be used to create extension products from and templated by a first nucleic acid.

The size of the primers or probes for interaction with the nucleic acids can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the nucleic acid of interest typically will be used to produce extension products and/or other replicated or amplified products that contain a region of the nucleic acid of interest. The size of the product can be such that the size can be accurately determined to within 3, or 2 or 1 nucleotides.

In certain embodiments the product can be, for example, at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product can be, for example, less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

Fluorescent Change Probes and Primers

Fluorescent change probes and fluorescent change primers refer to all probes and primers that involve a change in fluorescence intensity or wavelength based on a change in the form or conformation of the probe or primer and nucleic acid to be detected, assayed or replicated. Examples of fluorescent change probes and primers include molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, PNA probes and QPNA probes.

Fluorescent change probes and primers can be classified according to their structure and/or function. Fluorescent change probes include hairpin quenched probes, cleavage quenched probes, cleavage activated probes, and fluorescent activated probes. Fluorescent change primers include stem quenched primers and hairpin quenched primers.

Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted; the quenching moiety is no longer in proximity to the fluorescent label and fluorescence increases. Examples of hairpin quenched probes are molecular beacons, fluorescent triplex oligos, triplex molecular beacons, triplex FRET probes, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during amplification), the quenching moiety is no longer in proximity to the fluorescent label and fluorescence increases. TaqMan probes are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is increased or altered by hybridization of the probe to a target sequence. Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity. Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends of the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes.

Stem quenched primers are primers that when not hybridized to a complementary sequence form a stem structure (either an intramolecular stem structure or an intermolecular stem structure) that brings a fluorescent label and a quenching moiety into proximity such that fluorescence from the label is quenched. When the primer binds to a complementary sequence, the stem is disrupted; the quenching moiety is no longer in proximity to the fluorescent label and fluorescence increases. In the disclosed method, stem quenched primers are used as primers for nucleic acid synthesis and thus become incorporated into the synthesized or amplified nucleic acid. Examples of stem quenched primers are peptide nucleic acid quenched primers and hairpin quenched primers.

Peptide nucleic acid quenched primers are primers associated with a peptide nucleic acid quencher or a peptide nucleic acid fluor to form a stem structure. The primer contains a fluorescent label or a quenching moiety and is associated with either a peptide nucleic acid quencher or a peptide nucleic acid fluor, respectively. This puts the fluorescent label in proximity to the quenching moiety. When the primer is replicated, the peptide nucleic acid is displaced, thus allowing the fluorescent label to produce a fluorescent signal.

Hairpin quenched primers are primers that when not hybridized to a complementary sequence form a hairpin structure (and, typically, a loop) that brings a fluorescent label and a quenching moiety into proximity such that fluorescence from the label is quenched. When the primer binds to a complementary sequence, the stem is disrupted; the quenching moiety is no longer in proximity to the fluorescent label and fluorescence increases. Hairpin quenched primers are typically used as primers for nucleic acid synthesis and thus become incorporated into the synthesized or amplified nucleic acid. Examples of hairpin quenched primers are Amplifluor primers and scorpion primers.

Cleavage activated primers are similar to cleavage activated probes except that they are primers that are incorporated into replicated strands and are then subsequently cleaved.

Immunoassays

As shown herein, biomarkers can be detected by ELISPOT, ELISA, Flow Cytometry, or by an immuno array or similar protein array or microarray. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), enzyme linked immunospot assay (ELISPOT), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Labels

To aid in detection and quantitation of nucleic acids produced using the disclosed methods, labels can be directly incorporated into nucleotides and nucleic acids or can be coupled to detection molecules such as probes and primers. As used herein, a label is any molecule that can be associated with a nucleotide or nucleic acid, directly or indirectly, and which results in a measurable, detectable signal, either directly or indirectly. Many such labels for incorporation into nucleotides and nucleic acids or coupling to nucleic acid probes are known to those of skill in the art. Examples of labels suitable for use in the disclosed method are radioactive isotopes, fluorescent molecules, phosphorescent molecules, enzymes, antibodies, and ligands. Fluorescent labels, especially in the context of fluorescent change probes and primers, are useful for real-time detection of amplification.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, CASCADE BLUE®, OREGON GREEN®, pyrene, lissamine, xanthenes, acridines, oxazines, phycoerythrin, macrocyclic chelates of lanthanide ions such as quantum dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, BerberineSulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine 0, Coumarin-Phalloidin, CY3.1 8, CY5.1 8, CY7, Dans (1-Dimethyl Amino Naphaline 5 Sulphonic Acid), Dansa (DiaminoNaphtylSulphonic Acid), Dansyl NH-CH3, Diamino Phenyl Oxydiazole (DAO), Dimethylamino-5-Sulphonic acid, Dipyrrometheneboron-Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, IntrawhiteCf Liquid, Leucophor PAF, Leucophor SF, Leucophor WS, LissamineRhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green PyronineStilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Phycoerythrin B, PolyazaindacenePontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (StilbeneIsothiosulphonic acid), Stilbene, Snarf 1, sulphoRhodamine B Can C, SulphoRhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

The absorption and emission maxima, respectively, for some of these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Labeled nucleotides are a form of label that can be directly incorporated into the amplification products during synthesis. Examples of labels that can be incorporated into amplified nucleic acids include nucleotide analogs such as BrdUrd, aminoallyldeoxyuridine, 5-methylcytosine, bromouridine, and nucleotides modified with biotin or with suitable haptens such as digoxygenin. Suitable fluorescence-labeled nucleotides are Fluorescein-isothiocyanate-dUTP, Cyanine-3-dUTP and Cyanine-5-dUTP. One example of a nucleotide analog label for DNA is BrdUrd (bromodeoxyuridine, BrdUrd, BrdU, BUdR, Sigma-Aldrich Co). Other examples of nucleotide analogs for incorporation of label into DNA are AA-dUTP (aminoallyl-deoxyuridine triphosphate, Sigma-Aldrich Co.), and 5-methyl-dCTP (Roche Molecular Biochemicals). One example of a nucleotide analog for incorporation of label into RNA is biotin-16-UTP (biotin-16-uridine-5'-triphosphate, Roche Molecular Biochemicals). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl) phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Molecules that combine two or more of these labels are also considered labels. Any of the known labels can be used with the disclosed probes, tags, and method to label and detect nucleic acid amplified using the disclosed method. Methods for detecting and measuring signals generated by labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary label coupled to the antibody. As used herein, detection molecules are molecules which interact with amplified nucleic acid and to which one or more labels are coupled.

In one aspect disclosed herein are a population of cells determined to be produced by three dimensional culturing, wherein the determination of whether the stromal cell was cultured in a three dimensional culture can occur by any of the methods disclosed herein.

The skilled artisan can appreciate that the disclosed cultures can occur in any media appropriate for propogating the particular stromal cell population. Non-limiting examples of base media useful in culturing cells to derive ASCs include Minimum Essential Medium Eagle, ADC-1, LPM (Bovine Serum Albumin-free), F10(HAM), F12 (HAM), DCCM1, DCCM2, RPMI 1640, BGJ Medium (with and without Fitton-Jackson Modification), Basal Medium Eagle (BME-with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E-with Earle's sale base), Medium M199 (M199H-with Hank's salt base), Minimum Essential Medium Eagle (MEM-E-with Earle's salt base), Minimum Essential Medium Eagle (MEM-H-with Hank's salt base) and Minimum Essential Medium Eagle (MEM-NAA with non-essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. In some embodiments the medium is DMEM. These and other useful media are available from GIBCO, Grand Island, N.Y., USA and Biological Industries, Bet HaEmek, Israel, among others.

The medium may be supplemented such as with serum such as fetal serum of bovine or other species, and optionally or alternatively, growth factors, vitamins (e.g. ascorbic acid), cytokines, salts (e.g. B-glycerophosphate), steroids (e.g. dexamethasone) and hormones e.g., growth hormone, erythropoeitin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between picogram/ml to milligram/ml levels.

The skilled artisan will appreciate that additional components can be added to the culture medium. Such components may be antibiotics, antimycotics, albumin, amino acids, and other components known to the art for the culture of cells.

Examples of adherent materials that may be used to culture cells as described herein include, but are not limited to, a polyester, a polypropylene, a polyalkylene, a polyfluorochloroethylene, a polyvinyl chloride, a polystyrene, a polysulfone, a cellulose acetate, a glass fiber, a ceramic particle, a matrigel, an extra cellular matrix component (e.g., fibronectin, chondronectin, laminin), a collagen, a hydrogel, a poly L lactic acid and an inert metal fiber. These materials are exemplary only as the material used for the 2D or 3D substratum surface is immaterial so long as it permits the cells to adhere.

Even though exemplary culture methods are described for 2D and 3D surfaces, it is the dimensionality of the culture system (3D versus 2D) that is used in the description of the several embodiments that is the relevant factor. Thus, any of a variety of culture methods, including but not limited to suspension bioreactors, packed bed bioreactors, fixed bed bioreactors, rolling flasks, and any method of culturing cells in a liquid environment, may be used in the various aspects and embodiments of the invention.

Adherent material for the 3D aspect of the present invention is configured for 3D culturing thereby providing a growth matrix that substantially increases the available attachment surface for the adherence of the stromal cells so as to mimic the infrastructure of the tissue (e.g., placenta).

For example, for a growth matrix of 0.5 mm in height, the increase is by a factor of at least from 5 to 30 times, calculated by projection onto a base of the growth matrix. Such an increase by a factor of about 5 to 30 times, is per unit layer, and if a plurality of such layers, either stacked or separated by spacers or the like, is used, the factor of 5 to 30 times applies per each such structure. When the matrix is used in sheet form, preferably non-woven fiber sheets, or sheets of open-pore foamed polymers, the preferred thickness of the sheet is about 50 to 1000 μm or more, there being provided adequate porosity for cell entrance, entrance of nutrients and for removal of waste products from the sheet. According to a one embodiment the pores have an effective diameter of 10 μm to 300 μm. Such sheets can be prepared from fibers of various thicknesses, in one embodiment the fiber thickness or fiber diameter range is from about 0.5 μm to 100 μm, in other embodiments it is in the range of 10 μm to 15 μm in diameter.

The structures of the 3D culture system may be supported by, or even better bonded to, a porous support sheet or screen providing for dimensional stability and physical strength. Such matrix sheets may also be cut, punched, or shredded to provide particles with projected area of the order of about 0.2 $mm^2$ to about 10 $mm^2$, with the same order of thickness (about 50 to 1000 μm). Further details relating to the fabrication, use and/or advantages of the growth matrix which was used to reduce the present invention to practice are described in U.S. Pat. No. 5,168,085, and in particular, U.S. Pat. No. 5,266,476, both of which are incorporated herein by reference.

The adherent surface which comprises the 3D structure may be of any shape, including but not limited to squares, triangles, rings, disks, balls, ovals, cruciforms and any other shape that can be formed by a flexable or inflexible 3D structure.

For high scale production, culturing is preferably effected in a 3D bioreactor.

Examples of such bioreactors include, but are not limited to, a plug flow bioreactor, a continuous stirred tank bioreactor and a stationary-bed bioreactor. An example of a three dimensional (3D) plug flow bioreactor is described in U.S. Pat. No. 6,911,201 that is capable of supporting the growth and prolonged maintenance of stromal cells. In this bioreactor, stromal cells are seeded on porous carriers made of a non-woven fabric matrix of polyester, packed in a glass column, thereby enabling the propagation of large cell numbers in a relatively small volume.

The matrix used in the plug flow bioreactor can include, but is not limited to, sheet form, non-woven fiber sheets, or sheets of open-pore foamed polymers, the preferred thickness of the sheet is about 50 to 1000 μm or more, there being provided adequate porosity for cell entrance, entrance of nutrients and for removal of waste products from the sheet.

Other examples of 3D bioreactors include, but are not limited to, a plug flow bioreactor, a continuous stirred tank bioreactor, a stationary-bed bioreactor, a CelliGen Plus® bioreactor system (New Brunswick Scientific (NBS), and a BIOFLO 310 bioreactor system (New Brunswick Scientific (NBS). Other examples of bioreactors include an air-lift bioreactor where air is typically fed into the bottom of a central draught tube flowing up while forming bubbles; a cell seeding perfusion bioreactor with Polyactive foams [as described in Wendt, D. et al., Biotechnol Bioeng 84: 205-214, (2003)], tubular poly-L-lactic acid (PLLA) porous scaffolds in a radial-flow perfusion bioreactor [as described in Kitagawa et al., Biotechnology and Bioengineering 93(5): 947-954 (2006). Still other bioreactors which can be used are described in U.S. Pat. Nos. 6,277,151, 6,197,575, 6,139, 578, 6,132,463, 5,902,741 and 5,629,186.

In general, bioreactors are capable of 3D expansion of adherent cells under controlled conditions (e.g., pH, temperature and oxygen levels) and with constant cell growth medium perfusion. Furthermore, the cell cultures can be directly monitored for concentration levels of glucose, lactate, glutamine, glutamate and ammonium. The glucose consumption rate and the lactate formation rate of the adherent cells enable to measure cell growth rate and to determine the harvest time.

Cell seeding is preferably effected at a concentration of 20,000-1,500,000 cells/ml at seeding. In an exemplary embodiment a total of $150\pm30\times10^6$ cells are seeded, $3\text{-}5\times10^6$ cell/g carrier are seeded, or $0.015\text{-}0.1\times10^6$ cell/ml are seeded.

Cells can be harvested when at least about 10% of cells are proliferating while avoiding uncontrolled differentiation and senescence.

Culturing is effected for at least about 2 days, 3 days, 4 days, 5 days, 10 days, 20 days, a month or even more. It will be appreciated that culturing in a bioreactor can prolong this period.

Adherent cells of some embodiments of the present invention comprise at least about 10%, 28%, 30%, 50%, 80% or more proliferative cells (as can be assayed by FACS monitoring S and G2/M phases).

In order to provide 3D and 2D adherent cells, various manufacturing systems may be used. The examples provided below are illustrative only and additional methods are provided in the Examples. In any of the culture systems described that utilize placenta as the cells source, all placentas obtained were received from the maternity ward under approval of the Helsinki Committee of the medical facility. Accordingly, all placenta donors signed an informed consent and Donor Screening and Donor Testing was performed.

In general, to initiate any of the culture processes that involve placenta, the whole placenta is cut into pieces under aseptic conditions under laminar flow hood, washed with Hank's buffer solution and incubated for 3 hours at 37° C. with 0.1% Collagenase (1 mg Collagenase/ml tissue). 2D cell medium (2D-Medium comprising DMEM supplemented with 10% FBS, fungizone 0.25 µg/ml and gentamycine 50 µg/ml) is added and the digested tissue is roughly filtered through a sterile metal strainer, collected in a sterile beaker and centrifuged (10 minutes, 1200 RPM, 4° C.). Using gentle pipeting, suspended cells are then washed with 2D-Medium supplemented with antibiotics, seeded in 80 cm$^2$ flasks and incubated at 37° C. in a tissue culture incubator under humidified condition supplemented with 5% CO2. Following 2-3 days, in which the cells were allowed to adhere to the flask surface, they are washed with PBS and 2D-Medium was added.

While placenta is one source of ASC and is the ASC source used in the Examples, placenta is an exemplary source and other cells sources may be used. Examples of other ASC sources include adipose tissue, umbilical cord, blood, and bone marrow. Thus, in the various aspects and embodiments of the invention the ASC are not limited to placenta-derived ASC. However, in one embodiment, the ASC-2D, the ASC-3D, or both the ASC-2D and ASC-3D are placenta-derived ASC.

Manufacture of 2D Adherent Stromal Cells

When ASC-2D cells are used herein, they may be produced by any process using a 2D culture system, such as flasks or plates. In general, cells are seeded into a 2D vessel and allowed to adhere. The first passage is usually carried out after 10-15 days. Beginning at passage 2 and continuing until passage 6-8, cells are passaged when the culture reached 70-80% confluence, usually after about 3-5 days (1.5-2 doublings). The cells are detached from plates or flasks using 0.25% trypsin-EDTA (4 minutes at 37° C.) and seeded in a culture density of about $3\pm0.2\times10^3$ cells/cm$^2$. The size of the tissue culture flasks or plates can be increased as the passaging proceeds. For example, the culturing process may start in a 80 cm$^2$ tissue culture flask, continue in 175 cm$^2$, then in 500 cm$^2$ (Triple flask). In some embodiments, cells may be re-seeded into Cell Factory 10 tray (6320 cm$^2$).

ASC-2D are generally detached from the culture surface with Trypsin-EDTA (Biological Industries, Beit Ha'emek, Israel; 3-15 minutes with gentle agitation, 1-5 times), and are thereafter resuspended in DMEM and either used directly for testing or other uses or cryopreserved for later testing or use.

In one embodiment, the ASC-2D are placental-derived ASC-2D.

Manufacture of 3D Adherent Cells by PluriX™

In one embodiment, the ASC-3D cells are produced using a PluriX™ Plug Flow bioreactor (Pluristem, Haifa, Israel) as illustrated in U.S. Pat. No. 6,911,201. In general, the PluriX™ Plug Flow bioreactor is loaded with 1-100 ml packed 3D porous carriers (4 mm in diameter) made of a non woven fabric matrix of polyester. These carriers enable the propagation of large cell numbers in a relatively small volume. The bioreactor is maintained in an incubator of 37° C., with flow rate regulated and monitored by a valve, and peristaltic pump. The $O_2$ proportion is suited to the level of dissolved $O_2$ at the bioreactor exit, determined by a monitor.

Non-confluent primary human adherent 2D cell cultures are trypsinized, washed, resuspended in DMEM supplemented with 10% FBS, Pen-Strep-Nystatin mixture and 2 mM L-glutamine, and seeded ($10^3\text{-}10^5$ cells/ml) via an injection point onto the 3D carriers in a sterile Plug Flow bioreactor. Prior to inoculation, the bioreactor is generally filled with PBS-Ca—Mg (Biological Industries, Beit Ha'emek, Israel), autoclaved (120° C., 30 min) and washed with Dulbecco's growth medium containing 10% heat-inactivated fetal calf serum and a Pen-Strep-Nystatin mixture. Flow is kept at a rate of about 0.1-5 ml/min. The seeding process generally involves cessation of circulation for 2-48 hrs, which allow the cells to settle on the carriers. The bioreactor is generally kept under controlled temperature (37° C.) and pH conditions (pH=6.7-7.4); using an incubator supplied with sterile air and CO2 as needed. Growth medium is replaced 2-3 times a week. Circulation medium is replaced with fresh DMEM media, every 4 hr to 7 days. At a density of about $1\times10^6\text{-}1\times10^7$ cells/ml (generally following 12-40 days of growth), the total medium volume is removed from the bioreactor and bioreactor and carriers are washed 3-5 times with PBS. PluriX™ 3D-adherent cells are then detached from the carriers with Trypsin-EDTA; (Biological Industries, Beit Ha'emek, Israel; 3-15 minutes with gentle agitation, 1-5 times), and are thereafter resuspended in DMEM and either used directly for testing or other uses or cryopreserved for later testing or use.

In one embodiment, the PluriX™ ASC-3D are placental-derived ASC-3D.

Manufacture of 3D Adherent Cells by Celligen™

In another embodiment, the ASC-3D cells are produced using a Celligen™ Plug Flow bioreactor, as illustrated in US 2010/0209403 and WO 2009/037690. Generally speaking, the 3D growth phase is performed using an automatic CelliGen Plus® or BIOFLO 310 bioreactor system [(New Brunswick Scientific (NBS)] depicted in FIG. 8C of US 2010/0209403. The parameters of the process are monitored and controlled by a control console which included connectors for probes, motor and pumps, control loops for Dissolved Oxygen (DO), pH, perfusion and agitation (with a motor), a gases control system, water circulation and heating system for temperature control and an operator interface. The controlled process parameters (such as temperature, pH, DO etc.) can be displayed on the operator interface and monitored by a designated controller.

Generally, about $150\pm30\times10^6$ cells cryopreserved ASC-2D are thawed, washed and seeded in a sterile bioreactor.

The bioreactor generally contains 30-50 gr carriers (Fibra-Cel® disks, NBS), made of Polyester and Polypropylene and 1.5±0.1 L 3D-Medium. The growth medium in the bioreactor is kept at the following conditions: 37° C., 70% Dissolved Oxygen (DO) and pH 7.3. Filtered gases (Air, $CO_2$, $N_2$ and $O_2$) are supplied as determined by the control system in order to keep the DO value at 70% and the pH value at 7.3. For the first 24 hours, the medium is usually agitated at 50 Rounds Per Minutes (RPM) and increased up to 200 RPM by day 2. For the first 2-3 days, the cells are grown in a batch mode. Perfusion is initiated when the medium glucose concentration decreases below 550 mg/liter. The perfusion is adjusted in order to keep the glucose concentration constant at approximately 550±50 mg/liter. The glucose consumption rate and the lactate formation rate of the cell culture enables measure of the cell growth rate. These parameters are used to determine the harvest time based on accumulated experimental data.

The cell harvest process starts at the end of the growth phase (usually 4-10 days). The 3D-grown culture is usually harvested by emptying the bioreactor vessel using gravitation via tubing to a waste container. The vessel is opened and the carriers aseptically transferred from the basket to the upper basket net. The bioreactor vessel is then closed and refilled with pre-warmed PBS (37° C.). The agitation speed is increased to about 150 RPM for 2 minutes. The PBS is then drained and this washing procedure repeated twice.

In order to release the cells from the carriers, generally 1.5 L pre-warmed to 37° C. Trypsin-EDTA (Trypsin 0.25%, EDTA 1 mM) is added to the bioreactor vessel and carriers are agitated for 5 minutes in 150 RPM, 37° C. The cell suspension is collected to a sterile container containing 250 ml FBS. The cell suspension ("PLX-C") is then divided or further processed as needed for testing and use.

In one embodiment, the Celligen™ ASC-3D are placental-derived ASC-3D.

Some embodiments refer to a population of cells that is "positive" for at least one marker or at least one biomarker. A population is positive if it is positive by any of the assays described in the Examples.

Some embodiments refer to a population of cells that is "negative" for at least one marker or biomarker. A population is negative if the population contains so few cells positive for the marker that expression of the marker above a threshold level cannot be detected in the population as a whole. In some embodiments gene levels or expression levels are measured using any of the assay methods described in the Examples.

Methods of establishing threshold levels are known to the skilled artisan. For example, a threshold level in FACS analysis or western blotting may be established using an isotype control antibody. As described in the Examples, threshold levels in gene array assays may be set using a comparative source of nucleic acid (such as ASC-2D cDNA) and then measuring negative or positive changes (whether as a fold or percent change). Other methods of providing thresholds for determining whether a biomarker is positive, up-regulated, negative, down-regulated, or essentially unchanged are those used in the Examples section, and include the manufacturer's instructions for antibody array and gene array assays.

Methods for determining gene expression profiles, secretion profiles, and surface and/or intracellular protein expression profiles for ASC-3D and -2D are as set forth elsewhere in the Detailed Description and in the Examples section. It should be noted that although profiles for multiple genes, secreted proteins, and surface and/or intracellular proteins used a biomarkers are presented in the various examples, disclosure of any collection of genes, secreted proteins, and surface and/or intracellular proteins is also intended as an express disclosure of any one or a combination of the described genes, secreted proteins, and surface and/or intracellular proteins.

The present application provides biomarkers for adherent stromal cells (ASC) grown in three dimensional (3D) vs. two dimensional (2D) culture, methods and systems for using those biomarkers to distinguish between ASC-3D and -2D cells cultures, and kits comprising reagents for detecting these biomarkers. In some embodiments, the biomarkers are a panel that comprises two or more different biomarkers, and these biomarkers are measured or detected in an assay to determine whether an ASC was produced in 3D or 2D culture. A kit can be used to detect or measure the biomarkers. In various embodiments, the kits can be used to measure the levels of two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, or even more biomarkers.

In one aspect, aASC-3D is distinguished from a ASC-2D on the basis of the genes, secreted proteins, and surface and/or intracellular proteins profiles of any one, any sub-combination, or all, of the genes and proteins set forth in Tables 1-15. The tables provide reference gene and reference protein sequences from GenBank, a brief description of the genes and proteins, and common alternate names for the genes and proteins. Tables are subdivided by functions, but merely as a matter of convenience. There is overlap among the functional subdivisions (for example, CCL2 is an angiogenesis-related gene, a cytokine or chemokine gene, an inflammatory-related gene) and overlap or lack thereof should not be construed as in any way limiting the combinations of biomarkers that may be used within the various aspects and embodiments of the invention.

Manufacture of 3D Adherent Cells by Packed Bed Spinner Vessel

In one embodiment, the ASC-3D cells are produced using a packed bed spinner flask. The packed is base don a 500 ml glass spinner flask with a magnetic stirrer. The spinner flask if fitted with a packed bed apparatus similar to the Celligen™ Plug Flow bioreactor (see above) which is packed with 1.8gr of fibracel (or other carriers). The spinner is batch fed (rather than by perfusion), fitted with two 0.22 µm filters, and placed in a 37° c. 5% CO2 incubator. Cells are seeded onto the scaffold by introducing to the medium and allowing 4 hours of 40 RPM agitation. Subsequently the RPM is increased to 120 RPM. Medium is assessed daily for glucose level and replaced to maintain acceptable glucose concentration. At the end of the culture process, carriers are removed from the packed bed, washed twice with PBS, and processed or removed from the carriers by agitation and anzymatic digesyion for further use.

TABLE 1

Angiogenesis-related Genes for Use as Biomarkers

| GeneBank | Symbol | Description | Gene Name |
|---|---|---|---|
| NM_018046 | AGGF1 | Angiogenic factor with G patch and FHA domains 1 | FLJ10283, GPATC7, GPATCH7, HSU84971, HUS84971, VG5Q |
| NM_133265 | AMOT | Angiomotin | KIAA1071 |
| NM_001145 | ANG | Angiogenin, ribonuclease, RNase A family, 5 | ALS9, HEL168, MGC22466, MGC71966, RNASE4, RNASE5 |
| NM_001146 | ANGPT1 | Angiopoietin 1 | AGP1, AGPT, ANG1 |
| NM_001147 | ANGPT2 | Angiopoietin 2 | AGPT2, ANG2 |
| NM_004673 | ANGPTL1 | Angiopoietin-like 1 | ANG3, ANGPT3, ARP1, AngY, KIAA0351, UNQ162, dJ595C2.2 |
| NM_001702 | BAI1 | Brain-specific angiogenesis inhibitor 1 | FLJ41988, GDAIF |
| NM_001200 | BMP2 | Bone morphogenetic protein 2 | BMP2A |
| NM_001731 | BTG1 | B-cell translocation gene 1, anti-proliferative | — |
| NM_032965 | CCL15 | Chemokine (C-C motif) ligand 15 | HCC-2, HMRP-2B, LKN-1, LKN1, MIP-1D, MIP-5, MRP-2B, NCC-3, NCC3, SCYA15, SCYL3, SY15 |
| NM_002982 | CCL2 | Chemokine (C-C motif) ligand 2 | GDCF-2, HC11, HSMCR30, MCAF, MCP-1, MCP1, MGC9434, SCYA2, SMC-CF |
| NM_000574 | CD55 | CD55 molecule, decay accelerating factor for complement (Cromer blood group) | CR, CROM, DAF, TC |
| NM_000611 | CD59 | CD59 molecule, complement regulatory protein | 16.3A5, 1F5, EJ16, EJ30, EL32, FLJ38134, FLJ92039, G344, HRF-20, HRF20, MAC-IP, MACIF, MEM43, MGC2354, MIC11, MIN1, MIN2, MIN3, MIRL, MSK21, p18-20 |
| NM_001275 | CHGA | Chromogranin A (parathyroid secretory protein 1) | CGA |
| NM_030582 | COL18A1 | Collagen, type XVIII, alpha 1 | FLJ27325, FLJ34914, KNO, KNO1, KS, MGC74745 |
| NM_000091 | COL4A3 | Collagen, type IV, alpha 3 (Goodpasture antigen) | — |
| NM_000759 | CSF3 | Colony stimulating factor 3 (granulocyte) | C17orf33, CSF3OS, GCSF, MGC45931 |
| NM_001565 | CXCL10 | Chemokine (C-X-C motif) ligand 10 | C7, IFI10, INP10, IP-10, SCYB10, crg-2, gIP-10, mob-1 |
| NM_005409 | CXCL11 | Chemokine (C-X-C motif) ligand 11 | H174, I-TAC, IP-9, IP9, MGC102770, SCYB11, SCYB9B, b-R1 |
| NM_000609 | CXCL12 | Chemokine (C-X-C motif) ligand 12 | IRH, PBSF, SCYB12, SDF1, SDF1A, SDF1B, TLSF, TPAR1 |
| NM_006419 | CXCL13 | Chemokine (C-X-C motif) ligand 13 | ANGIE, ANGIE2, BCA-1, BCA1, BLC, BLR1L, SCYB13 |
| NM_004887 | CXCL14 | Chemokine (C-X-C motif) ligand 14 | BMAC, BRAK, KEC, KS1, MGC10687, MIP-2g, MIP2G, NJAC, SCYB14 |
| NM_002089 | CXCL2 | Chemokine (C-X-C motif) ligand 2 | CINC-2a, GRO2, GROb, MGSA-b, MIP-2a, MIP2, MIP2A, SCYB2 |
| NM_002090 | CXCL3 | Chemokine (C-X-C motif) ligand 3 | CINC-2b, GRO3, GROg, MIP-2b, MIP2B, SCYB3 |
| NM_002994 | CXCL5 | Chemokine (C-X-C motif) ligand 5 | ENA-78, SCYB5 |
| NM_002993 | CXCL6 | Chemokine (C-X-C motif) ligand 6 (granulocyte chemotactic protein 2) | CKA-3, GCP-2, GCP2, SCYB6 |
| NM_002416 | CXCL9 | Chemokine (C-X-C motif) ligand 9 | CMK, Humig, MIG, SCYB9, crg-10 |
| NM_001953 | TYMP | Thymidine phosphorylase | ECGF, ECGF1, MEDPS1, MNGIE, MTDPS1, PDECGF, TP, hPD-ECGF |
| NM_005711 | EDIL3 | EGF-like repeats and discoidin I-like domains 3 | DEL1, MGC26287 |
| NM_001432 | EREG | Epiregulin | ER |
| NM_000800 | FGF1 | Fibroblast growth factor 1 (acidic) | AFGF, ECGF, ECGF-beta, ECGFA, ECGFB, FGF-alpha, FGFA, GLIO703, HBGF1 |
| NM_004114 | FGF13 | Fibroblast growth factor 13 | FGF-13, FGF2, FHF-2, FHF2 |
| NM_002006 | FGF2 | Fibroblast growth factor 2 (basic) | BFGF, FGFB, HBGF-2 |
| NM_005130 | FGFBP1 | Fibroblast growth factor binding protein 1 | FGFBP, HBP17 |
| NM_004469 | FIGF | C-fos induced growth factor (vascular endothelial growth factor D) | VEGF-D, VEGFD |
| NM_002026 | FN1 | Fibronectin 1 | CIG, DKFZp686F10164, DKFZp686H0342, DKFZp686I1370, DKFZp686O13149, ED-B, FINC, FN, FNZ, GFND, GFND2, LETS, MSF |
| NM_006350 | FST | Follistatin | FS |
| NM_002087 | GRN | Granulin | GEP, GP88, PCDGF, PEPI, PGRN |
| NM_002091 | GRP | Gastrin-releasing peptide | BN, GRP-10, preproGRP, proGRP |
| NM_000601 | HGF | Hepatocyte growth factor (hepapoietin A; scatter factor) | DFNB39, F-TCF, HGFB, HPTA, SF |
| NM_024013 | IFNA1 | Interferon, alpha 1 | IFL, IFN, IFN-ALPHA, IFN-alphaD, IFNA13, IFNA, MGC138207, MGC138505, MGC138507 |
| NM_002176 | IFNB1 | Interferon, beta 1, fibroblast | IFB, IFF, IFNB, MGC96956 |
| NM_000619 | IFNG | Interferon, gamma | IFG, IFI |
| NM_000572 | IL10 | Interleukin 10 | CSIF, IL-10, IL10A, MGC126450, MGC126451, TGIF |
| NM_000882 | IL12A | Interleukin 12A (natural killer cell stimulatory factor 1, cytotoxic lymphocyte maturation factor 1, p35) | CLMF, IL-12A, NFSK, NKSF1, P35 |

TABLE 1-continued

Angiogenesis-related Genes for Use as Biomarkers

| GeneBank | Symbol | Description | Gene Name |
|---|---|---|---|
| NM_002187 | IL12B | Interleukin 12B (natural killer cell stimulatory factor 2, cytotoxic lymphocyte maturation factor 2, p40) | CLMF, CLMF2, IL-12B, NKSF, NKSF2 |
| NM_052872 | IL17F | Interleukin 17F | IL-17F, ML-1, ML1 |
| NM_000600 | IL6 | Interleukin 6 (interferon, beta 2) | BSF2, HGF, HSF, IFNB2, IL-6 |
| NM_000584 | IL8 | Interleukin 8 | CXCL8, GCP-1, GCP1, LECT, LUCT, LYNAP, MDNCF, MONAP, NAF, NAP-1, NAP1 |
| NM_003994 | KITLG | KIT ligand | DKFZp686F2250, FPH2, KL-1, Kill, MGF, SCF, SF, SHEP7 |
| NM_001648 | KLK3 | Kallikrein-related peptidase 3 | APS, KLK2A1.PSA, hK3 |
| NM_000230 | LEP | Leptin | FLJ94114, OB, OBS |
| NM_002391 | MDK | Midkine (neurite growth-promoting factor 2) | FLJ27379, MK, NEGF2 |
| NM_005938 | FOXO4 | Forkhead box O4 | AFX, AFX1, MGC120490, MLLT7 |
| NM_002521 | NPPB | Natriuretic peptide B | BNP |
| NM_000906 | NPR1 | Natriuretic peptide receptor A/guanylate cyclase A (atrionatriuretic peptide receptor A) | ANPRA, ANPa, GUC2A, GUCY2A, NPRA |
| NM_002608 | PDGFB | Platelet-derived growth factor beta polypeptide | FLJ12858, PDGF2, SIS, SSV, c-sis |
| NM_025208 | PDGFD | Platelet derived growth factor D | IEGF, MGC26867, SCDGF-B, SCDGFB |
| NM_002619 | PF4 | Platelet factor 4 | CXCL4, MGC 138298, SCYB4 |
| NM_002632 | PGF | Placental growth factor | D12S1900, PGFL, PLGF, PlGF-2, SHGC-10760 |
| NM_000301 | PLG | Plasminogen | DKFZp779M0222 |
| NM_002704 | PPBP | Pro-platelet basic protein (chemokine (C-X-C motif) ligand 7) | B-TG1, Beta-TG, CTAP-III, CTAP3, CTAPIII, CXCL7, LA-PF4, LDGF, MDGF, NAP-2, PBP, SCAR10, SCYB7, TC1, TC2, TGB, TGB1, THBGB, THBGB1 |
| NM_000948 | PRL | Prolactin | — |
| NM_032414 | PROK1 | Prokineticin 1 | EGVEGF, PK1, PRK1 |
| NM_002825 | PTN | Pleiotrophin | HARP, HBGF8, HBNF, NEGF1 |
| NM_004040 | RHOB | Ras homolog gene family, member B | ARH6, ARHB, MST081, MSTP081, RHOH6 |
| NM_002939 | RNH1 | Ribonuclease/angiogenin inhibitor 1 | MGC18200, MGC4569, MGC54054, RAI, RNH |
| NM_001754 | RUNX1 | Runt-related transcription factor 1 | AML1, AML1-EVI-1, AMLCR1, CBFA2, EVI-1, PEBP2aB |
| NM_000488 | SERPINC1 | Serpin peptidase inhibitor, clade C (antithrombin), member 1 | AT3, ATIII, MGC22579 |
| NM_000602 | SERPINE1 | Serpin peptidase inhibitor, clade E (nexin, plasminogen activator inhibitor type 1), member 1 | PAI, PAI-1, PAI1, PLANH1 |
| NM_002615 | SERPINF1 | Serpin peptidase inhibitor, clade F (alpha-2 antiplasmin, pigment epithelium derived factor), member 1 | EPC-1, PEDF |
| NM_006846 | SPINK5 | Serine peptidase inhibitor, Kazal type 5 | DKFZp686K19184, FLJ21544, FLJ97536, FLJ97596, FLJ99794, LEKTI, LETKI, NETS, NS, VAKTI |
| NM_015136 | STAB1 | Stabilin 1 | CLEVER-1, FEEL-1, FELE-1, FEX1, KIAA0246, STAB-1 |
| NM_003236 | TGFA | Transforming growth factor, alpha | TFGA |
| NM_000660 | TGFB1 | Transforming growth factor, beta 1 | CED, DPD1, LAP, TGFB, TGFbeta |
| NM_003246 | THBS1 | Thrombospondin 1 | THBS, THBS-1, TSP, TSP-1, TSP1 |
| NM_005424 | TIE1 | Tyrosine kinase with immunoglobulin-like and EGF-like domains 1 | JTK14, TIE |
| NM_003254 | TIMP1 | TIMP metallopeptidase inhibitor 1 | CLGI, EPA, EPO, FLJ90373, HCI, TIMP |
| NM_003255 | TIMP2 | TIMP metallopeptidase inhibitor 2 | CSC-21K |
| NM_000362 | TIMP3 | TIMP metallopeptidase inhibitor 3 | HSMRK222, K222, K222TA2, SFD |
| NM_000594 | TNF | Tumor necrosis factor | DIF, TNF-alpha, TNFA, TNFSF2 |
| NM_003282 | TNNI2 | Troponin I type 2 (skeletal, fast) | AMCD2B, DA2B, FSSV, fsTnI |
| NM_000363 | TNNI3 | Troponin I type 3 (cardiac) | CMD1FF, CMD2A, CMH7, MGC116817, RCM1, TNNC1, cTnI |
| NM_003376 | VEGFA | Vascular endothelial growth factor A | MGC70609, MVCD1, VEGF, VPF |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 2

Apoptosis-related Genes for Use as Biomarkers

| GeneBank | Symbol | Description | Gene Name |
|---|---|---|---|
| NM_005157 | ABL1 | C-abl oncogene 1, non-receptor tyrosine kinase | ABL, JTK7, bcr, abl, c-ABL, p150, v-abl |
| NM_005163 | AKT1 | V-akt murine thymoma viral oncogene homolog 1 | AKT, MGC99656, PKB, PKB-ALPHA, PRKBA, RAC, RAC-ALPHA |
| NM_001160 | APAF1 | Apoptotic peptidase activating factor 1 | APAF-1, CED4, DKFZp781B1145 |

TABLE 2-continued

Apoptosis-related Genes for Use as Biomarkers

| GeneBank | Symbol | Description | Gene Name |
|---|---|---|---|
| NM_004322 | BAD | BCL2-associated agonist of cell death | BBC2, BCL2L8 |
| NM_004323 | BAG1 | BCL2-associated athanogene | HAP, RAP46 |
| NM_004281 | BAG3 | BCL2-associated athanogene 3 | BAG-3, BIS, CAIR-1, MGC104307 |
| NM_004874 | BAG4 | BCL2-associated athanogene 4 | BAG-4, DKFZp586O2022, SODD |
| NM_001188 | BAK1 | BCL2-antagonist/killer 1 | BAK, BAK-LIKE, BCL2L7, CDN1, MGC117255, MGC3887 |
| NM_004324 | BAX | BCL2-associated X protein | BCL2L4 |
| NM_003921 | BCL10 | B-cell CLL/lymphoma 10 | CARMEN, CIPER, CLAP, c-E10, mE10 |
| NM_000633 | BCL2 | B-cell CLL/lymphoma 2 | Bcl-2 |
| NM_004049 | BCL2A1 | BCL2-related protein A1 | ACC-1, ACC-2, BCL2L5, BFL1, GRS, HBPA1 |
| NM_138578 | BCL2L1 | BCL2-like 1 | BCL-XL, S, BCL2L, BCLX, BCLXL, BCLXS, Bcl-X, DKFZp781P2092, bcl-xL, bcl-xS |
| NM_020396 | BCL2L10 | BCL2-like 10 (apoptosis facilitator) | BCL-B, Boo, Diva, MGC129810, MGC129811 |
| NM_006538 | BCL2L11 | BCL2-like 11 (apoptosis facilitator) | BAM, BIM, BIM-alpha6, BIM-beta6, BIM-beta7, BOD, BimEL, BimL |
| NM_004050 | BCL2L2 | BCL2-like 2 | BCL-W, BCL2-L-2, BCLW, KIAA0271 |
| NM_014739 | BCLAF1 | BCL2-associated transcription factor 1 | BTF, KIAA0164, bK211L9.1 |
| NM_016561 | BFAR | Bifunctional apoptosis regulator | BAR, RNF47 |
| NM_001196 | BID | BH3 interacting domain death agonist | FP497, MGC15319, MGC42355 |
| NM_001197 | BIK | BCL2-interacting killer (apoptosis-inducing) | BIP1, BP4, NBK |
| NM_004536 | NAIP | NLR family, apoptosis inhibitory protein | BIRC1, FLJ18088, FLJ42520, FLJ58811, NLRB1, psiNAIP |
| NM_001166 | BIRC2 | Baculoviral IAP repeat containing 2 | API1, HIAP2, Hiap-2, MIHB, RNF48, c-IAP1, cIAP1 |
| NM_001165 | BIRC3 | Baculoviral IAP repeat containing 3 | AIP1, API2, CIAP2, HAIP1, HIAP1, MALT2, MIHC, RNF49, c-IAP2 |
| NM_001167 | XIAP | X-linked inhibitor of apoptosis | API3, BIRC4, FLJ26913, IAP-3, ILP1, MIHA, XLP2, hIAP-3, hIAP3 |
| NM_016252 | BIRC6 | Baculoviral IAP repeat containing 6 | APOLLON, BRUCE, FLJ13726, FLJ13786, KIAA1289 |
| NM_033341 | BIRC8 | Baculoviral IAP repeat containing 8 | ILP-2, ILP2, hILP2 |
| NM_001205 | BNIP1 | BCL2/adenovirus E1B 19 kDa interacting protein 1 | NIP1, SEC20, TRG-8 |
| NM_004330 | BNIP2 | BCL2/adenovirus E1B 19 kDa interacting protein 2 | BNIP-2, NIP2 |
| NM_004052 | BNIP3 | BCL2/adenovirus E1B 19 kDa interacting protein 3 | NIP3 |
| NM_004331 | BNIP3L | BCL2/adenovirus E1B 19 kDa interacting protein 3-like | BNIP3a, NIX |
| NM_004333 | BRAF | V-raf murine sarcoma viral oncogene homolog B1 | B-RAF1, BRAF1, FLJ95109, MGC126806, MGC138284, NS7, RAFB1 |
| NM_006092 | NOD1 | Nucleotide-binding oligomerization domain containing 1 | CARD4, CLR7.1, NLRC1 |
| NM_032587 | CARD6 | Caspase recruitment domain family, member 6 | CINCIN1 |
| NM_014959 | CARD8 | Caspase recruitment domain family, member 8 | CARDINAL, DACAR, DAKAR, DKFZp779L0366, FLJ18119, FLJ18121, KIAA0955, MGC57162, NDPP, NDPP1, TUCAN |
| NM_033292 | CASP1 | Caspase 1, apoptosis-related cysteine peptidase (interleukin 1, beta, convertase) | ICE, IL1BC, P45 |
| NM_001230 | CASP10 | Caspase 10, apoptosis-related cysteine peptidase | ALPS2, FLICE2, MCH4 |
| NM_012114 | CASP14 | Caspase 14, apoptosis-related cysteine peptidase | MGC119078, MGC119079 |
| NM_032982 | CASP2 | Caspase 2, apoptosis-related cysteine peptidase | CASP-2, ICH1, NEDD-2, NEDD2 |
| NM_004346 | CASP3 | Caspase 3, apoptosis-related cysteine peptidase | CPP32, CPP32B, SCA-1 |
| NM_001225 | CASP4 | Caspase 4, apoptosis-related cysteine peptidase | ICE(rel)II, ICEREL-II, ICH-2, Mih1, TX, TX |
| NM_004347 | CASP5 | Caspase 5, apoptosis-related cysteine peptidase | ICE(rel)III, ICEREL-III, ICH-3, MGC141966 |
| NM_032992 | CASP6 | Caspase 6, apoptosis-related cysteine peptidase | MCH2 |
| NM_001227 | CASP7 | Caspase 7, apoptosis-related cysteine peptidase | CMH-1, ICE-LAP3, MCH3 |
| NM_001228 | CASP8 | Caspase 8, apoptosis-related cysteine peptidase | ALPS2B, CAP4, Casp-8, FLICE, FLJ17672, MACH, MCH5, MGC78473 |
| NM_001229 | CASP9 | Caspase 9, apoptosis-related cysteine peptidase | APAF-3, APAF3, CASPASE-9c, ICE-LAP6, MCH6 |
| NM_001250 | CD40 | CD40 molecule, TNF receptor superfamily member 5 | Bp50, CDW40, MGC9013, TNFRSF5, p50 |
| NM_000074 | CD40LG | CD40 ligand | CD154, CD40L, HIGM1, IGM, IMD3, T-BAM, TNFSF5, TRAP, gp39, hCD40L |
| NM_003879 | CFLAR | CASP8 and FADD-like apoptosis regulator | CASH, CASP8AP1, CLARP, Casper, FLAME, FLAME-1, FLAME1, FLIP, I-FLICE, MRIT, c-FLIP, c-FLIPL, c-FLIPR, c-FLIPS |
| NM_001279 | CIDEA | Cell death-inducing DFFA-like effector a | CIDE-A |
| NM_014430 | CIDEB | Cell death-inducing DFFA-like effector b | — |

TABLE 2-continued

Apoptosis-related Genes for Use as Biomarkers

| GeneBank | Symbol | Description | Gene Name |
|---|---|---|---|
| NM_003805 | CRADD | CASP2 and RIPK1 domain containing adaptor with death domain | MGC9163, RAIDD |
| NM_004938 | DAPK1 | Death-associated protein kinase 1 | DAPK, DKFZp781I035 |
| NM_004401 | DFFA | DNA fragmentation factor, 45 kDa, alpha polypeptide | DFF-45, DFF1, ICAD |
| NM_003824 | FADD | Fas (TNFRSF6)-associated via death domain | MGC8528, MORT1 |
| NM_000043 | FAS | Fas (TNF receptor superfamily, member 6) | ALPS1A, APO-1, APT1, CD95, FAS1, FASTM, TNFRSF6 |
| NM_000639 | FASLG | Fas ligand (TNF superfamily, member 6) | APT1LG1, CD178, CD95-L, CD95L, FASL, TNFSF6 |
| NM_001924 | GADD45A | Growth arrest and DNA-damage-inducible, alpha | DDIT1, GADD45 |
| NM_003806 | HRK | Harakiri, BCL2 interacting protein (contains only BH3 domain) | DP5, HARAKIRI |
| NM_000875 | IGF1R | Insulin-like growth factor 1 receptor | CD221, IGFIR, IGFR, JTK13, MGC142170, MGC142172, MGC18216 |
| NM_000595 | LTA | Lymphotoxin alpha (TNF superfamily, member 1) | LT, TNFB, TNFSF1 |
| NM_002342 | LTBR | Lymphotoxin beta receptor (TNFR superfamily, member 3) | CD18, D12S370, LT-BETA-R, TNF-R-III, TNFCR, TNFR-RP, TNFR2-RP, TNFRSF3 |
| NM_021960 | MCL1 | Myeloid cell leukemia sequence 1 (BCL2-related) | BCL2L3, EAT, MCL1-ES, MCL1L, MCL1S, MGC104264, MGC1839, Mcl-1, TM, bcl2-L-3, mcl1, EAT |
| NM_003946 | NOL3 | Nucleolar protein 3 (apoptosis repressor with CARD domain) | ARC, FLJ35304, MYP, NOP, NOP30 |
| NM_013258 | PYCARD | PYD and CARD domain containing | ASC, CARD5, MGC10332, TMS, TMS-1, TMS1 |
| NM_003821 | RIPK2 | Receptor-interacting serine-threonine kinase 2 | CARD3, CARDIAK, CCK, GIG30, RICK, RIP2 |
| NM_000594 | TNF | Tumor necrosis factor | DIF, TNF-alpha, TNFA, TNFSF2 |
| NM_003844 | TNFRSF10A | Tumor necrosis factor receptor superfamily, member 10a | APO2, CD261, DR4, MGC9365, TRAILR-1, TRAILR1 |
| NM_003842 | TNFRSF10B | Tumor necrosis factor receptor superfamily, member 10b | CD262, DR5, KILLER, KILLER, DR5, TRAIL-R2, TRAILR2, TRICK2, TRICK2A, TRICK2B, TRICKB, ZTNFR9 |
| NM_002546 | TNFRSF11B | Tumor necrosis factor receptor superfamily, member 11b | MGC29565, OCIF, OPG, TR1 |
| NM_001065 | TNFRSF1A | Tumor necrosis factor receptor superfamily, member 1A | CD120a, FPF, MGC19588, TBP1, TNF-R, TNF-R-I, TNF-R55, TNFAR, TNFR1, TNFR55, TNFR60, p55, p55-R, p60 |
| NM_014452 | TNFRSF21 | Tumor necrosis factor receptor superfamily, member 21 | BM-018, DR6, MGC31965 |
| NM_003790 | TNFRSF25 | Tumor necrosis factor receptor superfamily, member 25 | APO-3, DDR3, DR3, LARD, TNFRSF12, TR3, TRAMP, WSL-1, WSL-LR |
| NM_001242 | CD27 | CD27 molecule | MGC20393, S152, T14, TNFRSF7, Tp55 |
| NM_001561 | TNFRSF9 | Tumor necrosis factor receptor superfamily, member 9 | 4-1BB, CD137, CDw137, FLJ43501, ILA, MGC2172 |
| NM_003810 | TNFSF10 | Tumor necrosis factor (ligand) superfamily, member 10 | APO2L, Apo-2L, CD253, TL2, TRAIL |
| NM_001252 | CD70 | CD70 molecule | CD27L, CD27LG, TNFSF7 |
| NM_001244 | TNFSF8 | Tumor necrosis factor (ligand) superfamily, member 8 | CD153, CD30L, CD30LG, MGC138144 |
| NM_000546 | TP53 | Tumor protein p53 | FLJ92943, LFS1, P53, TRP53 |
| NM_005426 | TP53BP2 | Tumor protein p53 binding protein, 2 | 53BP2, ASPP2, BBP, P53BP2, PPP1R13A |
| NM_005427 | TP73 | Tumor protein p73 | P73 |
| NM_003789 | TRADD | TNFRSF1A-associated via death domain | Hs.89862, MGC11078 |
| NM_021138 | TRAF2 | TNF receptor-associated factor 2 | MGC: 45012, TRAP, TRAP3 |
| NM_003300 | TRAF3 | TNF receptor-associated factor 3 | CAP-1, CD40bp, CRAF1, LAP1 |
| NM_004295 | TRAF4 | TNF receptor-associated factor 4 | CART1, MLN62, RNF83 |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 3

Cell-Lineage-related Genes for Use as Biomarkers

| GeneBank | Symbol | Description | Gene Name |
|---|---|---|---|
| NM_000477 | ALB | Albumin | DKFZp779N1935, PRO0883, PRO0903, PRO1341 |
| NM_000042 | APOH | Apolipoprotein H (beta-2-glycoprotein I) | B2G1, B2GP1, BG |
| NM_198098 | AQP1 | Aquaporin 1 (Colton blood group) | AQP-CHIP, CHIP28, CO, MGC26324 |
| NM_130851 | BMP4 | Bone morphogenetic protein 4 | BMP2B, BMP2B1, MCOPS6, OFC11, ZYME |

TABLE 3-continued

Cell-Lineage-related Genes for Use as Biomarkers

| GeneBank | Symbol | Description | Gene Name |
|---|---|---|---|
| NM_000579 | CCR5 | Chemokine (C-C motif) receptor 5 | CC-CKR-5, CCCKR5, CD195, CKR-5, CKR5, CMKBR5, FLJ78003, IDDM22 |
| NM_001773 | CD34 | CD34 molecule | — |
| NM_000733 | CD3E | CD3e molecule, epsilon (CD3-TCR complex) | FLJ18683, T3E, TCRE |
| NM_001783 | CD79A | CD79a molecule, immunoglobulin-associated alpha | IGA, MB-1 |
| NM_020985 | CHAT | Choline O-acetyltransferase | CHOACTASE, CMS1A, CMS1A2 |
| NM_000493 | COL10A1 | Collagen, type X, alpha 1 | — |
| NM_000095 | COMP | Cartilage oligomeric matrix protein | EDM1, EPD1, MED, MGC131819, MGC149768, PSACH, THBS5 |
| NM_001868 | CPA1 | Carboxypeptidase A1 (pancreatic) | CPA |
| NM_000396 | CTSK | Cathepsin K | CTS02, CTSO, CTSO1, CTSO2, MGC23107, PKND, PYCD |
| NM_001920 | DCN | Decorin | CSCD, DSPG2, PG40, PGII, PGS2, SLRR1B |
| NM_178153 | DCX | Doublecortin | DBCN, DC, FLJ51296, LISX, SCLH, XLIS |
| NM_006892 | DNMT3B | DNA (cytosine-5-)-methyltransferase 3 beta | ICF, M.HsaIIIB |
| NM_001935 | DPP4 | Dipeptidyl-peptidase 4 | ADABP, ADCP2, CD26, DPPIV, TP103 |
| NM_001428 | ENO1 | Enolase 1, (alpha) | ENO1L1, MBP1, NNE, PPH |
| NM_001446 | FABP7 | Fatty acid binding protein 7, brain | B-FABP, BLBP, DKFZp547J2313, FABPB, MRG |
| NM_004464 | FGF5 | Fibroblast growth factor 5 | HBGF-5, Smag-82 |
| NM_004496 | FOXA1 | Forkhead box A1 | HNF3A, MGC33105, TCF3A |
| NM_012183 | FOXD3 | Forkhead box D3 | AIS1, Genesis, HFH2 |
| NM_005249 | FOXG1 | Forkhead box G1 | BF1, BF2, FHKL3, FKH2, FKHL1, FKHL2, FKHL3, FKHL4, FOXG1A, FOXG1B, FOXG1C, HBF-1, HBF-2, HBF-3, HBF-G2, HBF2, HFK1, HFK2, HFK3, KHL2, QIN |
| NM_000151 | G6PC | Glucose-6-phosphatase, catalytic subunit | G6PC1, G6PT, GSD1, GSD1a, MGC163350 |
| NM_000817 | GAD1 | Glutamate decarboxylase 1 (brain, 67 kDa) | FLJ45882, GAD, SCP |
| NM_000818 | GAD2 | Glutamate decarboxylase 2 (pancreatic islets and brain, 65 kDa) | GAD65, MGC161605, MGC161607 |
| NM_000153 | GALC | Galactosylceramidase | — |
| NM_002049 | GATA1 | GATA binding protein 1 (globin transcription factor 1) | ERYF1, GATA-1, GF-1, GF1, NFE1, XLTT |
| NM_032638 | GATA2 | GATA binding protein 2 | FLJ45948, MGC2306, NFE1B |
| NM_005257 | GATA6 | GATA binding protein 6 | — |
| NM_001485 | GBX2 | Gastrulation brain homeobox 2 | — |
| NM_020634 | GDF3 | Growth differentiation factor 3 | KFS3, MCOP7, MCOPCB6 |
| NM_002055 | GFAP | Glial fibrillary acidic protein | FLJ42474, FLJ45472 |
| NM_004821 | HAND1 | Heart and neural crest derivatives expressed 1 | Hxt, Thing1, bHLHa27, eHand |
| NM_021973 | HAND2 | Heart and neural crest derivatives expressed 2 | DHAND2, FLJ16260, Hed, MGC125303, MGC125304, Thing2, bHLHa26, dHand |
| NM_001010926 | HES5 | Hairy and enhancer of split 5 (*Drosophila*) | bHLHb38 |
| NM_178849 | HNF4A | Hepatocyte nuclear factor 4, alpha | FLJ39654, HNF4, HNF4a7, HNF4a8, HNF4a9, HNF4alpha, MODY, MODY1, NR2A1, NR2A21, TCF, TCF14 |
| NM_004967 | IBSP | Integrin-binding sialoprotein | BNSP, BSP, BSP-II, SP-II |
| NM_000612 | IGF2 | Insulin-like growth factor 2 (somatomedin A) | C11orf43, FLJ22066, FLJ44734, IGF-II, PP9974 |
| NM_000207 | INS | Insulin | IDDM2, ILPR, IRDN, MODY10 |
| NM_000213 | ITGB4 | Integrin, beta 4 | CD104 |
| NM_000421 | KRT10 | Keratin 10 | BCIE, BIE, CK10, EHK, K10, KPP |
| NM_000526 | KRT14 | Keratin 14 | CK14, EBS3, EBS4, K14, NFJ |
| NM_002276 | KRT19 | Keratin 19 | CK19, K19, K1CS, MGC15366 |
| NM_020997 | LEFTY1 | Left-right determination factor 1 | LEFTB, LEFTYB |
| NM_006301 | MAP3K12 | Mitogen-activated protein kinase kinase kinase 12 | DLK, MEKK12, MUK, ZPK, ZPKP1 |
| NM_017584 | MIOX | Myo-inositol oxygenase | ALDRL6, MGC90217 |
| NM_031944 | MIXL1 | Mix paired-like homeobox | MGC138179, MILD1, MIX, MIXL |
| NM_005823 | MSLN | Mesothelin | MPF, SMRP |
| NM_005963 | MYH1 | Myosin, heavy chain 1, skeletal muscle, adult | MGC133384, MYHSA1, MYHa, MyHC-2X, D, MyHC-2x |
| NM_022844 | MYH11 | Myosin, heavy chain 11, smooth muscle | AAT4, DKFZp686D10126, DKFZp686D19237, FAA4, FLJ35232, MGC126726, MGC32963, SMHC, SMMHC |
| NM_000257 | MYH7 | Myosin, heavy chain 7, cardiac muscle, beta | CMD1S, CMH1, DKFZp451F047, MGC138376, MGC138378, MPD1, MYHCB, SPMD, SPMM |
| NM_000258 | MYL3 | Myosin, light chain 3, alkali; ventricular, skeletal, slow | CMH8, MLC1SB, MLC1V, VLC1 |
| NM_024865 | NANOG | Nanog homeobox | — |
| NM_002500 | NEUROD1 | Neurogenic differentiation 1 | BETA2, BHF-1, MODY6, NEUROD, bHLHa3 |
| NM_024019 | NEUROG2 | Neurogenin 2 | Atoh4, MGC46562, Math4A, NGN2, bHLHa8, ngn-2 |
| NM_002509 | NKX2-2 | NK2 homeobox 2 | NKX2.2, NKX2B |
| NM_006172 | NPPA | Natriuretic peptide A | ANF, ANP, ATFB6, CDD-ANF, PND |
| NM_005806 | OLIG2 | Oligodendrocyte lineage transcription factor 2 | BHLHB1, OLIGO2, PRKCBP2, RACK17, bHLHe19 |

TABLE 3-continued

Cell-Lineage-related Genes for Use as Biomarkers

| GeneBank | Symbol | Description | Gene Name |
|---|---|---|---|
| NM_021728 | OTX2 | Orthodenticle homeobox 2 | MCOPS5, MGC45000 |
| NM_006206 | PDGFRA | Platelet-derived growth factor receptor, alpha polypeptide | CD140A, MGC74795, PDGFR2, RHEPDGFRA |
| NM_005397 | PODXL | Podocalyxin-like | Gp200, MGC138240, PC, PCLP, PCLP-1 |
| NM_004575 | POU4F2 | POU class 4 homeobox 2 | BRN3.2, BRN3B, Brn-3b |
| NM_002701 | POU5F1 | POU class 5 homeobox 1 | MGC22487, OCT3, OCT4, OTF-3, OTF3, OTF4, Oct-3, Oct-4 |
| NM_006017 | PROM1 | Prominin 1 | AC133, CD133, CORD12, MCDR2, PROML1, RP41, STGD4 |
| NM_138296 | PTCRA | Pre T-cell antigen receptor alpha | PT-ALPHA, PTA |
| NM_002903 | RCVRN | Recoverin | RCV1 |
| NM_001754 | RUNX1 | Runt-related transcription factor 1 | AML1, AML1-EVI-1, AMLCR1, CBFA2, EVI-1, PEBP2aB |
| NM_001035 | RYR2 | Ryanodine receptor 2 (cardiac) | ARVC2, ARVD2, RYR-2, VTSIP |
| NM_000542 | SFTPB | Surfactant protein B | PSP-B, SFTB3, SFTP3, SMDP1, SP-B |
| NM_003019 | SFTPD | Surfactant protein D | COLEC7, PSP-D, SFTP4, SP-D |
| NM_020346 | SLC17A6 | Solute carrier family 17 (sodium-dependent inorganic phosphate cotransporter), member 6 | DNPI, VGLUT2 |
| NM_020309 | SLC17A7 | Solute carrier family 17 (sodium-dependent inorganic phosphate cotransporter), member 7 | BNPI, VGLUT1 |
| NM_000340 | SLC2A2 | Solute carrier family 2 (facilitated glucose transporter), member 2 | GLUT2 |
| NM_080552 | SLC32A1 | Solute carrier family 32 (GABA vesicular transporter), member 1 | VGAT, VIAAT |
| NM_006932 | SMTN | Smoothelin | FLJ35168, FLJ35365, FLJ35620, FLJ38597 |
| NM_022454 | SOX17 | SRY (sex determining region Y)-box 17 | FLJ22252, VUR3 |
| NM_003106 | SOX2 | SRY (sex determining region Y)-box 2 | ANOP3, MCOPS3, MGC2413 |
| NM_031439 | SOX7 | SRY (sex determining region Y)-box 7 | MGC10895 |
| NM_003181 | T | T, brachyury homolog (mouse) | MGC104817, TFT |
| NM_000353 | TAT | Tyrosine aminotransferase | — |
| NM_000372 | TYR | Tyrosinase (oculocutaneous albinism IA) | CMM8, OCA1A, OCAIA, SHEP3 |
| NM_174900 | ZFP42 | Zinc finger protein 42 homolog (mouse) | REX1, ZNF754 |
| NM_003412 | ZIC1 | Zic family member 1 | ZIC, ZNF201 |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 4

Cytokine and Chemokine-related Genes for Use as Biomarkers

| GeneBank | Symbol | Description | Gene Name |
|---|---|---|---|
| NM_004797 | ADIPOQ | Adiponectin, C1Q and collagen domain containing | ACDC, ACRP30, ADIPQTL1, ADPN, APM-1, APM1, GBP28 |
| NM_004757 | AIMP1 | Aminoacyl tRNA synthetase complex-interacting multifunctional protein 1 | EMAP2, EMAPII, SCYE1, p43 |
| NM_005161 | APLNR | Apelin receptor | AGTRL1, APJ, APJR, FLJ90771, FLJ96609, HG11, MGC45246 |
| NM_004048 | B2M | Beta-2-microglobulin | — |
| NM_001709 | BDNF | Brain-derived neurotrophic factor | MGC34632 |
| NM_006129 | BMP1 | Bone morphogenetic protein 1 | FLJ44432, PCOLC, PCP, PCP2, TLD |
| NM_001200 | BMP2 | Bone morphogenetic protein 2 | BMP2A |
| NM_001201 | BMP3 | Bone morphogenetic protein 3 | BMP-3A |
| NM_130851 | BMP4 | Bone morphogenetic protein 4 | BMP2B, BMP2B1, MCOPS6, OFC11, ZYME |
| NM_021073 | BMP5 | Bone morphogenetic protein 5 | MGC34244 |
| NM_001718 | BMP6 | Bone morphogenetic protein 6 | VGR, VGR1 |
| NM_001719 | BMP7 | Bone morphogenetic protein 7 | OP-1 |
| NM_001720 | BMP8B | Bone morphogenetic protein 8b | BMP8, MGC131757, OP2 |
| NM_001735 | C5 | Complement component 5 | CPAMD4, FLJ17816, FLJ17822, MGC142298 |
| NM_001736 | C5AR1 | Complement component 5a receptor 1 | C5A, C5AR, C5R1, CD88 |
| NM_001296 | CCBP2 | Chemokine binding protein 2 | CCR10, CCR9, CMKBR9, D6, MGC126678, MGC138250, hD6 |
| NM_002981 | CCL1 | Chemokine (C-C motif) ligand 1 | I-309, P500, SCYA1, SISe, TCA3 |
| NM_002986 | CCL11 | Chemokine (C-C motif) ligand 11 | MGC22554, SCYA11 |
| NM_032965 | CCL15 | Chemokine (C-C motif) ligand 15 | HCC-2, HMRP-2B, LKN-1, LKN1, MIP-1D, MIP-5, MRP-2B, NCC-3, NCC3, SCYA15, SCYL3, SY15 |
| NM_004590 | CCL16 | Chemokine (C-C motif) ligand 16 | CKb12, HCC-4, ILINCK, LCC-1, LEC, LMC, MGC117051, Mtn-1, NCC-4, NCC4, SCYA16, SCYL4 |

TABLE 4-continued

Cytokine and Chemokine-related Genes for Use as Biomarkers

| GeneBank | Symbol | Description | Gene Name |
|---|---|---|---|
| NM_002987 | CCL17 | Chemokine (C-C motif) ligand 17 | A-152E5.3, ABCD-2, MGC138271, MGC138273, SCYA17, TARC |
| NM_002988 | CCL18 | Chemokine (C-C motif) ligand 18 (pulmonary and activation-regulated) | AMAC-1, AMAC1, CKb7, DC-CK1, DCCK1, MIP-4, PARC, SCYA18 |
| NM_006274 | CCL19 | Chemokine (C-C motif) ligand 19 | CKb11, ELC, MGC34433, MIP-3b, MIP3B, SCYA19 |
| NM_002982 | CCL2 | Chemokine (C-C motif) ligand 2 | GDCF-2, HC11, HSMCR30, MCAF, MCP-1, MCP1, MGC9434, SCYA2, SMC-CF |
| NM_004591 | CCL20 | Chemokine (C-C motif) ligand 20 | CKb4, LARC, MIP-3a, MIP3A, SCYA20, ST38 |
| NM_002989 | CCL21 | Chemokine (C-C motif) ligand 21 | 6Ckine, CKb9, ECL, MGC34555, SCYA21, SLC, TCA4 |
| NM_002990 | CCL22 | Chemokine (C-C motif) ligand 22 | ABCD-1, DC, B-CK, MDC, MGC34554, SCYA22, STCP-1 |
| NM_002991 | CCL24 | Chemokine (C-C motif) ligand 24 | Ckb-6, MPIF-2, MPIF2, SCYA24 |
| NM_002983 | CCL3 | Chemokine (C-C motif) ligand 3 | G0S19-1, LD78ALPHA, MIP-1-alpha, MIP1A, SCYA3 |
| NM_002984 | CCL4 | Chemokine (C-C motif) ligand 4 | ACT2, AT744.1, G-26, LAG1, MGC104418, MGC126025, MGC126026, MIP-1-beta, MIP1B, MIP1B1, SCYA2, SCYA4 |
| NM_002985 | CCL5 | Chemokine (C-C motif) ligand 5 | D17S136E, MGC17164, RANTES, SCYA5, SISd, TCP228 |
| NM_006273 | CCL7 | Chemokine (C-C motif) ligand 7 | FIC, MARC, MCP-3, MCP3, MGC138463, MGC138465, NC28, SCYA6, SCYA7 |
| NM_005623 | CCL8 | Chemokine (C-C motif) ligand 8 | HC14, MCP-2, MCP2, SCYA10, SCYA8 |
| NM_001295 | CCR1 | Chemokine (C-C motif) receptor 1 | CD191, CKR-1, CKR1, CMKBR1, HM145, MIP1aR, SCYAR1 |
| NM_016602 | CCR10 | Chemokine (C-C motif) receptor 10 | GPR2 |
| NM_001123396 | CCR2 | Chemokine (C-C motif) receptor 2 | CC-CKR-2, CCR2A, CCR2B, CD192, CKR2, CKR2A, CKR2B, CMKBR2, FLJ78302, MCP-1-R, MGC103828, MGC111760, MGC168006 |
| NM_001837 | CCR3 | Chemokine (C-C motif) receptor 3 | CC-CKR-3, CD193, CKR3, CMKBR3, MGC102841 |
| NM_005508 | CCR4 | Chemokine (C-C motif) receptor 4 | CC-CKR-4, CD194, CKR4, CMKBR4, ChemR13, HGCN:14099, K5-5, MGC88293 |
| NM_000579 | CCR5 | Chemokine (C-C motif) receptor 5 | CC-CKR-5, CCCKR5, CD195, CKR-5, CKR5, CMKBR5, FLJ78003, IDDM22 |
| NM_004367 | CCR6 | Chemokine (C-C motif) receptor 6 | BN-1, C-C CKR-6, CC-CKR-6, CCR-6, CD196, CKR-L3, CKRL3, CMKBR6, DCR2, DRY6, GPR29, GPRCY4, STRL22 |
| NM_001838 | CCR7 | Chemokine (C-C motif) receptor 7 | BLR2, CD197, CDw197, CMKBR7, EBI1 |
| NM_005201 | CCR8 | Chemokine (C-C motif) receptor 8 | CC-CKR-8, CCR-8, CDw198, CKRL1, CMKBR8, CMKBRL2, CY6, GPRCY6, MGC129966, MGC129973, TER1 |
| NM_016557 | CCRL1 | Chemokine (C-C motif) receptor-like 1 | CC-CKR-11, CCBP2, CCR-11, CCR10, CCR11, CCX CKR, CCX-CKR, CKR-11, PPR1, VSHK1 |
| NM_003965 | CCRL2 | Chemokine (C-C motif) receptor-like 2 | CKRX, CRAM, CRAM-A, CRAM-B, FLJ55815, HCR, MGC116710, MGC34104 |
| NM_000074 | CD40LG | CD40 ligand | CD154, CD40L, HIGM1, IGM, IMD3, T-BAM, TNFSF5, TRAP, gp39, hCD40L |
| NM_001252 | CD70 | CD70 molecule | CD27L, CD27LG, TNFSF7 |
| NM_181641 | CKLF | Chemokine-like factor | C32, CKLF1, CKLF2, CKLF3, CKLF4, UCK-1 |
| NM_004072 | CMKLR1 | CHEMOKINE-LIKE RECEPTOR 1 | CHEMERINR, ChemR23, DEZ, MGC126105, MGC126106 |
| NM_181269 | CMTM1 | CKLF-like MARVEL transmembrane domain containing 1 | CKLFH, CKLFH1, CKLFSF1, MGC71870 |
| NM_144673 | CMTM2 | CKLF-like MARVEL transmembrane domain containing 2 | CKLFSF2, MGC39436 |
| NM_144601 | CMTM3 | CKLF-like MARVEL transmembrane domain containing 3 | BNAS2, CKLFSF3, FLJ31762, MGC51956 |
| NM_178818 | CMTM4 | CKLF-like MARVEL transmembrane domain containing 4 | CKLFSF4 |
| NM_000614 | CNTF | Ciliary neurotrophic factor | HCNTF |
| NM_000757 | CSF1 | Colony stimulating factor 1 (macrophage) | MCSF, MGC31930 |
| NM_000758 | CSF2 | Colony stimulating factor 2 (granulocyte-macrophage) | GMCSF, MGC131935, MGC138897 |
| NM_000759 | CSF3 | Colony stimulating factor 3 (granulocyte) | C17orf33, CSF3OS, GCSF, MGC45931 |
| NM_002996 | CX3CL1 | Chemokine (C—X3—C motif) ligand 1 | ABCD-3, C3Xkine, CXC3, CXC3C, NTN, NTT, SCYD1, fractalkine, neurotactin |
| NM_001511 | CXCL1 | Chemokine (C—X—C motif) ligand 1 (melanoma growth stimulating activity, alpha) | FSP, GRO1, GROa, MGSA, MGSA-a, NAP-3, SCYB1 |
| NM_001565 | CXCL10 | Chemokine (C—X—C motif) ligand 10 | C7, IFI10, INP10, IP-10, SCYB10, crg-2, gIP-10, mob-1 |
| NM_005409 | CXCL11 | Chemokine (C—X—C motif) ligand 11 | H174, I-TAC, IP-9, IP9, MGC102770, SCYB11, SCYB9B, b-R1 |
| NM_000609 | CXCL12 | Chemokine (C—X—C motif) ligand 12 | IRH, PBSF, SCYB12, SDF1, SDF1A, SDF1B, TLSF, TPAR1 |

TABLE 4-continued

Cytokine and Chemokine-related Genes for Use as Biomarkers

| GeneBank | Symbol | Description | Gene Name |
|---|---|---|---|
| NM_006419 | CXCL13 | Chemokine (C—X—C motif) ligand 13 | ANGIE, ANGIE2, BCA-1, BCA1, BLC, BLR1L, SCYB13 |
| NM_022059 | CXCL16 | Chemokine (C—X—C motif) ligand 16 | CXCLG16, SR-PSOX, SRPSOX |
| NM_002089 | CXCL2 | Chemokine (C—X—C motif) ligand 2 | CINC-2a, GRO2, GROb, MGSA-b, MIP-2a, MIP2, MIP2A, SCYB2 |
| NM_002090 | CXCL3 | Chemokine (C—X—C motif) ligand 3 | CINC-2b, GRO3, GROg, MIP-2b, MIP2B, SCYB3 |
| NM_002994 | CXCL5 | Chemokine (C—X—C motif) ligand 5 | ENA-78, SCYB5 |
| NM_002993 | CXCL6 | Chemokine (C—X—C motif) ligand 6 (granulocyte chemotactic protein 2) | CKA-3, GCP-2, GCP2, SCYB6 |
| NM_002416 | CXCL9 | Chemokine (C—X—C motif) ligand 9 | CMK, Humig, MIG, SCYB9, crg-10 |
| NM_000634 | CXCR1 | Chemokine (C—X—C motif) receptor 1 | C-C, C-C-CKR-1, CD128, CD181, CDw128a, CKR-1, CMKAR1, IL8R1, IL8RA, IL8RBA |
| NM_001504 | CXCR3 | Chemokine (C—X—C motif) receptor 3 | CD182, CD183, CKR-L2, CMKAR3, GPR9, IP10-R, Mig-R, MigR |
| NM_003467 | CXCR4 | Chemokine (C—X—C motif) receptor 4 | CD184, D2S201E, FB22, HM89, HSY3RR, LAP3, LCR1, LESTR, NPY3R, NPYR, NPYRL, NPYY3R, WHIM |
| NM_001716 | CXCR5 | Chemokine (C—X—C motif) receptor 5 | BLR1, CD185, MDR15, MGC117347 |
| NM_006564 | CXCR6 | Chemokine (C—X—C motif) receptor 6 | BONZO, CD186, STRL33, TYMSTR |
| NM_014376 | CYFIP2 | Cytoplasmic FMR1 interacting protein 2 | PIR121 |
| NM_058186 | FAM3B | Family with sequence similarity 3, member B | 2-21, C21orf11, C21or176, ORF9, PANDER |
| NM_000639 | FASLG | Fas ligand (TNF superfamily, member 6) | APT1LG1, CD178, CD95-L, CD95L, FASL, TNFSF6 |
| NM_004469 | FIGF | C-fos induced growth factor (vascular endothelial growth factor D) | VEGF-D, VEGFD |
| NM_002046 | GAPDH | Glyceraldehyde-3-phosphate dehydrogenase | G3PD, GAPD, MGC88685 |
| NM_004962 | GDF10 | Growth differentiation factor 10 | BMP-3b, BMP3B |
| NM_005811 | GDF11 | Growth differentiation factor 11 | BMP-11, BMP11 |
| NM_016204 | GDF2 | Growth differentiation factor 2 | BMP-9, BMP9 |
| NM_020634 | GDF3 | Growth differentiation factor 3 | KFS3, MCOP7, MCOPCB6 |
| NM_000557 | GDF5 | Growth differentiation factor 5 | BMP14, CDMP1, LAP4, OS5, SYNS2 |
| NM_005260 | GDF9 | Growth differentiation factor 9 | — |
| NM_000175 | GPI | Glucose-6-phosphate isomerase | AMF, DKFZp686C13233, GNPI, NLK, PGI, PHI, SA-36, SA36 |
| NM_005299 | GPR31 | G protein-coupled receptor 31 | — |
| NM_032554 | HCAR1 | Hydroxycarboxylic acid receptor 1 | GPR104, GPR81, HCA1, LACR1, TA-GPCR |
| NM_001530 | HIF1A | Hypoxia inducible factor 1, alpha subunit (basic helix-loop-helix transcription factor) | HIF-1alpha, HIF1, HIF1-ALPHA, MOP1, PASD8, bHLHe78 |
| NM_000194 | HPRT1 | Hypoxanthine phosphoribosyltransferase 1 | HGPRT, HPRT |
| NM_024013 | IFNA1 | Interferon, alpha 1 | IFL, IFN, IFN-ALPHA, IFN-alphaD, IFNA13, IFNA@, MGC138207, MGC138505, MGC138507 |
| NM_000605 | IFNA2 | Interferon, alpha 2 | IFN-alphaA, IFNA, INFA2, MGC125764, MGC125765 |
| NM_000605 | IFNA2 | Interferon, alpha 2 | IFN-alphaA, IFNA, INFA2, MGC125764, MGC125765 |
| NM_021068 | IFNA4 | Interferon, alpha 4 | IFN-alpha4a, INFA4, MGC142200 |
| NM_002169 | IFNA5 | Interferon, alpha 5 | IFN-alphaG, INFA5 |
| NM_002170 | IFNA8 | Interferon, alpha 8 | IFN-alphaB |
| NM_002176 | IFNB1 | Interferon, beta 1, fibroblast | IFB, IFF, IFNB, MGC96956 |
| NM_000619 | IFNG | Interferon, gamma | IFG, IFI |
| NM_020124 | IFNK | Interferon, kappa | RP11-27J8.1 |
| NM_000572 | IL10 | Interleukin 10 | CSIF, IL-10, IL10A, MGC126450, MGC126451, TGIF |
| NM_000641 | IL11 | Interleukin 11 | AGIF, IL-11 |
| NM_000882 | IL12A | Interleukin 12A (natural killer cell stimulatory factor 1, cytotoxic lymphocyte maturation factor 1, p35) | CLMF, IL-12A, NFSK, NKSF1, P35 |
| NM_002187 | IL12B | Interleukin 12B (natural killer cell stimulatory factor 2, cytotoxic lymphocyte maturation factor 2, p40) | CLMF, CLMF2, IL-12B, NKSF, NKSF2 |
| NM_002188 | IL13 | Interleukin 13 | ALRH, BHR1, IL-13, MGC116786, MGC116788, MGC116789, P600 |
| NM_000585 | IL15 | Interleukin 15 | IL-15, MGC9721 |
| NM_004513 | IL16 | Interleukin 16 | FLJ16806, FLJ42735, FLJ44234, LCF, NIL16, PRIL16, prIL-16 |
| NM_014443 | IL17B | Interleukin 17B | IL-17B, IL-20, MGC138900, MGC138901, NIRF, ZCYTO7 |
| NM_013278 | IL17C | Interleukin 17C | CX2, IL-17C, IL-21, MGC126884, MGC138401 |
| NM_052872 | IL17F | Interleukin 17F | IL-17F, ML-1, ML1 |
| NM_001562 | IL18 | Interleukin 18 (interferon-gamma-inducing factor) | IGIF, IL-18, IL-1g, IL1F4, MGC12320 |
| NM_013371 | IL19 | Interleukin 19 | IL-10C, MDA1, NG.1, ZMDA1 |
| NM_000575 | IL1A | Interleukin 1, alpha | 1L-1A, IL1, IL1-ALPHA, IL1F1 |
| NM_000576 | IL1B | Interleukin 1, beta | IL-1, IL1-BETA, IL1F2 |

TABLE 4-continued

Cytokine and Chemokine-related Genes for Use as Biomarkers

| GeneBank | Symbol | Description | Gene Name |
|---|---|---|---|
| NM_173161 | IL1F10 | Interleukin 1 family, member 10 (theta) | FIL1-theta, IL-1HY2, IL1-theta, MGC119831, MGC119832, MGC119833 |
| NM_000577 | IL1RN | Interleukin 1 receptor antagonist | DIRA, ICIL-1RA, IL-1RN, IL-1ra, IL-1ra3, IL1F3, IL1RA, IRAP, MGC10430, MVCD4 |
| NM_000586 | IL2 | Interleukin 2 | IL-2, TCGF, lymphokine |
| NM_018724 | IL20 | Interleukin 20 | IL-20, IL10D, MGC96907, ZCYTO10 |
| NM_021803 | IL21 | Interleukin 21 | IL-21, Za11 |
| NM_020525 | IL22 | Interleukin 22 | IL-21, IL-22, IL-D110, IL-TIF, ILTIF, MGC79382, MGC79384, TIFIL-23, TIFa, zcyto18 |
| NM_016584 | IL23A | Interleukin 23, alpha subunit p19 | IL-23, IL-23A, IL23P19, MGC79388, P19, SGRF |
| NM_006850 | IL24 | Interleukin 24 | C49A, FISP, IL10B, MDA7, MOB5, ST16 |
| NM_022789 | IL25 | Interleukin 25 | IL17E |
| NM_145659 | IL27 | Interleukin 27 | IL-27, IL-27A, IL27A, IL27p28, IL30, MGC71873, p28 |
| NM_000588 | IL3 | Interleukin 3 (colony-stimulating factor, multiple) | IL-3, MCGF, MGC79398, MGC79399, MULTI-CSF |
| NM_014440 | IL36A | Interleukin 36, alpha | FIL1, FIL1(EPSILON), FIL1E, IL-1F6, IL1(EPSILON), IL1F6, MGC129552, MGC129553 |
| NM_173178 | IL36B | Interleukin 36, beta | FIL1, FIL1-(ETA), FIL1H, FILI-(ETA), IL-1F8, IL-1H2, IL1-ETA, IL1F8, IL1H2, MGC126880, MGC126882 |
| NM_019618 | IL36G | Interleukin 36, gamma | IL-1F9, IL-1H1, IL-1RP2, IL1E, IL1F9, IL1H1, IL1RP2 |
| NM_012275 | IL36RN | Interleukin 36 receptor antagonist | FIL1, FIL1(DELTA), FIL1D, IL1F5, IL1HY1, IL1L1, IL1RP3, IL36RA, MGC29840 |
| NM_173205 | IL37 | Interleukin 37 | FIL1, FIL1(ZETA), FIL1Z, IL-1F7, IL-1H, IL-1H4, IL-1RP1, IL-37, IL1F7, IL1H4, IL1RP1 |
| NM_000589 | IL4 | Interleukin 4 | BCGF-1, BCGF1, BSF-1, BSF1, IL-4, MGC79402 |
| NM_000879 | IL5 | Interleukin 5 (colony-stimulating factor, eosinophil) | EDF, IL-5, TRF |
| NM_000600 | IL6 | Interleukin 6 (interferon, beta 2) | BSF2, HGF, HSF, IFNB2, IL-6 |
| NM_000880 | IL7 | Interleukin 7 | IL-7 |
| NM_000584 | IL8 | Interleukin 8 | CXCL8, GCP-1, GCP1, LECT, LUCT, LYNAP, MDNCF, MONAP, NAF, NAP-1, NAP1 |
| NM_000590 | IL9 | Interleukin 9 | HP40, IL-9, P40 |
| NM_002191 | INHA | Inhibin, alpha | — |
| NM_002192 | INHBA | Inhibin, beta A | EDF, FRP |
| NM_003240 | LEFTY2 | Left-right determination factor 2 | EBAF, LEFTA, LEFTYA, MGC46222, TGFB4 |
| NM_002309 | LIF | Leukemia inhibitory factor (cholinergic differentiation factor) | CDF, DIA, HILDA |
| NM_000595 | LTA | Lymphotoxin alpha (TNF superfamily, member 1) | LT, TNFB, TNFSF1 |
| NM_002341 | LTB | Lymphotoxin beta (TNF superfamily, member 3) | TNFC, TNFSF3, p33 |
| NM_002341 | LTB | Lymphotoxin beta (TNF superfamily, member 3) | TNFC, TNFSF3, p33 |
| NM_181657 | LTB4R | Leukotriene B4 receptor | BLT1, BLTR, CMKRL1, GPR16, LTB4R1, LTBR1, P2RY7, P2Y7 |
| NM_002415 | MIF | Macrophage migration inhibitory factor (glycosylation-inhibiting factor) | GIF, GLIF, MMIF |
| NM_004530 | MMP2 | Matrix metallopeptidase 2 (gelatinase A, 72 kDa gelatinase, 72 kDa type IV collagenase) | CLG4, CLG4A, MMP-II, MONA, TBE-1 |
| NM_002423 | MMP7 | Matrix metallopeptidase 7 (matrilysin, uterine) | MMP-7, MPSL1, PUMP-1 |
| NM_005259 | MSTN | Myostatin | GDF8 |
| NM_002468 | MYD88 | Myeloid differentiation primary response gene (88) | MYD88D |
| NM_003998 | NFKB1 | Nuclear factor of kappa light polypeptide gene enhancer in B-cells 1 | DKFZp686C01211, EBP-1, KBF1, MGC54151, NF-kappa-B, NF-kappaB, NFKB-p105, NFKB-p50, NFkappaB, p105, p50 |
| NM_018055 | NODAL | Nodal homolog (mouse) | MGC138230 |
| NM_020530 | OSM | Oncostatin M | MGC20461 |
| NM_002607 | PDGFA | Platelet-derived growth factor alpha polypeptide | PDGF-A, PDGF1 |
| NM_002704 | PPBP | Pro-platelet basic protein (chemokine (C—X—C motif) ligand 7) | B-TG1, Beta-TG, CTAP-III, CTAP3, CTAPIII, CXCL7, LA-PF4, LDGF, MDGF, NAP-2, PBP, SCAR10, SCYB7, TC1, TC2, TGB, TGB1, THBGB, THBGB1 |
| NM_012423 | RPL13A | Ribosomal protein L13a | L13A, TSTA1 |
| NM_006923 | SDF2 | Stromal cell-derived factor 2 | — |
| NM_004787 | SLIT2 | Slit homolog 2 (Drosophila) | FLJ14420, SLIL3, Slit-2 |
| NM_000582 | SPP1 | Secreted phosphoprotein 1 | BNSP, BSPI, ETA-1, MGC110940, OPN |
| NM_004610 | TCP10 | T-complex 10 homolog (mouse) | MGC34049, TCP10A |
| NM_003236 | TGFA | Transforming growth factor, alpha | TFGA |
| NM_000660 | TGFB1 | Transforming growth factor, beta 1 | CED, DPD1, LAP, TGFB, TGFbeta |
| NM_003238 | TGFB2 | Transforming growth factor, beta 2 | MGC116892, TGF-beta2 |
| NM_003239 | TGFB3 | Transforming growth factor, beta 3 | ARVD, FLJ16571, TGF-beta3 |

TABLE 4-continued

Cytokine and Chemokine-related Genes for Use as Biomarkers

| GeneBank | Symbol | Description | Gene Name |
|---|---|---|---|
| NM_000460 | THPO | Thrombopoietin | MGC163194, MGDF, MKCSF, ML, MPLLG, TPO |
| NM_003264 | TLR2 | Toll-like receptor 2 | CD282, TIL4 |
| NM_138554 | TLR4 | Toll-like receptor 4 | ARMD10, CD284, TOLL, hToll |
| NM_000594 | TNF | Tumor necrosis factor | DIF, TNF-alpha, TNFA, TNFSF2 |
| NM_002546 | TNFRSF11B | Tumor necrosis factor receptor superfamily, member 11b | MGC29565, OCIF, OPG, TR1 |
| NM_001065 | TNFRSF1A | Tumor necrosis factor receptor superfamily, member 1A | CD120a, FPF, MGC19588, TBP1, TNF-R, TNF-R-I, TNF-R55, TNFAR, TNFR1, TNFR55, TNFR60, p55, p55-R, p60 |
| NM_003810 | TNFSF10 | Tumor necrosis factor (ligand) superfamily, member 10 | APO2L, Apo-2L, CD253, TL2, TRAIL |
| NM_003701 | TNFSF11 | Tumor necrosis factor (ligand) superfamily, member 11 | CD254, ODF, OPLL, OPTB2, RANKL, TRANCE, hRANKL2, sOdf |
| NM_003809 | TNFSF12 | Tumor necrosis factor (ligand) superfamily, member 12 | APO3L, DR3LG, MGC129581, MGC20669, TWEAK |
| NM_006573 | TNFSF13B | Tumor necrosis factor (ligand) superfamily, member 13b | BAFF, BLYS, CD257, DTL, TALL-1, TALL1, THANK, TNFSF20, ZTNF4 |
| NM_003807 | TNFSF14 | Tumor necrosis factor (ligand) superfamily, member 14 | CD258, HVEML, LIGHT, LTg, TR2 |
| NM_003326 | TNFSF4 | Tumor necrosis factor (ligand) superfamily, member 4 | CD134L, CD252, GP34, OX-40L, OX4OL, TXGP1 |
| NM_001244 | TNFSF8 | Tumor necrosis factor (ligand) superfamily, member 8 | CD153, CD30L, CD30LG, MGC138144 |
| NM_018643 | TREM1 | Triggering receptor expressed on myeloid cells 1 | TREM-1 |
| NM_175852 | TXLNA | Taxilin alpha | DKFZp451J0118, IL14, MGC118870, MGC118871, RP4-622L5.4, TXLN |
| NM_001953 | TYMP | Thymidine phosphorylase | ECGF, ECGF1, MEDPS1, MNGIE, MTDPS1, PDECGF, TP, hPD-ECGF |
| NM_003376 | VEGFA | Vascular endothelial growth factor A | MGC70609, MVCD1, VEGF, VPF |
| NM_000551 | VHL | Von Hippel-Lindau tumor suppressor | HRCA1, RCA1, VHL1 |
| NM_002995 | XCL1 | Chemokine (C motif) ligand 1 | ATAC, LPTN, LTN, SCM-1, SCM-1a, SCM1, SCM1A, SCYC1 |
| NM_005283 | XCR1 | Chemokine (C motif) receptor 1 | CCXCR1, GPR5 |

TABLE 5

Cytoskeleton-related Genes for Use as Biomarkers

| GeneBank | Symbol | Description | Gene Name |
|---|---|---|---|
| NM_005722 | ACTR2 | ARP2 actin-related protein 2 homolog (yeast) | ARP2 |
| NM_005721 | ACTR3 | ARP3 actin-related protein 3 homolog (yeast) | ARP3 |
| NM_012402 | ARFIP2 | ADP-ribosylation factor interacting protein 2 | FLJ18046, FLJ18697, FLJ99239, POR1 |
| NM_013423 | ARHGAP6 | Rho GTPase activating protein 6 | RHOGAP6, RHOGAPX-1 |
| NM_001175 | ARHGDIB | Rho GDP dissociation inhibitor (GDI) beta | D4, GDIA2, GDID4, LYGDI, Ly-GDI, RAP1GN1, RhoGDI2 |
| NM_198236 | ARHGEF11 | Rho guanine nucleotide exchange factor (GEF) 11 | DKFZp667F1223, GTRAP48, KIAA0380, PDZ-RHOGEF |
| NM_005720 | ARPC1B | Actin related protein 2/3 complex, subunit 1B, 41 kDa | ARC41, p40-ARC, p41-ARC |
| NM_005731 | ARPC2 | Actin related protein 2/3 complex, subunit 2, 34 kDa | ARC34, PNAS-139, p34-Arc |
| NM_005719 | ARPC3 | Actin related protein 2/3 complex, subunit 3, 21 kDa | ARC21, p21-Arc |
| NM_005718 | ARPC4 | Actin related protein 2/3 complex, subunit 4, 20 kDa | ARC20, MGC13544, P20-ARC |
| NM_005717 | ARPC5 | Actin related protein 2/3 complex, subunit 5, 16 kDa | ARC16, MGC88523, dJ127C7.3, p16-Arc |
| NM_003600 | AURKA | Aurora kinase A | AIK, ARK1, AURA, AURORA2, BTAK, MGC34538, STK15, STK6, STK7 |
| NM_004217 | AURKB | Aurora kinase B | AIK2, AIM-1, AIM1, ARK2, AurB, IPL1, STK12, STK5, aurkb-sv1, aurkb-sv2 |
| NM_003160 | AURKC | Aurora kinase C | AIE2, AIK3, ARK3, AurC, STK13, aurora-C |
| NM_006340 | BAIAP2 | BAI1-associated protein 2 | BAP2, FLAF3, IRSP53 |
| NM_004342 | CALD1 | Caldesmon 1 | CDM, H-CAD, HCAD, L-CAD, LCAD, MGC21352, NAG22 |
| NM_006888 | CALM1 | Calmodulin 1 (phosphorylase kinase, delta) | CALM2, CALM3, CALML2, CAMI, DD132, PHKD, caM |
| NM_003688 | CASK | Calcium/calmodulin-dependent serine protein kinase (MAGUK family) | CAGH39, CAMGUK, CMG, FGS4, FLJ22219, FLJ31914, LIN2, MICPCH, TNRC8 |
| NM_003914 | CCNA1 | Cyclin A1 | — |
| NM_004701 | CCNB2 | Cyclin B2 | HsT17299 |

TABLE 5-continued

Cytoskeleton-related Genes for Use as Biomarkers

| GeneBank | Symbol | Description | Gene Name |
|---|---|---|---|
| NM_001791 | CDC42 | Cell division cycle 42 (GTP binding protein, 25 kDa) | CDC42Hs, G25K |
| NM_003607 | CDC42BPA | CDC42 binding protein kinase alpha (DMPK-like) | DKFZp686L1738, DKFZp686P1738, FLJ23347, KIAA0451, MRCK, MRCKA, PK428 |
| NM_006779 | CDC42EP2 | CDC42 effector protein (Rho GTPase binding) 2 | BORG1, CEP2 |
| NM_006449 | CDC42EP3 | CDC42 effector protein (Rho GTPase binding) 3 | BORG2, CEP3, FLJ46903, UB1 |
| NM_004935 | CDK5 | Cyclin-dependent kinase 5 | PSSALRE |
| NM_003885 | CDK5R1 | Cyclin-dependent kinase 5, regulatory subunit 1 (p35) | CDK5P35, CDK5R, MGC33831, NCK5A, p23, p25, p35, p35nck5a |
| NM_015242 | ARAP1 | ArfGAP with RhoGAP domain, ankyrin repeat and PH domain 1 | CENTD2, KIAA0782 |
| NM_005507 | CFL1 | Cofilin 1 (non-muscle) | CFL |
| NM_007174 | CIT | Citron (rho-interacting, serine/threonine kinase 21) | CRIK, KIAA0949, STK21 |
| NM_015282 | CLASP1 | Cytoplasmic linker associated protein 1 | DKFZp686D1968, DKFZp686H2039, FLJ33821, FLJ41222, KIAA0622, MAST1, MGC131895 |
| NM_015097 | CLASP2 | Cytoplasmic linker associated protein 2 | — |
| NM_002956 | CLIP1 | CAP-GLY domain containing linker protein 1 | CLIP, CLIP-170, CLIP170, CYLN1, MGC131604, RSN |
| NM_003388 | CLIP2 | CAP-GLY domain containing linker protein 2 | CLIP, CLIP-115, CYLN2, KIAA0291, MGC11333, WBSCR3, WBSCR4, WSCR3, WSCR4 |
| NM_016823 | CRK | V-crk sarcoma virus CT10 oncogene homolog (avian) | CRKII |
| NM_005231 | CTTN | Cortactin | EMS1, FLJ34459 |
| NM_014608 | CYFIP1 | Cytoplasmic FMR1 interacting protein 1 | FLJ45151, P140SRA-1, SHYC, SRA1 |
| NM_014376 | CYFIP2 | Cytoplasmic FMR1 interacting protein 2 | PIR121 |
| NM_005219 | DIAPH1 | Diaphanous homolog 1 (*Drosophila*) | DFNA1, DIA1, DRF1, FLJ25265, LFHL1, hDIA1 |
| NM_006870 | DSTN | Destrin (actin depolymerizing factor) | ACTDP, ADF, bA462D18.2 |
| NM_003379 | EZR | Ezrin | CVIL, CVL, DKFZp762H157, FLJ26216, MGC1584, VIL2 |
| NM_017737 | FNBP1L | Formin binding protein 1-like | C1orf139, TOCA1 |
| NM_012418 | FSCN2 | Fascin homolog 2, actin-bundling protein, retinal (Strongylocentrotus purpuratus) | RFSN, RP30 |
| NM_000177 | GSN | Gelsolin | ADF, AGEL, DKFZp313L0718 |
| NM_003870 | IQGAP1 | IQ motif containing GTPase activating protein 1 | HUMORFA01, KIAA0051, SARI, p195 |
| NM_006633 | IQGAP2 | IQ motif containing GTPase activating protein 2 | — |
| NM_002314 | LIMK1 | LIM domain kinase 1 | LIMK, LIMK-1 |
| NM_005569 | LIMK2 | LIM domain kinase 2 | — |
| NM_004140 | LLGL1 | Lethal giant larvae homolog 1 (*Drosophila*) | DLG4, HUGL, HUGL-1, HUGL1, LLGL |
| NM_012090 | MACF1 | Microtubule-actin crosslinking factor 1 | ABP620, ACF7, FLJ45612, FLJ46776, KIAA0465, KIAA1251, MACF, OFC4 |
| NM_002419 | MAP3K11 | Mitogen-activated protein kinase kinase kinase 11 | MEKK11, MGC17114, MLK-3, MLK3, PTK1, SPRK |
| NM_002375 | MAP4 | Microtubule-associated protein 4 | DKFZp779A1753, MGC8617 |
| NM_002754 | MAPK13 | Mitogen-activated protein kinase 13 | MGC99536, PRKM13, SAPK4, p38delta |
| NM_012325 | MAPRE1 | Microtubule-associated protein, RP/EB family, member 1 | EB1, MGC117374, MGC129946 |
| NM_014268 | MAPRE2 | Microtubule-associated protein, RP/EB family, member 2 | EB1, EB2, RP1 |
| NM_005910 | MAPT | Microtubule-associated protein tau | DDPAC, FLJ31424, FTDP-17, MAPTL, MGC138549, MSTD, MTBT1, MTBT2, PPND, TAU |
| NM_004954 | MARK2 | MAP/microtubule affinity-regulating kinase 2 | EMK-1, EMK1, MGC99619, PAR-1, Par1b |
| NM_000381 | MID1 | Midline 1 (Opitz/BBB syndrome) | BBBG1, FLJ57031, FLJ58683, FLJ76288, FXY, GBBB1, MIDIN, OGS1, OS, OSX, RNF59, TRIM18, XPRF, ZNFXY |
| NM_002444 | MSN | Moesin | — |
| NM_053025 | MYLK | Myosin light chain kinase | DKFZp686I10125, FLJ12216, KRP, MLCK, MLCK1, MLCK108, MLCK210, MSTP083, MYLK1, smMLCK |
| NM_033118 | MYLK2 | Myosin light chain kinase 2 | KMLC, MLCK, MLCK2, skMLCK |
| NM_006153 | NCK1 | NCK adaptor protein 1 | MGC12668, NCK, NCKalpha, nck-1 |
| NM_003581 | NCK2 | NCK adaptor protein 2 | GRB4, NCKbeta |
| NM_002576 | PAK1 | P21 protein (Cdc42/Rac)-activated kinase 1 | MGC130000, MGC130001, PAKalpha |
| NM_005884 | PAK4 | P21 protein (Cdc42/Rac)-activated kinase 4 | — |
| NM_002628 | PFN2 | Profilin 2 | D3S1319E, PFL |
| NM_145753 | PHLDB2 | Pleckstrin homology-like domain, family B, member 2 | DKFZp313O2433, DKFZp434G227, DKFZp686J05113, FLJ21791, LL5b, LL5beta |
| NM_015040 | PIKFYVE | Phosphoinositide kinase, FYVE finger containing | CFD, FAB1, FLJ37746, KIAA0981, MGC40423, PIP5K, PIP5K3 |
| NM_002480 | PPP1R12A | Protein phosphatase 1, regulatory (inhibitor) subunit 12A | MBS, MGC133042, MYPT1 |
| NM_002481 | PPP1R12B | Protein phosphatase 1, regulatory (inhibitor) subunit 12B | FLJ40942, MGC131980, MGC87886, MYPT2 |

TABLE 5-continued

Cytoskeleton-related Genes for Use as Biomarkers

| GeneBank | Symbol | Description | Gene Name |
|---|---|---|---|
| NM_000944 | PPP3CA | Protein phosphatase 3, catalytic subunit, alpha isozyme | CALN, CALNA, CALNA1, CCN1, CNA1, PPP2B |
| NM_021132 | PPP3CB | Protein phosphatase 3, catalytic subunit, beta isozyme | CALNA2, CALNB, CNA2, PP2Bbeta |
| NM_006908 | RAC1 | Ras-related C3 botulinum toxin substrate 1 (rho family, small GTP binding protein Rac1) | MGC111543, Rac-1, TC-25, p21-Rac1 |
| NM_013277 | RACGAP1 | Rac GTPase activating protein 1 | HsCYK-4, ID-GAP, MgcRacGAP |
| NM_002906 | RDX | Radixin | DFNB24 |
| NM_001664 | RHOA | Ras homolog gene family, member A | ARH12, ARHA, RHO12, RHOH12 |
| NM_005406 | ROCK1 | Rho-associated, coiled-coil containing protein kinase 1 | MGC131603, MGC43611, P160ROCK, PR00435 |
| NM_018984 | SSH1 | Slingshot homolog 1 (*Drosophila*) | FLJ21928, FLJ38102, KIAA1298, SSH1L |
| NM_033389 | SSH2 | Slingshot homolog 2 (*Drosophila*) | KIAA1725, MGC78588, SSH-2 |
| NM_005563 | STMN1 | Stathmin 1 | C1or1215, FLJ32206, LAP18, Lag, MGC138869, MGC138870, OP18, PP17, PP19, PR22, SMN |
| NM_003253 | TIAM1 | T-cell lymphoma invasion and metastasis 1 | FLJ36302 |
| NM_003370 | VASP | Vasodilator-stimulated phosphoprotein | — |
| NM_000377 | WAS | Wiskott-Aldrich syndrome (eczema-thrombocytopenia) | IMD2, THC, THC1, WASP |
| NM_003931 | WASF1 | WAS protein family, member 1 | FLJ31482, KIAA0269, SCAR1, WAVE, WAVE1 |
| NM_003941 | WASL | Wiskott-Aldrich syndrome-like | DKFZp779G0847, MGC48327, N-WASP, NWASP |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 6

Embryonic Stem Cell-related Genes for Use as Biomarkers

| GeneBank | Symbol | Description | Gene Name |
|---|---|---|---|
| NM_001134 | AFP | Alpha-fetoprotein | FETA, HPAFP |
| NM_018321 | BRIX1 | BRX1, biogenesis of ribosomes, homolog (*S. cerevisiae*) | BRIX, BXDC2, FLJ11100 |
| NM_001773 | CD34 | CD34 molecule | — |
| NM_001769 | CD9 | CD9 molecule | BTCC-1, DRAP-27, FLJ99568, MIC3, MRP-1, TSPAN-29, TSPAN29 |
| NM_001795 | CDH5 | Cadherin 5, type 2 (vascular endothelium) | 7B4, CD144, FLJ17376 |
| NM_001265 | CDX2 | Caudal type homeobox 2 | CDX-3, CDX3 |
| NM_000088 | COL1A1 | Collagen, type I, alpha 1 | OI4 |
| NM_012071 | COMMD3 | COMM domain containing 3 | BUP, C10or18, DKFZp686K0399, FLJ45471 |
| NM_001878 | CRABP2 | Cellular retinoic acid binding protein 2 | CRABP-II, RBP6 |
| NM_024415 | DDX4 | DEAD (Asp-Glu-Ala-Asp) box polypeptide 4 | MGC111074, VASA |
| NM_001927 | DES | Desmin | CMD1I, CSM1, CSM2, FLJ12025, FLJ39719, FLJ41013, FLJ41793 |
| NM_006729 | DIAPH2 | Diaphanous homolog 2 (*Drosophila*) | DIA, DIA2, DRF2, FLJ11167, POF, POF2 |
| NM_006892 | DNMT3B | DNA (cytosine-5-)-methyltransferase 3 beta | ICF, M.HsaIIIB |
| NM_000115 | EDNRB | Endothelin receptor type B | ABCDS, ET-B, ET-BR, ETB, ETBR, ETRB, HSCR, HSCR2, WS4A |
| NM_005442 | EOMES | Eomesodermin | TBR2 |
| NM_002007 | FGF4 | Fibroblast growth factor 4 | HBGF-4, HST, HST-1, HSTF1, K-FGF, KFGF |
| NM_004464 | FGF5 | Fibroblast growth factor 5 | HBGF-5, Smag-82 |
| NM_002019 | FLT1 | Fms-related tyrosine kinase 1 (vascular endothelial growth factor/vascular permeability factor receptor) | FLT, VEGFR1 |
| NM_002026 | FN1 | Fibronectin 1 | CIG, DKFZp686F10164, DKFZp686H0342, DKFZp68611370, DKFZp686O13149, ED-B, FINC, FN, FNZ, GFND, GFND2, LETS, MSF |
| NM_021784 | FOXA2 | Forkhead box A2 | HNF3B, MGC19807, TCF3B |
| NM_012183 | FOXD3 | Forkhead box D3 | AIS1, Genesis, HFH2 |
| NM_000814 | GABRB3 | Gamma-aminobutyric acid (GABA) A receptor, beta 3 | ECA5, MGC9051 |
| NM_015973 | GAL | Galanin prepropeptide | GALN, GLNN, GMAP, MGC40167 |
| NM_002052 | GATA4 | GATA binding protein 4 | MGC126629 |
| NM_005257 | GATA6 | GATA binding protein 6 | — |
| NM_001485 | GBX2 | Gastrulation brain homeobox 2 | — |
| NM_002054 | GCG | Glucagon | GLP1, GLP2, GRPP |
| NM_003643 | GCM1 | Glial cells missing homolog 1 (*Drosophila*) | GCMA, hGCMa |
| NM_020634 | GDF3 | Growth differentiation factor 3 | KFS3, MCOP7, MCOPCB6 |
| NM_005310 | GRB7 | Growth factor receptor-bound protein 7 | — |
| NM_000518 | HBB | Hemoglobin, beta | CD113t-C, beta-globin |
| NM_005332 | HBZ | Hemoglobin, zeta | — |

TABLE 6-continued

Embryonic Stem Cell-related Genes for Use as Biomarkers

| GeneBank | Symbol | Description | Gene Name |
| --- | --- | --- | --- |
| NM_002110 | HCK | Hemopoietic cell kinase | JTK9 |
| NM_000415 | IAPP | Islet amyloid polypeptide | DAP, IAP |
| NM_003641 | IFITM1 | Interferon induced transmembrane protein 1 (9-27) | 9-27, CD225, IFI17, LEU13 |
| NM_006435 | IFITM2 | Interferon induced transmembrane protein 2 (1-8D) | 1-8D |
| NM_006548 | IGF2BP2 | Insulin-like growth factor 2 mRNA binding protein 2 | IMP-2, IMP2, VICKZ2, p62 |
| NM_002184 | IL6ST | Interleukin 6 signal transducer (gp130, oncostatin M receptor) | CD130, CDW130, DKFZp564F053, GP130, IL-6RB |
| NM_000207 | INS | Insulin | IDDM2, ILPR, IRDN, MODY10 |
| NM_000222 | KIT | V-kit Hardy-Zuckerman 4 feline sarcoma viral oncogene homolog | C-Kit, CD117, PBT, SCFR |
| NM_006121 | KRT1 | Keratin 1 | CK1, EHK, EHK1, EPPK, K1, KRT1A, NEPPK |
| NM_005559 | LAMA1 | Laminin, alpha 1 | LAMA, S-LAM-alpha |
| NM_002291 | LAMB1 | Laminin, beta 1 | CLM, MGC142015 |
| NM_002293 | LAMC1 | Laminin, gamma 1 (formerly LAMB2) | LAMB2, MGC87297 |
| NM_020997 | LEFTY1 | Left-right determination factor 1 | LEFTB, LEFTYB |
| NM_003240 | LEFTY2 | Left-right determination factor 2 | EBAF, LEFTA, LEFTYA, MGC46222, TGFB4 |
| NM_002310 | LIFR | Leukemia inhibitory factor receptor alpha | CD118, FLJ98106, FLJ99923, LIF-R, SJS2, STWS, SWS |
| NM_024674 | LIN28A | Lin-28 homolog A (C. elegans) | CSDD1, FLJ12457, LIN-28, LIN28, ZCCHC1 |
| NM_005593 | MYF5 | Myogenic factor 5 | bHLHc2 |
| NM_002478 | MYOD1 | Myogenic differentiation 1 | MYF3, MYOD, PUM, bHLHc1 |
| NM_024865 | NANOG | Nanog homeobox | — |
| NM_006617 | NES | Nestin | FLJ21841 |
| NM_002500 | NEUROD1 | Neurogenic differentiation 1 | BETA2, BHF-1, MODY6, NEUROD, bHLHa3 |
| NM_018055 | NODAL | Nodal homolog (mouse) | MGC138230 |
| NM_005450 | NOG | Noggin | SYM1, SYNS1 |
| NM_003822 | NR5A2 | Nuclear receptor subfamily 5, group A, member 2 | B1F, B1F2, CPF, FTF, FTZ-F1, FTZ-F1beta, LRH-1, LRH1, hB1F-2 |
| NM_001489 | NR6A1 | Nuclear receptor subfamily 6, group A, member 1 | GCNF, GCNF1, NR61, RTR |
| NM_003744 | NUMB | Numb homolog (Drosophila) | S171 |
| NM_005806 | OLIG2 | Oligodendrocyte lineage transcription factor 2 | BHLHB1, OLIGO2, PRKCBP2, RACK17, bHLHe19 |
| NM_006193 | PAX4 | Paired box 4 | KPD, MGC129960, MODY9 |
| NM_000280 | PAX6 | Paired box 6 | AN, AN2, D11S812E, MGC17209, MGDA, WAGR |
| NM_000209 | PDX1 | Pancreatic and duodenal homeobox 1 | GSF, IDX-1, IPF1, IUF1, MODY4, PDX-1, STF-1 |
| NM_000442 | PECAM1 | Platelet/endothelial cell adhesion molecule | CD31, FLJ34100, FLJ58394, PECAM-1 |
| NM_005397 | PODXL | Podocalyxin-like | Gp200, MGC138240, PC, PCLP, PCLP-1 |
| NM_002701 | POU5F1 | POU class 5 homeobox 1 | MGC22487, OCT3, OCT4, OTF-3, OTF3, OTF4, Oct-3, Oct-4 |
| NM_000314 | PTEN | Phosphatase and tensin homolog | 10q23del, BZS, DEC, GLM2, MGC11227, MHAM, MMAC1, PTEN1, TEP1 |
| NM_178161 | PTF1A | Pancreas specific transcription factor, 1a | PTF1-p48, bHLHa29 |
| NM_005612 | REST | RE1-silencing transcription factor | NRSF, XBR |
| NM_004348 | RUNX2 | Runt-related transcription factor 2 | AML3, CBFA1, CCD, CCD1, MGC120022, MGC120023, OSF-2, OSF2, PEA2aA, PEBP2A2, PEBP2aA, PEBP2aA1 |
| NM_006080 | SEMA3A | Sema domain, immunoglobulin domain (Ig), short basic domain, secreted, (semaphorin) 3A | Hsema-I, Hsema-III, MGC133243, SEMA1, SEMAD, SEMAIII, SEMAL, SemD, coll-1 |
| NM_000295 | SERPINA1 | Serpin peptidase inhibitor, clade A (alpha-1 antiproteinase, antitrypsin), member 1 | A1A, A1AT, AAT, MGC23330, MGC9222, PI, PI1, PRO2275, alpha1AT |
| NM_003013 | SFRP2 | Secreted frizzled-related protein 2 | FRP-2, SARP1, SDF-5 |
| NM_022454 | SOX17 | SRY (sex determining region Y)-box 17 | FLJ22252, VUR3 |
| NM_003106 | SOX2 | SRY (sex determining region Y)-box 2 | ANOP3, MCOPS3, MGC2413 |
| NM_001048 | SST | Somatostatin | SMST |
| NM_153694 | SYCP3 | Synaptonemal complex protein 3 | COR1, MGC71888, SCP3 |
| NM_003181 | T | T, brachyury homolog (mouse) | MGC104817, TFT |
| NM_000353 | TAT | Tyrosine aminotransferase | — |
| NM_003212 | TDGF1 | Teratocarcinoma-derived growth factor 1 | CR, CRGF, CRIPTO |
| NM_198253 | TERT | Telomerase reverse transcriptase | EST2, TCS1, TP2, TRT, hEST2, hTRT |
| NM_014553 | TFCP2L1 | Transcription factor CP2-like 1 | CRTR1, LBP-9, LBP9 |
| NM_003577 | UTF1 | Undifferentiated embryonic cell transcription factor 1 | — |
| NM_000378 | WT1 | Wilms tumor 1 | AWT1, GUD, NPHS4, WAGR, WIT-2, WT33 |
| NM_174900 | ZFP42 | Zinc finger protein 42 homolog (mouse) | REX1, ZNF754 |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 7

Endothelial Cell-related Genes for Use as Biomarkers

| GeneBank | Symbol | Description | Gene Name |
| --- | --- | --- | --- |
| NM_000789 | ACE | Angiotensin I converting enzyme (peptidyl-dipeptidase A) 1 | ACE1, CD143, DCP, DCP1, MGC26566, MVCD3 |
| NM_003183 | ADAM17 | ADAM metallopeptidase domain 17 | ADAM18, CD156B, CSVP, MGC71942, TACE |
| NM_000029 | AGT | Angiotensinogen (serpin peptidase inhibitor, clade A, member 8) | ANHU, FLJ92595, FLJ97926, SERPINA8 |
| NM_031850 | AGTR1 | Angiotensin II receptor, type 1 | AG2S, AGTR1A, AGTR1B, AT1, AT1B, AT1R, AT2R1, AT2R1A, AT2R1B, HAT1R |
| NM_000698 | ALOX5 | Arachidonate 5-lipoxygenase | 5-LO, 5-LOX, 5LPG, LOG5, MGC163204 |
| NM_001146 | ANGPT1 | Angiopoietin 1 | AGP1, AGPT, ANG1 |
| NM_001154 | ANXA5 | Annexin A5 | ANX5, ENX2, PP4 |
| NM_004324 | BAX | BCL2-associated X protein | BCL2L4 |
| NM_000633 | BCL2 | B-cell CLL/lymphoma 2 | Bcl-2 |
| NM_004049 | BCL2A1 | BCL2-related protein A1 | ACC-1, ACC-2, BCL2L5, BFL1, GRS, HBPA1 |
| NM_138578 | BCL2L1 | BCL2-like 1 | BCL-XL, S, BCL2L, BCLX, BCLXL, BCLXS, Bcl-X, DKFZp781P2092, bcl-xL, bcl-xS |
| NM_001716 | CXCR5 | Chemokine (C—X—C motif) receptor 5 | BLR1, CD185, MDR15, MGC117347 |
| NM_033292 | CASP1 | Caspase 1, apoptosis-related cysteine peptidase (interleukin 1, beta, convertase) | ICE, IL1BC, P45 |
| NM_004346 | CASP3 | Caspase 3, apoptosis-related cysteine peptidase | CPP32, CPP32B, SCA-1 |
| NM_032992 | CASP6 | Caspase 6, apoptosis-related cysteine peptidase | MCH2 |
| NM_002982 | CCL2 | Chemokine (C-C motif) ligand 2 | GDCF-2, HC11, HSMCR30, MCAF, MCP-1, MCP1, MGC9434, SCYA2, SMC-CF |
| NM_002985 | CCL5 | Chemokine (C-C motif) ligand 5 | D17S136E, MGC17164, RANTES, SCYA5, SISd, TCP228 |
| NM_001795 | CDH5 | Cadherin 5, type 2 (vascular endothelium) | 7B4, CD144, FLJ17376 |
| NM_003879 | CFLAR | CASP8 and FADD-like apoptosis regulator | CASH, CASP8AP1, CLARP, Casper, FLAME, FLAME-1, FLAME1, FLIP, I-FLICE, MRIT, c-FLIP, c-FLIPL, c-FLIPR, c-FLIPS |
| NM_030582 | COL18A1 | Collagen, type XVIII, alpha 1 | FLJ27325, FLJ34914, KNO, KNO1, KS, MGC74745 |
| NM_001872 | CPB2 | Carboxypeptidase B2 (plasma) | CPU, PCPB, TAFI |
| NM_003805 | CRADD | CASP2 and RIPK1 domain containing adaptor with death domain | MGC9163, RAIDD |
| NM_000758 | CSF2 | Colony stimulating factor 2 (granulocyte-macrophage) | GMCSF, MGC131935, MGC138897 |
| NM_002996 | CX3CL1 | Chemokine (C—X3—C motif) ligand 1 | ABCD-3, C3Xkine, CXC3, CXC3C, NTN, NTT, SCYD1, fractalkine, neurotactin |
| NM_001953 | TYMP | Thymidine phosphorylase | ECGF, ECGF1, MEDPS1, MNGIE, MTDPS1, PDECGF, TP, hPD-ECGF |
| NM_001955 | EDN1 | Endothelin 1 | ET1, HDLCQ7, PPET1 |
| NM_001956 | EDN2 | Endothelin 2 | ET2, PPET2 |
| NM_001957 | EDNRA | Endothelin receptor type A | ETA, ETAR, ETRA |
| NM_000043 | FAS | Fas (TNF receptor superfamily, member 6) | ALPS1A, APO-1, APT1, CD95, FAS1, FASTM, TNFRSF6 |
| NM_000639 | FASLG | Fas ligand (TNF superfamily, member 6) | APT1LG1, CD178, CD95-L, CD95L, FASL, TNFSF6 |
| NM_000800 | FGF1 | Fibroblast growth factor 1 (acidic) | AFGF, ECGF, ECGF-beta, ECGFA, ECGFB, FGF-alpha, FGFA, GLIO703, HBGF1 |
| NM_002019 | FLT1 | Fms-related tyrosine kinase 1 (vascular endothelial growth factor/vascular permeability factor receptor) | FLT, VEGFR1 |
| NM_002026 | FN1 | Fibronectin 1 | CIG, DKFZp686F10164, DKFZp686H0342, DKFZp686I1370, DKFZp686O13149, ED-B, FINC, FN, FNZ, GFND, GFND2, LETS, MSF |
| NM_000201 | ICAM1 | Intercellular adhesion molecule 1 | BB2, CD54, P3.58 |
| NM_002176 | IFNB1 | Interferon, beta 1, fibroblast | IFB, IFF, IFNB, MGC96956 |
| NM_000641 | IL11 | Interleukin 11 | AGIF, IL-11 |
| NM_000576 | IL1B | Interleukin 1, beta | IL-1, IL1-BETA, IL1F2 |
| NM_000588 | IL3 | Interleukin 3 (colony-stimulating factor, multiple) | IL-3, MCGF, MGC79398, MGC79399, MULTI-CSF |
| NM_000600 | IL6 | Interleukin 6 (interferon, beta 2) | BSF2, HGF, HSF, IFNB2, IL-6 |
| NM_000880 | IL7 | Interleukin 7 | IL-7 |
| NM_002205 | ITGA5 | Integrin, alpha 5 (fibronectin receptor, alpha polypeptide) | CD49e, FNRA, VLA5A |
| NM_002210 | ITGAV | Integrin, alpha V (vitronectin receptor, alpha polypeptide, antigen CD51) | CD51, DKFZp686A08142, MSK8, VNRA |
| NM_002211 | ITGB1 | Integrin, beta 1 (fibronectin receptor, beta polypeptide, antigen CD29 includes MDF2, MSK12) | CD29, FNRB, GPIIA, MDF2, MSK12, VLA-BETA, VLAB |
| NM_000212 | ITGB3 | Integrin, beta 3 (platelet glycoprotein IIIa, antigen CD61) | CD61, GP3A, GPIIIa |
| NM_002253 | KDR | Kinase insert domain receptor (a type III receptor tyrosine kinase) | CD309, FLK1, VEGFR, VEGFR2 |

TABLE 7-continued

Endothelial Cell-related Genes for Use as Biomarkers

| GeneBank | Symbol | Description | Gene Name |
| --- | --- | --- | --- |
| NM_000222 | KIT | V-kit Hardy-Zuckerman 4 feline sarcoma viral oncogene homolog | C-Kit, CD117, PBT, SCFR |
| NM_001648 | KLK3 | Kallikrein-related peptidase 3 | APS, KLK2A1, PSA, hK3 |
| NM_002421 | MMP1 | Matrix metallopeptidase 1 (interstitial collagenase) | CLG, CLGN |
| NM_004530 | MMP2 | Matrix metallopeptidase 2 (gelatinase A, 72 kDa gelatinase, 72 kDa type IV collagenase) | CLG4, CLG4A, MMP-II, MONA, TBE-1 |
| NM_004994 | MMP9 | Matrix metallopeptidase 9 (gelatinase B, 92 kDa gelatinase, 92 kDa type IV collagenase) | CLG4B, GELB, MANDP2, MMP-9 |
| NM_000625 | NOS2 | Nitric oxide synthase 2, inducible | HEP-NOS, INOS, NOS, NOS2A |
| NM_000603 | NOS3 | Nitric oxide synthase 3 (endothelial cell) | ECNOS, eNOS |
| NM_002521 | NPPB | Natriuretic peptide B | BNP |
| NM_000906 | NPR1 | Natriuretic peptide receptor A/guanylate cyclase A (atrionatriuretic peptide receptor A) | ANPRA, ANPa, GUC2A, GUCY2A, NPRA |
| NM_002538 | OCLN | Occludin | BLCPMG, FLJ08163, FLJ18079, FLJ77961, FLJ94056, MGC34277 |
| NM_006206 | PDGFRA | Platelet-derived growth factor receptor, alpha polypeptide | CD140A, MGC74795, PDGFR2, RHEPDGFRA |
| NM_000442 | PECAM1 | Platelet/endothelial cell adhesion molecule | CD31, FLJ34100, FLJ58394, PECAM-1 |
| NM_002619 | PF4 | Platelet factor 4 | CXCL4, MGC138298, SCYB4 |
| NM_002632 | PGF | Placental growth factor | D12S1900, PGFL, PLGF, PIGF-2, SHGC-10760 |
| NM_003706 | PLA2G4C | Phospholipase A2, group IVC (cytosolic, calcium-independent) | CPLA2-gamma, DKFZp586C0423, FLJ42247, FLJ44164 |
| NM_000930 | PLAT | Plasminogen activator, tissue | DKFZp686I03148, T-PA, TPA |
| NM_002658 | PLAU | Plasminogen activator, urokinase | ATF, UPA, URK, u-PA |
| NM_000301 | PLG | Plasminogen | DKFZp779M0222 |
| NM_000961 | PTGIS | Prostaglandin I2 (prostacyclin) synthase | CYP8, CYP8A1, MGC126858, MGC126860, PGIS, PTGI |
| NM_004040 | RHOB | Ras homolog gene family, member B | ARH6, ARHB, MST081, MSTP081, RHOH6 |
| NM_003804 | RIPK1 | Receptor (TNFRSF)-interacting serine-threonine kinase 1 | FLJ39204, RIP, RIP1 |
| NM_000450 | SELE | Selectin E | CD62E, ELAM, ELAM1, ESEL, LECAM2 |
| NM_000655 | SELL | Selectin L | CD62L, LAM1, LECAM1, LEU8, LNHR, LSEL, LYAM1, PLNHR, TQ1 |
| NM_003006 | SELPLG | Selectin P ligand | CD162, CLA, PSGL-1, PSGL1 |
| NM_000602 | SERPINE1 | Serpin peptidase inhibitor, clade E (nexin, plasminogen activator inhibitor type 1), member 1 | PAI, PAI-1, PAI1, PLANH1 |
| NM_000454 | SOD1 | Superoxide dismutase 1, soluble | ALS, ALS1, IPOA, SOD, hSod1, homodimer |
| NM_021972 | SPHK1 | Sphingosine kinase 1 | SPHK |
| NM_000459 | TEK | TEK tyrosine kinase, endothelial | CD202B, TIE-2, TIE2, VMCM, VMCM1 |
| NM_006287 | TFPI | Tissue factor pathway inhibitor (lipoprotein-associated coagulation inhibitor) | EPI, LACI, TFI, TFPI1 |
| NM_000361 | THBD | Thrombomodulin | AHUS6, BDCA3, CD141, THRM, TM |
| NM_003246 | THBS1 | Thrombospondin 1 | THBS, THBS-1, TSP, TSP-1, TSP1 |
| NM_003254 | TIMP1 | TIMP metallopeptidase inhibitor 1 | CLG1, EPA, EPO, FLJ90373, HCI, TIMP |
| NM_000594 | TNF | Tumor necrosis factor | DIF, TNF-alpha, TNFA, TNFSF2 |
| NM_006290 | TNFAIP3 | Tumor necrosis factor, alpha-induced protein 3 | A20, MGC104522, MGC138687, MGC138688, OTUD7C, TNFA1P2 |
| NM_003841 | TNFRSF10C | Tumor necrosis factor receptor superfamily, member 10c, decoy without an intracellular domain | CD263, DCR1, DCR1-TNFR, LIT, MGC149501, MGC149502, TRAIL-R3, TRAILR3, TRID |
| NM_003810 | TNFSF10 | Tumor necrosis factor (ligand) superfamily, member 10 | APO2L, Apo-2L, CD253, TL2, TRAIL |
| NM_001078 | VCAM1 | Vascular cell adhesion molecule 1 | CD106, DKFZp779G2333, INCAM-100, MGC99561 |
| NM_003376 | VEGFA | Vascular endothelial growth factor A | MGC70609, MVCD1, VEGF, VPF |
| NM_000552 | VWF | Von Willebrand factor | F8VWF, VWD |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 8

Epithelial to Mesencymal Transition-related Genes for Use as Biomarkers

| GeneBank | Symbol | Description | Gene Name |
| --- | --- | --- | --- |
| NM_024060 | AHNAK | AHNAK nucleoprotein | AHNAKRS, MGC5395 |
| NM_005163 | AKT1 | V-akt murine thymoma viral oncogene homolog 1 | AKT, MGC99656, PKB, PKB-ALPHA, PRKBA, RAC, RAC-ALPHA |
| NM_006129 | BMP1 | Bone morphogenetic protein 1 | FLJ44432, PCOLC, PCP, PCP2, TLD |
| NM_001719 | BMP7 | Bone morphogenetic protein 7 | OP-1 |

TABLE 8-continued

Epithelial to Mesencymal Transition-related Genes for Use as Biomarkers

| GeneBank | Symbol | Description | Gene Name |
|---|---|---|---|
| NM_004342 | CALD1 | Caldesmon 1 | CDM, H-CAD, HCAD, L-CAD, LCAD, MGC21352, NAG22 |
| NM_018584 | CAMK2N1 | Calcium/calmodulin-dependent protein kinase II inhibitor 1 | MGC22256, PRO1489, RP11-401M16.1 |
| NM_001233 | CAV2 | Caveolin 2 | CAV, MGC12294 |
| NM_004360 | CDH1 | Cadherin 1, type 1, E-cadherin (epithelial) | Arc-1, CD324, CDHE, ECAD, LCAM, UVO |
| NM_001792 | CDH2 | Cadherin 2, type 1, N-cadherin (neuronal) | CD325, CDHN, CDw325, NCAD |
| NM_000089 | COL1A2 | Collagen, type I, alpha 2 | OI4 |
| NM_000090 | COL3A1 | Collagen, type III, alpha 1 | EDS4A, FLJ34534 |
| NM_000393 | COL5A2 | Collagen, type V, alpha 2 | MGC105115 |
| NM_001904 | CTNNB1 | Catenin (cadherin-associated protein), beta 1, 88 kDa | CTNNB, DKFZp686D02253, FLJ25606, FLJ37923 |
| NM_004949 | DSC2 | Desmocollin 2 | ARVD11, CDHF2, DG2, DGII, III, DKFZp686I11137, DSC3 |
| NM_004415 | DSP | Desmoplakin | DP, DPI, DPII |
| NM_005228 | EGFR | Epidermal growth factor receptor | ERBB, ERBB1, HER1, PIG61, mENA |
| NM_001982 | ERBB3 | V-erb-b2 erythroblastic leukemia viral oncogene homolog 3 (avian) | ErbB-3, HER3, LCCS2, MDA-BF-1, MGC88033, c-erbB-3, c-erbB3, erbB3-S, p180-ErbB3, p45-sErbB3, p85-sErbB3 |
| NM_000125 | ESR1 | Estrogen receptor 1 | DKFZp686N23123, ER, ESR, ESRA, Era, NR3A1 |
| NM_016946 | F11R | F11 receptor | CD321, JAM, JAM1, JAMA, JCAM, KAT, PAM-1 |
| NM_005130 | FGFBP1 | Fibroblast growth factor binding protein 1 | FGFBP, HBP17 |
| NM_002026 | FN1 | Fibronectin 1 | CIG, DKFZp686F10164, DKFZp686H0342, DKFZp686I1370, DKFZp686O13149, ED-B, FINC, FN, FNZ, GFND, GFND2, LETS, MSF |
| NM_005251 | FOXC2 | Forkhead box C2 (MFH-1, mesenchyme forkhead 1) | FKHL14, LD, MFH-1, MFH1 |
| NM_003507 | FZD7 | Frizzled family receptor 7 | FzE3 |
| NM_004126 | GNG11 | Guanine nucleotide binding protein (G protein), gamma 11 | GNGT11 |
| NM_173849 | GSC | Goosecoid homeobox | — |
| NM_002093 | GSK3B | Glycogen synthase kinase 3 beta | |
| NM_001552 | IGFBP4 | Insulin-like growth factor binding protein 4 | BP-4, HT29-IGFBP, IBP4, IGFBP-4 |
| NM_000577 | IL1RN | Interleukin 1 receptor antagonist | DIRA, ICIL-1RA, IL-1RN, IL-1ra, IL-1ra3, IL1F3, IL1RA, IRAP, MGC10430, MVCD4 |
| NM_004517 | ILK | Integrin-linked kinase | DKFZp686F1765, ILK-2, P59 |
| NM_002205 | ITGA5 | Integrin, alpha 5 (fibronectin receptor, alpha polypeptide) | CD49e, FNRA, VLA5A |
| NM_002210 | ITGAV | Integrin, alpha V (vitronectin receptor, alpha polypeptide, antigen CD51) | CD51, DKFZp686A08142, MSK8, VNRA |
| NM_002211 | ITGB1 | Integrin, beta 1 (fibronectin receptor, beta polypeptide, antigen CD29 includes MDF2, MSK12) | CD29, FNRB, GPIIA, MDF2, MSK12, VLA-BETA, VLAB |
| NM_000214 | JAG1 | Jagged 1 | AGS, AHD, AWS, CD339, HJ1, JAGL1, MGC104644 |
| NM_000526 | KRT14 | Keratin 14 | CK14, EBS3, EBS4, K14, NFJ |
| NM_002276 | KRT19 | Keratin 19 | CK19, K19, K1CS, MGC15366 |
| NM_005556 | KRT7 | Keratin 7 | CK7, K2C7, K7, MGC129731, MGC3625, SCL |
| NM_005909 | MAP1B | Microtubule-associated protein 1B | DKFZp686E1099, DKFZp686F1345, FLJ38954, FUTSCH, MAP5 |
| NM_000248 | MITF | Microphthalmia-associated transcription factor | MI, WS2, WS2A, bHLHe32 |
| NM_004530 | MMP2 | Matrix metallopeptidase 2 (gelatinase A, 72 kDa gelatinase, 72 kDa type IV collagenase) | CLG4, CLG4A, MMP-II, MONA, TBE-1 |
| NM_002422 | MMP3 | Matrix metallopeptidase 3 (stromelysin 1, progelatinase) | CHDS6, MGC126102, MGC126103, MGC126104, MMP-3, SL-1, STMY, STMY1, STR1 |
| NM_004994 | MMP9 | Matrix metallopeptidase 9 (gelatinase B, 92 kDa gelatinase, 92 kDa type IV collagenase) | CLG4B, GELB, MANDP2, MMP-9 |
| NM_002444 | MSN | Moesin | — |
| NM_002447 | MST1R | Macrophage stimulating 1 receptor (c-met-related tyrosine kinase) | CD136, CDw136, PTK8, RON |
| NM_018055 | NODAL | Nodal homolog (mouse) | MGC138230 |
| NM_017617 | NOTCH1 | Notch 1 | TAN1, hN1 |
| NM_015901 | NUDT13 | Nudix (nucleoside diphosphate linked moiety X)-type motif 13 | — |
| NM_002538 | OCLN | Occludin | BLCPMG, FLJ08163, FLJ18079, FLJ77961, FLJ94056, MGC34277 |
| NM_002609 | PDGFRB | Platelet-derived growth factor receptor, beta polypeptide | CD140B, JTK12, PDGFR, PDGFR1 |
| NM_016445 | PLEK2 | Pleckstrin 2 | |
| NM_015704 | PPPDE2 | PPPDE peptidase domain containing 2 | D15Wsu75e, DJ347H13.4, FAM152B, MGC138384 |
| NM_005607 | PTK2 | PTK2 protein tyrosine kinase 2 | FADK, FAK, FAK1, FRNK, pp125FAK |
| NM_003463 | PTP4A1 | Protein tyrosine phosphatase type IVA, member 1 | DKFZp779M0721, HH72, PRL-1, PRL1, PTP(CAAX1), PTPCAAX1 |

TABLE 8-continued

Epithelial to Mesencymal Transition-related Genes for Use as Biomarkers

| GeneBank | Symbol | Description | Gene Name |
|---|---|---|---|
| NM_006908 | RAC1 | Ras-related C3 botulinum toxin substrate 1 (rho family, small GTP binding protein Rac1) | MGC111543, Rac-1, TC-25, p21-Rac1 |
| NM_002923 | RGS2 | Regulator of G-protein signaling 2, 24 kDa | G0S8 |
| NM_000602 | SERPINE1 | Serpin peptidase inhibitor, clade E (nexin, plasminogen activator inhibitor type 1), member 1 | PAI, PAI-1, PAI1, PLANH1 |
| NM_003616 | SIP1 | Survival of motor neuron protein interacting protein 1 | GEMIN2, SIP1-delta |
| NM_005901 | SMAD2 | SMAD family member 2 | JV18, JV18-1, MADH2, MADR2, MGC22139, MGC34440, hMAD-2, hSMAD2 |
| NM_005985 | SNAI1 | Snail homolog 1 (*Drosophila*) | SLUGH2, SNA, SNAH, SNAIL, SNAIL1, dJ710H13.1 |
| NM_003068 | SNAI2 | Snail homolog 2 (*Drosophila*) | MGC10182, SLUG, SLUGH1, SNAIL2, WS2D |
| NM_178310 | SNAI3 | Snail homolog 3 (*Drosophila*) | MGC129606, SMUC, SNAIL3, ZNF293, Zfp293 |
| NM_006941 | SOX10 | SRY (sex determining region Y)-box 10 | DOM, MGC15649, PCWH, WS2E, WS4, WS4C |
| NM_003118 | SPARC | Secreted protein, acidic, cysteine-rich (osteonectin) | ON |
| NM_000582 | SPP1 | Secreted phosphoprotein 1 | BNSP, BSPI, ETA-1, MGC110940, OPN |
| NM_003150 | STAT3 | Signal transducer and activator of transcription 3 (acute-phase response factor) | APRF, FLJ20882, HIES, MGC16063 |
| NM_012449 | STEAP1 | Six transmembrane epithelial antigen of the prostate 1 | MGC19484, PRSS24, STEAP |
| NM_003200 | TCF3 | Transcription factor 3 (E2A immunoglobulin enhancer binding factors E12/E47) | E2A, E47, ITF1, MGC129647, MGC129648, VDIR, bHLHb21 |
| NM_003199 | TCF4 | Transcription factor 4 | E2-2, ITF2, MGC149723, MGC149724, PTHS, SEF2, SEF2-1, SEF2-1A, SEF2-1B, bHLHb19 |
| NM_006528 | TFPI2 | Tissue factor pathway inhibitor 2 | FLJ21164, PP5, REF1, TFPI-2 |
| NM_000660 | TGFB1 | Transforming growth factor, beta 1 | CED, DPD1, LAP, TGFB, TGFbeta |
| NM_003238 | TGFB2 | Transforming growth factor, beta 2 | MGC116892, TGF-beta2 |
| NM_003239 | TGFB3 | Transforming growth factor, beta 3 | ARVD, FLJ16571, TGF-beta3 |
| NM_003254 | TIMP1 | TIMP metallopeptidase inhibitor 1 | CLGI, EPA, EPO, FLJ90373, HCI, TIMP |
| NM_003692 | TMEFF1 | Transmembrane protein with EGF-like and two follistatin-like domains 1 | C9orf2, CT120.1, H7365, TR-1 |
| NM_178031 | TMEM132A | Transmembrane protein 132A | DKFZp547E212, FLJ20539, GBP, HSPA5BP1, MGC138669 |
| NM_014399 | TSPAN13 | Tetraspanin 13 | FLJ22934, NET-6, NET6, TM4SF13 |
| NM_000474 | TWIST1 | Twist homolog 1 (*Drosophila*) | ACS3, BPES2, BPES3, CRS1, SCS, TWIST, bHLHa38 |
| NM_004385 | VCAN | Versican | CSPG2, DKFZp686K06110, ERVR, GHAP, PG-M, WGN, WGN1 |
| NM_003380 | VIM | Vimentin | FLJ36605 |
| NM_033305 | VPS13A | Vacuolar protein sorting 13 homolog A (*S. cerevisiae*) | CHAC, CHOREIN, FLJ42030, KIAA0986 |
| NM_004626 | WNT11 | Wingless-type MMTV integration site family, member 11 | HWNT11, MGC141946, MGC141948 |
| NM_003392 | WNT5A | Wingless-type MMTV integration site family, member 5A | hWNT5A |
| NM_032642 | WNT5B | Wingless-type MMTV integration site family, member 5B | MGC2648 |
| NM_030751 | ZEB1 | Zinc finger E-box binding homeobox 1 | AREB6, BZP, DELTAEF1, FECD6, MGC133261, NIL2A, PPCD3, TCF8, ZFHEP, ZFHX1A |
| NM_014795 | ZEB2 | Zinc finger E-box binding homeobox 2 | FLJ42816, HSPC082, KIAA0569, SIP-1, SIP1, SMADIP1, ZFHX1B |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 9

Extracellular Matrix and Adhesion Genes for Use as Biomarkers

| GeneBank | Symbol | Description | Gene Name |
|---|---|---|---|
| NM_006988 | ADAMTS1 | ADAM metallopeptidase with thrombospondin type 1 motif, 1 | C3-C5, KIAA1346, METH1 |
| NM_139025 | ADAMTS13 | ADAM metallopeptidase with thrombospondin type 1 motif, 13 | C9orf8, DKFZp434C2322, FLJ42993, MGC118899, MGC118900, TTP, VWFCP, vWF-CP |
| NM_007037 | ADAMTS8 | ADAM metallopeptidase with thrombospondin type 1 motif, 8 | ADAM-TS8, FLJ41712, METH2 |
| NM_000610 | CD44 | CD44 molecule (Indian blood group) | CDW44, CSPG8, ECMR-III, HCELL, HUTCH-I, IN, LHR, MC56, MDU2, MDU3, MGC10468, MIC4, Pgp1 |

TABLE 9-continued

Extracellular Matrix and Adhesion Genes for Use as Biomarkers

| GeneBank | Symbol | Description | Gene Name |
|---|---|---|---|
| NM_004360 | CDH1 | Cadherin 1, type 1, E-cadherin (epithelial) | Arc-1, CD324, CDHE, ECAD, LCAM, UVO |
| NM_001843 | CNTN1 | Contactin 1 | F3, GP135 |
| NM_080629 | COL11A1 | Collagen, type XI, alpha 1 | CO11A1, COLL6, STL2 |
| NM_004370 | COL12A1 | Collagen, type XII, alpha 1 | BA209D8.1, COL12A1L, DJ234P15.1 |
| NM_021110 | COL14A1 | Collagen, type XIV, alpha 1 | UND |
| NM_001855 | COL15A1 | Collagen, type XV, alpha 1 | FLJ38566 |
| NM_001856 | COL16A1 | Collagen, type XVI, alpha 1 | 447AA |
| NM_000088 | COL1A1 | Collagen, type I, alpha 1 | OI4 |
| NM_001846 | COL4A2 | Collagen, type IV, alpha 2 | DKFZp686I14213, FLJ22259 |
| NM_000093 | COL5A1 | Collagen, type V, alpha 1 | — |
| NM_001848 | COL6A1 | Collagen, type VI, alpha 1 | OPLL |
| NM_001849 | COL6A2 | Collagen, type VI, alpha 2 | DKFZp586E1322, FLJ46862, PP3610 |
| NM_000094 | COL7A1 | Collagen, type VII, alpha 1 | EBD1, EBDCT, EBR1 |
| NM_001850 | COL8A1 | Collagen, type VIII, alpha 1 | C3orf7, MGC9568 |
| NM_004385 | VCAN | Versican | CSPG2, DKFZp686K06110, ERVR, GHAP, PG-M, WGN, WGN1 |
| NM_001901 | CTGF | Connective tissue growth factor | CCN2, HCS24, IGFBP8, MGC102839, NOV2 |
| NM_001903 | CTNNA1 | Catenin (cadherin-associated protein), alpha 1, 102 kDa | CAP102, FLJ36832, FLJ52416 |
| NM_001904 | CTNNB1 | Catenin (cadherin-associated protein), beta 1, 88 kDa | CTNNB, DKFZp686D02253, FLJ25606, FLJ37923 |
| NM_001331 | CTNND1 | Catenin (cadherin-associated protein), delta 1 | CAS, CTNND, KIAA0384, P120CAS, P120CTN, p120, p120(CAS), p120(CTN) |
| NM_001332 | CTNND2 | Catenin (cadherin-associated protein), delta 2 (neural plakophilin-related arm-repeat protein) | GT24, NPRAP |
| NM_004425 | ECM1 | Extracellular matrix protein 1 | |
| NM_002026 | FN1 | Fibronectin 1 | CIG, DKFZp686F10164, DKFZp686H0342, DKFZp686I1370, DKFZp686O13149, ED-B, FINC, FN, FNZ, GFND, GFND2, LETS, MSF |
| NM_001523 | HAS1 | Hyaluronan synthase 1 | HAS |
| NM_000201 | ICAM1 | Intercellular adhesion molecule 1 | BB2, CD54, P3.58 |
| NM_181501 | ITGA1 | Integrin, alpha 1 | CD49a, VLA1 |
| NM_002203 | ITGA2 | Integrin, alpha 2 (CD49B, alpha 2 subunit of VLA-2 receptor) | BR, CD49B, GPIa, VLA-2, VLAA2 |
| NM_002204 | ITGA3 | Integrin, alpha 3 (antigen CD49C, alpha 3 subunit of VLA-3 receptor) | CD49C, FLJ34631, FLJ34704, GAP-B3, GAPB3, MSK18, VCA-2, VL3A, VLA3a |
| NM_000885 | ITGA4 | Integrin, alpha 4 (antigen CD49D, alpha 4 subunit of VLA-4 receptor) | CD49D, IA4, MGC90518 |
| NM_002205 | ITGA5 | Integrin, alpha 5 (fibronectin receptor, alpha polypeptide) | CD49e, FNRA, VLA5A |
| NM_000210 | ITGA6 | Integrin, alpha 6 | CD49f, DKFZp686J01244, FLJ18737, ITGA6B, VLA-6 |
| NM_002206 | ITGA7 | Integrin, alpha 7 | FLJ25220 |
| NM_003638 | ITGA8 | Integrin, alpha 8 | — |
| NM_002209 | ITGAL | Integrin, alpha L (antigen CD11A (p180), lymphocyte function-associated antigen 1; alpha polypeptide) | CD11A, LFA-1, LFA1A |
| NM_000632 | ITGAM | Integrin, alpha M (complement component 3 receptor 3 subunit) | CD11B, CR3A, MAC-1, MAC1A, MGC117044, MO1A, SLEB6 |
| NM_002210 | ITGAV | Integrin, alpha V (vitronectin receptor, alpha polypeptide, antigen CD51) | CD51, DKFZp686A08142, MSK8, VNRA |
| NM_002211 | ITGB1 | Integrin, beta 1 (fibronectin receptor, beta polypeptide, antigen CD29 includes MDF2, MSK12) | CD29, FNRB, GPIIA, MDF2, MSK12, VLA-BETA, VLAB |
| NM_000211 | ITGB2 | Integrin, beta 2 (complement component 3 receptor 3 and 4 subunit) | CD18, LAD, LCAMB, LFA-1, MAC-1, MF17, MFI7 |
| NM_000212 | ITGB3 | Integrin, beta 3 (platelet glycoprotein IIIa, antigen CD61) | CD61, GP3A, GPIIIa |
| NM_000213 | ITGB4 | Integrin, beta 4 | CD104 |
| NM_002213 | ITGB5 | Integrin, beta 5 | FLJ26658 |
| NM_000216 | KAL1 | Kallmann syndrome 1 sequence | ADMLX, HHA, KAL, KALIG-1, KMS |
| NM_005559 | LAMA1 | Laminin, alpha 1 | LAMA, S-LAM-alpha |
| NM_000426 | LAMA2 | Laminin, alpha 2 | LAMM |
| NM_000227 | LAMA3 | Laminin, alpha 3 | BM600, E170, LAMNA, LOCS, lama3a |
| NM_002291 | LAMB1 | Laminin, beta 1 | CLM, MGC142015 |
| NM_000228 | LAMB3 | Laminin, beta 3 | BM600-125 KDA, FLJ99565, LAMS, LAMNB1 |
| NM_002293 | LAMC1 | Laminin, gamma 1 (formerly LAMB2) | LAMB2, MGC87297 |
| NM_002421 | MMP1 | Matrix metallopeptidase 1 (interstitial collagenase) | CLG, CLGN |
| NM_002425 | MMP10 | Matrix metallopeptidase 10 (stromelysin 2) | SL-2, STMY2 |
| NM_005940 | MMP11 | Matrix metallopeptidase 11 (stromelysin 3) | SL-3, ST3, STMY3 |
| NM_002426 | MMP12 | Matrix metallopeptidase 12 (macrophage elastase) | HME, ME, MGC138506, MME, MMP-12 |
| NM_002427 | MMP13 | Matrix metallopeptidase 13 (collagenase 3) | CLG3, MANDP1 |
| NM_004995 | MMP14 | Matrix metallopeptidase 14 (membrane-inserted) | 1, MMP-14, MMP-X1, MT-MMP, MT-MMP 1, MT1-MMP, MT1MMP, MTMMP1 |

TABLE 9-continued

Extracellular Matrix and Adhesion Genes for Use as Biomarkers

| GeneBank | Symbol | Description | Gene Name |
|---|---|---|---|
| NM_002428 | MMP15 | Matrix metallopeptidase 15 (membrane-inserted) | MT2-MMP, MTMMP2, SMCP-2 |
| NM_005941 | MMP16 | Matrix metallopeptidase 16 (membrane-inserted) | C8orf57, DKFZp761D112, MMP-X2, MT-MMP2, MT-MMP3, MT3-MMP |
| NM_004530 | MMP2 | Matrix metallopeptidase 2 (gelatinase A, 72 kDa gelatinase, 72 kDa type IV collagenase) | CLG4, CLG4A, MMP-II, MONA, TBE-1 |
| NM_002422 | MMP3 | Matrix metallopeptidase 3 (stromelysin 1, progelatinase) | CHDS6, MGC126102, MGC126103, MGC126104, MMP-3, SL-1, STMY, STMY1, STR1 |
| NM_002423 | MMP7 | Matrix metallopeptidase 7 (matrilysin, uterine) | MMP-7, MPSL1, PUMP-1 |
| NM_002424 | MMP8 | Matrix metallopeptidase 8 (neutrophil collagenase) | CLG1, HNC, MMP-8, PMNL-CL |
| NM_004994 | MMP9 | Matrix metallopeptidase 9 (gelatinase B, 92 kDa gelatinase, 92 kDa type IV collagenase) | CLG4B, GELB, MANDP2, MMP-9 |
| NM_000615 | NCAM1 | Neural cell adhesion molecule 1 | CD56, MSK39, NCAM |
| NM_000442 | PECAM1 | Platelet/endothelial cell adhesion molecule | CD31, FLJ34100, FLJ58394, PECAM-1 |
| NM_000450 | SELE | Selectin E | CD62E, ELAM, ELAM1, ESEL, LECAM2 |
| NM_000655 | SELL | Selectin L | CD62L, LAM1, LECAM1, LEU8, LNHR, LSEL, LYAM1, PLNHR, TQ1 |
| NM_003005 | SELP | Selectin P (granule membrane protein 140 kDa, antigen CD62) | CD62, CD62P, FLJ45155, GMP140, GRMP, LECAM3, PADGEM, PSEL |
| NM_003919 | SGCE | Sarcoglycan, epsilon | DYT11, ESG |
| NM_003118 | SPARC | Secreted protein, acidic, cysteine-rich (osteonectin) | ON |
| NM_003119 | SPG7 | Spastic paraplegia 7 (pure and complicated autosomal recessive) | CAR, CMAR, FLJ37308, MGC126331, MGC126332, PGN, SPG5C |
| NM_000582 | SPP1 | Secreted phosphoprotein 1 | BNSP, BSPI, ETA-1, MGC110940, OPN |
| NM_000358 | TGFBI | Transforming growth factor, beta-induced, 68 kDa | BIGH3, CDB1, CDG2, CDGG1, CSD, CSD1, CSD2, CSD3, EBMD, LCD1 |
| NM_003246 | THBS1 | Thrombospondin 1 | THBS, THBS-1, TSP, TSP-1, TSP1 |
| NM_003247 | THBS2 | Thrombospondin 2 | TSP2 |
| NM_007112 | THBS3 | Thrombospondin 3 | MGC119564, MGC119565, TSP3 |
| NM_003254 | TIMP1 | TIMP metallopeptidase inhibitor 1 | CLGI, EPA, EPO, FLJ90373, HCI, TIMP |
| NM_003255 | TIMP2 | TIMP metallopeptidase inhibitor 2 | CSC-21K |
| NM_000362 | TIMP3 | TIMP metallopeptidase inhibitor 3 | HSMRK222, K222, K222TA2, SFD |
| NM_003278 | CLEC3B | C-type lectin domain family 3, member B | DKFZp686H17246, TN, TNA |
| NM_002160 | TNC | Tenascin C | 150-225, GMEM, GP, HXB, JI, MGC167029, TN, TN-C |
| NM_001078 | VCAM1 | Vascular cell adhesion molecule 1 | CD106, DKFZp779G2333, INCAM-100, MGC99561 |
| NM_000638 | VTN | Vitronectin | V75, VN, VNT |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 10

Fibrosis-related Genes for Use as Biomarkers

| GeneBank | Symbol | Description | Gene Name |
|---|---|---|---|
| NM_001613 | ACTA2 | Actin, alpha 2, smooth muscle, aorta | AAT6, ACTSA |
| NM_000029 | AGT | Angiotensinogen (serpin peptidase inhibitor, clade A, member 8) | ANHU, FLJ92595, FLJ97926, SERPINA8 |
| NM_005163 | AKT1 | V-akt murine thymoma viral oncogene homolog 1 | AKT, MGC99656, PKB, PKB-ALPHA, PRKBA, RAC, RAC-ALPHA |
| NM_000633 | BCL2 | B-cell CLL/lymphoma 2 | Bcl-2 |
| NM_001719 | BMP7 | Bone morphogenetic protein 7 | OP-1 |
| NM_001753 | CAV1 | Caveolin 1, caveolae protein, 22 kDa | BSCL3, CGL3, MSTP085, VIP21 |
| NM_002986 | CCL11 | Chemokine (C-C motif) ligand 11 | MGC22554, SCYA11 |
| NM_002982 | CCL2 | Chemokine (C-C motif) ligand 2 | GDCF-2, HC11, HSMCR30, MCAF, MCP-1, MCP1, MGC9434, SCYA2, SMC-CF |
| NM_002983 | CCL3 | Chemokine (C-C motif) ligand 3 | G0S19-1, LD78ALPHA, MIP-1-alpha, MIP1A, SCYA3 |
| NM_001123396 | CCR2 | Chemokine (C-C motif) receptor 2 | CC-CKR-2, CCR2A, CCR2B, CD192, CKR2, CKR2A, CKR2B, CMKBR2, FLJ78302, MCP-1-R, MGC103828, MGC111760, MGC168006 |
| NM_005194 | CEBPB | CCAAT/enhancer binding protein (C/EBP), beta | C, EBP-beta, CRP2, IL6DBP, LAP, MGC32080, NF-IL6, TCF5 |
| NM_000089 | COL1A2 | Collagen, type I, alpha 2 | OI4 |
| NM_000090 | COL3A1 | Collagen, type III, alpha 1 | EDS4A, FLJ34534 |
| NM_001901 | CTGF | Connective tissue growth factor | CCN2, HCS24, IGFBP8, MGC102839, NOV2 |

TABLE 10-continued

Fibrosis-related Genes for Use as Biomarkers

| GeneBank | Symbol | Description | Gene Name |
|---|---|---|---|
| NM_003467 | CXCR4 | Chemokine (C—X—C motif) receptor 4 | CD184, D2S201E, FB22, HM89, HSY3RR, LAP3, LCR1, LESTR, NPY3R, NPYR, NPYRL, NPYY3R, WHIM |
| NM_001920 | DCN | Decorin | CSCD, DSPG2, PG40, PGII, PGS2, SLRR1B |
| NM_001955 | EDN1 | Endothelin 1 | ET1, HDLCQ7, PPET1 |
| NM_001963 | EGF | Epidermal growth factor | HOMG4, URG |
| NM_000118 | ENG | Endoglin | CD105, END, FLJ41744, HHT1, ORW, ORW1 |
| NM_000639 | FASLG | Fas ligand (TNF superfamily, member 6) | APT1LG1, CD178, CD95-L, CD95L, FASL, TNFSF6 |
| NM_013372 | GREM1 | Gremlin 1 | CKTSF1B1, DAND2, DRM, GREMLIN, IHG-2, MGC126660 |
| NM_000601 | HGF | Hepatocyte growth factor (hepapoietin A; scatter factor) | DFNB39, F-TCF, HGFB, HPTA, SF |
| NM_000619 | IFNG | Interferon, gamma | IFG, IFI |
| NM_000572 | IL10 | Interleukin 10 | CSIF, IL-10, IL10A, MGC126450, MGC126451, TGIF |
| NM_002188 | IL13 | Interleukin 13 | ALRH, BHR1, IL-13, MGC116786, MGC116788, MGC116789, P600 |
| NM_000640 | IL13RA2 | Interleukin 13 receptor, alpha 2 | CD213A2, CT19, IL-13R, IL13BP |
| NM_000575 | IL1A | Interleukin 1, alpha | IL-1A, IL1, IL1-ALPHA, IL1F1 |
| NM_000576 | IL1B | Interleukin 1, beta | IL-1, IL1-BETA, IL1F2 |
| NM_000589 | IL4 | Interleukin 4 | BCGF-1, BCGF1, BSF-1, BSF1, IL-4, MGC79402 |
| NM_000879 | IL5 | Interleukin 5 (colony-stimulating factor, eosinophil) | EDF, IL-5, TRF |
| NM_004517 | ILK | Integrin-linked kinase | DKFZp686F1765, ILK-2, P59 |
| NM_031479 | INHBE | inhibin, beta E | MGC4638 |
| NM_181501 | ITGA1 | Integrin, alpha 1 | CD49a, VLA1 |
| NM_002203 | ITGA2 | Integrin, alpha 2 (CD49B, alpha 2 subunit of VLA-2 receptor) | BR, CD49B, GPIa, VLA-2, VLAA2 |
| NM_002204 | ITGA3 | Integrin, alpha 3 (antigen CD49C, alpha 3 subunit of VLA-3 receptor) | CD49C, FLJ34631, FLJ34704, GAP-B3, GAPB3, MSK18, VCA-2, VL3A, VLA3a |
| NM_002210 | ITGAV | Integrin, alpha V (vitronectin receptor, alpha polypeptide, antigen CD51) | CD51, DKFZp686A08142, MSK8, VNRA |
| NM_002211 | ITGB1 | Integrin, beta 1 (fibronectin receptor, beta polypeptide, antigen CD29 includes MDF2, MSK12) | CD29, FNRB, GPIIA, MDF2, MSK12, VLA-BETA, VLAB |
| NM_000212 | ITGB3 | Integrin, beta 3 (platelet glycoprotein IIIa, antigen CD61) | CD61, GP3A, GPIIIa |
| NM_002213 | ITGB5 | Integrin, beta 5 | FLJ26658 |
| NM_000888 | ITGB6 | Integrin, beta 6 | — |
| NM_002214 | ITGB8 | Integrin, beta 8 | — |
| NM_002228 | JUN | Jun proto-oncogene | AP-1, AP1, c-Jun |
| NM_002317 | LOX | Lysyl oxidase | MGC105112 |
| NM_000627 | LTBP1 | Latent transforming growth factor beta binding protein 1 | MGC163161 |
| NM_002421 | MMP1 | Matrix metallopeptidase 1 (interstitial collagenase) | CLG, CLGN |
| NM_002427 | MMP13 | Matrix metallopeptidase 13 (collagenase 3) | CLG3, MANDP1 |
| NM_004995 | MMP14 | Matrix metallopeptidase 14 (membrane-inserted) | 1, MMP-14, MMP-X1, MT-MMP, MT-MMP 1, MT1-MMP, MT1MMP, MTMMP1 |
| NM_004530 | MMP2 | Matrix metallopeptidase 2 (gelatinase A, 72 kDa gelatinase, 72 kDa type IV collagenase) | CLG4, CLG4A, MMP-II, MONA, TBE-1 |
| NM_002422 | MMP3 | Matrix metallopeptidase 3 (stromelysin 1, progelatinase) | CHDS6, MGC126102, MGC126103, MGC126104, MMP-3, SL-1, STMY, STMY1, STR1 |
| NM_002424 | MMP8 | Matrix metallopeptidase 8 (neutrophil collagenase) | CLG1, HNC, MMP-8, PMNL-CL |
| NM_004994 | MMP9 | Matrix metallopeptidase 9 (gelatinase B, 92 kDa gelatinase, 92 kDa type IV collagenase) | CLG4B, GELB, MANDP2, MMP-9 |
| NM_002467 | MYC | V-myc myelocytomatosis viral oncogene homolog (avian) | MRTL, bHLHe39, c-Myc |
| NM_003998 | NFKB1 | Nuclear factor of kappa light polypeptide gene enhancer in B-cells 1 | DKFZp686C01211, EBP-1, KBF1, MGC54151, NF-kappa-B, NF-kappaB, NFKB-p105, NFKB-p50, NFkappaB, p105, p50 |
| NM_002607 | PDGFA | Platelet-derived growth factor alpha polypeptide | PDGF-A, PDGF1 |
| NM_002608 | PDGFB | Platelet-derived growth factor beta polypeptide | FLJ12858, PDGF2, SIS, SSV, c-sis |
| NM_000930 | PLAT | Plasminogen activator, tissue | DKFZp686I03148, T-PA, TPA |
| NM_002658 | PLAU | Plasminogen activator, urokinase | ATF, UPA, URK, u-PA |
| NM_000301 | PLG | Plasminogen | DKFZp779M0222 |
| NM_000295 | SERPINA1 | Serpin peptidase inhibitor, clade A (alpha-1 antiproteinase, antitrypsin), member 1 | A1A, A1AT, AAT, MGC23330, MGC9222, PI, PI1, PRO2275, alpha1AT |
| NM_000602 | SERPINE1 | Serpin peptidase inhibitor, clade E (nexin, plasminogen activator inhibitor type 1), member 1 | PAI, PAI-1, PAI1, PLANH1 |

TABLE 10-continued

Fibrosis-related Genes for Use as Biomarkers

| GeneBank | Symbol | Description | Gene Name |
| --- | --- | --- | --- |
| NM_001235 | SERPINH1 | Serpin peptidase inhibitor, clade H (heat shock protein 47), member 1, (collagen binding protein 1) | AsTP3, CBP1, CBP2, HSP47, PPROM, RA-A47, SERPINH2, gp46 |
| NM_005901 | SMAD2 | SMAD family member 2 | JV18, JV18-1, MADH2, MADR2, MGC22139, MGC34440, hMAD-2, hSMAD2 |
| NM_005902 | SMAD3 | SMAD family member 3 | DKFZp586N0721, DKFZp686J10186, HSPC193, HsT17436, JV15-2, MADH3, MGC60396 |
| NM_005359 | SMAD4 | SMAD family member 4 | DPC4, JIP, MADH4 |
| NM_005585 | SMAD6 | SMAD family member 6 | HsT17432, MADH6, MADH7 |
| NM_005904 | SMAD7 | SMAD family member 7 | CRCS3, FLJ16482, MADH7, MADH8 |
| NM_005985 | SNAI1 | Snail homolog 1 (*Drosophila*) | SLUGH2, SNA, SNAH, SNAIL, SNAIL1, dJ710H13.1 |
| NM_138473 | SP1 | Sp1 transcription factor | — |
| NM_007315 | STAT1 | Signal transducer and activator of transcription 1, 91 kDa | DKFZp686B04100, ISGF-3, STAT91 |
| NM_003153 | STAT6 | Signal transducer and activator of transcription 6, interleukin-4 induced | D12S1644, IL-4-STAT, STAT6B, STAT6C |
| NM_000660 | TGFB1 | Transforming growth factor, beta 1 | CED, DPD1, LAP, TGFB, TGFbeta |
| NM_003238 | TGFB2 | Transforming growth factor, beta 2 | MGC116892, TGF-beta2 |
| NM_003239 | TGFB3 | Transforming growth factor, beta 3 | ARVD, FLJ16571, TGF-beta3 |
| NM_004612 | TGFBR1 | Transforming growth factor, beta receptor 1 | AAT5, ACVRLK4, ALK-5, ALK5, LDS1A, LDS2A, SKR4, TGFR-1 |
| NM_003242 | TGFBR2 | Transforming growth factor, beta receptor II (70/80 kDa) | AAT3, FAA3, LDS1B, LDS2B, MFS2, RIIC, TAAD2, TGFR-2, TGFbeta-RII |
| NM_003244 | TGIF1 | TGFB-induced factor homeobox 1 | HPE4, MGC39747, MGC5066, TGIF |
| NM_003246 | THBS1 | Thrombospondin 1 | THBS, THBS-1, TSP, TSP-1, TSP1 |
| NM_003247 | THBS2 | Thrombospondin 2 | TSP2 |
| NM_003254 | TIMP1 | TIMP metallopeptidase inhibitor 1 | CLGI, EPA, EPO, FLJ90373, HCI, TIMP |
| NM_003255 | TIMP2 | TIMP metallopeptidase inhibitor 2 | CSC-21K |
| NM_000362 | TIMP3 | TIMP metallopeptidase inhibitor 3 | HSMRK222, K222, K222TA2, SFD |
| NM_003256 | TIMP4 | TIMP metallopeptidase inhibitor 4 | — |
| NM_000594 | TNF | Tumor necrosis factor | DIF, TNF-alpha, TNFA, TNFSF2 |
| NM_003376 | VEGFA | Vascular endothelial growth factor A | MGC70609, MVCD1, VEGF, VPF |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 11

Growth Factor Genes for Use as Biomarkers

| GeneBank | Symbol | Description | Gene Name |
| --- | --- | --- | --- |
| NM_000479 | AMH | Anti-Mullerian hormone | MIF, MIS |
| NM_016442 | ERAP1 | Endoplasmic reticulum aminopeptidase 1 | A-LAP, ALAP, APPILS, ARTS-1, ARTS1, ERAAP, ERAAP1, KIAA0525, PILS-AP, PILSAP |
| NM_001709 | BDNF | Brain-derived neurotrophic factor | MGC34632 |
| NM_006129 | BMP1 | Bone morphogenetic protein 1 | FLJ44432, PCOLC, PCP, PCP2, TLD |
| NM_014482 | BMP10 | Bone morphogenetic protein 10 | MGC126783 |
| NM_001200 | BMP2 | Bone morphogenetic protein 2 | BMP2A |
| NM_001201 | BMP3 | Bone morphogenetic protein 3 | BMP-3A |
| NM_130851 | BMP4 | Bone morphogenetic protein 4 | BMP2B, BMP2B1, MCOPS6, OFC11, ZYME |
| NM_021073 | BMP5 | Bone morphogenetic protein 5 | MGC34244 |
| NM_001718 | BMP6 | Bone morphogenetic protein 6 | VGR, VGR1 |
| NM_001719 | BMP7 | Bone morphogenetic protein 7 | OP-1 |
| NM_001720 | BMP8B | Bone morphogenetic protein 8b | BMP8, MGC131757, OP2 |
| NM_177405 | CECR1 | Cat eye syndrome chromosome region, candidate 1 | ADA2, ADGF, IDGFL |
| NM_001828 | CLC | Charcot-Leyden crystal protein | GAL10, Gal-10, LGALS10, LGALS10A, LPPL_HUMAN, MGC149659 |
| NM_000757 | CSF1 | Colony stimulating factor 1 (macrophage) | MCSF, MGC31930 |
| NM_000758 | CSF2 | Colony stimulating factor 2 (granulocyte-macrophage) | GMCSF, MGC131935, MGC138897 |
| NM_000759 | CSF3 | Colony stimulating factor 3 (granulocyte) | C17orf33, CSF3OS, GCSF, MGC45931 |
| NM_006574 | CSPG5 | Chondroitin sulfate proteoglycan 5 (neuroglycan C) | MGC44034, NGC |
| NM_001511 | CXCL1 | Chemokine (C—X—C motif) ligand 1 (melanoma growth stimulating activity, alpha) | FSP, GRO1, GROa, MGSA, MGSA-a, NAP-3, SCYB1 |
| NM_012242 | DKK1 | Dickkopf homolog 1 (*Xenopus laevis*) | DKK-1, SK |
| NM_001953 | TYMP | Thymidine phosphorylase | ECGF, ECGF1, MEDPS1, MNGIE, MTDPS1, PDECGF, TP, hPD-ECGF |

TABLE 11-continued

Growth Factor Genes for Use as Biomarkers

| GeneBank | Symbol | Description | Gene Name |
| --- | --- | --- | --- |
| NM_001432 | EREG | Epiregulin | ER |
| NM_000800 | FGF1 | Fibroblast growth factor 1 (acidic) | AFGF, ECGF, ECGF-beta, ECGFA, ECGFB, FGF-alpha, FGFA, GLIO703, HBGF1 |
| NM_004112 | FGF11 | Fibroblast growth factor 11 | FHF3, FLJ16061, MGC102953, MGC45269 |
| NM_004114 | FGF13 | Fibroblast growth factor 13 | FGF-13, FGF2, FHF-2, FHF2 |
| NM_004115 | FGF14 | Fibroblast growth factor 14 | FGF-14, FHF-4, FHF4, MGC119129, SCA27 |
| NM_003867 | FGF17 | Fibroblast growth factor 17 | FGF-13 |
| NM_005117 | FGF19 | Fibroblast growth factor 19 | — |
| NM_002006 | FGF2 | Fibroblast growth factor 2 (basic) | BFGF, FGFB, HBGF-2 |
| NM_020637 | FGF22 | Fibroblast growth factor 22 | — |
| NM_020638 | FGF23 | Fibroblast growth factor 23 | ADHR, HPDR2, HYPF, PHPTC |
| NM_004464 | FGF5 | Fibroblast growth factor 5 | HBGF-5, Smag-82 |
| NM_020996 | FGF6 | Fibroblast growth factor 6 | HBGF-6, HST2 |
| NM_002009 | FGF7 | Fibroblast growth factor 7 | HBGF-7, KGF |
| NM_002010 | FGF9 | Fibroblast growth factor 9 (glia-activating factor) | GAF, HBFG-9, MGC119914, MGC119915, SYNS3 |
| NM_004469 | FIGF | C-fos induced growth factor (vascular endothelial growth factor D) | VEGF-D, VEGFD |
| NM_004962 | GDF10 | Growth differentiation factor 10 | BMP-3b, BMP3B |
| NM_005811 | GDF11 | Growth differentiation factor 11 | BMP-11, BMP11 |
| NM_005259 | MSTN | Myostatin | GDF8 |
| NM_000514 | GDNF | Glial cell derived neurotrophic factor | ATF1, ATF2, HFB1-GDNF, HSCR3 |
| NM_000175 | GPI | Glucose-6-phosphate isomerase | AMF, DKFZp686C13233, GNPI, NLK, PGI, PHI, SA-36, SA36 |
| NM_001945 | HBEGF | Heparin-binding EGF-like growth factor | DTR, DTS, DTSF, HEGFL |
| NM_000618 | IGF1 | Insulin-like growth factor 1 (somatomedin C) | IGF-I, IGF1A, IGFI |
| NM_000612 | IGF2 | Insulin-like growth factor 2 (somatomedin A) | C11orf43, FLJ22066, FLJ44734, IGF-II, PP9974 |
| NM_000572 | IL10 | Interleukin 10 | CSIF, IL-10, IL10A, MGC126450, MGC126451, TGIF |
| NM_000641 | IL11 | Interleukin 11 | AGIF, IL-11 |
| NM_002187 | IL12B | Interleukin 12B (natural killer cell stimulatory factor 2, cytotoxic lymphocyte maturation factor 2, p40) | CLMF, CLMF2, IL-12B, NKSF, NKSF2 |
| NM_001562 | IL18 | Interleukin 18 (interferon-gamma-inducing factor) | IGIF, IL-18, IL-1g, IL1F4, MGC12320 |
| NM_000575 | IL1A | Interleukin 1, alpha | IL-1A, IL1, IL1-ALPHA, IL1F1 |
| NM_000576 | IL1B | Interleukin 1, beta | IL-1, IL1-BETA, IL1F2 |
| NM_000586 | IL2 | Interleukin 2 | IL-2, TCGF, lymphokine |
| NM_000588 | IL3 | Interleukin 3 (colony-stimulating factor, multiple) | IL-3, MCGF, MGC79398, MGC79399, MULTI-CSF |
| NM_000589 | IL4 | Interleukin 4 | BCGF-1, BCGF1, BSF-1, BSF1, IL-4, MGC79402 |
| NM_002191 | INHA | Inhibin, alpha | — |
| NM_002192 | INHBA | Inhibin, beta A | EDF, FRP |
| NM_002193 | INHBB | Inhibin, beta B | MGC157939 |
| NM_000214 | JAG1 | Jagged 1 | AGS, AHD, AWS, CD339, HJ1, JAGL1, MGC104644 |
| NM_002226 | JAG2 | Jagged 2 | HJ2, SER2 |
| NM_020997 | LEFTY1 | Left-right determination factor 1 | LEFTB, LEFTYB |
| NM_003240 | LEFTY2 | Left-right determination factor 2 | EBAF, LEFTA, LEFTYA, MGC46222, TGFB4 |
| NM_002309 | LIF | Leukemia inhibitory factor (cholinergic differentiation factor) | CDF, DIA, HILDA |
| NM_003573 | LTBP4 | Latent transforming growth factor beta binding protein 4 | FLJ46318, FLJ90018, LTBP-4, LTBP4L, LTBP4S |
| NM_002391 | MDK | Midkine (neurite growth-promoting factor 2) | FLJ27379, MK, NEGF2 |
| NM_000266 | NDP | Norrie disease (pseudoglioma) | EVR2, FEVR, ND |
| NM_002506 | NGF | Nerve growth factor (beta polypeptide) | Beta-NGF, HSAN5, MGC161426, MGC161428, NGFB |
| NM_018055 | NODAL | Nodal homolog (mouse) | MGC138230 |
| NM_013957 | NRG1 | Neuregulin 1 | ARIA, GGF, GGF2, HGL, HRG, HRG1, HRGA, MST131, NDF, SMDF |
| NM_013982 | NRG2 | Neuregulin 2 | DON1, HRG2, NTAK |
| NM_001010848 | NRG3 | Neuregulin 3 | HRG3, pro-NRG3 |
| NM_004558 | NRTN | Neurturin | NTN |
| NM_002527 | NTF3 | Neurotrophin 3 | HDNF, MGC129711, NGF-2, NGF2, NT3 |
| NM_182981 | OSGIN1 | Oxidative stress induced growth inhibitor 1 | BDGI, OKL38 |
| NM_016205 | PDGFC | Platelet derived growth factor C | FALLOTEIN, SCDGF |
| NM_002632 | PGF | Placental growth factor | D12S1900, PGFL, PLGF, PlGF-2, SHGC-10760 |
| NM_004158 | PSPN | Persephin | PSP |
| NM_002825 | PTN | Pleiotrophin | HARP, HBGF8, HBNF, NEGF1 |
| NM_021094 | SLCO1A2 | Solute carrier organic anion transporter family, member 1A2 | OATP, OATP-A, OATP1A2, SLC21A3 |
| NM_000582 | SPP1 | Secreted phosphoprotein 1 | BNSP, BSPI, ETA-1, MGC110940, OPN |
| NM_003212 | TDGF1 | Teratocarcinoma-derived growth factor 1 | CR, CRGF, CRIPTO |

TABLE 11-continued

Growth Factor Genes for Use as Biomarkers

| GeneBank | Symbol | Description | Gene Name |
| --- | --- | --- | --- |
| NM_000660 | TGFB1 | Transforming growth factor, beta 1 | CED, DPD1, LAP, TGFB, TGFbeta |
| NM_000460 | THPO | Thrombopoietin | MGC163194, MGDF, MKCSF, ML, MPLLG, TPO |
| NM_003283 | TNNT1 | Troponin T type 1 (skeletal, slow) | ANM, FLJ98147, MGC104241, STNT, TNT, TNTS |
| NM_003376 | VEGFA | Vascular endothelial growth factor A | MGC70609, MVCD1, VEGF, VPF |
| NM_005429 | VEGFC | Vascular endothelial growth factor C | Flt4-L, VRP |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 12

Inflammatory-related Genes for Use as Biomarkers

| GeneBank | Symbol | Description | Gene Name |
| --- | --- | --- | --- |
| NM_001090 | ABCF1 | ATP-binding cassette, sub-family F (GCN20), member 1 | ABC27, ABC50 |
| NM_001706 | BCL6 | B-cell CLL/lymphoma 6 | BCL5, BCL6A, LAZ3, ZBTB27, ZNF51 |
| NM_000064 | C3 | Complement component 3 | AHUS5, ARMD9, ASP, CPAMD1 |
| NM_007293 | C4A | Complement component 4A (Rodgers blood group) | C4, C4A2, C4A3, C4A4, C4A6, C4S, CO4, CPAMD2, MGC164979, RG |
| NM_001735 | C5 | Complement component 5 | CPAMD4, FLJ17816, FLJ17822, MGC142298 |
| NM_002981 | CCL1 | Chemokine (C-C motif) ligand 1 | I-309, P500, SCYA1, SISe, TCA3 |
| NM_002986 | CCL11 | Chemokine (C-C motif) ligand 11 | MGC22554, SCYA11 |
| NM_005408 | CCL13 | Chemokine (C-C motif) ligand 13 | CKb10, MCP-4, MGC17134, NCC-1, NCC1, SCYA13, SCYL1 |
| NM_032965 | CCL15 | Chemokine (C-C motif) ligand 15 | HCC-2, HMRP-2B, LKN-1, LKN1, MIP-1D, MIP-5, MRP-2B, NCC-3, NCC3, SCYA15, SCYL3, SY15 |
| NM_004590 | CCL16 | Chemokine (C-C motif) ligand 16 | CKb12, HCC-4, ILINCK, LCC-1, LEC, LMC, MGC117051, Mtn-1, NCC-4, NCC4, SCYA16, SCYL4 |
| NM_002987 | CCL17 | Chemokine (C-C motif) ligand 17 | A-152E5.3, ABCD-2, MGC138271, MGC138273, SCYA17, TARC |
| NM_002988 | CCL18 | Chemokine (C-C motif) ligand 18 (pulmonary and activation-regulated) | AMAC-1, AMAC1, CKb7, DC-CK1, DCCK1, MIP-4, PARC, SCYA18 |
| NM_006274 | CCL19 | Chemokine (C-C motif) ligand 19 | CKb11, ELC, MGC34433, MIP-3b, MIP3B, SCYA19 |
| NM_002982 | CCL2 | Chemokine (C-C motif) ligand 2 | GDCF-2, HC11, HSMCR30, MCAF, MCP-1, MCP1, MGC9434, SCYA2, SMC-CF |
| NM_004591 | CCL20 | Chemokine (C-C motif) ligand 20 | CKb4, LARC, MIP-3a, MIP3A, SCYA20, ST38 |
| NM_002989 | CCL21 | Chemokine (C-C motif) ligand 21 | 6Ckine, CKb9, ECL, MGC34555, SCYA21, SLC, TCA4 |
| NM_005064 | CCL23 | Chemokine (C-C motif) ligand 23 | CK-BETA-8, CKb8, Ckb-8, Ckb-8-1, MIP-3, MIP3, MPIF-1, SCYA23 |
| NM_002991 | CCL24 | Chemokine (C-C motif) ligand 24 | Ckb-6, MPIF-2, MPIF2, SCYA24 |
| NM_005624 | CCL25 | Chemokine (C-C motif) ligand 25 | Ckb15, MGC150327, SCYA25, TECK |
| NM_006072 | CCL26 | Chemokine (C-C motif) ligand 26 | IMAC, MGC126714, MIP-4a, MIP-4alpha, SCYA26, TSC-1 |
| NM_002983 | CCL3 | Chemokine (C-C motif) ligand 3 | G0S19-1, LD78ALPHA, MIP-1-alpha, MIP1A, SCYA3 |
| NM_002984 | CCL4 | Chemokine (C-C motif) ligand 4 | ACT2, AT744.1, G-26, LAG1, MGC104418, MGC126025, MGC126026, MIP-1-beta, MIP1B, MIP1B1, SCYA2, SCYA4 |
| NM_002985 | CCL5 | Chemokine (C-C motif) ligand 5 | D17S136E, MGC17164, RANTES, SCYA5, SISd, TCP228 |
| NM_006273 | CCL7 | Chemokine (C-C motif) ligand 7 | FIC, MARC, MCP-3, MCP3, MGC138463, MGC138465, NC28, SCYA6, SCYA7 |
| NM_005623 | CCL8 | Chemokine (C-C motif) ligand 8 | HC14, MCP-2, MCP2, SCYA10, SCYA8 |
| NM_001295 | CCR1 | Chemokine (C-C motif) receptor 1 | CD191, CKR-1, CKR1, CMKBR1, HM145, MIP1aR, SCYAR1 |
| NM_001123396 | CCR2 | Chemokine (C-C motif) receptor 2 | CC-CKR-2, CCR2A, CCR2B, CD192, CKR2, CKR2A, CKR2B, CMKBR2, FLJ78302, MCP-1-R, MGC103828, MGC111760, MGC168006 |
| NM_001837 | CCR3 | Chemokine (C-C motif) receptor 3 | CC-CKR-3, CD193, CKR3, CMKBR3, MGC102841 |
| NM_005508 | CCR4 | Chemokine (C-C motif) receptor 4 | CC-CKR-4, CD194, CKR4, CMKBR4, ChemR13, HGCN:14099, K5-5, MGC88293 |
| NM_000579 | CCR5 | Chemokine (C-C motif) receptor 5 | CC-CKR-5, CCCKR5, CD195, CKR-5, CKR5, CMKBR5, FLJ78003, IDDM22 |

TABLE 12-continued

Inflammatory-related Genes for Use as Biomarkers

| GeneBank | Symbol | Description | Gene Name |
| --- | --- | --- | --- |
| NM_004367 | CCR6 | Chemokine (C-C motif) receptor 6 | BN-1, C-C CKR-6, CC-CKR-6, CCR-6, CD196, CKR-L3, CKRL3, CMKBR6, DCR2, DRY6, GPR29, GPRCY4, STRL22 |
| NM_001838 | CCR7 | Chemokine (C-C motif) receptor 7 | BLR2, CD197, CDw197, CMKBR7, EBI1 |
| NM_005201 | CCR8 | Chemokine (C-C motif) receptor 8 | CC-CKR-8, CCR-8, CDw198, CKRL1, CMKBR8, CMKBRL2, CY6, GPRCY6, MGC129966, MGC129973, TER1 |
| NM_006641 | CCR9 | Chemokine (C-C motif) receptor 9 | CDw199, GPR-9-6, GPR28 |
| NM_005194 | CEBPB | CCAAT/enhancer binding protein (C/EBP), beta | C, EBP-beta, CRP2, IL6DBP, LAP, MGC32080, NF-IL6, TCF5 |
| NM_000567 | CRP | C-reactive protein, pentraxin-related | MGC149895, MGC88244, PTX1 |
| NM_001337 | CX3CR1 | Chemokine (C—X3—C motif) receptor 1 | CCRL1, CMKBRL1, CMKDR1, GPR13, GPRV28, V28 |
| NM_001511 | CXCL1 | Chemokine (C—X—C motif) ligand 1 (melanoma growth stimulating activity, alpha) | FSP, GRO1, GROa, MGSA, MGSA-a, NAP-3, SCYB1 |
| NM_001565 | CXCL10 | Chemokine (C—X—C motif) ligand 10 | C7, IFI10, INP10, IP-10, SCYB10, crg-2, gIP-10, mob-1 |
| NM_005409 | CXCL11 | Chemokine (C—X—C motif) ligand 11 | H174, I-TAC, IP-9, IP9, MGC102770, SCYB11, SCYB9B, b-R1 |
| NM_000609 | CXCL12 | Chemokine (C—X—C motif) ligand 12 | IRH, PBSF, SCYB12, SDF1, SDF1A, SDF1B, TLSF, TPAR1 |
| NM_006419 | CXCL13 | Chemokine (C—X—C motif) ligand 13 | ANGIE, ANGIE2, BCA-1, BCA1, BLC, BLR1L, SCYB13 |
| NM_004887 | CXCL14 | Chemokine (C—X—C motif) ligand 14 | BMAC, BRAK, KEC, KS1, MGC10687, MIP-2g, MIP2G, NJAC, SCYB14 |
| NM_002089 | CXCL2 | Chemokine (C—X—C motif) ligand 2 | CINC-2a, GRO2, GROb, MGSA-b, MIP-2a, MIP2, MIP2A, SCYB2 |
| NM_002090 | CXCL3 | Chemokine (C—X—C motif) ligand 3 | CINC-2b, GRO3, GROg, MIP-2b, MIP2B, SCYB3 |
| NM_002994 | CXCL5 | Chemokine (C—X—C motif) ligand 5 | ENA-78, SCYB5 |
| NM_002993 | CXCL6 | Chemokine (C—X—C motif) ligand 6 (granulocyte chemotactic protein 2) | CKA-3, GCP-2, GCP2, SCYB6 |
| NM_002416 | CXCL9 | Chemokine (C—X—C motif) ligand 9 | CMK, Humig, MIG, SCYB9, crg-10 |
| NM_021571 | CARD18 | Caspase recruitment domain family, member 18 | ICEBERG, UNQ5804, pseudo-ICE |
| NM_000605 | IFNA2 | Interferon, alpha 2 | IFN-alphaA, IFNA, INFA2, MGC125764, MGC125765 |
| NM_000572 | IL10 | Interleukin 10 | CSIF, IL-10, IL10A, MGC126450, MGC126451, TGIF |
| NM_001558 | IL10RA | Interleukin 10 receptor, alpha | CDW210A, HIL-10R, IL-10R1, IL10R |
| NM_000628 | IL10RB | Interleukin 10 receptor, beta | CDW210B, CRF2-4, CRFB4, D21S58, D21S66, IL-10R2 |
| NM_002188 | IL13 | Interleukin 13 | ALRH, BHR1, IL-13, MGC116786, MGC116788, MGC116789, P600 |
| NM_001560 | IL13RA1 | Interleukin 13 receptor, alpha 1 | CD213A1, IL-13Ra, NR4 |
| NM_013278 | IL17C | Interleukin 17C | CX2, IL-17C, IL-21, MGC126884, MGC138401 |
| NM_000575 | IL1A | Interleukin 1, alpha | IL-1A, IL1, IL1-ALPHA, IL1F1 |
| NM_000576 | IL1B | Interleukin 1, beta | IL-1, IL1-BETA, IL1F2 |
| NM_173161 | IL1F10 | Interleukin 1 family, member 10 (theta) | FIL1-theta, IL-1HY2, IL1-theta, MGC119831, MGC119832, MGC119833 |
| NM_012275 | IL36RN | Interleukin 36 receptor antagonist | FIL1, FIL1(DELTA), FIL1D, IL1F5, IL1HY1, IL1L1, IL1RP3, IL36RA, MGC29840 |
| NM_014440 | IL36A | Interleukin 36, alpha | FIL1, FIL1(EPSILON), FIL1E, IL-1F6, IL1(EPSILON), IL1F6, MGC129552, MGC129553 |
| NM_173205 | IL37 | Interleukin 37 | FIL1, FIL1(ZETA), FIL1Z, IL-1F7, IL-1H, IL-1H4, IL-1RP1, IL-37, IL1F7, IL1H4, IL1RP1 |
| NM_173178 | IL36B | Interleukin 36, beta | FIL1, FIL1-(ETA), FIL1H, FILI-(ETA), IL-1F8, IL-1H2, IL1-ETA, IL1F8, IL1H2, MGC126880, MGC126882 |
| NM_019618 | IL36G | Interleukin 36, gamma | IL-1F9, IL-1H1, IL-1RP2, IL1E, IL1F9, IL1H1, IL1RP2 |
| NM_000877 | IL1R1 | Interleukin 1 receptor, type I | CD121A, D2S1473, IL-1R-alpha, IL1R, IL1RA, P80 |
| NM_000577 | IL1RN | Interleukin 1 receptor antagonist | DIRA, ICIL-1RA, IL-1RN, IL-1ra, IL-1ra3, IL1F3, IL1RA, IRAP, MGC10430, MVCD4 |
| NM_020525 | IL22 | Interleukin 22 | IL-21, IL-22, IL-D110, IL-TIF, ILTIF, MGC79382, MGC79384, TIFIL-23, TIFa, zcyto18 |
| NM_000879 | IL5 | Interleukin 5 (colony-stimulating factor, eosinophil) | EDF, IL-5, TRF |
| NM_000564 | IL5RA | Interleukin 5 receptor, alpha | CD125, CDw125, HSIL5R3, IL5R, MGC26560 |
| NM_000584 | IL8 | Interleukin 8 | CXCL8, GCP-1, GCP1, LECT, LUCT, LYNAP, MDNCF, MONAP, NAF, NAP-1, NAP1 |
| NM_000634 | CXCR1 | Chemokine (C—X—C motif) receptor 1 | C-C, C-C-CKR-1, CD128, CD181, CDw128a, CKR-1, CMKAR1, IL8R1, IL8RA, IL8RBA |
| NM_001557 | CXCR2 | Chemokine (C—X—C motif) receptor 2 | CD182, CDw128b, CMKAR2, IL8R2, IL8RA, IL8RB |

TABLE 12-continued

Inflammatory-related Genes for Use as Biomarkers

| GeneBank | Symbol | Description | Gene Name |
| --- | --- | --- | --- |
| NM_000590 | IL9 | Interleukin 9 | HP40, IL-9, P40 |
| NM_002186 | IL9R | Interleukin 9 receptor | CD129 |
| NM_000595 | LTA | Lymphotoxin alpha (TNF superfamily, member 1) | LT, TNFB, TNFSF1 |
| NM_002341 | LTB | Lymphotoxin beta (TNF superfamily, member 3) | TNFC, TNFSF3, p33 |
| NM_181657 | LTB4R | Leukotriene B4 receptor | BLT1, BLTR, CMKRL1, GPR16, LTB4R1, LTBR1, P2RY7, P2Y7 |
| NM_002415 | MIF | Macrophage migration inhibitory factor (glycosylation-inhibiting factor) | GIF, GLIF, MMIF |
| NM_004757 | AIMP1 | Aminoacyl tRNA synthetase complex-interacting multifunctional protein 1 | EMAP2, EMAPII, SCYE1, p43 |
| NM_000582 | SPP1 | Secreted phosphoprotein 1 | BNSP, BSPI, ETA-1, MGC110940, OPN |
| NM_000594 | TNF | Tumor necrosis factor | DIF, TNF-alpha, TNFA, TNFSF2 |
| NM_000074 | CD40LG | CD40 ligand | CD154, CD40L, HIGM1, IGM, IMD3, T-BAM, TNFSF5, TRAP, gp39, hCD40L |
| NM_019009 | TOLLIP | Toll interacting protein | FLJ33531, IL-1RAcPIP |
| NM_005283 | XCR1 | Chemokine (C motif) receptor 1 | CCXCR1, GPR5 |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 13

MSC Genes for Use as Biomarkers

| GeneBank | Symbol | Description | Gene Name |
| --- | --- | --- | --- |
| NM_000927 | ABCB1 | ATP-binding cassette, sub-family B (MDR/TAP), member 1 | ABC20, CD243, CLCS, GP170, MDR1, MGC163296, P-GP, PGY1 |
| NM_001627 | ALCAM | Activated leukocyte cell adhesion molecule | CD166, FLJ38514, MEMD, MGC71733 |
| NM_001150 | ANPEP | Alanyl (membrane) aminopeptidase | APN, CD13, GP150, LAP1, P150, PEPN |
| NM_001154 | ANXA5 | Annexin A5 | ANX5, ENX2, PP4 |
| NM_001709 | BDNF | Brain-derived neurotrophic factor | MGC34632 |
| NM_199173 | BGLAP | Bone gamma-carboxyglutamate (gla) protein | BGP, OC |
| NM_001200 | BMP2 | Bone morphogenetic protein 2 | BMP2A |
| NM_130851 | BMP4 | Bone morphogenetic protein 4 | BMP2B, BMP2B1, MCOPS6, OFC11, ZYME |
| NM_001718 | BMP6 | Bone morphogenetic protein 6 | VGR, VGR1 |
| NM_001719 | BMP7 | Bone morphogenetic protein 7 | OP-1 |
| NM_004346 | CASP3 | Caspase 3, apoptosis-related cysteine peptidase | CPP32, CPP32B, SCA-1 |
| NM_000610 | CD44 | CD44 molecule (Indian blood group) | CDW44, CSPG8, ECMR-III, HCELL, HUTCH-I, IN, LHR, MC56, MDU2, MDU3, MGC10468, MIC4, Pgp1 |
| NM_000088 | COL1A1 | Collagen, type I, alpha 1 | OI4 |
| NM_000758 | CSF2 | Colony stimulating factor 2 (granulocyte-macrophage) | GMCSF, MGC131935, MGC138897 |
| NM_000759 | CSF3 | Colony stimulating factor 3 (granulocyte) | C17orf33, CSF3OS, GCSF, MGC45931 |
| NM_001904 | CTNNB1 | Catenin (cadherin-associated protein), beta 1, 88 kDa | CTNNB, DKFZp686D02253, FLJ25606, FLJ37923 |
| NM_001963 | EGF | Epidermal growth factor | HOMG4, URG |
| NM_000118 | ENG | Endoglin | CD105, END, FLJ41744, HHT1, ORW, ORW1 |
| NM_004448 | ERBB2 | V-erb-b2 erythroblastic leukemia viral oncogene homolog 2, neuro/glioblastoma derived oncogene homolog (avian) | CD340, HER-2, HER-2, neu, HER2, MLN 19, NEU, NGL, TKR1 |
| NM_004465 | FGF10 | Fibroblast growth factor 10 | — |
| NM_002006 | FGF2 | Fibroblast growth factor 2 (basic) | BFGF, FGFB, HBGF-2 |
| NM_000148 | FUT1 | Fucosyltransferase 1 (galactoside 2-alpha-L-fucosyltransferase, H blood group) | H, HH, HSC |
| NM_002033 | FUT4 | Fucosyltransferase 4 (alpha (1,3) fucosyltransferase, myeloid-specific) | CD15, ELFT, FCT3A, FUC-TIV, FUTIV, LeX, SSEA-1 |
| NM_003508 | FZD9 | Frizzled family receptor 9 | CD349, FZD3 |
| NM_004864 | GDF15 | Growth differentiation factor 15 | GDF-15, MIC-1, MIC1, NAG-1, PDF, PLAB, PTGFB |
| NM_000557 | GDF5 | Growth differentiation factor 5 | BMP14, CDMP1, LAP4, OS5, SYNS2 |
| NM_001001557 | GDF6 | Growth differentiation factor 6 | BMP13, CDMP2, KFM, KFS, KFS1, KFSL, MCOP4, MCOPCB6, MGC158100, MGC158101, SCDO4, SGM1 |
| NM_182828 | GDF7 | Growth differentiation factor 7 | BMP12 |
| NM_002097 | GTF3A | General transcription factor IIIA | AP2, TFIIIA |
| NM_003642 | HAT1 | Histone acetyltransferase 1 | KAT1 |
| NM_004964 | HDAC1 | Histone deacetylase 1 | DKFZp686H12203, GON-10, HD1, RPD3, RPD3L1 |

TABLE 13-continued

MSC Genes for Use as Biomarkers

| GeneBank | Symbol | Description | Gene Name |
| --- | --- | --- | --- |
| NM_000601 | HGF | Hepatocyte growth factor (hepapoietin A; scatter factor) | DFNB39, F-TCF, HGFB, HPTA, SF |
| NM_000545 | HNF1A | HNF1 homeobox A | HNF-1A, HNF1, IDDM20, LFB1, MODY3, TCF-1, TCF1 |
| NM_000201 | ICAM1 | Intercellular adhesion molecule 1 | BB2, CD54, P3.58 |
| NM_000619 | IFNG | Interferon, gamma | IFG, IFI |
| NM_000618 | IGF1 | Insulin-like growth factor 1 (somatomedin C) | IGF-I, IGF1A, IGFI |
| NM_000572 | IL10 | Interleukin 10 | CSIF, IL-10, IL10A, MGC126450, MGC126451, TGIF |
| NM_000576 | IL1B | Interleukin 1, beta | IL-1, IL1-BETA, IL1F2 |
| NM_000600 | IL6 | Interleukin 6 (interferon, beta 2) | BSF2, HGF, HSF, IFNB2, IL-6 |
| NM_000207 | INS | Insulin | IDDM2, ILPR, IRDN, MODY10 |
| NM_000210 | ITGA6 | Integrin, alpha 6 | CD49f, DKFZp686J01244, FLJ18737, ITGA6B, VLA-6 |
| NM_002210 | ITGAV | Integrin, alpha V (vitronectin receptor, alpha polypeptide, antigen CD51) | CD51, DKFZp686A08142, MSK8, VNRA |
| NM_000887 | ITGAX | Integrin, alpha X (complement component 3 receptor 4 subunit) | CD11C, SLEB6 |
| NM_002211 | ITGB1 | Integrin, beta 1 (fibronectin receptor, beta polypeptide, antigen CD29 includes MDF2, MSK12) | CD29, FNRB, GPIIA, MDF2, MSK12, VLA-BETA, VLAB |
| NM_000214 | JAG1 | Jagged 1 | AGS, AHD, AWS, CD339, HJ1, JAGL1, MGC104644 |
| NM_002253 | KDR | Kinase insert domain receptor (a type III receptor tyrosine kinase) | CD309, FLK1, VEGFR, VEGFR2 |
| NM_003994 | KITLG | KIT ligand | DKFZp686F2250, FPH2, KL-1, Kitl, MGF, SCF, SF, SHEP7 |
| NM_002309 | LIF | Leukemia inhibitory factor (cholinergic differentiation factor) | CDF, DIA, HILDA |
| NM_006500 | MCAM | Melanoma cell adhesion molecule | CD146, MUC18 |
| NM_000248 | MITF | Microphthalmia-associated transcription factor | MI, WS2, WS2A, bHLHe32 |
| NM_004530 | MMP2 | Matrix metallopeptidase 2 (gelatinase A, 72 kDa gelatinase, 72 kDa type IV collagenase) | CLG4, CLG4A, MMP-II, MONA, TBE-1 |
| NM_006617 | NES | Nestin | FLJ21841 |
| NM_002507 | NGFR | Nerve growth factor receptor | CD271, Gp80-LNGFR, TNFRSF16, p75(NTR), p75NTR |
| NM_017617 | NOTCH1 | Notch 1 | TAN1, hN1 |
| NM_002526 | NT5E | 5'-nucleotidase, ecto (CD73) | CD73, NT5, NT, NT5, NTE, eN, eNT |
| NM_007083 | NUDT6 | Nudix (nucleoside diphosphate linked moiety X)-type motif 6 | ASFGF2, FGF-AS, FGF2AS, gfg, gfg-1 |
| NM_003884 | KAT2B | K(lysine) acetyltransferase 2B | CAF, P, P, CAF, PCAF |
| NM_002609 | PDGFRB | Platelet-derived growth factor receptor, beta polypeptide | CD140B, JTK12, PDGFR, PDGFR1 |
| NM_033198 | PIGS | Phosphatidylinositol glycan anchor biosynthesis, class S | DKFZp686K20216, FLJ45226 |
| NM_002701 | POU5F1 | POU class 5 homeobox 1 | MGC22487, OCT3, OCT4, OTF-3, OTF3, OTF4, Oct-3, Oct-4 |
| NM_015869 | PPARG | Peroxisome proliferator-activated receptor gamma | CIMT1, GLM1, NR1C3, PPARG1, PPARG2, PPARgamma |
| NM_006017 | PROM1 | Prominin 1 | AC133, CD133, CORD12, MCDR2, PROML1, RP41, STGD4 |
| NM_005607 | PTK2 | PTK2 protein tyrosine kinase 2 | FADK, FAK, FAK1, FRNK, pp125FAK |
| NM_002838 | PTPRC | Protein tyrosine phosphatase, receptor type, C | B220, CD45, CD45R, GP180, L-CA, LCA, LY5, T200 |
| NM_001664 | RHOA | Ras homolog gene family, member A | ARH12, ARHA, RHO12, RHOH12 |
| NM_004348 | RUNX2 | Runt-related transcription factor 2 | AML3, CBFA1, CCD, CCD1, MGC120022, MGC120023, OSF-2, OSF2, PEA2aA, PEBP2A1, PEBP2A2, PEBP2aA, PEBP2aA1 |
| NM_012434 | SLC17A5 | Solute carrier family 17 (anion/sugar transporter), member 5 | AST, FLJ22227, FLJ23268, ISSD, NSD, SD, SIALIN, SIASD, SLD |
| NM_005359 | SMAD4 | SMAD family member 4 | DPC4, JIP, MADH4 |
| NM_020429 | SMURF1 | SMAD specific E3 ubiquitin protein ligase 1 | KIAA1625 |
| NM_022739 | SMURF2 | SMAD specific E3 ubiquitin protein ligase 2 | DKFZp686F0270, MGC138150 |
| NM_003106 | SOX2 | SRY (sex determining region Y)-box 2 | ANOP3, MCOPS3, MGC2413 |
| NM_000346 | SOX9 | SRY (sex determining region Y)-box 9 | CMD1, CMPD1, SRA1 |
| NM_181486 | TBX5 | T-box 5 | HOS |
| NM_198253 | TERT | Telomerase reverse transcriptase | EST2, TCS1, TP2, TRT, hEST2, hTRT |
| NM_000660 | TGFB1 | Transforming growth factor, beta 1 | CED, DPD1, LAP, TGFB, TGFbeta |
| NM_003239 | TGFB3 | Transforming growth factor, beta 3 | ARVD, FLJ16571, TGF-beta3 |
| NM_006288 | THY1 | Thy-1 cell surface antigen | CD90, FLJ33325 |
| NM_000594 | TNF | Tumor necrosis factor | DIF, TNF-alpha, TNFA, TNFSF2 |
| NM_001078 | VCAM1 | Vascular cell adhesion molecule 1 | CD106, DKFZp779G2333, INCAM-100, MGC99561 |
| NM_003376 | VEGFA | Vascular endothelial growth factor A | MGC70609, MVCD1, VEGF, VPF |
| NM_003380 | VIM | Vimentin | FLJ36605 |
| NM_000552 | VWF | Von Willebrand factor | F8VWF, VWD |

TABLE 13-continued

MSC Genes for Use as Biomarkers

| GeneBank | Symbol | Description | Gene Name |
| --- | --- | --- | --- |
| NM_033131 | WNT3A | Wingless-type MMTV integration site family, member 3A | MGC119418, MGC119419, MGC119420 |
| NM_174900 | ZFP42 | Zinc finger protein 42 homolog (mouse) | REX1, ZNF754 |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 14

Wound Healing Genes for Use as Biomarkers

| GeneBank | Symbol | Description | Gene Name |
| --- | --- | --- | --- |
| NM_001613 | ACTA2 | Actin, alpha 2, smooth muscle, aorta | AAT6, ACTSA |
| NM_005159 | ACTC1 | Actin, alpha, cardiac muscle 1 | ACTC, ASD5, CMD1R, CMH11, LVNC4 |
| NM_001146 | ANGPT1 | Angiopoietin 1 | AGP1, AGPT, ANG1 |
| NM_002982 | CCL2 | Chemokine (C-C motif) ligand 2 | GDCF-2, HC11, HSMCR30, MCAF, MCP-1, MCP1, MGC9434, SCYA2, SMC-CF |
| NM_006273 | CCL7 | Chemokine (C-C motif) ligand 7 | FIC, MARC, MCP-3, MCP3, MGC138463, MGC138465, NC28, SCYA6, SCYA7 |
| NM_000074 | CD40LG | CD40 ligand | CD154, CD40L, HIGM1, IGM, IMD3, T-BAM, TNFSF5, TRAP, gp39, hCD40L |
| NM_004360 | CDH1 | Cadherin 1, type 1, E-cadherin (epithelial) | Arc-1, CD324, CDHE, ECAD, LCAM, UVO |
| NM_021110 | COL14A1 | Collagen, type XIV, alpha 1 | UND |
| NM_000088 | COL1A1 | Collagen, type I, alpha 1 | OI4 |
| NM_000089 | COL1A2 | Collagen, type I, alpha 2 | OI4 |
| NM_000090 | COL3A1 | Collagen, type III, alpha 1 | EDS4A, FLJ34534 |
| NM_001845 | COL4A1 | Collagen, type IV, alpha 1 | arresten |
| NM_000091 | COL4A3 | Collagen, type IV, alpha 3 (Goodpasture antigen) | — |
| NM_000093 | COL5A1 | Collagen, type V, alpha 1 | — |
| NM_000393 | COL5A2 | Collagen, type V, alpha 2 | MGC105115 |
| NM_015719 | COL5A3 | Collagen, type V, alpha 3 | — |
| NM_000758 | CSF2 | Colony stimulating factor 2 (granulocyte-macrophage) | GMCSF, MGC131935, MGC138897 |
| NM_000759 | CSF3 | Colony stimulating factor 3 (granulocyte) | C17orf33, CSF3OS, GCSF, MGC45931 |
| NM_001901 | CTGF | Connective tissue growth factor | CCN2, HCS24, IGFBP8, MGC102839, NOV2 |
| NM_001904 | CTNNB1 | Catenin (cadherin-associated protein), beta 1, 88 kDa | CTNNB, DKFZp686D02253, FLJ25606, FLJ37923 |
| NM_001911 | CTSG | Cathepsin G | CATG, CG, MGC23078 |
| NM_000396 | CTSK | Cathepsin K | CTS02, CTSO, CTSO1, CTSO2, MGC23107, PKND, PYCD |
| NM_001333 | CTSL2 | Cathepsin L2 | CATL2, CTSU, CTSV, MGC125957 |
| NM_001511 | CXCL1 | Chemokine (C—X—C motif) ligand 1 (melanoma growth stimulating activity, alpha) | FSP, GRO1, GROa, MGSA, MGSA-a, NAP-3, SCYB1 |
| NM_005409 | CXCL11 | Chemokine (C—X—C motif) ligand 11 | H174, I-TAC, IP-9, IP9, MGC102770, SCYB11, SCYB9B, b-R1 |
| NM_002089 | CXCL2 | Chemokine (C—X—C motif) ligand 2 | CINC-2a, GRO2, GROb, MGSA-b, MIP-2a, MIP2, MIP2A, SCYB2 |
| NM_002994 | CXCL5 | Chemokine (C—X—C motif) ligand 5 | ENA-78, SCYB5 |
| NM_001963 | EGF | Epidermal growth factor | HOMG4, URG |
| NM_005228 | EGFR | Epidermal growth factor receptor | ERBB, ERBB1, HER1, PIG61, mENA |
| NM_000129 | F13A1 | Coagulation factor XIII, A1 polypeptide | F13A |
| NM_001993 | F3 | Coagulation factor III (thromboplastin, tissue factor) | CD142, FLJ17960, TF, TFA |
| NM_000508 | FGA | Fibrinogen alpha chain | Fib2, MGC119422, MGC119423, MGC119425 |
| NM_004465 | FGF10 | Fibroblast growth factor 10 | — |
| NM_002006 | FGF2 | Fibroblast growth factor 2 (basic) | BFGF, FGFB, HBGF-2 |
| NM_002009 | FGF7 | Fibroblast growth factor 7 | HBGF-7, KGF |
| NM_001945 | HBEGF | Heparin-binding EGF-like growth factor | DTR, DTS, DTSF, HEGFL |
| NM_000601 | HGF | Hepatocyte growth factor (hepapoietin A; scatter factor) | DFNB39, F-TCF, HGFB, HPTA, SF |
| NM_000619 | IFNG | Interferon, gamma | IFG, IFI |
| NM_000618 | IGF1 | Insulin-like growth factor 1 (somatomedin C) | IGF-I, IGF1A, IGFI |
| NM_000572 | IL10 | Interleukin 10 | CSIF, IL-10, IL10A, MGC126450, MGC126451, TGIF |
| NM_000576 | IL1B | Interleukin 1, beta | IL-1, IL1-BETA, IL1F2 |
| NM_000586 | IL2 | Interleukin 2 | IL-2, TCGF, lymphokine |
| NM_000589 | IL4 | Interleukin 4 | BCGF-1, BCGF1, BSF-1, BSF1, IL-4, MGC79402 |

TABLE 14-continued

Wound Healing Genes for Use as Biomarkers

| GeneBank | Symbol | Description | Gene Name |
| --- | --- | --- | --- |
| NM_000600 | IL6 | Interleukin 6 (interferon, beta 2) | BSF2, HGF, HSF, IFNB2, IL-6 |
| NM_002184 | IL6ST | Interleukin 6 signal transducer (gp130, oncostatin M receptor) | CD130, CDW130, DKFZp564F053, GP130, IL-6RB |
| NM_181501 | ITGA1 | Integrin, alpha 1 | CD49a, VLA1 |
| NM_002203 | ITGA2 | Integrin, alpha 2 (CD49B, alpha 2 subunit of VLA-2 receptor) | BR, CD49B, GPIa, VLA-2, VLAA2 |
| NM_002204 | ITGA3 | Integrin, alpha 3 (antigen CD49C, alpha 3 subunit of VLA-3 receptor) | CD49C, FLJ34631, FLJ34704, GAP-B3, GAPB3, MSK18, VCA-2, VL3A, VLA3a |
| NM_000885 | ITGA4 | Integrin, alpha 4 (antigen CD49D, alpha 4 subunit of VLA-4 receptor) | CD49D, IA4, MGC90518 |
| NM_002205 | ITGA5 | Integrin, alpha 5 (fibronectin receptor, alpha polypeptide) | CD49e, FNRA, VLA5A |
| NM_000210 | ITGA6 | Integrin, alpha 6 | CD49f, DKFZp686J01244, FLJ18737, ITGA6B, VLA-6 |
| NM_002210 | ITGAV | Integrin, alpha V (vitronectin receptor, alpha polypeptide, antigen CD51) | CD51, DKFZp686A08142, MSK8, VNRA |
| NM_002211 | ITGB1 | Integrin, beta 1 (fibronectin receptor, beta polypeptide, antigen CD29 includes MDF2, MSK12) | CD29, FNRB, GPIIA, MDF2, MSK12, VLA-BETA, VLAB |
| NM_000212 | ITGB3 | Integrin, beta 3 (platelet glycoprotein IIIa, antigen CD61) | CD61, GP3A, GPIIIa |
| NM_002213 | ITGB5 | Integrin, beta 5 | FLJ26658 |
| NM_000888 | ITGB6 | Integrin, beta 6 | — |
| NM_002745 | MAPK1 | Mitogen-activated protein kinase 1 | ERK, ERK2, ERT1, MAPK2, P42MAPK, PRKM1, PRKM2, p38, p40, p41, p41mapk |
| NM_002746 | MAPK3 | Mitogen-activated protein kinase 3 | ERK1, HS44KDAP, HUMKER1A, MGC20180, P44ERK1, P44MAPK, PRKM3 |
| NM_002415 | MIF | Macrophage migration inhibitory factor (glycosylation-inhibiting factor) | GIF, GLIF, MMIF |
| NM_002421 | MMP1 | Matrix metallopeptidase 1 (interstitial collagenase) | CLG, CLGN |
| NM_004530 | MMP2 | Matrix metallopeptidase 2 (gelatinase A, 72 kDa gelatinase, 72 kDa type IV collagenase) | CLG4, CLG4A, MMP-II, MONA, TBE-1 |
| NM_002423 | MMP7 | Matrix metallopeptidase 7 (matrilysin, uterine) | MMP-7, MPSL1, PUMP-1 |
| NM_004994 | MMP9 | Matrix metallopeptidase 9 (gelatinase B, 92 kDa gelatinase, 92 kDa type IV collagenase) | CLG4B, GELB, MANDP2, MMP-9 |
| NM_002607 | PDGFA | Platelet-derived growth factor alpha polypeptide | PDGF-A, PDGF1 |
| NM_000930 | PLAT | Plasminogen activator, tissue | DKFZp686I03148, T-PA, TPA |
| NM_002658 | PLAU | Plasminogen activator, urokinase | ATF, UPA, URK, u-PA |
| NM_002659 | PLAUR | Plasminogen activator, urokinase receptor | CD87, U-PAR, UPAR, URKR |
| NM_000301 | PLG | Plasminogen | DKFZp779M0222 |
| NM_000314 | PTEN | Phosphatase and tensin homolog | 10q23del, BZS, DEC, GLM2, MGC11227, MHAM, MMAC1, PTEN1, TEP1 |
| NM_000963 | PTGS2 | Prostaglandin-endoperoxide synthase 2 (prostaglandin G/H synthase and cyclooxygenase) | COX-2, COX2, GRIPGHS, PGG, HS, PGHS-2, PHS-2, hCox-2 |
| NM_006908 | RAC1 | Ras-related C3 botulinum toxin substrate 1 (rho family, small GTP binding protein Rac1) | MGC111543, Rac-1, TC-25, p21-Rac1 |
| NM_001664 | RHOA | Ras homolog gene family, member A | ARH12, ARHA, RHO12, RHOH12 |
| NM_000602 | SERPINE1 | Serpin peptidase inhibitor, clade E (nexin, plasminogen activator inhibitor type 1), member 1 | PAI, PAI-1, PAI1, PLANH1 |
| NM_003150 | STAT3 | Signal transducer and activator of transcription 3 (acute-phase response factor) | APRF, FLJ20882, HIES, MGC16063 |
| NM_003186 | TAGLN | Transgelin | DKFZp686B01212, DKFZp686P11128, SM22, SMCC, TAGLN1, WS3-10 |
| NM_003236 | TGFA | Transforming growth factor, alpha | TFGA |
| NM_000660 | TGFB1 | Transforming growth factor, beta 1 | CED, DPD1, LAP, TGFB, TGFbeta |
| NM_003243 | TGFBR3 | Transforming growth factor, beta receptor III | BGCAN, betaglycan |
| NM_003254 | TIMP1 | TIMP metallopeptidase inhibitor 1 | CLGI, EPA, EPO, FLJ90373, HCI, TIMP |
| NM_000594 | TNF | Tumor necrosis factor | DIF, TNF-alpha, TNFA, TNFSF2 |
| NM_003376 | VEGFA | Vascular endothelial growth factor A | MGC70609, MVCD1, VEGF, VPF |
| NM_000638 | VTN | Vitronectin | V75, VN, VNT |
| NM_003882 | WISP1 | WNT1 inducible signaling pathway protein 1 | CCN4, FLJ14388, WISP1c, WISP1i, WISP1tc |
| NM_003392 | WNT5A | Wingless-type MMTV integration site family, member 5A | hWNT5A |
| NM_004048 | B2M | Beta-2-microglobulin | — |
| NM_000194 | HPRT1 | Hypoxanthine phosphoribosyltransferase 1 | HGPRT, HPRT |
| NM_012423 | RPL13A | Ribosomal protein L13a | L13A, TSTA1 |
| NM_002046 | GAPDH | Glyceraldehyde-3-phosphate dehydrogenase | G3PD, GAPD, MGC88685 |

TABLE 15

Proteins for Use as Biomarkers

| Cytokine Name | Official Symbol | Full Name | Genbank | Related Names |
|---|---|---|---|---|
| 4-1BB | TNFRSF9 | Tumor necrosis factor receptor superfamily member 9 | NP_001552.2. | CD137, ILA, 4-1BB ligand receptor |
| 6Ckine | CCL21 | 6-Cysteine Chemokine | NM_002989 | Small-inducible cytokine A21, Beta chemokine exodus-2, Secondary lymphoid-tissue chemokine, SLC, SCYA21 |
| ACE | ACE | Angiotensin-converting enzyme | NP_000780.1. NP_690043.1. | CD143, DCP, DCP1 |
| ACE-2 | ACE2 | Angiotensin-converting enzyme 2 | NP_068576.1 | ACE-related carboxypeptidase, Angiotensin-converting enzyme homolog |
| ACTH | ACTH | Adrenocorticotropic hormone | NP_000930.1. NP_001030333.1 | POMC, Pro-opiomelanocortin, Corticotropin-lipotropin, NPP, Melanotropin gamma, Gamma-MSH, Potential peptide, Corticotropin, Melanotropin alpha, Alpha-MSH, Corticotropin-like intermediary peptide, CLIP, Lipotropin beta, Beta-LPH, Lipotropin gamma, Gamma-LPH, Melanotropin beta, Beta-MSH, Beta-endorphin, Met-enkephalin |
| ACTHR | ACTHR | Adrenocorticotropic hormone receptor | NP_000520.1 | Melanocortin receptor 2, MC2-R |
| Activin A | INHBA | Activin A | NM_002192 | Activin beta-A chain, Erythroid differentiation protein, EDF, INHBA |
| Activin B | INHBB | Activin B | NM_002193 | Inhibin beta B chain, Activin beta-B chain |
| Activin C | INHBC | Activin C | NM005538 | Inhibin, beta C |
| Activin RIA | ACVR1 | Activin receptor type-1 | NM_001105 | Activin receptor type I, ACTR-I, Serine/threonine-protein kinase receptor R1, SKR1, Activin receptor-like kinase 2, ALK-2, TGF-B superfamily receptor type I, TSR-I, ACVRLK2 |
| Activin RIB | ACVR1B | Activin receptor type-1B | NM_020328 | ACTR-IB, Serine/threonine-protein kinase receptor R2, SKR2, Activin receptor-like kinase 4, ALK-4, ACVRLK4, ALK4 |
| Activin RII A/B | ACVR2B | Activin receptor type-2B | NM_001106 | Activin receptor type IIB, ACTR-IIB |
| Activin RIIA | ACVR2A | Activin receptor type-2A | NM_001616 | Activin receptor type IIA |
| ADAM17 | ADAM17 | Disintegrin and metalloproteinase domain-containing protein 17 | NP_003174.3 | TNF-alpha-converting enzyme, TNF-alpha convertase, Snake venom-like protease, CD156b, CSVP, TACE |
| ADFP | ADFP | Adipose differentiation-related protein | NP_001113.2 | Adipophilin, ADRP |
| Adipsin | Adipsin | Adipsin | NP_001919.2 | C3 convertase activator, Properdin factor D, CFD, DF, PFD, complement factor D |
| AFP | AFP | Alpha-1-fetoprotein | NP_001125.1 | Alpha-fetoglobulin, HPAFP |
| AMPKa1 | AMPKa1 | 5-AMP-activated protein kinase catalytic subunit alpha-1 | NP_006242.5. NP_996790.3. | PRKAA1, AMPK1 |
| Amylin | Amylin | Islet amyloid polypeptide | NP_000406.1. | Amylin, Diabetes-associated peptide, DAP, Insulinoma amyloid peptide, IAPP |
| AGRP | AGRP | Agouti related protein | NM_001138 | AGRT, ART |
| ALCAM | ALCAM | CD166 antigen | NM_001627 | Activated leukocyte cell adhesion molecule, CD166, ALCAM, MEMD |
| Amphiregulin | AREG | Amphiregulin | NM_001657 | Colorectum cell-derived growth factor, AR, CRDGF, AREG, SDGF |
| ANG | ANG | Angiogenin | NM_001145 | ANG, RNASE5, Ribonuclease 5 |
| ANG-1 | ANGPT-1 | Angiopoietin-1 | NM_001146, NM_139290 | ANGPT1, KIAA0003 |
| Angiopoietin-4 | ANGPT4 | Angiopoietin-4 | NM_015985 | ANG3, ANG4 |
| Angiopoietin-like 1 | ANGPTL1 | Angiopoietin-like 1 | NM_004673 | ARP-1 |
| Angiopoietin-like 2 | ANGPTL2 | Angiopoietin-like 2 | NM_012098 | ARP-2 |
| Angiopoietin-like 3 | ANGPTL3 | Angiopoietin-like 3 | NP_055310.1 | Angiopoietin 5, Angiopoietin-like 3, Angiopoietin-related protein 3, ANG-5 |
| Angiopoietin-like 4 | ANGPTL4 | Angiopoietin-like 4 | NP_001034756.1 NP_647475.1 | ARP4, HFARP, PGAR, Angiopoietin-related protein 4 |
| Angiostatin | PLG | Angiostatin | NM_000301, NP_000292 | 98-465AA OF PLASMINOGEN |
| Apelin | Apelin | Apelin | NP_059109.3 | APLN, APEL, AGTRL1 ligand |
| ApoA2 | ApoA2 | Apolipoprotein A-II | NP_001634.1 | Apolipoprotein A-II(1-76) |
| ApoB | ApoB | Apolipoprotein B | NP_000375.2 | Apolipoprotein B-100, Apo B-48, APOB |
| ApoE | ApoE | Apolipoprotein E | NP_000032.1 | Apo-E |
| Apolipoprotein AI | Apo-AI | Apolipoprotein A-I | NP_000030.1 | ApoA-I |

TABLE 15-continued

Proteins for Use as Biomarkers

| Cytokine Name | Official Symbol | Full Name | Genbank | Related Names |
|---|---|---|---|---|
| APLNR | AGTRL1 | Apelin receptor | NM_005161 | HG11, APLNR, AGTRL1, APJ |
| APRIL | TNFSF13 | Tumor necrosis factor ligand superfamily member 13 | NM_003808 | A proliferation-inducing ligand, TNF- and APOL-related leukocyte expressed ligand 2, TALL-2, TNF-related death ligand 1, TRDL-1, CD256, TNFSF13, APRIL, TALL2, ZTNF2 |
| Artemin | ARTN | Artemin | NM_057160 | Enovin, Neublastin, ARTN, EVN |
| Axl | UFO | Tyrosine-protein kinase receptor UFO | | AXL oncogene, UFO |
| B7-1 (CD80) | CD80 | T-lymphocyte activation antigen CD80 | NM_005191 | Activation B7-1 antigen, CTLA-4 counter-receptor B7.1, B7, BB1, CD80, CD28LG, CD28LG1, LAB7 |
| Bad | BAD | Bcl2 antagonist of cell death | NP_004313.1, NP_116784.1 | Bcl-2-binding component 6, Bcl-2-like protein 8, BBC6, BCL2L8 |
| Bax | Bax | Apoptosis regulator BAX | NP_004315.1, NP_620116.1, NP_620118.1, NP_620119.1, NP_620120.1 | Bcl-2-like protein 4, Bcl2-L-4, |
| BCAM | BCAM | Lutheran blood group glycoprotein | NP_001013275.1, NP_005572.2 | B-CAM cell surface glycoprotein, Auberger B antigen, F8/G253 antigen, LU, MSK19, CD239 |
| Bcl-2 | BCL2 | Apoptosis regulator Bcl-2 | NP_000624.2 | B-cell CLL/lymphoma 2, |
| Bcl-w | BCL2L2 | Bcl-2-like protein 2 | NP_004041.1 | Bcl2-L-2, BCLW, KIAA0271, Apoptosis regulator Bcl-W |
| BAFF | TNFSF13B | B-cell-activating factor belonging to the TNF family | NM_006573 | TNF- and APOL-related leukocyte expressed ligand 1, TALL-1, B lymphocyte stimulator, BLyS, B cell-activating factor, BAFF, Dendritic cell-derived TNF-like molecule, CD257 |
| BAFF R/ TNFRSF13C | TNFRSF13C | B-Cell Activating Factor Receptor | NM_052945 | B cell-activating factor receptor, BAFF receptor, BAFF-R, BLyS receptor 3, CD268, TNFRSF13C, BAFFR, BR3 |
| BCMA/ TNFRSF17 | TNFRSF17 | Tumor necrosis factor receptor superfamily member 17 | NM_001192 | B-cell maturation protein, CD269, TNFRSF17, BCM, BCMA |
| BD-1 | DEFB1 | Beta Defensin-1 | NM_005218 | Defensin, beta 1, DEFB1, BD1, HBD1 |
| BDNF | BDNF | Brain-derived neurotrophic factor | NM_170735 | Abrineurin |
| Beta 2M | B2M | Beta-2-microglobulin | NP_004039.1 | |
| Beta-Catenin | CTNNB1 | Catenin beta-1 | XM_001133660 | CTNNB, Beta-catenin |
| Beta-Defensin 2 | DEFB4 | Beta Defensin 2 | NM_004942 | Defensin, beta 2, Skin-antimicrobial peptide 1, SAP1, DEFB4, DEFB102, DEFB2 |
| Beta IG-H3 | Beta IG-H3 | Transforming growth factor-beta-induced protein ig-h3 | NP_000349.1 | Transforming growth factor, beta-induced, 68 kDa, RGD-containing collagen-associated protein, BIGH3, BGH3 |
| beta-NGF | NGFB | Nerve growth factor-beta | NM_002506 | Beta-NGF |
| BID | BID | BH3-interacting domain death agonist | NP_001187.1, NP_932070.1, NP_932071.1 | p22 BID |
| BIK | BIK | B-cell lymphocyte | NM_001197 | Apoptosis inducer NBK, BP4, BIP1, NBK |
| BIM | Bcl2-L-11 | Bcl-2-like protein 11 | NP_006529.1, NP_619527.1, NP_996885.1 | Bcl2-interacting mediator of cell death |
| BLC | CXCL13 | B-lymphocyte chemoattractant | NM_006419 | Small-inducible cytokine B13, B lymphocyte chemoattractant, CXC chemokine BLC, B cell-attracting chemokine 1, BCA-1, ANGIE, BLC, SCYB13 |
| BMP-15 | BMP15 | Bone morphogenetic protein 15 | NM_005448 | Growth/differentiation factor 9B, GDF-9B |
| BMP-2 | BMP2 | Bone morphogenetic protein 2 | NM_001200 | BMP-2A |
| BMP-3 | BMP3 | Bone morphogenetic protein 3 | NM_001201 | Osteogenin, BMP-3A |
| BMP-3b | BMP3B | Bone morphogenetic protein 3b | NM_004962 | Growth/differentiation factor 10, GDF-10, Bone-inducing protein, BIP |
| BMP-4 | BMP4 | Bone morphogenetic protein 4 | NM_130850 | BMP-2B, DVR4 |
| BMP-5 | BMP5 | Bone morphogenetic protein 5 | NM_021073 | BMP-5 |
| BMP-6 | BMP6 | Bone morphogenetic protein 6 | NM_001718 | VGR, BMP-6 |
| BMP-7 | BMP7 | Bone morphogenetic protein 7 | NM_001719 | Osteogenic protein 1, OP-1, INN = Eptotermin alfa |
| BMP-8 | BMP8 | Bone morphogenetic protein 8 | NM_001720 | Osteogenic protein 2, OP-2, BMP8B, Bone morphogenetic protein 8B |

TABLE 15-continued

Proteins for Use as Biomarkers

| Cytokine Name | Official Symbol | Full Name | Genbank | Related Names |
|---|---|---|---|---|
| BMPR-1A | BMPR1A | Bone morphogenetic proteins receptor IA | NM_004329 | Serine/threonine-protein kinase receptor R5, SKR5, Activin receptor-like kinase 3, ALK-3, CD292, ACVRLK3 |
| BMPR-1B | BMPR1B | Bone morphogenetic proteins receptor IB | NM_001203 | CDw293 |
| BMPR-II | BMPR2 | Bone morphogenetic proteins receptor II | NM_001204 | BMP type II receptor, BMPR-II, BMPR2, PPH1 |
| BTC | BTC | Betacellulin | NM_001729 | Probetacellulin |
| C3a des Arg | C3a | Complement C3 | NP_000055.2 | Complement component 3, C3 and PZP-like alpha-2-macroglobulin domain-containing protein 1 |
| CA125 | MUC-16 | Mucin-16 | NP_078966.2 | Ovarian carcinoma antigen CA125, Ovarian cancer-related tumor marker CA125 |
| CA15-3 | | | | |
| CA19-9 | | | | |
| Calcitonin | CALC1 | Calcitonin | NP_001029124.1, NP_001029125.1, NP_001732.1 | CALCA |
| Carbonic Anhydrase IX | CA-IX | Carbonic anhydrase 9 | NP_001207.2. | G250, MN, CAIX, Carbonate dehydratase IX, Membrane antigen MN, P54/58N, Renal cell carcinoma-associated antigen G250 |
| CART | CART | Cocaine- and amphetamine-regulated transcript protein | NP_004282.1 | CARTPT |
| Caspase-3 | CASP-3 | Caspase-3 | NP_004337.2, NP_116786.1 | Apopain, Cysteine protease CPP32, CPP-32, Yama protein, SREBP cleavage activity 1, SCA-1, apoptosis-related cysteine peptidase |
| Caspase-8 | CASP-8 | Caspase-8 | NP_001073593.1. NP_001073594.1. NP_001219.2. NP_203519.1. NP_203520.1. NP_203522.1 | ICE-like apoptotic protease 5, MORT1-associated CED-3 homolog, MACH, FADD-homologous ICE/CED-3-like protease, FLICE, Apoptotic cysteine protease, Apoptotic protease Mch-5, CAP4, MCH5 |
| Cathepsin B | CTSB | Cathepsin B | NP_001899.1. NP_680090.1. NP_680091.1. NP_680092.1. NP_680093.1 | Cathepsin B1, APP secretase, APPS, CPSB |
| Cathepsin S | CTSS | Cathepsin S | NP_004070.3 | |
| CCL14 | CCL14 | C-C motif chemokine 14 | NM_032962 | Small-inducible cytokine A14, Chemokine CC-1/CC-3, HCC-1/HCC-3, HCC-1(1-74), NCC-2 |
| CCL28 | CCL28 | C-C motif chemokine 28 | NM_148672 | Small-inducible cytokine A28, Mucosae-associated epithelial chemokine, MEC, Protein CCK1, SCYA28 |
| CCR1 | CCR1 | CC-Chemokine receptor-1 | NM_001295 | CC-CKR1, HM145, YT4 |
| CCR2 | CCR2 | CC-Chemokine receptor-2 | NM_000647 | Monocyte chemoattractant protein 1 receptor, MCP-1-R, CD192, CCR2, CMKBR2 |
| CCR3 | CCR3 | CC-Chemokine receptor-3 | NM_178329 | CMKBR3, Eosinophil eotaxin receptor, CD193 |
| CCR4 | CCR4 | CC-Chemokine receptor-4 | NM_005508 | K5-5, CD194, CMKBR4 |
| CCR5 | CCR5 | CC-Chemokine receptor-5 | NP_000570.1, NP_001093638.1. | HIV-1 fusion coreceptor, CHEMR13, CD195, CMKBR5 |
| CCR6 | CCR6 | CC-Chemokine receptor-6 | NM_031409 | LARC receptor, GPR-CY4, GPRCY4, Chemokine receptor-like 3, CKR-L3, DRY6, G-protein coupled receptor 29, CD196, CKRL3, CMKBR6, GPR29, STRL22 |
| CCR7 | CCR7 | CC-Chemokine receptor-7 | NM_001838 | MIP-3 beta receptor, EBV-induced G-protein coupled receptor 1, BLR2, CDw197, CD197, CMKBR7, EBI1, EVI1 |
| CCR8 | CCR8 | CC-Chemokine receptor-8 | NM_005201 | GPR-CY6, GPRCY6, Chemokine receptor-like 1, CKR-L1, TER1, CMKBRL2, CC-chemokine receptor CHEMR1, CDw198, CKRL1, CMKBR8 |
| CCR9 | CCR9 | CC-Chemokine receptor-9 | NM_006641 | GPR-9-6, G-protein coupled receptor 28, CDw199, CMKBR9, GPR28 |
| CD 163 | CD163 | Scavenger receptor cysteine-rich type 1 protein M130 | NM_004244, NM_203416 | M130, Hemoglobin scavenger receptor |
| CD14 | CD14 | Monocyte differentiation antigen CD14 | NP_000582.1. NP_001035110.1 | Myeloid cell-specific leucine-rich glycoprotein |
| CD23/Fc epsilon RII | FCER2 | Low affinity immunoglobulin epsilon Fc receptor | NP_001993.2 | Lymphocyte IgE receptor, Fc-epsilon-RII, BLAST-2, Immunoglobulin E-binding factor, CD23, CD23A, FCE2, IGEBF |
| CD27 | TNFRSF7 | Tumor necrosis factor receptor superfamily member 7 | NM_001242 | CD27L receptor, T-cell activation antigen CD27, T14 |

TABLE 15-continued

Proteins for Use as Biomarkers

| Cytokine Name | Official Symbol | Full Name | Genbank | Related Names |
|---|---|---|---|---|
| CD30 | TNFRSF8 | Tumor necrosis factor receptor superfamily member 8 | NM_001243 | CD30L receptor, Lymphocyte activation antigen CD30, KI-1 antigen, CD30, D1S166E |
| CD30 Ligand | TNFSF8 | Tumor necrosis factor ligand superfamily member 8 | NM_001244 | CD30 ligand, CD30-L, CD153, CD30LG |
| CD36 | CD36 | Platelet glycoprotein 4 | NP_000063.2, NP_001001547.1, NP_001001548.1, NP_001120915.1, NP_001120916.1 | Platelet glycoprotein IV, GPIV, Glycoprotein IIIb, Leukocyte differentiation antigen CD36, PAS IV, PAS-4, Platelet collagen receptor, Fatty acid translocase, FAT, Thrombospondin receptor, GP3B, GP4 |
| CD38 | CD38 | ADP-ribosyl cyclase 1 | NP_001766.2 | Cyclic ADP-ribose hydrolase 1, cADPr hydrolase 1, T10 |
| CD40 | CD40 | Tumor necrosis factor receptor superfamily member 5 | NP_001241.1. NP_690593.1 | TNFRSF5, CD40L receptor, B-cell surface antigen CD40, Bp50, CDw40 |
| CD40 Ligand | CD40LG | CD40 Ligand | NM_000074 | CD40L, TNF-related activation protein, TRAP, T-cell antigen Gp39, CD154, TNFSF5, TRAP |
| CD90 | CD90 | Cluster of Differentiation 90 | NP_006279.2 | Thy1, Thy-1 membrane glycoprotein, Thy-1 antigen, CDw90 |
| CEA | CEA | Carcinoembryonic antigen | NP_004354.2 | CEACAM5, Carcinoembryonic antigen, Meconium antigen 100, CD66e, Carcinoembryonic antigen-related cell adhesion molecule 5 |
| CEACAM-1 | CEACAM-1 | Carcinoembryonic antigen-related cell adhesion molecule 1 | NP_001020083.1 | |
| Cerberus 1 | CER1 | Cerberus 1 | NM_005454 | Cerberus-related protein, DAN domain family member 4, DAND4 |
| Chem R23 | RARRES2 | Retinoic acid receptor responder protein 2 | NM_002889 | Tazarotene-induced gene 2 protein, RAR-responsive protein TIG2, TIG2 |
| Chordin-Like 1 | CHRDL1 | Chordin-Like 1 | NM_145234 | Neuralin-1, Ventroptin, Neurogenesin-1, NRLN1 |
| Chordin-Like 2 | CHRDL2 | Chordin-Like 2 | NP_056239.3 | Chordin-related protein 2, Breast tumor novel factor 1, BNF-1, BNF1, CHL2 |
| cIAP-2 | BIRC3 | Baculoviral IAP repeat-containing protein 3 | NP_001156.1, NP_892007.1 | API2, IAP1, MIHC, RNF49, Inhibitor of apoptosis protein 1, HIAP-1, C-IAP2, TNFR2-TRAF-signaling complex protein 1, IAP homolog C, Apoptosis inhibitor 2, API2, RING finger protein 49 |
| Ck beta 8-1 | CCL23 | Chemokine-beta-8 | NM_145898 NM_005064 | MIP-3-beta, orELC, MPIF-1[Myeloid progenitor inhibitory factor-1] |
| Claudin-3 | CLDN3 | Claudin-3 | NP_001297.1 | Clostridium perfringens enterotoxin receptor 2, CPE-receptor 2, CPE-R 2, Ventral prostate.1 protein homolog, HRVP1, C7orf1, CPETR2 |
| Claudin-4 | CLDN4 | Claudin-4 | NP_001296.1 | Clostridium perfringens enterotoxin receptor, CPE-receptor, CPE-R, Williams-Beuren syndrome chromosomal region 8 protein, CLDN4, CPER, CPETR1, WBSCR8 |
| CLC | CLC | Eosinophil lysophospholipase | NM_001828 | Charcot-Leyden crystal protein, Lysolecithin acylhydrolase, Galectin-10 |
| Clusterin | CLU | Clusterin | NP_001822.2, NP_976084.1 | Complement-associated protein SP-40, Complement cytolysis inhibitor, CLI, NA1/NA2, Apolipoprotein J, Apo-J, Testosterone-repressed prostate message 2, TRPM-2, Ku70-binding protein 1, Aging-associated gene 4 protein, APOJ, CLI, KUB1 |
| CNTF R alpha | CNTFR | Ciliary neuronotrophic factor receptor alpha | NM_001842 | |
| CNTF | CNTF | Ciliary neuronotrophic factor | NM_000614 | |
| CRIM 1 | CRIM1 | Cysteine-rich motor neuron 1 protein | NM_016441 | Cysteine-rich repeat-containing protein S52, CRIM1, S52 |
| Cripto-1 | CRGF | Cripto-1 growth factor | NM_003212 | Teratocarcinoma-derived growth factor 1, Epidermal growth factor-like cripto protein CR1, TDGF1, CRIPTO |
| CRP | CRP | C-Reactive Protein | NP_000558.2 | PTX1 |
| CRTH-2 | GPR44 | Putative G-protein coupled receptor 44 | NM_004778 | CD294 antigen, CRTH2, DL1R, Chemoattractant receptor-homologous molecule expressed on Th2 cells |
| Cryptic | CFC1 | Cryptic | NM_032545 | |
| CT-1 | CTF-1 | Cardiotrophin-1 | NM_001330 | |
| CTACK | CCL27 | C-C motif chemokine 27 | NM_006664 | Small-inducible cytokine A27, CC chemokine ILC, IL-11 R-alpha-locus chemokine, Skinkine, Eskine, Cutaneous T-cell-attracting chemokine, ILC, SCYA27 |

TABLE 15-continued

Proteins for Use as Biomarkers

| Cytokine Name | Official Symbol | Full Name | Genbank | Related Names |
|---|---|---|---|---|
| CTGF | CTGF | Connective Tissue Growth Factor | NM_001901 | Hypertrophic chondrocyte-specific protein 24, CCN2, HCS24, IGFBP8 |
| CTLA-4 | CTLA4 | Cytotoxic T-lymphocyte associated antigen 4 | NM_005214 | CTLA-4, CD152 |
| CV-2 | hCV2 | Protein crossveinless-2 | NM_133468 | Bone morphogenetic protein-binding endothelial cell precursor-derived regulator, BMP-binding endothelial regulator protein, KIAA1965, BMPER |
| CXCL14 | CXCL14 | C—X—C motif chemokine 14 | NM_004887 | Small-inducible cytokine B14, Chemokine BRAK, NJAC, SCYB14 |
| CXCL16 | CXCL16 | C—X—C motif chemokine 16 | NM_022059 | Small-inducible cytokine B16, Transmembrane chemokine CXCL16, SR-PSOX, Scavenger receptor for phosphatidylserine and oxidized low density lipoprotein, SCYB16, SRPSOX |
| CXCR1 | IL8RA | High affinity interleukin-8 receptor A | NM_000634 | IL-8 receptor type 1, CXCR-1, CDw128a, CD181, IL8RA, CMKAR1 |
| CXCR2 | IL8RB | High affinity interleukin-8 receptor B | NM_001557 | GRO/MGSA receptor, IL-8 receptor type 2, CDw128b, CD182 |
| CXCR3 | CXCR3 | CXC-Chemokine receptor 3 | NM_001504 | Interferon-inducible protein 10 receptor, IP-10 receptor, CKR-L2, G protein-coupled receptor 9, CD183, GPR9 |
| CXCR4 | CXCR4 | CXC-Chemokine receptor 4 | NM_003467 | Stromal cell-derived factor 1 receptor, SDF-1 receptor, Fusin, Leukocyte-derived seven transmembrane domain receptor, LESTR, LCR1, FB22, NPYRL, HM89, CD184 |
| CXCR5 | CXCR5 | CXC-Chemokine receptor 5 | NM_001716 | Burkitt lymphoma receptor 1, Monocyte-derived receptor 15, MDR-15, CD185, BLR1, MDR15 |
| CXCR6 | CXCR6 | CXC-Chemokine receptor 6 | NM_006564 | G-protein coupled receptor bonzo, G-protein coupled receptor STRL33, CDw186, CD186, BONZO, STRL33, TYMSTR |
| Cyclin D1 | CCND1 | Cyclin D1 | NP_444284.1 | G1/S-specific cyclin-D, BCL1, PRAD1 |
| Cystatin A | CSTA | Cystatin A | NP_005204.1 | Cystatin-AS, Stefin-A, STF1, STFA |
| Cystatin B | CSTB | Cystatin B | NP_000091.1 | Stefin-B, Liver thiol proteinase inhibitor, CPI-B, CST6, STFB |
| Cystatin C | CST3 | Cystatin C | NP_000090.1 | Cystatin-3, Neuroendocrine basic polypeptide, Gamma-trace, Post-gamma-globulin |
| Cytochrome C | CYC1 | Cytochrome c-1 | NP_001907.2 | Cytochrome c1, heme protein, mitochondrial, Ubiquinol-cytochrome-c reductase complex cytochrome c1 subunit, Cytochrome c-1, Cytochrome b-c1 complex subunit 4, Complex III subunit 4, Complex III subunit IV |
| Cytokeratin 8 | KRT8 | Cytokeratin 8 | NP_002264.1 | CK-8, Keratin-8, K8, CYK8 |
| D6 | CCBP2 | Chemokine-binding protein 2 | NM_001296 | Chemokine-binding protein D6, C-C chemokine receptor D6, CCR10, CMKBR9 |
| DAN | NBL1 | Neuroblastoma suppressor of tumorigenicity 1 | NM_005380 | Zinc finger protein DAN, N03, DAN domain family member 1, DAND1 |
| DANCE | DANCE | Developmental arteries and neural crest EGF-like protein | NM_006329 | Fibulin-5, Urine p50 protein, UP50, FBLN5 |
| DcR3 | TNFRSF6B | Tumor necrosis factor receptor superfamily member 6B | NM_032945 | Decoy receptor for Fas ligand, Decoy receptor 3, M68, DCR3, TR6 |
| Decorin | DCN | Decorin | NM_133507 | Bone proteoglycan II, PG-S2, PG40, SLRR1B |
| Dkk-1 | DKK1 | Dickkopf-related protein 1 | NM_012242 | SK |
| Dkk-3 | DKK3 | Dickkopf-related protein 3 | NM_013253 | REIC |
| Dkk-4 | DKK4 | Dickkopf-related protein 4 | NM_014420 | |
| DPPIV | DPP4 | Dipeptidyl peptidase 4 | NP_001926.2 | Dipeptidyl peptidase IV, DPP IV, T-cell activation antigen CD26, TP103, Adenosine deaminase complexing protein 2, ADABP, CD26, ADCP2 |
| DR3 | TNFRSF25 | Tumor necrosis factor receptor superfamily member 25 | NM_148965 | WSL-1 protein, Apoptosis-mediating receptor DR3, Apoptosis-mediating receptor TRAMP, Death domain receptor 3, Apoptosis-inducing receptor AIR, Apo-3, Lymphocyte-associated receptor of death, LARD, TNFRSF25, APO3, DDR3, DR3, TNFRSF12 |
| DR6 | TNFRSF21 | Tumor necrosis factor receptor superfamily member 21 | NM_014452 | TNFR-related death receptor 6, Death receptor 6 |
| Dtk | Dtk | Tyrosine-protein kinase receptor TYRO3 | NP_006284.2 | BYK, RSE, SKY |
| E-Cadherin | CDH1 | Epithelial cadherin | NP_004351.1 | Uvomorulin, CAM 120/80, CD324, CDHE, UVO, Cadherin-1 |
| EDA-A2 | EDA2R | X-linked ectodysplasin-A2 receptor | NP_068555.1 | TNFRSF27, XEDAR, Tumor necrosis factor receptor superfamily member 27 |

TABLE 15-continued

Proteins for Use as Biomarkers

| Cytokine Name | Official Symbol | Full Name | Genbank | Related Names |
|---|---|---|---|---|
| EDAR | EDAR | Tumor necrosis factor receptor superfamily member EDAR | NM_022336 | Anhidrotic ectodysplasin receptor 1, Ectodysplasin-A receptor, EDA-A1 receptor, Ectodermal dysplasia receptor, Downless homolog |
| EDG-1 | EDG1 | Endothelial Differentiation Gene-1 | NM_001400 | Sphingosine 1-phosphate receptor 1, Sphingosine 1-phosphate receptor Edg-1, S1P receptor Edg-1, Endothelial differentiation G-protein coupled receptor 1, S1PR1, CHEDG1, EDG1 |
| EGF | EGF | Epidermal growth factor | NM_001963 | |
| EGFR | ErbB-1 | Epidermal growth factor receptor | NP_005219.2, NP_958439.1, NP_958440.1, NP_958441.1 | Receptor tyrosine-protein kinase ErbB-1, ERBB1 |
| EG-VEGF | PROK1 | Endocrine Gland-derived Vascular Endothelial cell Growth Factor | NM_032414 | Prokineticin-1, Mambakine |
| Elafin | Elafin | Elafin | NP_002629.1 | Elastase-specific inhibitor, ESI, Skin-derived antileukoproteinase, SKALP, Peptidase inhibitor 3, WAP four-disulfide core domain protein 14, Protease inhibitor WAP3, PI3, WAP3, WFDC14 |
| EMAP-II | EML2 | Echinoderm microtubule-associated protein-like 2 | NM_012155 | HuEMAP-2, EMAP2, EMAPL2 |
| ENA-78 | CXCL5 | Epithelial neutrophil-activating protein 78 | NM_002994 | Epithelial cell-derived neutrophil attractant-78 |
| Endocan | ESM1 | Endocan | NM_007036 | Endothelial cell-specific molecule 1 |
| Endoglin | ENG | Endoglin | NM_000118 | CD105 |
| Endorphin Beta | Endorphin B | Beta-endorphin | NP_000930.1, NP_001030333.1 | Cleavage product of POMC |
| Endostatin | COL18A1 | Endostatin | NM_030582 | Collagen alpha-1(XVIII) chain, COL18A1 |
| Endothelin-1 | EDN1 | Endothelin-1 | NP_001946.3 | Preproendothelin-1, PPET1 |
| EN-RAGE | S100A12 | RAGE-binding protein | NM_005621 | |
| Eotaxin | CCL11 | Eotaxin | NM_002986 | CCL11, SCYA11, C-C motif chemokine 11, Small-inducible cytokine A11, Eosinophil chemotactic protein |
| Eotaxin-2 | CCL24 | Eotaxin-2 | NM_002991 | Small-inducible cytokine A24, Myeloid progenitor inhibitory factor 2, MPIF-2, CK-beta-6, Eosinophil chemotactic protein 2, CCL24, SCYA24 |
| Eotaxin-3 | CCL26 | Eotaxin-3 | NM_006072 | Small-inducible cytokine A26, Macrophage inflammatory protein 4-alpha, MIP-4-alpha, Thymic stroma chemokine-1, TSC-1, CC chemokine IMAC |
| Epiregulin | EPR | Epiregulin | NM_001432 | |
| EpCAM | EPCAM | Epithelial Cell Adhesion Molecule | NP_002345.2 | TROP1, tumor-associated calcium signal transducer-1 |
| Epo | EPX | Eosinophil peroxidase | NM_000502 | EPER, EPO, EPP |
| ErbB2 | ERBB2 | Receptor tyrosine-protein kinase erbB-2 | NM_001005862 | p185erbB2, C-erbB-2, NEU proto-oncogene, Tyrosine kinase-type cell surface receptor HER2, MLN 19, CD340 |
| ErbB3 | ERBB3 | Receptor tyrosine-protein kinase erbB-3 | NP_001005915.1. NP_001973.2 | HER3, Tyrosine kinase-type cell surface receptor HER3 |
| ErbB4 | ERBB4 | Receptor tyrosine-protein kinase erbB-4 | NM_005235 | p180erbB4, Tyrosine kinase-type cell surface receptor HER4, HER4 |
| E-selectin | SELE | E-selectin | NM_000450 | |
| ETL | ETL protein | EGF, latrophilin and seven transmembrane domain-containing protein 1 | NP_071442.2 | ELTD1, EGF-TM7-latrophilin-related protein, ETL protein |
| FABP4 | FABP4 | Fatty acid-binding protein, adipocyte | NP_001433.1 | A-FABP, AFABP, Fatty acid-binding protein 4, Adipocyte lipid-binding protein, ALBP |
| FADD | FADD | Fas-Associating protein with Death Domain | NM_003824 | MORT-1 |
| FAM3B | FAM3B | Family with sequence similarity 3, Member B isoform B | NM_058186 | PANDER |
| Fas/TNFRSF6 | FAS | Tumor necrosis factor receptor superfamily member 6 | NP_000034.1. NP_690610.1. NP_690611.1. NP_690612.1. NP_690613.1. NP_690614.1. NP_690615.1. NP_690616.1 | APT1, FAS1 |
| FasL | FASLG | Fas Ligand | NM_000639 | CD95 ligand, Apo-1 ligand |
| FCGR2B | Fc-gamma-RIIb | Low affinity immunoglobulin gamma | NP_001002273.1, NP_001002274.1, | IgG Fc receptor II-b, Fc-gamma RII-b, Fc-gamma-RIIb, FcRII-b, CDw32, CD32, FCG2, IGFR2 |

TABLE 15-continued

Proteins for Use as Biomarkers

| Cytokine Name | Official Symbol | Full Name | Genbank | Related Names |
|---|---|---|---|---|
| | | Fc region receptor II-b | NP_001002275.1, NP_003992.3 | |
| Ferritin-L | FTL | Ferritin light chain | NP_000137.2 | Ferritin L subunit |
| Ferritin-H | FTH | Ferritin heavy chain | NP_002023.2 | Ferritin H subunit, Cell proliferation-inducing gene 15 protein, FTH1, FTHL6 |
| FGF Basic | bFGF | Basic Fibroblast Growth Factor | NP_001997.5 | FGF2, Heparin-binding growth factor 2 |
| FGF R3 | FGFR3 | Fibroblast growth factor receptor 3 | NM_022965 | FGFR3, JTK4, CD333 |
| FGF R4 | FGFR4 | Fibroblast growth factor receptor 4 | NM_022963 | FGFR4, JTK2, TKF, CD334 |
| FGF R5 | FGFRL1 | Fibroblast growth factor receptor 5 | NM_021923 | Fibroblast growth factor receptor-like 1, FGFR-like protein, FGF homologous factor receptor, FGFRL1, FGFR5, FHFR |
| FGF-10 | FGF10 | Fibroblast growth factor-10 | NM_004465 | Keratinocyte growth factor 2 |
| FGF-11 | FGF11 | Fibroblast growth factor-11 | NM_004112 | FHF-3, Fibroblast growth factor homologous factor 3 |
| FGF-12 | FGF12 | Fibroblast growth factor-12 | NM_021032 | Fibroblast growth factor homologous factor 1, FHF-1, Myocyte-activating factor, FGF12B |
| FGF-13 1B | FGF13 | Fibroblast growth factor 13 | NM_004114 | FHF-2, Fibroblast growth factor homologous factor 2 |
| FGF-16 | FGF16 | Fibroblast growth factor-16 | NM_003868 | |
| FGF-17 | FGF17 | Fibroblast growth factor-17 | NM_003867 | |
| FGF-18 | FGF18 | Fibroblast growth factor-18 | NM_033649, NM_003862 | zFGF5 |
| FGF-19 | FGF19 | Fibroblast growth factor-19 | NM_005117 | |
| FGF-2 | FGF2 | Heparin-binding growth factor 2 | NM_002006 | bFGF, Basic fibroblast growth factor |
| FGF-20 | FGF20 | Fibroblast growth factor-20 | NM_019851 | |
| FGF-21 | FGF21 | Fibroblast growth factor-21 | NM_019113 | |
| FGF-23 | FGF23 | Fibroblast growth factor-23 | NM_020638 | Tumor-derived hypophosphatemia-inducing factor, Phosphatonin, HYPF |
| FGF-4 | FGF4 | Fibroblast growth factor-4 | NM_002007 | HST, HSTF1, KS3, Heparin secretory-transforming protein, HST-1, Transforming protein KS3, Heparin-binding growth factor 4 |
| FGF-5 | FGF5 | Fibroblast growth factor-5 | NM_004464 | HBGF-5 (heparin binding growth factor-5), hst-1 or HSTF-1 |
| FGF-6 | FGF6 | Fibroblast growth factor-6 | NM_020996 | HBGF-6, HST-2, Heparin-binding growth factor 6 |
| FGF-7 | FGF7 | Fibroblast growth factor-7 | NM_002009 | Heparin-binding growth factor 7, HBGF-7 |
| FGF-8 | FGF8 | Fibroblast growth factor-8 | NM_006119/ NM_033165 | Heparin-binding growth factor 8, HBGF-8, Androgen-induced growth factor, AIGF |
| FGF-9 | FGF9 | Fibroblast growth factor-9 | NM_002010 | Glia-activating factor, GAF, HBGF-9 |
| FGF-BP | FGFBP1 | Fibroblast growth factor-binding protein | NM_005130 | 17 kDa heparin-binding growth factor-binding protein, 17 kDa HBGF-binding protein, HBp17, FGFBP, HBP17 |
| FLRG | FSTL3 | Follistatin-Related gene protein | NM_005860 | Follistatin-like 3 |
| Flt-3 Ligend | FLT3 | Fms-like tyrosine kinase-3 Ligand | NM_004119 | STK-1 ligand |
| Follistatin | FS | Follistatin | NP_037541.1 | Activin-binding protein |
| Follistatin-like 1 | FSTL1 | Follistatin-like protein 1 | NM_007085 | TSC-36 |
| Fractalkine | CX3CL1 | Fractalkine | NP_002987.1 | C—X3—C motif chemokine 1, Neurotactin, CX3C membrane-anchored chemokine, Small-inducible cytokine D1, FKN, NTT, SCYD1 |
| Frizzled-1 | FZD1 | Frizzled-1 | NM_003505 | FzD1, Fz1 |
| Frizzled-3 | FZD3 | Frizzled-3 | NM_017412 | FzD3, Fz3 |
| Frizzled-4 | FZD4 | Frizzled-4 | NM_012193 | FzD4, CD344 |
| Frizzled-5 | FZD5 | Frizzled-5 | NM_003468 | FzD5, HFZ5 |
| Frizzled6 | FZD6 | Frizzled-6 | NM_003506 | FzD6 |
| Frizzled-7 | FZD7 | Frizzled-7 | NM_003507 | FzD7 |
| FSHR | FSH-R | Follicle-stimulating hormone receptor | NP_000136.2, NP_852111.1 | FSH-R, Follitropin receptor, LGR1 |
| Furin | Fur | Furin | NP_002560.1 | Paired basic amino acid residue cleaving enzyme, PACE, Dibasic-processing enzyme, FUR, PCSK3 |
| Galectin-1 | LGALS1 | Galectin-1 | NP_002296.1 | Lectin galactoside-binding soluble, Beta-galactoside-binding lectin L-14-I, Lactose-binding lectin 1, S-Lac lectin 1, Galaptin, 14 kDa lectin, HPL, HBL, Putative MAPK-activating protein PM12 |

TABLE 15-continued

Proteins for Use as Biomarkers

| Cytokine Name | Official Symbol | Full Name | Genbank | Related Names |
|---|---|---|---|---|
| Galectin-3 | LGALS3 | Galectin-3 | NP_002297.2 | Galactose-specific lectin 3, Mac-2 antigen, IgE-binding protein, 35 kDa lectin, Carbohydrate-binding protein 35, CBP 35, Laminin-binding protein, Lectin L-29, L-31, Galactoside-binding protein, GALBP |
| Galectin-7 | LGALS7 | Galectin-7 | NP_001035972.1. NP_002298.1. XP_001721023.1 | HKL-14, PI7, p53-induced gene 1 protein, PIG1 |
| GASP-1/ WFIKKNRP | WFIKKN2 | GDF Associated Serum Protein 1 | NM_175575 | Growth and differentiation factor-associated serum protein-1 |
| GASP-2/ WFIKKN | WFIKKN1 | GDF Associated Serum Protein 2 | NM_053284 | Growth and differentiation factor-associated serum protein-2 |
| GATA-4 | GATA4 | Transcription factor GATA-4 | NP_002043.2 | GATA-binding factor 4 |
| GCP-2 | CXCL6 | Granulocyte Chemotactic Protein 2 | NM_002993 | Granulocyte chemoattractant protein-2 |
| GCSF | GCSF | Granulocyte-colony Stimulating Factor | NM_172220 | Pluripoietin, INN = Filgrastim, INN = Lenograstim, CSF3 |
| G-CSF R | GCSFR | Granulocyte-colony Stimulating Factor receptor | NM_156039 | CD114, CSF3R |
| GDF1 | GDF1 | Embryonic growth/differentiation factor 1 | NM_001492 | GDF-1 |
| GDF11 | GDF11 | Growth/differentiation factor 11 | NM_005811 | Bone morphogenetic protein 11, BMP11 |
| GDF-15 | GDF15 | Growth differentiation factor-15 | NM_004864 | Placental bone morphogenetic protein, Placental TGF-beta, Macrophage inhibitory cytokine 1, MIC-1, Prostate differentiation factor, NSAID-activated gene 1 protein, NAG-1, NSAID-regulated gene 1 protein, NRG-1, PDF, PLAB, PTGFB |
| GDF3 | GDF3 | Growth/differentiation factor 3 | NM_020634 | GDF-3 |
| GDF5 | GDF5 | Growth/differentiation factor 5 | NM_000557 | Cartilage-derived morphogenetic protein 1, CDMP-1, Radotermin, GDF5 |
| GDF8 | GDF8 | Growth/differentiation factor 8 | NM_005259 | Myostatin, MSTN |
| GDF9 | GDF9 | Growth/differentiation factor 9 | NM_005260 | |
| GDNF | GDNF | Glial-derived Neurotrophic Factor | NM_000514 | Astrocyte-derived trophic factor, ATF, hGDNF |
| GFR alpha-1 | GFRA1 | GDNF Family Receptor alpha 1 | NM_145793 | TGF-beta-related neurotrophic factor receptor 1, RET ligand 1, GFRA1, GDNFRA, RETL1, TRNR1 |
| GFR alpha-2 | GFRA2 | GDNF family receptor alpha-2 | NM_001495 | Neurturin receptor alpha, NRTNR-alpha, NTNR-alpha, TGF-beta-related neurotrophic factor receptor 2, GDNF receptor beta, GDNFR-beta, RET ligand 2, GFRA2, GDNFRB, RETL2, TRNR2 |
| GFR alpha-3 | GFRA3 | GDNF family receptor alpha-3 | NM_001496 | GFR-alpha-3 |
| GFR alpha-4 | GFRA4 | GDNF receptor alpha 4 | NP_071422.1. NP_665705.1 | GFR-alpha-4, Persephin receptor |
| Ghrelin | GHRL | Ghrelin | NP_001128413.1. NP_057446.1 | Appetite-regulating hormone, Growth hormone secretagogue, Growth hormone-releasing peptide, Motilin-related peptide, M46 protein, cleaved into the following 3 chains: Ghrelin-27, Ghrelin-28, Obestatin, GHRL, MTLRP |
| GLP-1 (7-37) | GLP-1(7-37) | Glucagon-like peptide 1(7-37) | NP_002045.1 | Glucagon: Cleaved into the following 8 chains: 1-Glicentin, 2-Glicentin-related polypeptide, 3-Oxyntomodulin, 4-Glucagon, 5-Glucagon-like peptide 1, 6-Glucagon-like peptide 1(7-37), 7-Glucagon-like peptide 1(7-36), 8-Glucagon-like peptide 2 |
| Glucagon | GCG | Glucagon | NM_002054 | |
| Glutathione Peroxidase 1 | GPX1 | Glutathione Peroxidase 1 | NP_000572.2. NP_958799.1 | GSHPx-1, GPx-1, Cellular glutathione peroxidase |
| Glutathione Peroxidase 3 | GPX3 | Glutathione peroxidase 3 | NP_002075.2. | GSHPx-3, GPx-3, Extracellular glutathione peroxidase, Plasma glutathione peroxidase, GSHPx-P, GPx-P |
| Glut1 | SLC2A1 | Glucose transporter 1 | NM_006516 | Glucose transporter type 1, erythrocyte/brain, GLUT-1, HepG2 glucose transporter |
| Glut2 | SLC2A2 | Glucose transporter 2 | NM_000340 | Solute carrier family 2, facilitated glucose transporter member 2, Glucose transporter type 2, GLUT-2, SLC2A2 |

TABLE 15-continued

Proteins for Use as Biomarkers

| Cytokine Name | Official Symbol | Full Name | Genbank | Related Names |
|---|---|---|---|---|
| Glut3 | SLC2A3 | Glucose transporter 3 | NM_006931 | Solute carrier family 2, facilitated glucose transporter member 14, Glucose transporter type 14, GLUT-14, SLC2A14, GLUT3 |
| Glut5 | SLC2A5 | Glucose transporter 5 | NM_003039 | Solute carrier family 2, facilitated glucose transporter member 5, Glucose transporter type 5, GLUT-5, Fructose transporter, SLC2A5 |
| Glypican 3 | GPC3 | Glypican 3 | NM_00484 | Intestinal protein OCI-5, GTR2-2, MXR7 |
| Glypican 5 | GPC5 | Glypican 5 | NM_004466 | Secreted glypican-5 |
| GM-CSF | CSF2 | Granulocyte-macrophage colony stimulating factor | NM_000758 | Colony-stimulating factor, CSF, Sargramostim, Molgramostin |
| GM-CSF R alpha | GMR | Granulocyte macrophage colony stimulatingfactor receptor alpha | NM_172247 | CSF2R, CSF2RY, CD116 |
| GPR-39 | GPR39 | G-protein coupled receptor 39 | NP_001499.1 | |
| Granzyme A | GZMA | Granzyme A | NM_006144 | Granzyme-1, Cytotoxic T-lymphocyte proteinase 1, Hanukkah factor, H factor, HF, CTL tryptase, Fragmentin-1, CTLA3, HFSP |
| GREMLIN | GREM1 | GREMLIN (C-term) | NM_013372 | Cysteine KNOT superfamily 1, BMP antagonist 1 |
| GRO-a | CXCL1 | Growth-regulated alpha protein | NM_001511 | C—X—C motif chemokine 1, Melanoma growth stimulatory activity, MGSA, Neutrophil-activating protein 3, NAP-3, GRO-alpha(1-73), GRO, GRO1, GROA, MGSA, SCYB1 |
| GRO-b | CXCL2 | Growth-regulated protein beta | NP_002080.1 | C—X—C motif chemokine 2, Macrophage inflammatory protein 2-alpha, GRO2, GROB, MIP2A, SCYB2 |
| GRO-g | CXCL3 | Growth-regulated protein gamma | NP_002081.2 | C—X—C motif chemokine 3, Macrophage inflammatory protein 2-beta, MIP2-beta, Growth-regulated protein gamma, GRO-gamma, GRO-gamma(1-73), GRO3, GROG, SCYB3 |
| Growth Hormone | GH1 | Growth Hormone | NM_000515 | Somatotropic hormone |
| Growth Hormone R | GHR | Growth Hormone Receptor | NM_000163 | Somatotropin receptor |
| HB-EGF | HBEGF | Heparin-binding Epidermal Growth factor | NM_001945 | DTR, DTS, HEGFL |
| HCC-4 | CCL16 | Hemofiltrate CC Chemokine 4 | NM_004590 | NCC-4, LEC, LMC, and LCC-1 |
| HCR | CCHCR1 | Coiled-coil alpha-helical rod protein 1 | NM_019052 | Alpha-helical coiled-coil rod protein, Putative gene 8 protein, Pg8, C6orf18, HCR |
| Hepassocin | FGL1 | Hepassocin | NM_004467 | Fibrinogen-like 1 |
| Heregulin | HRG | Heregulin | NP_004486.2. NP_039250.2. NP_039251.2. NP_039252.2. NP_039253.1. NP_039254.1. NP_039255.1. NP_039256.2. NP_039258.1. | GGF, HGL, HRGA, NDF, SMDF, Pro-neuregulin-1, Neuregulin-1, membrane-bound isoform, Neu differentiation factor, Breast cancer cell differentiation factor p45, Acetylcholine receptor-inducing activity, ARIA, Sensory and motor neuron-derived factor, Glial growth factor |
| HGF | HGF | Hepatocyte growth factor | NM_001010934 | Scatter factor, SF, Hepatopoeitin-A |
| HGFR | HGF receptor | Hepatocyte growth factor receptor | NP_000236.2 NP_001120972.1 | |
| HRG-alpha | HPRG | Histidine-rich glycoprotein | NP_000403.1 | |
| HSP27 | HspB1 | Heat shock protein beta-1 | NP_001531.1 | Heat shock 27 kDa protein, HSP 27, Stress-responsive protein 27, Estrogen-regulated 24 kDa protein, 28 kDa heat shock protein |
| HSP60 | Hsp60 | 60 kDa heat shock protein, mitochondrial | NP_511115.2, NP_727489.1 | Hsp60, 60 kDa chaperonin, CPN60, Heat shock protein 60, HSP-60, Mitochondrial matrix protein P1, Mmp-P1 |
| HSP70 | HSPA1A | Heat shock 70 kDa protein 1 | NP_005336.3, NP_005337.2 | HSP70.1, HSP70-1/HSP70-2, HSPA1 |
| HTRA2 | HTRA2 | Serine protease HTRA2, mitochondrial | NP_037379.1, NP_659540.1. | High temperature requirement protein A2, HtrA2, Omi stress-regulated endoprotease, Serine proteinase OMI, Serine protease 25 |
| LAP | TGFB1 | Transforming growth factor beta-1 | NM_000660 | TGF-beta-1 |
| HVEM | TNFRSF14 | Herpesvirus entry mediator | NM_003820 | HveA, Herpes simplex virus entry protein A, HveAt, HVEA, HVEM, Tumor necrosis factor receptor superfamily member 14 |

TABLE 15-continued

Proteins for Use as Biomarkers

| Cytokine Name | Official Symbol | Full Name | Genbank | Related Names |
|---|---|---|---|---|
| I-309 | CCL1 | T lymphocyte-secreted protein I-309 | NM_002981 | Small-inducible cytokine A1, T lymphocyte-secreted protein I-309, CCL1, SCYA1 |
| IBSP | IBSP | Bone sialoprotein 2 | NP_004958.2. | Bone sialoprotein II, BSP II, Cell-binding sialoprotein, Integrin-binding sialoprotein, BNSP |
| ICAM-1 | ICAM-1 | Intercellular adhesion molecule 1 | NP_000192.2 | CD54 antigen, Major group rhinovirus receptor |
| ICAM-2 | ICAM2 | Intercellular adhesion molecule 2 | NM_000873 | CD102 |
| ICAM-3 | ICAM3 | Intercellular Adhesion Molecule 3 | NM_002162 | ICAM-R, CDw50, CD50 |
| ICAM-5 | ICAM5 | Intercellular Adhesion Molecule 5 | NM_003259 | Telencephalin, TLCN, TLN |
| IFN-beta | IFN-beta | Interferon beta | NP_002167.1 | IFB, IFNB, Fibroblast interferon |
| IFN-gamma | IFNG | Interferon gamma | NM_000619 | Immune interferon, IFNG |
| IFN-gamma R1 | IFNGR1 | Interferon gamma receptor 1 | NM_000416 | Interferon-gamma receptor alpha chain, IFN-gamma-R1, CDw119, CD119 |
| IFN-omega 1 | IFNW1 | Interferon omega 1 | NM_002177 | Interferon alpha-II-1 |
| IGFBP-1 | IGFBP1 | Insulin-like growth factor binding proteins 1 | NM_001013029 | IGF-binding protein, IBP-1, Placental protein 12, PP12 |
| IGFBP-2 | IGFBP2 | Insulin-like growth factor binding proteins 2 | NM_000597 | BP2, IBP2, |
| IGFBP-3 | IGFBP3 | Insulin-like growth factor binding proteins 3 | NM_001013398 | IBP3, IGF-binding protein 3 |
| IGFBP-4 | IGFBP4 | Insulin-like growth factor binding proteins 4 | NM_001552 | IBP4, IGF-binding protein 4 |
| IGFBP-5 | IGFBP5 | Insulin-like growth factor-binding protein 5 | NP_000590.1 | IBP5, IGF-binding protein 5 |
| IGFBP-6 | IGFBP6 | Insulin-like growth factor-binding protein 6 | NP_002169.1 | IBP6, IGF-binding protein 6 |
| IGFBP-7 | IGFBP7 | Insulin-like growth factor-binding protein 7 | NM_001553 | MAC25, PSF, IGF-binding protein 7, Prostacyclin-stimulating factor, PGI2-stimulating factor, IGFBP-rP1, Tumor-derived adhesion factor |
| IGF-I R | IGF1R | Insulin-like growth factor 1 receptor | NP_000866.1 | Insulin-like growth factor I receptor, IGF-I receptor, CD221 |
| IGF-I | IGF1 | Insulin-like growth factor-1 | NM_000618 | Somatomedin-C, Mechano growth factor, MGF, IBP1 |
| IGF-II R | IGF2R | Insulin-like growth factor II receptor | NM_000876 | Cation-independent mannose-6-phosphate receptor, MPRI |
| IGF-II | IGF2 | Insulin-like growth factor-2 | NM_000612 | Somatomedin-A |
| IL-1F10 | IL1F10 | Human Interleukin 1 family member 10 | NM_173161 | FIL1T, IL1HY2, IL-1HY2 |
| IL-1 F5 | IL1F5 | Human Interleukin 1 family member 5 | NM_173170 | FIL1D, IL1HY1, IL1L1, IL1RP3, Interleukin-1 delta |
| IL-1 F6 | IL1F6 | Human Interleukin 1 family member 6 | NM_014440 | FIL1E, IL1E, Interleukin-1 epsilon, IL-1 epsilon, FIL1 epsilon |
| IL-1 F7 | IL1F7 | Human Interleukin 1 family member 7 | NM_173205 | FIL1Z, IL1H4, IL1RP1, Interleukin-1 zeta |
| IL-1 F8 | IL1F8 | Human Interleukin 1 family member 8 | NM_173178 | IL1H2, Interleukin-1 eta, IL-1 eta |
| IL-1 F9 | IL1F9 | Human Interleukin 1 family member 9 | NM_019618 | IL1E, IL1H1, IL1RP2, Interleukin-1 homolog 1, IL-1H1, Interleukin-1 epsilon, IL-1 epsilon, IL-1-related protein 2, IL-1RP2 |
| IL1RAP | IL1RAP | Interleukin-1 receptor accessory protein | NM_002182 | IL-1RAcP |
| IL1RL1 | IL1RL1 | Interleukin 1 receptor-like 1 | NP_003847.2, NP_057316.3 | Protein ST2, DER4, ST2, T1 |
| IL1RL2 | IL1RL2 | Interleukin-1 receptor-like 2 | NP_003845.2 | IL-1Rrp2, Interleukin-1 receptor-related protein 2 |
| IL-1 R8 | IL1R8 | Interleukin 1 receptor 8 | NM_014271 | IL1 RAPL, X-linked interleukin-1 receptor accessory protein-like 1, IL1RAPL-1, Oligophrenin-4, Three immunoglobulin domain-containing IL-1 receptor-related 2, TIGIRR-2, IL1RAPL1, OPHN4 |
| IL-1 R9 | IL1R9 | Interleukin-1 receptor 9 | NM_017416 | IL1 RAPL2, X-linked interleukin-1 receptor accessory protein-like 2, IL-1 receptor accessory protein-like 2, IL1RAPL-2-related protein, Three immunoglobulin domain-containing IL-1 receptor-related 1, TIGIRR-1 |
| IL-1 RI | IL-1 RI | Interleukin-1 receptor type I | NP_000868.1 | IL-1R-1, IL-1RT1, IL-1R-alpha, p80, CD121 antigen-like family member A, CD121a, IL1R1, IL1R, IL1RA, IL1RT1 |
| IL-1 RII | IL-1 RII | Interleukin-1 receptor type II | NP_004624.1. NP_775465.1 | IL-1R-2, IL-1R-beta, CD121 antigen-like family member B, CDw121b, CD121b antigen, CD121 |

TABLE 15-continued

Proteins for Use as Biomarkers

| Cytokine Name | Official Symbol | Full Name | Genbank | Related Names |
|---|---|---|---|---|
| IL-10 | IL10 | Interleukin 10 | NM_000572 | Cytokine synthesis inhibitory factor, CSIF |
| IL-10 R alpha | IL10RA | Interleukin 10 receptor alpha | NM_001558 | IL-10R-A, IL-10R1, CDw210a |
| IL-10 R beta | IL10RB | Interleukin 10 receptor beta | NM_000628 | IL-10R-B, IL-10R2, Cytokine receptor class-II member 4, Cytokine receptor family 2 member 4, CRF2-4, CDw210b, IL10RB, CRFB4, D21S58, D21S66 |
| IL-11 | IL11 | Interleukin 11 | NM_000641 | Adipogenesis inhibitory factor, AGIF, Oprelvekin |
| IL-12 R beta 1 | IL12RB1 | Interleukin 12 receptor beta 1 | NM_005535 | IL-12R-beta-1, Interleukin-12 receptor beta, IL-12 receptor beta component, IL-12RB1, CD212, IL12RB1, IL12R, IL12RB |
| IL-12 R beta 2 | IL12RB2 | Interleukin 12 receptor beta 2 | NM_001559 | IL-12R-beta-2, Interleukin-12 receptor beta-2 chain |
| IL-13 | IL13 | Interleukin 13 | NM_002188 | NC30 |
| IL-13 R alpha 1 | IL13RA1 | Interleukin 13 receptor alpha 1 | NM_001560 | IL-13 receptor alpha-1, IL-13R-alpha-1, IL-13RA-1, Cancer/testis antigen 19, CT19, CD213a1, IL13RA1, IL13R, IL13RA |
| IL-13 R alpha 2 | IL13RA2 | Interleukin 13 receptor alpha 2 | NM_000640 | IL-13R-alpha-2, IL-13RA-2, Interleukin-13-binding protein, CD213a2, IL13RA2, IL13R |
| IL-15 | IL15 | Interleukin 15 | NM_000585 | |
| IL-15 R alpha | IL15RA | Interleukin 15 receptor alpha | NM_172200/ NM_002189 | |
| IL-16 | IL16 | Interleukin 16 | NM_172217 | Pro-interleukin-16, Lymphocyte chemoattractant factor, LCF |
| IL-17 | IL17A | Interleukin 17 | NM_002190 | IL-17A, Cytotoxic T-lymphocyte-associated antigen 8, CTLA-8 |
| IL-17B | IL17B | Interleukin 17B | NM_014443 | Cytokine-like protein Zcyto7, Neuronal interleukin-17-related factor, Interleukin-20, IL-20, NIRF, ZCYTO7 |
| IL-17B R | IL17RB | Interleukin 17B receptor | NM_172234 | Interleukin-17B receptor, IL-17B receptor, IL-17 receptor homolog 1, IL-17Rh1, IL17Rh1, Cytokine receptor CRL4, IL17RB, EVI27, IL17BR |
| IL-17C | IL17C | Interleukin 17C | NM_013278 | Cytokine CX2 |
| IL-17D | IL17D | Interleukin 17D | NM_138284 | Interleukin-27 |
| IL-17E | IL25 | Interleukin 17E | NM_172314 | IL-25, Interleukin-17E, IL-17E |
| IL-17F | IL17F | Interleukin 17F | NM_052872 | Interleukin-17F, Interleukin-24, IL-24, Cytokine ML-1, IL17F |
| IL-17R | IL17RA | Interleukin 17 receptor A | NM_014339 | CD217 |
| IL-17RC | IL17RC | Interleukin 17 receptor C | NM_032732 | Interleukin-17 receptor-like protein, IL-17RL, Interleukin-17 receptor homolog, IL17Rhom |
| IL-17RD | IL17RC | Interleukin-17 receptor D | NM_017563 | IL-17RD, IL17Rhom, Interleukin-17 receptor-like protein, Sef homolog, hSef, IL17RD, IL17RLM |
| IL-18 BPa | IL-18 BPa | Interleukin-18-binding protein | NP_001034748.1, NP_001034749.1, NP_001138527.1, NP_001138529.1, NP_766630.2 | Tadekinig-alfa |
| IL-18 R alpha | IL18R1 | Interleukin-18 receptor 1 | NP_003846.1 | IL1 receptor-related protein, IL-1Rrp, CD218 antigen-like family member A, CDw218a, CD218a |
| IL-18 R beta | IL18RAP | Interleukin-18 receptor accessory protein | NP_003844.1 | Interleukin-18 receptor accessory protein-like, IL-18Rbeta, IL-1R accessory protein-like, IL-1RAcPL, Accessory protein-like, IL-1R7, CD218 antigen-like family member B, CDw218b, CD218b |
| IL-18 | IL18 | Interleukin 18 | NM_001562 | IGIF, IL1F4, Interferon-gamma-inducing factor, Interleukin-1 gamma, Iboctadekin |
| IL-19 | IL19 | Interleukin 19 | NM_153758 | Melanoma differentiation-associated protein-like protein, NG.1, ZMDA1 |
| IL-1alpha | IL1A | Interleukin-1 alpha | NM_000575 | Hematopoietin-1, IL1F1, pro-interleukin-1-alpha |
| IL-1beta | IL1B | Interleukin-1 beta | NM_000576 | Catabolin, IL1F2, pro-interleukin-1-beta |
| IL-1ra | IL1RA | Interleukin-1 receptor antagonist protein | NM_173842 | IL1F3, IL1 inhibitor, ICIL-1RA, IL1RN |
| IL-2 | IL2 | Interleukin 2 | NM_000586 | T-cell growth factor, TCGF, Aldesleukin |
| IL-2 R alpha | IL2RA | Interleukin-2 receptor alpha chain | NM_000417 | p55, TAC antigen, CD25 |
| IL-2 R beta | IL2RB | Interleukin-2 receptor subunit beta | NM_000878 | High affinity IL-2 receptor subunit beta, IL-2 receptor, P70-75, p75, CD122 |
| IL-2 R gamma | IL2RG | Cytokine receptor common gamma chain | NM_000206 | Interleukin-2 receptor gamma chain, IL-2R gamma chain, p64, CD132 |
| IL-20 | IL20 | Interleukin 20 | NM_018724 | Four alpha helix cytokine Zcyto10, ZCYTO10 |
| IL-20 R alpha | IL20RA | Interleukin-20 receptor alpha chain | NM_014432 | IL-20R1, Cytokine receptor class-II member 8, Cytokine receptor family 2 member 8, CRF2-8, ZcytoR7 |
| IL-20 R beta | IL20RB | Interleukin 20 receptor beta | NM_144717 | IL-20R2, DIRS1, IL-20R-beta |
| IL-21 | IL21 | Interleukin-21 | NM_021803 | Za11 |

TABLE 15-continued

Proteins for Use as Biomarkers

| Cytokine Name | Official Symbol | Full Name | Genbank | Related Names |
|---|---|---|---|---|
| IL-21 R | IL21R | Interleukin 21 receptor | NM_021798 | NILR, Novel interleukin receptor |
| IL-22 | IL22 | Interleukin-22 | NM_020525 | IL-10-related T-cell-derived-inducible factor, IL-TIF, ILTIF |
| IL-22 BP | IL22RA2 | Interleukin-22 receptor subunit alpha-2 | NM_181310 | IL-TIF, CRF2-10, CRF2-X, IL-22 RA2 |
| IL-22 R | IL-22 R | Interleukin-22 receptor subunit alpha-1 | NP_067081.2 | Cytokine receptor family 2 member 9, CRF2-9, IL22RA1 |
| IL-23 | IL23A | Interleukin-23 subunit alpha | NM_016584 | Interleukin-23 subunit p19, IL-23p19, IL23A, SGRF |
| IL-23 R | IL23R | Interleukin 23 receptor | NM_144701 | |
| IL-24 | IL24 | Interleukin-24 | NM_006850 | Suppression of tumorigenicity 16 protein, Melanoma differentiation-associated gene 7 protein, MDA-7 |
| IL-26 | IL26 | Interleukin-26 | NM_018402 | AK155 protein |
| IL-27 | IL27 | Interleukin-27 subunit alpha | NM_145659 | p28 |
| IL-28A | IL28A | Interleukin-28A | NM_172138 | Interferon lambda-2, IFN-lambda-2, Cytokine ZCYTO20 |
| IL-29 | IL29 | Interleukin-29 | NM_172140 | Interferon lambda-1, Cytokine ZCYTO21, IL29, IFNL1, ZCYTO21 |
| IL-3 | IL3 | Interleukin 3 | NM_000588 | Multipotential colony-stimulating factor, Hematopoietic growth factor, P-cell-stimulating factor, Mast cell growth factor, MCGF |
| IL-3 R alpha | IL3RA | Interleukin-3 receptor subunit alpha | NM_002183 | IL-3R-alpha, CD123 |
| IL-31 | IL31 | Interleukin-31 | NM_001014336 | |
| IL-31 RA | IL31RA | Interleukin-31 Receptor A | NM_139017 | Interleukin-31 receptor A, IL-31RA, Cytokine receptor-like 3, Gp130-like monocyte receptor, HGLM-R, GLM-R, IL31RA, CRL3, GPL |
| IL-4 | IL4 | Interleukin 4 | NM_172348 | B-cell stimulatory factor 1, BSF-1, Lymphocyte stimulatory factor 1, Binetrakin, Pitrakinra |
| IL-4 R | IL4R | Interleukin-4 receptor alpha chain | NM_001008699 | IL4RA, IL-4R-alpha, CD124 |
| IL-5 | IL5 | Interleukin 5 | NM_000879 | T-cell replacing factor, TRF, Eosinophil differentiation factor, B-cell differentiation factor I |
| IL-5 R alpha | IL5RA | Interleukin-5 receptor subunit alpha | NM_175724 | IL-5R-alpha, CDw125, CD125 |
| IL-6 | IL6 | Interleukin 6 | NM_000600 | B-cell stimulatory factor 2, BSF-2, Interferon beta-2, Hybridoma growth factor, CTL differentiation factor, CDF |
| IL-6 R | IL6R | Interleukin-6 receptor subunit alpha | NP_000556.1, NP_852004.1 | IL-6R 1, Membrane glycoprotein 80, gp80, CD126 |
| IL-7 | IL7 | Interleukin 7 | NM_000880 | |
| IL-7 R alpha | IL7R | Interleukin-7 receptor subunit alpha | NP_002176.2 | CDw127, CD127 |
| IL-8 | IL8 | Interleukin 8 | NM_000584 | C—X—C motif chemokine 8, Monocyte-derived neutrophil chemotactic factor, MDNCF, T-cell chemotactic factor, Neutrophil-activating protein 1, NAP-1, Protein 3-10C, Granulocyte chemotactic protein 1, GCP-1, Monocyte-derived neutrophil-activating peptide, MONAP, Emoctakin |
| IL-9 R | IL9R | Interleukin-9 receptor | NM_002186 | CD129 |
| IL-9 | IL9 | Interleukin-9 | NM_000590 | T-cell growth factor P40, P40 cytokine |
| Inhibin A | INHBA | Inhibin beta A chain | NP_002183.1 | Activin beta-A chain, Erythroid differentiation protein, EDF, INHBA |
| Inhibin B | INHBB | Inhibin beta B chain | NP_002184.2 | |
| INSL3 | INSL3 | Insulin-like 3 | NP_005534.2 | Leydig insulin-like peptide, Ley-l-L, Relaxin-like factor, RLF, RLNL |
| INSRR | INSRR | Insulin receptor-related protein | NP_055030.1 | IR-related receptor, IRR |
| Insulin R | INSR | Insulin Receptor | NM_000208 | CD220, IR |
| Insulysin | IDE | Insulin-degrading enzyme | NM_004969 | Insulin protease, Insulinase, Insulysin |
| IP-10 | CXCL10 | Interferon-inducible protein-10 | NM_001565 | INP10, SCYB10, C—X—C motif chemokine 10, Small-inducible cytokine B10, 10 kDa interferon-gamma-induced protein, Gamma-IP10, IP-10, CXCL10(1-73) |
| I-TAC | CXCL11 | Interferon-inducible T cell Alpha Chemoattractant | NM_005409 | C—X—C motif chemokine 11, Small-inducible cytokine B11, Interferon-inducible T-cell alpha chemoattractant, Interferon-gamma-inducible protein 9, IP-9, H174, Beta-R1, CXCL11, SCYB11, SCYB9B |
| Kallikrein 1 | KLK1 | Kallikrein-1 | NP_002248.1 | Tissue kallikrein, Kidney/pancreas/salivary gland kallikrein |
| Kallikrein 3 | KLK3 | Kallikrein-3 | NP_001025218.1, NP_001025219.1, | Kallikrein-3, Semenogelase, Gamma-seminoprotein, Seminin, P-30 antigen, Prostate- |

TABLE 15-continued

Proteins for Use as Biomarkers

| Cytokine Name | Official Symbol | Full Name | Genbank | Related Names |
|---|---|---|---|---|
| | | | NP_001025220.1, NP_001639.1 | specific antigen, APS |
| Kallikrein 5 | KLK5 | Kallikrein-5 | NP_001070959.1, NP_001070960.1, NP_036559.1 | Stratum corneum tryptic enzyme, Kallikrein-like protein 2, KLK-L2, KLK5, SCTE |
| Kallikrein 6 | KLK6 | Kallikrein-6 | NP_001012982.1, NP_002765.1 | Protease M, Neurosin, Zyme, SP59, Serine protease 9, Serine protease 18, KLK6, PRSS18, PRSS9 |
| Kallikrein 7 | KLK7 | Kallikrein-7 | NP_005037.1, NP_644806.1 | Stratum corneum chymotryptic enzyme, hSCCE, Serine protease 6, KLK7, PRSS6, SCCE |
| Kallikrein 8 | KLK8 | Kallikrein-8 | NP_009127.1, NP_653088.1, NP_653089.1, NP_653090.1 | Neuropsin, NP, Ovasin, Serine protease TADG-14, Tumor-associated differentially expressed gene 14 protein, Serine protease 19, NRPN, PRSS19, TADG14 |
| Kallikrein 11 | KLK11 | Kallikrein-11 | NP_006844.1, NP_659196.1 | Hippostasin, Trypsin-like protease, Serine protease 20, PRSS20, TLSP |
| Kallikrein 14 | KLK14 | Kallikrein-14 | NP_071329.2 | Kallikrein-like protein 6, KLK-L6 |
| Kininostatin/kininogen | KNG1 | Kininostatin | NM_000893 | High molecular weight kininogen, HMWK, Williams-Fitzgerald-Flaujeac factor, Fitzgerald factor, Alpha-2-thiol proteinase inhibitor, BDK, KNG |
| Kremen-1 | KREMEN1 | Kremen-1 | NM-001039571 | Kremen protein 1, Kringle-containing protein marking the eye and the nose, Kringle domain-containing transmembrane protein 1, Dickkopf receptor, KREMEN, KRM1 |
| Kremen-2 | KREMEN2 | Kremen-2 | NM_024507 | Kringle-containing protein marking the eye and the nose, Kringle domain-containing transmembrane protein 2, Dickkopf receptor 2, KRM2 |
| LAP | TGF-beta-1 | Latency-associated peptide | NP_000651.3 | Transforming growth factor beta-1 |
| Latent TGF-beta bp1 | LTBP-1 | Latent-transforming growth factor beta-binding protein 1 | NP_000618.2. NP_996826.1 | Transforming growth factor beta-1-binding protein 1, TGF-beta1-BP-1, LTBP1 |
| LBP | LBP | Lipopolysaccharide-binding protein | NM_004139 | LPS binding protein/LIF binding protein |
| LECT2 | LECT2 | Leukocyte cell-derived chemotaxin-2 | NM_002302 | |
| Lefty-A | LEFTY2 | Left-right determination factor 2 | NM_003240 | Protein lefty-2, Left-right determination factor A, Protein lefty-A, Transforming growth factor beta-4, TGF-beta-4, Endometrial bleeding-associated factor, LEFTY2, EBAF, LEFTA, LEFTYA, TGFB4 |
| Lep | LEP | Leptin | NM_000230 | Obesity factor, Obese protein, LEP, OB, OBS |
| Leptin R | LEPR | Leptin Receptor | NM_002303 | OB receptor, OB-R, HuB219, CD295, LEPR, DB, OBR |
| LFA-1 alpha | ITGAL | Integrin alpha-L | NM_002209 | Leukocyte adhesion glycoprotein LFA-1 alpha chain, LFA-1A, Leukocyte function-associated molecule 1 alpha chain, CD11 antigen-like family member A, CD11a, ITGAL, CD11A |
| LHR | LHR | Luteinizing hormone receptor | NP_000224.2 | LH/CG-R, LSH-R, Luteinizing hormone receptor, LHR, LHCGR, LCGR, LGR2, LHRHR |
| LIF R alpha | LIFR | Leukemia inhibitory factor receptor | NM_002310 | LIF receptor, LIF-R, CD118 |
| LIF | LIF | Leukemia Inhibitoty Factor | NM_002309 | Differentiation-stimulating factor, D factor, Melanoma-derived LPL inhibitor, MLPLI, Emflermin, LIF, HILDA |
| LIGHT | TNFSF14 | Tumor necrosis factor ligand superfamily member 14 | NM_172014 | Herpesvirus entry mediator-ligand, HVEM-L, CD258 |
| Lipocalin-1 | LCN1 | Lipocalin-1 | NM_002297 | Von Ebner gland protein, VEG protein, Tear prealbumin, TP, Tear lipocalin, Tlc, LCN1, VEGP |
| Livin | BIRC7 | Baculoviral IAP repeat-containing protein 7 | NP_071444.1, NP_647478.1 | KIAP, LIVIN, MLIAP, RNF50, Kidney inhibitor of apoptosis protein, KIAP, Melanoma inhibitor of apoptosis protein, ML-IAP, RING finger protein 50 |
| Lox-1 | OLR1 | Oxidized low-density lipoprotein receptor 1 | NP_002534.1 | Lectin-type oxidized LDL receptor 1, Lectin-like oxidized LDL receptor 1, Lectin-like oxLDL receptor 1, hLOX-1, LOX-1 |
| LRP-1 | LRP1 | Prolow-density lipoprotein receptor-related protein 1 | NM_002332 | Alpha-2-macroglobulin receptor, A2MR, Apolipoprotein E receptor, APOER, CD91, APR |
| LRP-6 | LRP6 | Low-density lipoprotein receptor-related protein 6 | NM_002336 | |
| L-selectin | SELL | L-selectin | NM_000655 | Lymph node homing receptor, Leukocyte adhesion molecule 1, LAM-1, Leukocyte surface antigen Leu-8, TQ1, gp90-MEL, Leukocyte-endothelial cell adhesion molecule 1, LECAM1, CD62 antigen-like family member L, CD62L, LNHR, LYAM1 |

TABLE 15-continued

Proteins for Use as Biomarkers

| Cytokine Name | Official Symbol | Full Name | Genbank | Related Names |
|---|---|---|---|---|
| Ltn/Lptn | XCL1 | Lymphotactin | NM_002995 | C motif chemokine 1, Cytokine SCM-1, ATAC, Lymphotaxin, SCM-1-alpha, Small-inducible cytokine C1, XC chemokine ligand 1 |
| Luciferase | Luciferase | Luciferin 4-monooxygenase | NP_002333.1 | |
| Lymphotoxin beta | LTB | Lymphotoxin beta | NM_009588 | LT-beta, Tumor necrosis factor C, TNF-C, Tumor necrosis factor ligand superfamily member 3, LTB, TNFC, TNFSF3 |
| Lymphotoxin beta R | LTBR | Lymphotoxin beta receptor | NM_002342 | Tumor necrosis factor receptor superfamily member 3, Lymphotoxin-beta receptor, Tumor necrosis factor receptor 2-related protein, Tumor necrosis factor C receptor, LTBR, D12S370, TNFCR, TNFRSF3 |
| LYVE-1 | LYVE1 | Lymphatic vessel endothelial hyaluronic acid receptor 1 | NP_006682.2 | Cell surface retention sequence-binding protein 1, CRSBP-1, Hyaluronic acid receptor, Extracellular link domain-containing protein 1, CRSBP1, HAR, XLKD1 |
| MAC-1 | ITGAM | Integrin alpha-M | NM_000632 | Cell surface glycoprotein MAC-1 subunit alpha, CR-3 alpha chain, Leukocyte adhesion receptor MO1, Neutrophil adherence receptor, CD11 antigen-like family member B, CD11b, ITGAM, CD11B, CR3A |
| Marapsin | MPN | Marapsin | NP_114154.1 | Pancreasin, Channel-activating protease 2, CAPH2, Serine protease 27 |
| MCP-1 | CCL2 | C-C motif chemokine 2 | NM_002982 | Small-inducible cytokine A2, Monocyte chemoattractant protein 1, Monocyte chemotactic protein 1, MCP-1, Monocyte chemotactic and activating factor, MCAF, Monocyte secretory protein JE, HC11, CCL2, MCP1, SCYA2 |
| MCP-2 | CCL8 | C-C motif chemokine 8 | NM_005623 | Small-inducible cytokine A8, Monocyte chemoattractant protein 2, Monocyte chemotactic protein 2, MCP2, SCYA10, SCYA8 |
| MCP-3 | CCL7 | C-C motif chemokine 7 | NM_006273 | Small-inducible cytokine A7, Monocyte chemoattractant protein 3, Monocyte chemotactic protein 3 |
| MCP-4 | CCL13 | C-C motif chemokine 13 | NM_005408 | Small-inducible cytokine A13, Monocyte chemoattractant protein 4, Monocyte chemotactic protein 4, MCP-4, CK-beta-10, NCC-1, SCYA13 |
| MCSF | CSF1 | Macrophage colony-stimulating factor 1 | NM_000757 | Macrophage colony-stimulating factor 1, CSF-1, MCSF, M-CSF, Lanimostim |
| M-CSF R | CSF1R | Macrophage colony-stimulating factor 1 receptor | NP_005202.2 | Fms proto-oncogene, c-fms, CD115 |
| MDC | CCL22 | C-C motif chemokine 22 | NM_002990 | Small-inducible cytokine A22, Macrophage-derived chemokine, MDC(1-69), Stimulated T-cell chemotactic protein 1, CC chemokine STCP-1 |
| Mesothelin | MSLN | Mesothelin | NP_005814.2, NP_037536.2 | Pre-pro-megakaryocyte-potentiating factor, CAK1 antigen, MPF |
| MFG-E8 | MFGE8 | Lactadherin | NM_005928 | Milk fat globule-EGF factor 8, MFG-E8, HMFG, Breast epithelial antigen BA46, MFGM |
| MFRP | MFRP | Membrane frizzled-related protein | NM_031433 | Membrane-type frizzled-related protein |
| MICA | MIC-A | MHC class I polypeptide-related sequence A | NP_000238.1 | PERB11.1 |
| MICB | MIC-B | MHC class I polypeptide-related sequence B | NP_005922.2 | PERB11.2 |
| Midkine | MDK | Midkine | NP_001012333.1, NP_001012334.1, NP_002382.1 | Neurite outgrowth-promoting protein, Midgestation and kidney protein, Amphiregulin-associated protein, ARAP, Neurite outgrowth-promoting factor 2, MK1, NEGF2, MK |
| MIF | MIF | Macrophage migration inhibitory factor | NM_002415 | Phenylpyruvate tautomerase, L-dopachrome tautomerase, L-dopachrome isomerase, Glycosylation-inhibiting factor, GIF, MIF, GLIF, MMIF |
| MIP 2 | Gro-beta | C—X—C motif chemokine 2 | NP_002080.1 | Macrophage inflammatory protein 2-alpha, MIP2-alpha, Growth-regulated protein beta, Gro-beta, GRO2, GROB, MIP2A, SCYB2 |
| MIP-1alpha | CCL3 | C-C motif chemokine 3 | NM_002983 | Small-inducible cytokine A3, Macrophage inflammatory protein 1-alpha, MIP-1-alpha, Tonsillar lymphocyte LD78 alpha protein, G0/G1 switch regulatory protein 19-1, G0S19-1 protein, SIS-beta, PAT 464.1, G0S19-1, MIP1A, SCYA3 |
| MIP-1beta | CCL4 | C-C motif chemokine 4 | NM_002984 | Small-inducible cytokine A4, Macrophage inflammatory protein 1-beta, MIP-1-beta, MIP-1- |

TABLE 15-continued

Proteins for Use as Biomarkers

| Cytokine Name | Official Symbol | Full Name | Genbank | Related Names |
|---|---|---|---|---|
| | | | | beta(1-69), T-cell activation protein 2, ACT-2, PAT 744, Protein H400, SIS-gamma, Lymphocyte activation gene 1 protein, LAG-1, HC21, G-26 T-lymphocyte-secreted protein, LAG1, MIP1B, SCYA4 |
| MIP-1delta | CCL15 | C-C motif chemokine 15 | NM_032965 | Small-inducible cytokine A15, Macrophage inflammatory protein 5, MIP-5, Chemokine CC-2, HCC-2, NCC-3, MIP-1 delta, Leukotactin-1, LKN-1, Mrp-2b |
| MIP-3 alpha | CCL20 | C-C motif chemokine 20 | NM_004591 | Small-inducible cytokine A20, Macrophage inflammatory protein 3 alpha, MIP-3-alpha, Liver and activation-regulated chemokine, CC chemokine LARC, Beta chemokine exodus-1, MIP3A, SCYA20 |
| MIP-3 beta | CCL19 | C-C motif chemokine 19 | NM_006274 | Small-inducible cytokine A19, Macrophage inflammatory protein 3 beta, MIP-3-beta, EBI1-ligand chemokine, ELC, Beta chemokine exodus-3, CK beta-11, CCL19, ELC, MIP3B, SCYA19 |
| MIS | AMH | Mullerian inhibiting factor | NM_000479 | MIS, Anti-Muellerian hormone, AMH, Muellerian-inhibiting substance, MIF |
| MMP-1 | MMP1 | Interstitial collagenase | NM_002421 | Matrix metalloproteinase-1, MMP-1, Fibroblast collagenase |
| MMP-2 | | 72 kDa type IV collagenase | NP_001121363.1, NP_004521.1 | 72 kDa gelatinase, Matrix metalloproteinase-2, MMP-2, Gelatinase A, TBE-1, CLG4A |
| MMP-10 | MMP10 | Stromelysin-2 | NM_002425 | Matrix metalloproteinase-10, Transin-2, MMP10, STMY2 |
| MMP-11 | MMP11 | Stromelysin-3 | NM_005940 | Stromelysin-3, Matrix metalloproteinase-11, STMY3, SL-3, ST3 |
| MMP-12 | MMP12 | Macrophage metalloelastase | NM_002426 | Macrophage elastase, HME, Matrix metalloproteinase-12 |
| MMP-13 | MMP13 | Collagenase 3 | NM_002427 | Matrix metalloproteinase-13 |
| MMP-14 | MMP14 | Matrix metalloproteinase-14 | NM_004995 | Membrane-type matrix metalloproteinase 1, MT-MMP 1, MMP-X1 |
| MMP-15 | MMP-15 | Matrix metalloproteinase-15 | NM_002428 | Membrane-type matrix metalloproteinase 2, MT-MMP 2, MTMMP2, SMCP-2 |
| MMP-16 | MMP-16 | Matrix metalloproteinase-16 | NM_005941 | Membrane-type matrix metalloproteinase 3, MT-MMP 3, MMP-X2 |
| MMP-19 | MMP-19 | Matrix metalloproteinase-19 | NM_002429 | Matrix metalloproteinase RASI, MMP-18 |
| MMP-20 | MMP-20 | Matrix metalloproteinase-20 | NM_004771 | Enamel metalloproteinase, Enamelysin |
| MMP-24 | MMP-24 | Matrix metalloproteinase-24 | NM_006690 | Membrane-type matrix metalloproteinase 5, MT-MMP 5, MT5-MMP, MMP24, MT5MMP |
| MMP-25 | MMP-25 | Matrix metalloproteinase-25 | NM_022468 | Membrane-type matrix metalloproteinase 6, MT-MMP 6, Membrane-type-6 matrix metalloproteinase, Leukolysin, MMP20, MMPL1, MT6MMP |
| MMP-3 | MMP-3 | Matrix metalloproteinase-3 | NM_002422 | Stromelysin-1, Transin-1, MMP3, STMY1 |
| MMP-7 | MMP-7 | Matrix metalloproteinase-7 | NM_002423 | Matrilysin, Pump-1 protease, Uterine metalloproteinase, Matrin, MPSL1, PUMP1 |
| MMP-8 | MMP-8 | Matrix metalloproteinase-8 | NM_002424 | PMNL collagenase, PMNL-CL, CLG1 |
| MMP-9 | MMP-9 | Matrix metalloproteinase-9 | NM_004994 | 92 kDa type IV collagenase, 92 kDa gelatinase, Gelatinase B, GELB, CLG4B |
| NAIP | NAIP | Neuronal apoptosis inhibitory protein | NP_004527.2 | Baculoviral IAP repeat-containing protein 1, BIRC1 |
| Nanog | Nanog | Homeobox protein NANOG | NP_079141.2 | Homeobox transcription factor Nanog, hNanog |
| NAP-2 | NAP-2 | Neutrophil-activating peptide 2 | NM_002704 | Platelet basic protein, C—X—C motif chemokine 7, Small-inducible cytokine B7, Leukocyte-derived growth factor, LDGF, Macrophage-derived growth factor, MDGF |
| NCAM-1 | NCAM-1 | Neural cell adhesion molecule 1 | NP_002695.1 | CD56 |
| Neprilysin | EPN | Neprilysin | NP_000893.2, NP_009218.2, NP_009219.2, NP_009220.2 | Neutral endopeptidase 24.11, Neutral endopeptidase, NEP, Enkephalinase, Atriopeptidase, Common acute lymphocytic leukemia antigen, CALLA, CD10, MME |
| Nesfatin | Nefa | Nucleobindin-2 | NP_005004.1 | DNA-binding protein NEFA, Nucb2, Nefa |
| Nestin | NES | Nestin | NP_006608.1 | |
| Neuritin | Neuritin | Neuritin | NRN | NRN1 |
| NeuroD1 | NEUROD1 | Neurogenic differentiation factor 1 | NM_002500 | |
| Neuropilin-2 | NRP2 | Neuropilin-2 | NM_018534 | Vascular endothelial cell growth factor 165 receptor 2, NRP2, VEGF165R2 |

TABLE 15-continued

Proteins for Use as Biomarkers

| Cytokine Name | Official Symbol | Full Name | Genbank | Related Names |
|---|---|---|---|---|
| Neuropeptide Y | NPY | Neuropeptide Y | NP_000896.1 | Neuropeptide tyrosine, C-flanking peptide of NPY, CPON |
| NGF R | NGFR | Tumor necrosis factor receptor superfamily member 16 | NM_002507 | Low-affinity nerve growth factor receptor, NGF receptor, Gp80-LNGFR, p75 ICD, Low affinity neurotrophin receptor p75NTR, CD271, NGFR, TNFRSF16 |
| Nidogen-1 | NID-1 | Nidogen-1 | NP_002499.2 | Entactin, NID |
| NOV | NOV | Protein NOV homolog | NM_002514 | Nephroblastoma overexpressed gene protein homolog, NOV, CCN3, IGFBP9, NOVH |
| NrCAM | NRCAM | Neuronal cell adhesion molecule | NP_001032209.1. NP_005001.3 | NgCAM-related cell adhesion molecule, hBravo, KIAA0343 |
| NRG2 | NRG2 | Pro-neuregulin-2, membrane-bound isoform | XM_001129975 | Pro-NRG2, NTAK |
| NRG3 | NRG3 | Pro-neuregulin-3, membrane-bound isoform | XM_166086 | Pro-NRG3, |
| NT-3 | NTF3 | Neurotrophin-3 | NM_002527 | Neurotrophic factor, HDNF, Nerve growth factor 2, NGF-2, NTF3 |
| NT-4 | NTF4 | Neurotrophin-4 | NM_006179 | Neurotrophin-4, NT-4, Neutrophic factor 4, Neurotrophin-5, NT-5, NTF5 |
| NTN | NRTN | Neurturin | NP_004549.1 | |
| 03-Oct | POU5F1 | POU domain, class 5, transcription factor 1 | NP_002692.2. NP_976034.3 | Octamer-binding transcription factor 3, Oct-4, OTF3 |
| Omentin | ITLN-1 | Omentin | NP_060095.2 | Intelectin-1, ITLN-1, Intestinal lactoferrin receptor, Galactofuranose-binding lectin, Endothelial lectin HL-1, ITLN1, INTL, ITLN, LFR |
| Osteoprotegerin | OPG | Tumor necrosis factor receptor superfamily member 11B | NM_002546 | Osteoprotegerin, Osteoclastogenesis inhibitory factor, TNFRSF11B, OCIF, OPG |
| Orexin | OX | Orexin | O43612 | Hypocretin, Hcrt, OX, PPORX, PPDX |
| Oncostatin M | OSM | Oncostatin-M | NM_020530 | |
| Osteocalcin | OSTCN | Osteocalcin | NP_954642.1 | Gamma-carboxyglutamic acid-containing protein, Bone Gla protein, BGP |
| Osteocrin | OSTN | Osteocrin | NM_198184 | Musclin |
| Osteopontin | OPN | Osteopontin | NP_000573.1, NP_001035147.1 | BNSP, OPN, Bone sialoprotein 1, Secreted phosphoprotein 1, SPP-1, Urinary stone protein, Nephropontin, Uropontin |
| Osteoprotegerin | OPG | Osteoprotegerin | NP_002537.3 | Osteoclastogenesis inhibitory factor, OCIF, Tumor necrosis factor receptor superfamily member 11B |
| OX40 Ligand | TNFSF4 | OX40 ligand | NM_003326 | Tumor necrosis factor ligand superfamily member 4, Glycoprotein Gp34, TAX transcriptionally-activated glycoprotein 1, CD252, TNFSF4, TXGP1 |
| p53 | TP53 | Cellular tumor antigen p53 | NP_000537.3, NP_001119584.1 | Tumor suppressor p53, Phosphoprotein p53, Antigen NY-CO-13, P53 |
| PAI-1 | | Plasminogen activator inhibitor 1 | NP_000593.1 | Endothelial plasminogen activator inhibitor, SERPINE1, PAI1, PLANH1 |
| PARC | CCL18 | C-C motif chemokine 18 | NM_002988 | Small-inducible cytokine A18, Macrophage inflammatory protein 4, MIP-4, Pulmonary and activation-regulated chemokine, CC chemokine PARC, Alternative macrophage activation-associated CC chemokine 1, AMAC-1, Dendritic cell chemokine 1, DC-CK1 |
| P-Cadherin | CDH3 | Placental cadherin | NP_001784.2 | Cadherin-3 |
| PD-ECGF | ECGF1 | Platelet-derived endothelial cell growth factor | NM_001953 | Thymidine phosphorylase, EC = 2.4.2.4, TdRPase, TP, Gliostatin, TYMP |
| PDGF R alpha | PDGFRA | Alpha-type platelet-derived growth factor receptor | NM_006206 | PDGF-R-alpha, CD140 antigen-like family member A, CD140a antigen, CD140a |
| PDGF R beta | PDGFRB | Beta-type platelet-derived growth factor receptor | NM_002609 | PDGF-R-beta, CD140 antigen-like family member B, CD140b, PDGFRB |
| PDGF-AA | PDGFA | Platelet-derived growth factor subunit A | NP_002598.4, NP_148983.1 | Platelet-derived growth factor A chain, Platelet-derived growth factor alpha polypeptide, PDGF-1 |
| PDGF-BB | PDGFB | Platelet-derived growth factor subunit B | NP_002599.1 | Platelet-derived growth factor B chain, Platelet-derived growth factor beta polypeptide, PDGF-2, c-sis, INN = Becaplermin, PDGF2, SIS |
| PDGF-C | PDGFC | Platelet-derived growth factor C | NM_016205 | Spinal cord-derived growth factor, SCDGF, Fallotein, VEGF-E |
| PDGF-D | PDGFD | Platelet-derived growth factor D | NM_025208 | Iris-expressed growth factor, Spinal cord-derived growth factor B |

TABLE 15-continued

Proteins for Use as Biomarkers

| Cytokine Name | Official Symbol | Full Name | Genbank | Related Names |
|---|---|---|---|---|
| PDX-1 | PDX-1 | Pancreas/duodenum homeobox protein 1 | NP_000200.1 | Insulin promoter factor 1, IPF-1, Islet/duodenum homeobox-1, IDX-1, Somatostatin-transactivating factor 1, STF-1, Insulin upstream factor 1, IUF-1, Glucose-sensitive factor, GSF |
| PECAM-1 | PECAM-1 | Platelet endothelial cell adhesion molecule | NM_000442 | PECAM-1, EndoCAM, GPIIA, CD31 |
| PEDF | PEDF | Pigment epithelium-derived factor | | Serpin-F1, EPC-1 |
| Peptide YY | PYY2 | Putative peptide YY-2 | | |
| PTX3 | PTX3 | Pentraxin-related protein PTX3 | NM_002852 | Pentaxin-related protein PTX3, Tumor necrosis factor-inducible gene 14 protein, TSG-14, TNFAIP5, TSG14 |
| Persephin | PSPN | Persephin | NP_004149.1 | PSP |
| PF4 | PF4 | Platelet factor 4 | NM_002619 | C—X—C motif chemokine 4, Oncostatin-A, Iroplact |
| PIGF | PGF | Placenta growth factor | NM_002632 | PGFL, PLGF |
| PLUNC | PLUNC | Protein Plunc | NM_130852 | Palate lung and nasal epithelium clone protein, Lung-specific protein X, Nasopharyngeal carcinoma-related protein, Tracheal epithelium-enriched protein, Secretory protein in upper respiratory tracts, Von Ebner protein HI, LUNX, NASG, SPURT |
| PPARG | PPARG | Peroxisome proliferator-activated receptor gamma | NP_056953.2, NP_619725.2, NP_619726.2 | PPAR-gamma, Nuclear receptor subfamily 1 group C member 3, NR1C3 |
| PR | PGR | Progesterone receptor | NP_000917.3 | Nuclear receptor subfamily 3 group C member 3, NR3C3 |
| Progranulin | GRN | Granulins | NM_002087 | Proepithelin, PEPI |
| Prohibitin | PHB | Prohibitin | NP_002625.1 | |
| Prolactin | PRL | Prolactin | NM_000948 | |
| PSA | PSA | Puromycin-sensitive aminopeptidase | NP_006301.3 | NPEPPS |
| P-selectin | SELP | P-selectin | NM_003005 | Granule membrane protein 140, GMP-140, PADGEM, Leukocyte-endothelial cell adhesion molecule 3, LECAM3, CD62 antigen-like family member P, CD62P, SELP, GMRP, GRMP |
| RAGE | RAGE | Advanced glycosylation end product-specific receptor | NM_001136 | Receptor for advanced glycosylation end products, AGER |
| RANK | TNFRSF11A | Tumor necrosis factor receptor superfamily member 11A | NM_003839 | Receptor activator of NF-KB, Osteoclast differentiation factor receptor, ODFR, CD265 |
| RANTES | CCL5 | C-C motif chemokine 5 | NM_002985 | Small-inducible cytokine A5, T-cell-specific protein RANTES, SIS-delta, T cell-specific protein P228, TCP228, Eosinophil-chemotactic cytokine, EoCP, D17S136E, SCYA5 |
| RBP4 | RBP4 | Retinol-binding protein 4 | NP_006735.2 | Plasma retinol-binding protein, PRBP, RBP |
| RELM beta | RELMB | Resistin-like beta | NM_032579 | Cysteine-rich secreted protein FIZZ2, Colon and small intestine-specific cysteine-rich protein, Cysteine-rich secreted protein A12-alpha-like 1, Colon carcinoma-related gene protein, CCRG, FIZZ2, HXCP2, RETNL2 |
| RELT | RELT | Receptor expressed in lymphoid tissues | NM_152222 | TNFRSF19L, Tumor necrosis factor receptor superfamily member 19L |
| Resistin | RETN | Resistin | NP_065148.1 | Cysteine-rich secreted protein FIZZ3, Adipose tissue-specific secretory factor, ADSF, C/EBP-epsilon-regulated myeloid-specific secreted cysteine-rich protein, Cysteine-rich secreted protein A12-alpha-like 2, FIZZ3, HXCP1, RSTN |
| ROBO4 | ROBO4 | Roundabout homolog 4 | NM_019055 | Magic roundabout |
| S100 A8 | S100 A8 | Protein S100-A8 | NM_002964 | S100 calcium-binding protein A8, Calgranulin-A, Migration inhibitory factor-related protein 8, MRP-8, P8, Cystic fibrosis antigen, CFAG, Leukocyte L1 complex light chain, Calprotectin L1L subunit, Urinary stone protein band A, CAGA, CFAG, MRP8 |
| S100 A9 | S100 A9 | Protein S100-A9 | NM_002965 | S100 calcium-binding protein A9, Calgranulin-B, Migration inhibitory factor-related protein 14, MRP-14, P14, Leukocyte L1 complex heavy chain, Calprotectin L1H subunit, CAGB, CFAG, MRP14 |
| S100A10 | S100A10 | Protein S100-A10 | NM_002966 | S100 calcium-binding protein A10, Calpactin-1 light chain, Calpactin I light chain, p10 protein, p11, Cellular ligand of annexin II, S100A10, ANX2LG, CAL1L, CLP11 |
| S100B | S100B | Protein S100-B | NP_006263.1 | S100 calcium-binding protein B, S-100 protein subunit beta, S-100 protein beta chain |

TABLE 15-continued

Proteins for Use as Biomarkers

| Cytokine Name | Official Symbol | Full Name | Genbank | Related Names |
|---|---|---|---|---|
| SAA | SAA1 | Serum amyloid A protein | NM_199161 | SAA2 |
| SCF | SCF | Stem Cell Factor | NP_000890.1, NP_003985.2 | Kit ligand, C-kit ligand, Mast cell growth factor, MGF, KITLG |
| SCF R | SCFR | Mast/stem cell growth factor receptor | NP_000213.1. NP_001087241.1 | Proto-oncogene tyrosine-protein kinase Kit, c-kit, CD117, KIT |
| SDF-1 | CXCL12 | Stromal cell-derived factor 1 | NM_000609 | C—X—C motif chemokine 12, Pre-B cell growth-stimulating factor, PBSF, hIRH |
| Semaphorin-3A | SEMA3A | Semaphorin-3A | NP_006071.1 | Semaphorin III, Sema III, SEMAD |
| Serotonin-2A | HTR2 | Serotonin receptor 2A | NP_000612.1 | 5-hydroxytryptamine receptor 2A, HTR2A, 5-HT-2A, 5-HT-2 |
| SERPINA1 | SERPINA1 | Alpha-1-antitrypsin | NP_000286.3, NP_001002235.1, NP_001002236.1, NP_001121172.1, NP_001121173.1, NP_001121174.1, NP_001121175.1, NP_001121176.1, NP_001121177.1, NP_001121178.1, NP_001121179.1 | Alpha-1 protease inhibitor, Alpha-1-antiproteinase, AAT, PI |
| Serpin A8 | SERPINA8 | Angiotensinogen | NP_000020.1 | AGT |
| sFRP-1 | SFRP1 | Secreted frizzled-related protein 1 | NM_003012 | Secreted apoptosis-related protein 2, SARP-2, FRP, FRP1, SARP2 |
| sFRP-3 | SFRP3 | Secreted frizzled-related protein 3 | NM_001463 | Frizzled-related protein 1, FrzB-1, Frezzled, Fritz, FRZB, FIZ, FRE, FRP, FRZB1 |
| sFRP-4 | SFRP4 | Secreted frizzled-related protein 4 | NM_003014 | FRPHE, Frizzled protein, human endometrium |
| SIGIRR | SIGIRR | Single Ig IL-1-related receptor | NM_021805 | Single Ig IL-1R-related molecule, Single immunoglobulin domain-containing IL1R-related protein, Toll/interleukin-1 receptor 8 |
| Siglec-5 | SIGLEC5 | Sialic acid-binding Ig-like lectin 5 | NP_003821.1 | Obesity-binding protein 2, OB-binding protein 2, OB-BP2, CD33 antigen-like 2, CD170, CD33L2, OBBP2 |
| Siglec-9 | Siglec-9 | Sialic acid-binding Ig-like lectin 9 | NP_055256.1 | Protein FOAP-9 |
| SLPI | SLPI | Antileukoproteinase | NM_003064 | Secretory leukocyte protease inhibitor, HUSI-1, Seminal proteinase inhibitor, BLPI, Mucus proteinase inhibitor, MPI, WAP four-disulfide core domain protein 4, Protease inhibitor WAP4, WAP4, WFDC4 |
| SMAC | DIABLO | Diablo homolog, mitochondrial | NP_063940.1, NP_620307.1 | Second mitochondria-derived activator of caspase, Smac protein, Direct IAP-binding protein with low pI |
| Smad 1 | Smad 1 | Mothers against decapentaplegic homolog 1 | NM_005900 | Mothers against decapentaplegic homolog 1, Mothers against DPP homolog 1, Mad-related protein 1, hSMAD1, Transforming growth factor-beta-signaling protein 1, BSP-1, JV4-1, MADH1, MADR1 |
| Smad 4 | Smad 4 | Mothers against decapentaplegic homolog 4 | NP_005350.1 | SMAD 4, hSMAD4, Deletion target in pancreatic carcinoma 4, DPC4, MADH4 |
| Smad 5 | Smad 5 | Mothers against decapentaplegic homolog 5 | NP_001001419.1, NP_001001420.1, NP_005894.3 | hSmad5, JV5-1, MADH5 |
| Smad 7 | Smad 7 | Mothers against decapentaplegic homolog 7 | NP_005895.1 | MADH7, MADH8, hSMAD7 |
| Smad 8 | Smad 8 | Mothers against decapentaplegic homolog 9 | NP_001120689.1. NP_005896.1 | Madh6, SMAD9, MADH6, MADH9 |
| Soggy-1 | SGY-1 | Protein soggy-1 | NP_055234.1 | Dickkopf-like protein 1, Cancer/testis antigen 34, CT34, DKKL1 |
| Sonic Hedgehog | SHH | Sonic hedgehog protein | NM_000193 | HHG-1 |
| SOX2 | SOX2 | Transcription factor SOX-2 | NP_003097.1 | |
| SOX17 | SOX17 | Transcription factor SOX-17 | NP_071899.1 | |
| SPARC | SPARC | SPARC | NM_003118 | Secreted protein acidic and rich in cysteine, Osteonectin, ON, Basement-membrane protein 40, BM-40 |
| Spinesin | TMPRSS5 | Transmembrane protease, serine 5 | NM_030770 | |

TABLE 15-continued

Proteins for Use as Biomarkers

| Cytokine Name | Official Symbol | Full Name | Genbank | Related Names |
|---|---|---|---|---|
| SSTR2 | SSTR2 | Somatostatin receptor type 2 | NP_001041.1 | SS2R, SRIF-1 |
| Survivin | BIRC5 | Baculoviral IAP repeat-containing protein 5 | NP_001012270.1, NP_001012271.1, NP_001159.2. | Apoptosis inhibitor survivin, Apoptosis inhibitor 4, API4, IAP4 |
| Syndecan-3 | SDC3 | Syndecan-3 | NP_055469.3 | KIAA0468, SYND3 |
| TNFRSF13B | TNFRSF13B | Tumor necrosis factor receptor superfamily member 13B | NM_012452 | Transmembrane activator and CAML interactor, CD267, TACI |
| TARC | CCL17 | Thymus and activation-regulated chemokine | NP_002978.1 | Small-inducible cytokine A17, Thymus and activation-regulated chemokine, CC chemokine TARC, SCYA17, |
| TCCR | IL27RA | Interleukin-27 receptor subunit alpha | NM_004843 | WSX-1, Type I T-cell cytokine receptor, Protein CRL1, CRL1, WSX1 |
| TECK | CCL25 | Thymus-expressed chemokine | NM_005624 | C-C motif chemokine 25, Small-inducible cytokine A25, Thymus-expressed chemokine, Chemokine TECK, SCYA25 |
| TFPI | TFPI | Tissue factor pathway inhibitor | NM_006287 | Lipoprotein-associated coagulation inhibitor, LACI, Extrinsic pathway inhibitor, EPI, |
| TGF-alpha | TGFA | Protransforming growth factor alpha | NM_003236 | Transforming growth factor alpha, TGF-alpha, EGF-like TGF, ETGF, TGF type 1, TGFA |
| TGF-beta 1 | TGFB1 | Transforming growth factor beta-1 | NM_000660 | Latency-associated peptide, LAP, TGFB |
| TGF-beta 2 | TGFB2 | Transforming growth factor beta-2 | NM_003238 | Glioblastoma-derived T-cell suppressor factor, G-TSF, BSC-1 cell growth inhibitor, Polyergin, Cetermin |
| TGF-beta 3 | TGFB3 | Transforming growth factor beta-3 | NM_003239 | |
| TGF-beta RI | TGFBR1 | TGF-beta receptor type-1 | NM_004612 | Transforming growth factor-beta receptor type I, TGF-beta receptor type I, TGF-beta type I receptor, TbetaR-I, TGFR-1, Serine/threonine-protein kinase receptor R4, Activin receptor-like kinase 5, ALK-5 |
| TGF-beta RII | TGFBR2 | TGF-beta receptor type-2 | NM_001024847 | Transforming growth factor-beta receptor type II, TGF-beta receptor type II, TGF-beta type II receptor, TbetaR-II, TGFR-2 |
| TGF-beta RIII | TGFBR3 | TGF-beta receptor type III | NM_003243 | TGFR-3, Transforming growth factor beta receptor III, Betaglycan |
| Thrombin | Thrombin | Prothrombin | NP_000497.1 | Coagulation factor II, F2 |
| Thrombopoietin | THPO | Thrombopoietin | NM_000460 | TPO, Megakaryocyte colony-stimulating factor, Myeloproliferative leukemia virus oncogene ligand, C-mpl ligand, ML, Megakaryocyte growth and development factor, MGDF |
| Thrombospondin-1 | THBS1 | Thrombospondin-1 | NM_003246 | TSP, TSP1 |
| Thrombospondin-2 | THBS2 | Thrombospondin-2 | NM_003247 | TSP2 |
| Thrombospondin-4 | THBS4 | Thrombospondin-4 | NM_003248 | TSP4 |
| Thymopoietin | Thymopoietin | Thymopoietin | NP_003267.1 | TP, Lamina-associated polypeptide 2, isoform alpha, TP alpha, TP beta, Splenin, Thymopentin, TP5, LAP2, Lamina-associated polypeptide 2, isoforms beta/gamma |
| Thyroglobulin | TG | Thyroglobulin | NP_003226.4 | |
| Tie-1 | Tie-1 | Tyrosine-protein kinase receptor Tie-1 | MGI: 99906 | TIE |
| Tie-2 | TEK | Angiopoietin-1 receptor | NM_000459 | Tyrosine-protein kinase receptor TIE-2, hTIE2, Tyrosine-protein kinase receptor TEK, Tunica interna endothelial cell kinase, p140 TEK, CD202b |
| TIM-1 | TIM-1 | Hepatitis A virus cellular receptor 1 | NP_001092884.1, NP_036338.2 | HAVcr-1, T-cell immunoglobulin and mucin domain-containing protein 1, TIMD-1, T-cell membrane protein 1, TIM, HAVCR1, TIM1, TIMD1 |
| TIMP-1 | TIMP-1 | Metalloproteinase inhibitor 1 | NM_003254 | Tissue inhibitor of metalloproteinases, Erythroid-potentiating activity, EPA, Fibroblast collagenase inhibitor, Collagenase inhibitor, CLGI, TIMP |
| TIMP-2 | TIMP-2 | Metalloproteinase inhibitor 2 | NP_003246.1 | Tissue inhibitor of metalloproteinases 2, CSC-21K |
| TIMP-3 | TIMP-3 | Metalloproteinase inhibitor 3 | NM_000362 | Tissue inhibitor of metalloproteinases 3, TIMP-3, Protein MIG-5 |
| TIMP-4 | TIMP-4 | Metalloproteinase inhibitor 4 | NM_003256 | Tissue inhibitor of metalloproteinases 4 |
| Tissue Factor | TF | Tissue factor | NP_001984.1 | Coagulation factor III, Thromboplastin, CD142, F3 |
| TL1 | TNFSF15 | Tumor necrosis factor ligand superfamily member 15 | NM_005118 | Vascular endothelial cell growth inhibitor, TNF ligand-related molecule 1, TL1, VEGI |
| TLR1 | TLR1 | Toll-like receptor 1 | NM_003263 | Toll/interleukin-1 receptor-like protein, TIL, CD281, KIAA0012 |

TABLE 15-continued

Proteins for Use as Biomarkers

| Cytokine Name | Official Symbol | Full Name | Genbank | Related Names |
|---|---|---|---|---|
| TLR2 | TLR2 | Toll-like receptor 2 | NM_003264 | Toll/interleukin-1 receptor-like protein 4, CD282, TIL4 |
| TLR3 | TLR3 | Toll-like receptor 3 | NM_003265 | CD283 |
| TLR4 | TLR4 | Toll-like receptor 4 | NM_138554 | hToll, CD284 |
| TMEFF1 | TMEFF1 | Tomoregulin-1 | NM_003692 | Transmembrane protein with EGF-like and one follistatin-like domain, TR-1, H7365, C9orf2 |
| TMEFF2 | TMEFF2 | Tomoregulin-2 | NM_016192 | Transmembrane protein with EGF-like and two follistatin-like domains, TR-2, Hyperplastic polyposis protein 1, HPP1, TENB2, TPEF |
| TNF RI | TNFRSF1A | Tumor necrosis factor receptor superfamily member 1A | NM_001065 | p60, TNF-R1, TNFR-I, p55, CD120a |
| TNF RII | TNFRSF1B | Tumor necrosis factor receptor superfamily member 1B | NM_001066 | Tumor necrosis factor receptor 2, TNF-R2, Tumor necrosis factor receptor type II, p75, p80 TNF-alpha receptor, CD120b, Etanercept |
| TNF-alpha | TNF | Tumor necrosis factor | NP_000585.2 | TNFA, TNFSF2 |
| TNF-beta | LTA | Tumor necrosis factor beta | NP_000586.2 | Lymphotoxin-alpha, Tumor necrosis factor ligand superfamily member 1, TNFB, TNFSF1 |
| TNFRF18 | TNFRF18 | Tumor necrosis factor receptor superfamily member 18 | NP_004186.1, NP_683699.1, NP_683700.1 | Glucocorticoid-induced TNFR-related protein, Activation-inducible TNFR family receptor, AITR, GITR |
| TNFSF18 L | TNFSF18L | Tumor necrosis factor ligand superfamily member 18 | NP_005083.2 | Glucocorticoid-induced TNF-related ligand, hGITRL, Activation-inducible TNF-related ligand, AITRL, TL6 |
| TRADD | TRADD | Tumor necrosis factor receptor type 1-associated DEATH domain protein | NM_003789 | TNFRSF1A-associated via death domain |
| TRAIL R1 | TNFRSF10A | Tumor necrosis factor receptor superfamily member 10A | NP_003835.2 | Death receptor 4, TNF-related apoptosis-inducing ligand receptor 1, TRAIL receptor 1, CD261, APO2, DR4, TRAILR1 |
| TRAIL R2 | TNFRSF10B | Tumor necrosis factor receptor superfamily member 10B | NP_003833.4, NP_671716.2 | Death receptor 5, TNF-related apoptosis-inducing ligand receptor 2, TRAIL-R2, CD262, DR5, KILLER, TRAILR2, TRICK2, ZTNFR9 |
| TRAIL | TNFSF10 | Tumor necrosis factor ligand superfamily member 10 | NP_003801.1 | TNF-related apoptosis-inducing ligand, Protein TRAIL, Apo-2 ligand, CD253, APO2L |
| TRANCE | TNFSF11 | TNF-related activation-induced cytokine | NM_033012 | Tumor necrosis factor ligand superfamily member 11, Receptor activator of nuclear factor kappa B ligand, RANKL, Osteoprotegerin ligand, OPGL, Osteoclast differentiation factor, ODF, CD254 |
| TREM-1 | TREM-1 | Triggering receptor expressed on myeloid cells 1 | NM_018643 | Triggering receptor expressed on monocytes 1 |
| TROY | TNFRSF19 | Tumor necrosis factor receptor superfamily member 19 | NM_018647 | Toxicity and JNK inducer, TRADE, TAJ |
| TSG-6 | TNFAIP6 | TNF-stimulated gene 6 protein | NM_007115 | TNF-stimulated gene 6 protein, Tumor necrosis factor, alpha-induced protein 6, Hyaluronate-binding protein |
| TSHR | TSHR | Thyrotropin receptor | | Thyroid-stimulating hormone receptor, TSH-R, TSHR, LGR3 |
| TWEAK | TNFSF12 | TNF-related weak inducer of apoptosis | NP_003800.1 | TNF-related weak inducer of apoptosis, APO3 ligand, APO3L, DR3LG |
| TWEAK R | TNFRSF12A | Tweak-receptor | NP_057723.1 | Tumor necrosis factor receptor superfamily member 12A, Fibroblast growth factor-inducible immediate-early response protein 14, FGF-inducible 14, CD266, TNFRSF12A Synonyms: FN14 |
| Ubiquitin | Ubiquitin | Ubiquitin | NP_061828.1, NP_066289.2 | UBA80, UBCEP1 |
| uPA | PLAU | Urokinase-type plasminogen activator | NM_002658 | U-plasminogen activator |
| uPAR | PLAUR | Urokinase plasminogen activator surface receptor | NP_001005376.1, NP_001005377.1, NP_002650.1 | Monocyte activation antigen Mo3, CD87, MO3, UPAR |
| Vasorin | VASN | Vasorin | NM_138440 | Protein slit-like 2, SLITL2 |
| VCAM-1 | VCAM-1 | Vascular cell adhesion protein 1 | NP_001069.1, NP_542413.1 | V-CAM 1, INCAM-100, CD106, L1CAM |
| VE-Cadherin | CDH5 | Vascular endothelial cadherin | NM_001795 | Cadherin-5, 7B4 antigen, CD144 |
| VEGF | VEGFA | Vascular endothelial growth factor A | NM_001025366 | Vascular permeability factor, VPF |
| VEGF R2 | CD309 antigen | Vascular endothelial growth factor receptor 2 | NP_002244.1. | Kinase insert domain receptor, Protein-tyrosine kinase receptor Flk-1, CD309, KDR, FLK1 |

TABLE 15-continued

Proteins for Use as Biomarkers

| Cytokine Name | Official Symbol | Full Name | Genbank | Related Names |
|---|---|---|---|---|
| VEGF R3 | VEGF R3 | Vascular endothelial growth factor receptor 3 | NP_002011.2 | Tyrosine-protein kinase receptor FLT4 |
| VEGF-B | VEGFB | Vascular endothelial growth factor B | NM_003377 | VEGF-related factor, VRF |
| VEGF-C | VEGFC | Vascular endothelial growth factor C | NM_005429 | Vascular endothelial growth factor-related protein, VRP, Flt4 ligand, Flt4-L |
| VEGF-D | FIGF | Vascular endothelial growth factor D | NM_004469 | c-fos-induced growth factor, VEGFD |
| WIF-1 | WIF1 | Wnt inhibitory factor 1 | NM_007191 | |
| Vaspin | Vaspin | Visceral adipose tissue-derived serine protease inhibitor | NP_776249.1 | Serpin A12, Visceral adipose-specific serpin, OL-64 |
| Visfatin | NAMPT | Visfatin | NP_005737.1 | Nicotinamide phosphoribosyltransferase, NAmPRTase, EC = 2.4.2.12, Pre-B-cell colony-enhancing factor 1, Pre-B cell-enhancing factor, PBEF, PBEF1 |
| WISP-1 | WISP1 | WNT1-inducible-signaling pathway protein 1 | NP_003873.1, NP_543028.1 | Wnt-1-induced secreted protein, CCN4 |
| XEDAR | EDA2R | X-linked ectodysplasin-A2 receptor | NM_021783 | Tumor necrosis factor receptor superfamily member 27, TNFRSF27, EDA-A2 receptor |
| XIAP | XIAP | Baculoviral IAP repeat-containing protein 4 | NP_001158.2 | E3 ubiquitin-protein ligase XIAP, Inhibitor of apoptosis protein 3, X-linked inhibitor of apoptosis protein, X-linked IAP, IAP-like protein, HILP, XIAP, API3, BIRC4, IAP3 |

Thus, the disclosure provides biomarkers that distinguish between 3D and 2D cultured adherent stromal cells. In certain aspects and embodiments, the ASC are derived from placenta. Any one or a combination of at least two of the biomarkers can be used to identify an ASC-3D, to identify a ASC-2D, or to distinguish cells produced by a 3D vs a 2D method. Any one or a combination of at least two of the biomarkers can also be used to correlate the therapeutic efficacy of a cell population by differentiating between populations having biological properties characteristic of ASC-3D cells. Thus, in one aspect the invention also provides cells or a population of cells characterized by one or a combination of the biomarkers, whether gene or protein, as set forth herein.

Compositions Comprising Adherent Stromal Cells and Uses Thereof

In another aspect, the invention comprises a cell or a population of cells characterized by at least one biomarker or any subcombination or combination of biomarkers as described herein. Thus, in various embodiments, the cell or population of cells are characterized by biomarkers as set forth in any of the preceding paragraphs. In one aspect, the cell or population of cells is a cell or population of cells that is an adherent cell from placenta or a population of adherent cells from placenta.

In some embodiments, the population of cells is capable of suppressing immune reaction in a subject. As used herein the phrase "suppressing immune reaction in a subject" refers to decreasing or inhibiting the immune reaction occurring in a subject in response to an antigen (e.g., a foreign cell or a portion thereof). The immune response which can be suppressed by the adherent cells include the humoral immune responses, and cellular immune responses, which involve specific recognition of pathogen antigens via antibodies and T-lymphocytes (proliferation of T cells), respectively.

As used herein the term "treating" refers to inhibiting or arresting the development of a disease or condition and/or causing the reduction, remission, or regression of the disease or condition. In some embodiments the inhibition or arrest is accompanied by the reduction, remission, or regression or at least one symptom of the disease or condition. Those of skill in the art will understand that various methodologies and assays can be used to assess the development of a disease or condition, and similarly, various methodologies and assays may be used to assess the reduction, remission or regression of a disease or condition.

Cells or cellular compositions which may be administered in accordance with treating aspects of the invention include any of the adherent cells described herein, which may be cultured in three-dimensional or two dimensional settings. Administered cells may further include mesenchymal and-non mesenchymal partially or terminally differentiated derivatives of same.

Methods of deriving lineage specific cells from the adherent stromal cells are well known in the art. See for example, U.S. Pat. Nos. 5,486,359, 5,942,225, 5,736,396, 5,908,784 and 5,902,741.

The cells may be naive or genetically modified such as to derive a lineage of interest (see U.S. Pat. Appl. No. 20030219423).

The cells may be of autologous or non-autologous source (i.e., allogeneic or xenogeneic) of fresh or frozen (e.g., cryo-preserved) preparations.

Depending on the medical condition, the subject may be administered with additional chemical drugs (e.g., immuno-modulatory, chemotherapy etc.) or cells.

Since non-autologous cells may induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu MZ, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu MZ, et al., A novel cell encapsulation method using photosensitive poly(allylamine alpha-cyanocinnamylideneacetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 µm. Such microcapsules can be further encapsulated with additional 2-5 µm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al., Improving cell encapsulation through size control. J Biomater Sci Polym Ed. 2002;13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T.A. Microfabrication technology for pancreatic cell encapsulation. Expert Opin Biol Ther. 2002, 2: 633-46).

In any of the methods described herein, the cells can be administered either per se or, preferably as a part of a pharmaceutical composition that further comprises a pharmaceutically acceptable carrier. Also, as noted above, the cells can be placental-derived, thus, the compositions and pharmaceutical compositions for use in any of the various methods can be placental-derived adherent stromal cells. The placental-derived ASC may be ASC-3D or ASC-2D.

As used herein a "pharmaceutical composition" refers to a preparation of the adherent cells of the invention (i.e., adherent cells of a tissue selected from the group consisting of placenta and adipose tissue, which are obtained from a three-dimensional culture), with other chemical components such as pharmaceutically suitable carriers and excipients. The purpose of a pharmaceutical composition is to facilitate administration of the cells to a subject.

Hereinafter, the term "pharmaceutically acceptable carrier" refers to a carrier or a diluent that does not cause significant irritation to a subject and does not abrogate the biological activity and properties of the administered compound. Examples of carriers include, without limitation, propylene glycol, saline, emulsions and mixtures of organic solvents with water.

The term "excipient" refers to an inert substance added to a pharmaceutical composition to further facilitate administration of a compound. Examples of excipients include, without limitation, calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

One may administer the pharmaceutical composition in a systemic manner (as detailed hereinabove). Alternatively, one may administer the pharmaceutical composition locally, for example, via injection of the pharmaceutical composition directly into a tissue region of a patient.

Pharmaceutical compositions of the invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, physiological salt buffer, or freezing medium containing cryopreservents. For transmucosal administration, penetrants appropriate to the barrier to be permeated are used in the formulation. Such penetrants are generally known in the art.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans. Toxicity and therapeutic efficacy of the active ingredients described herein can be determined by standard pharmaceutical procedures in vitro, in cell cultures or experimental animals.

The data obtained from the in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1).

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually to levels of the active ingredient which are sufficient to effectively regulate the neurotransmitter synthesis by the implanted cells. Dosages necessary to achieve the desired effect can depend on individual characteristics and route of administration. Detection assays can be used to determine plasma concentrations. Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition.

Compositions including the preparation of the invention formulated in a compatible pharmaceutical carrier may also be prepared, placed in an appropriate container, and labeled for treatment of an indicated condition.

Compositions of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The adherent cells of the invention can be suitably formulated as pharmaceutical compositions which can be suitably packaged as an article of manufacture. Such an article of manufacture comprises a packaging material which comprises a label for use in a method of treating any of the diseases or conditions described herein.

It will be appreciated that the adherent cells of the present invention are capable of inducing immunosuppression and/or tolerance in a subject. Thus, the adherent cells may be used to treat any condition in need of immunosuppression and/or tolerance. Such conditions included, but are not limited to, autoimmune diseases and inflammatory diseases (including acute and chronic inflammatory diseases) including, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases. Accordingly, disclosed herein are methods of determining whether an adherent stromal cell was produced by three dimensional culture further comprising administering an adherent stromal cell found to be produced by three dimensional culture to a subject for treating autoimmune diseases and inflammatory diseases (including acute and chronic inflammatory diseases) including, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases as described herein.

Examples of autoimmune cardiovascular diseases include, but are not limited to atherosclerosis (Matsuura E. et al., Lupus. 1998; 7 Suppl 2:S 135), myocardial infarction (Vaarala 0. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J. Cardiol. 1999 Jun. 17; 83 (12A):75H), thrombocytopenic purpura (Moccia F. Ann Ital Med. Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., HistolHistopathol 2000 July; 15 (3):791; Tisch R, McDevitt H 0. ProcNatlAcadSci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res ClinPract 1996 October; 34 Suppl: S125), autoimmune thyroid diseases, Graves' disease (Orgiazzi J. EndocrinolMetabClin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J ReprodImmunol 1998 February; 37 (2):87), autoimmune anti-sperm infertility (Diekman A B. et al., Am J ReprodImmunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., GastroenterolHepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., ClinImmunolImmunopathol 1990 March; 54 (3):382), primary biliary cirrhosis (Jones D E. ClinSci (Colch) 1996 November; 91 (5):551; Strassburg C P. et al., Eur J GastroenterolHepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J ClinNeurosci. 2000 May; 7 (3):191); Guillain-Barre syndrome and autoimmune neuropathies (Kusunoki S. Am J Med. Sci. 2000 April; 319 (4):234), myasthenia, Lambert-Eaton myasthenic syndrome (Takamori M. Am J Med. Sci. 2000 April; 319 (4):204); paraneoplastic neurological diseases, cerebellar atrophy, paraneoplastic cerebellar atrophy and stiff-man syndrome (Hiemstra H S. et al., ProcNatlAcadSci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., ElectroencephalogrClinNeurophysiolSuppl 1999; 50:419); acquired neuromyotonia, arthrogryposis multiplex congenita (Vincent A. et al., Ann N Y Acad. Sci. 1998 May 13; 841:482), neuritis, optic neuritis (Soderstrom M. et al., J NeurolNeurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am SocNephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., ClinDiagn Lab Immunol. 1999 March; 6 (2):156); Chan 0 T. et al., Immunol Rev 1999 June; 169:107).

Furthermore, the adherent cells may be used to treat diseases associated with transplantation of a graft including, but are not limited to, graft rejection, chronic graft rejection, subacute graft rejection, hyperacute graft rejection, acute graft rejection and graft versus host disease.

The adherent cells are capable of connective tissue regeneration and/or repair. Thus, according to yet an additional aspect of the invention, there is provided a method of treating a medical condition requiring connective tissue regeneration and/or repair in a subject in need thereof. The phrase "connective tissue" refers to a supporting framework tissue comprising strands of collagen, elastic fibers (e.g., between and around muscle and blood vessels) and simple cells. Examples of connective tissues include, but are not limited to dense connective tissue (e.g., ligament, tendon, periodontal ligament), areolar connective tissue (e.g., with proteinaceous fibers such as collagen and elastin), reticular connective tissue, adipose tissue, blood, bone, cartilage, skin, intervertebral disc, dental pulp, dentin, gingival, extracellular matrix (ECM)-forming cells, loose connective tissue and smooth muscle cells. The phrase "medical condition requiring connective tissue regeneration and/or repair" refers to any pathology characterized by connective tissue damage (i.e., non-functioning tissue, cancerous or pre-cancerous tissue, broken tissue, fractured tissue, fibrotic tissue, or ischemic tissue) or loss (e.g., following a trauma, an infectious disease, a genetic disease, and the like). Non-limiting examples of such pathologies include, bone fracture, bone cancer (e.g., osteosarcoma, bone cancer metastasis), burn wound, articular cartilage defect and deep wound.

The phrase "administering to the subject" refers to the introduction of the cells described herein to target tissue. The cells can be derived from the recipient or from an allogeneic or xenogeneic donor. This phrase also encompasses "transplantation", "cell replacement" or "grafting" of the cells of the invention into the subject.

The adherent cells may also be used to treat conditions including subchondral-bone cysts, bone fractures, osteoporosis, osteoarthritis, degenerated bone, various cancers associated with connective tissue loss (e.g., bone cancer, osteosarcoma, bone metastases), cartilage damage, articular cartilage defect, degenerative disc disease, osteogenesisimperfecta (OI), burns, burn wounds, deep wounds, delayed wound-healing, injured ligaments and injured tendons.

The subject may be any mammal in treatment, including e.g. human or domesticated animals including, but not limited to, horses (i.e. equine), cattle, goat, sheep, pig, dog, cat, camel, alpaca, llama and yak.

As used herein the term "about" refers to ±0.10%.

Additional objects, advantages, and novel features of the invention will become apparent to one ordinarily skilled in the art upon examination of the following examples, which are not intended to be limiting. Additionally, each of the various embodiments and aspects of the invention as delineated hereinabove and as claimed in the claims section below finds experimental support in the following examples.

EXAMPLES

Example 1

Preparation of Placental ASC-2D and ASC-3D Cell Samples

Initial Seeding of ASC

Placental ASCs were prepared as previously described. Initial seeding in tissue culture plate surfaces ("TCPS") flasks and packed bed spinners with Fibracel disks was as follows. Briefly, ASCs (passage 4 cells) at $5-10 \times 10^6$ were thawed and ASC were plated at $1.5 \times 10^6$ in each of 3 triple flasks with full DMEM. After 3-4 days post first seeding (-70% confluence) the cells were harvested and used to seed 5 triple flasks. Three to four days following the second seeding (~70% confluence), cells were harvested and seeded four spinners with $8.1 \times 10^6$ ASC each and 4 175 cm2 flasks with $0.5 \times 10^6$ ASC each. Three days after the third seeding, the four flasks were harvested and seeded into 8 flasks (175 $cm^2$) with $0.5 \times 10^6$ ASC each.

TCPS Flasks

After 3 additional days, i.e., once cells in flask reached 70-80% confluence two flasks were used for RNA collection, two flasks for cell lysate, and two flasks for collection of condition media.

RNA was prepared from the 2D flasks by removing the media from one flask and washing with DPBS.5 ml RNA extraction lysis buffer was then added to the flask and it was incubated at room temperature ("RT") for 2 min, followed by a short vortex. Thee mL of the lysate is then transferred to a 15 ml tube and 3 ml 70% ethanol added. The mixture was then loaded on 4 RNA extraction columns—2×700 µl for each column—and the extraction continued according to Qiagen RNA extraction kit protocol. Once the eppendorf tubes with RNA were placed at −80° C., the process was repeated for the second flask. RNA purity was assessed using nanodrop and Bioanalyzer. The RNA was used to make cDNA according to the SAbiosciencecDNA kit instructions. Purity of cDNA was assessed using nanodrop. The cDNA was then used to analyze gene expression according to RT2 kit instructions.

Cell lysates were prepared from 2D flasks by adding proteinase inhibitors (100 µl of Sigma P8340) to Raybio cell lysis buffer brought to 2× with 10 mL distilled water. The media was removed from one flask and the flask washed twice with DPBS. Following removal of the DPBS, 3 ml of lx RayBio Cell Lysis Buffer was added and incubated for 1 minute. Cell lysis was verified by microscope. Lysis supernatant was collected and spun at 4600 rpm for 10 min at 4° C. Aliquots were prepared and frozen in liquid nitrogen. The procedure was then repeated for the second flask.

Cell counts were also determined using flasks designated for cell counting. This number was used to determine how much EBM/blocking reagent, if at all, to add to cell lysate for use in protein array. This number was also used for normalization of results.

Condition media was prepared from 2D flasks by washing the flasks with DPBS twice. Fifty milliliters of EBM was added and the flasks placed in an incubator for 24 hours. EBM was then collected, spun down at 4600 for 1 min at 4° C., and 6 aliquots of 10 ml prepared that were snap frozen in liquid nitrogen and placed at −80° C. TryplE was added to flasks and the cells collected for cell count (for CM normalization).

Spinner Flasks

Spinner flasks were used at day 6 post seeding ("6 dps") and RNA, cell lysate, and conditioned media prepared.

RNA was prepared by adding 350 µl RNA extraction lysis buffer to each of 4 eppendorf tubes. Twenty Fibracel disks were removed from the basket and placed in 50 mL tubes with 10 mL of wash medium. Following washing with DPBS, three Fibracel were placed in each eppendorf tube containing RNA lysis buffer, then vortexed for 2 minutes. Essentially as described above, RNA was prepared using the Qiagen RNA extraction kit, RNA purity measured, and cDNA prepared using the SAbiosciencecDNA kit. The second spinner flask was then processed. The cDNA was used to analyze gene expression according to RT2 kit instructions.

Cell lysates were prepared by removing 20 Fibracel from the basket at 6 dps and placed in 50 mL tubes with 10 mL of wash medium. Following washing with DPBS, 3 mL if 1X RayBio Cell Lysis Buffer was added, vortexed for 1 minute, then pipetted up and down 10 times with a 1000 µL pipette to remove cell lysate from Fibracel. The supernatant was removed, spun down at 4600 rpm for 10 minutes at 4° C. Aliquots of 5×0.6 mL were prepared and frozen at −80° C. The second spinner flask was then processed by collecting 30 additional FibraCel. For the second flask, cells were removed, counted, stained (before and after removal) and visualized under a microscope for cell quantification (for CL normalization). 2.3 gr of FibraCel (wet weight) was used for cell removal and freezing in freezing medium for future analysis. FibraCel was also saved in 4% PFA for future analysis.

Conditioned medium was prepared from the spinner flasks by removing the DMEM at 6 days post seeding. The basket was washed twice with DPBS and 150 mL EBM added. Following a 24 hour incubation in an incubator, the EBM was collected, spun down at 4600 rpm for 1 minute, and 6 aliquot of 10 mL prepared and snap frozen in liquid nitrogen. Twenty of the FibraCel were then collected and cells removed for counting, cell staining (before and after removal) and visualization under a microscope (for CM normalization). The FibraCel were saved in 4% PFA.

Example 2

Selection of Genes and Proteins for Differential Analysis

A panel of genes and proteins that are potentially differentially regulated in placental ASC-3D vs -2D cells was determined based on consideration of relevant biological pathways. The screening panels are presented in Tables 1-15, above.

Example 3

Analysis of Proteins Secreted into Culture Medium and in Cell Lysates

Conditioned medium and cell lysates were prepared as described in Example 1 was analyzed using RayBio® Human Angiogenesis and Human Inflammation Arrays (G series) (RayBiotech, Inc.) arrays according to the manufacture's instructions. Fluorescence was detected using a laser scanner and normalized, also according to the manufacture's instructions.

Tables 16 and 17 summarize the results of this experiment.

TABLE 16

| | Proteins Up-regulated in 3D Culture Medium | | | | | |
|---|---|---|---|---|---|---|
| | Data | | | | | |
| | PD280311 | | PD061210 | | t-Tests | |
| Protein | CM 2D | CM 3D | CM 2D | CM 3D | PD280311 | PD061210 |
| Angiogenin | | 425.5 | 4270.4 | 8555.3 | NA | 0.002049 |
| | | 2233.6 | 4425.5 | 8547.8 | | |
| | | 4189.7 | 5055.9 | 10860 | | |
| | 808.22 | 3938.9 | 4803.5 | 10846.4 | | |

TABLE 16-continued

Proteins Up-regulated in 3D Culture Medium

| | Data | | | | t-Tests | |
|---|---|---|---|---|---|---|
| | PD280311 | | PD061210 | | | |
| Protein | CM 2D | CM 3D | CM 2D | CM 3D | PD280311 | PD061210 |
| AVG | 808.22 | 2696.95 | 4625.09 | 9594.01 | | |
| St Dev | NA | 1933.79 | 391.90 | 1620.78 | | |
| IL-6 | | 4820.8 | 0 | 1888.8 | 0.000479 | <.0001 |
| | | 4819.2 | 0 | 1651.6 | | |
| | 87.4 | 5971.6 | 0 | 2710.6 | | |
| | 257.6 | 5971.7 | 0 | 2284.2 | | |
| AVG | 172.56 | 5395.85 | 0 | 2110.07 | | |
| St Dev | NA | 814.30 | 0 | 510.98 | | |
| Angiopoietin 1 | 622.55 | 814.5 | 1013.3 | 1525 | 0.602176 | 0.004104 |
| | 6651.1 | 814.2 | 991.4 | 1428.5 | | |
| | 45.35 | 1213.4 | 705.4 | 2217.5 | | |
| | 173.9 | 1128 | 862.4 | 1906.5 | | |
| AVG | 376.73 | 992.52 | 890.92 | 1749.41 | | |
| St Dev | 377.72 | 252.01 | 157.57 | 410.92 | | |
| MCP-3 | 2307.6 | 4270 | 171 | 539.6 | 0.002578 | 0.002794 |
| | 2401.7 | 4189 | 336.9 | 500.5 | | |
| | 83.5 | 4778.3 | 105.7 | 843.3 | | |
| | 211.1 | 4781.8 | 138.1 | 722.2 | | |
| AVG | 1274.50 | 4504.77 | 187.61 | 644.18 | | |
| St Dev | 1594.1 | 389.29 | 93.83 | 184.44 | | |
| uPAR | 2608.1 | 1561.4 | 445.9 | 1729.3 | 0.654952 | <.0001 |
| | 2579.8 | 1735 | 339.5 | 1641.3 | | |
| | 478.3 | 2057.8 | 347.6 | 1646 | | |
| | 527.4 | 2004.4 | 328.5 | 1916.9 | | |
| AVG | 1557.40 | 1839.67 | 364.44 | 1713.86 | | |
| St Dev | 1491.33 | 270.76 | 39.93 | 69.28 | | |

TABLE 17

Proteins Down-regulated in 3D Culture Medium

| | Data | | | | t-Tests | |
|---|---|---|---|---|---|---|
| | PD280311 | | PD061210 | | | |
| Protein | CM 2D | CM 3D | CM 2D | CM 3D | PD280311 | PD061210 |
| TIMP-1 | 520.3 | 376.7 | 3297.3 | 1048.3 | 0.049432 | 0.000211 |
| | | 414.98 | 3706.9 | 1116 | | |
| | 2124.5 | 493.7 | 3360.7 | 1903.1 | | |
| | 2114.1 | 443 | 3689.3 | 1863.3 | | |
| AVG | 1319.77 | 432.12 | 3503.70 | 1466.33 | | |
| St Dev | 1130.72 | 51.27 | 2.26 | 561.86 | | |
| TIMP-2 | 20428.7 | 1317.6 | 45729.6 | 7269.6 | <.0001 | <.0001 |
| | 13038.5 | 1293.5 | 47553 | 7200.6 | | |
| | 16611.43 | 1495.7 | 42444.3 | 8978 | | |
| | 17630.2 | 1381.2 | 43495 | 8995.5 | | |
| AVG | 16927.22 | 1371.98 | 44685.61 | 8020.03 | | |
| St Dev | 273.75 | 93.99 | 2765.77 | 1234.02 | | |
| IL-8 | 15215.79 | 3697.3 | 1941 | 966.8 | 0.003555 | 0.001433 |
| | | 3238.3 | 1781.6 | 933 | | |
| | 8561 | 3832.5 | 2566.4 | 1260.1 | | |
| | 12300.6 | 3851.5 | 2220 | 1151.8 | | |
| AVG | 12823.32 | 3654.91 | 2120.61 | 1065.90 | | |
| St Dev | 3383.46 | 264.58 | 366.67 | 180.34 | | |

A bar graph comparing several of the proteins up-regulated in ASC-3D vs ASC-2D culture medium are presented in FIG. 1. Based on these results, angiogenin, IL-6, angiopoietin-1 MCP-3 and uPAR are all upregulated in ASC-3D since there is a relative increase of these proteins in the culture medium of ASC-3D cells. Thus, any one of these protein biomarkers, a subcombination of them, or all of them in combination, may be used in identifying ASC-3D. Angiopoietin-1 and MCP-3 have been tested and found upregulated in all three batches tested to date.

Figure 2:
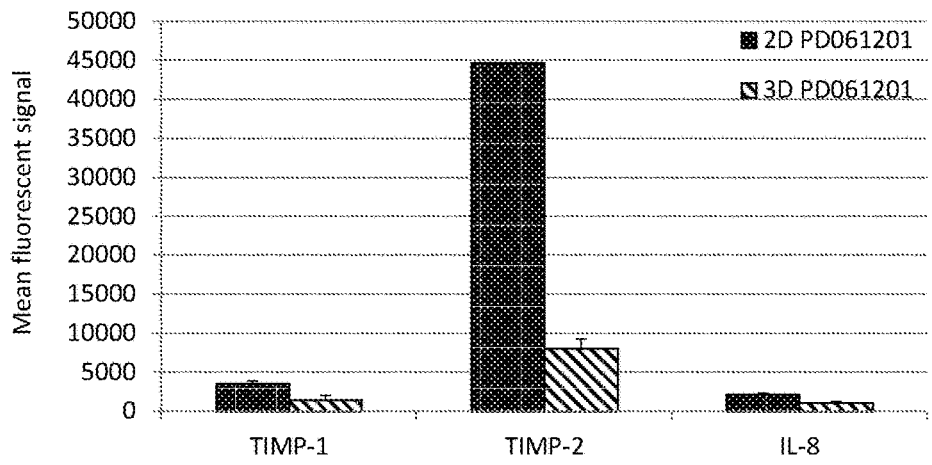
FIG. 2 is a bar graph presenting levels of secreted proteins that are downregulated in 3D (fibracel) Vs. 2D (flask) growth: TIMP-1, TIMP-2 and IL-8.

A bar graph comparing proteins down-regulated in ASC-3D vs ASC-2D culture medium are presented in FIG. 2. Based on these results, TIMP-1, TIMP-2, and IL-8 are all downregulated in ASC-3D since there is a relative decrease of these proteins in the culture medium of ASC-3D cells. Thus, any one of these protein biomarkers, a subcombination of them, or all of them in combination, may be used in identifying ASC-3D. TIMP-2 has been tested and found downregulated in all three batches tested to date.

Other proteins have also been tested. Of note, MMP-1 protein in culture medium was about the same irrespective of whether the culture medium was from ASC-3D or ASC-2D cells.

When cellular lysates were examined, the angiogenesis-related proteins bFGF, TIMP-2, and Angiopoietin-1 and the inflammatory-related protein ICAM-1 were found at similar levels in the culture lysate from both ASC-3D and ASC-2D in all three batches tested to date.

Example 4

Analysis of Gene Expression cDNA for gene analysis was prepared as described in Example 1. Expression profiles were analyzed using the $RT^2$ ProfilerTM PCR Array kit (SABioscience). The analysis was done for two general functional classes of genes—those related to angiogenesis and those related to inflammation. As indicated by the shared genes between the panels, there is considerable overlap between "angiogenesis-related" and "inflammatory-related" genes.

Tables 18, 19, and 20 summarize the results for the angiogenesis-related panel:.

TABLE 18

Angiogenesis-related Analysis - Genes Overexpressed in ASC-3D

| Gene Symbol | Fold Regulation | Comments |
|---|---|---|
| ANG | 1.9507 | OKAY |
| ANGPT1 | 1.5305 | OKAY |
| BTG1 | 1.1599 | OKAY |
| CCL2 | 5.6923 | OKAY |
| COL18A1 | 1.7459 | OKAY |
| CSF3 | 34.5114 | A |
| CXCL2 | 10.2603 | OKAY |
| CXCL3 | 9.0882 | OKAY |
| CXCL5 | 3.5776 | OKAY |
| CXCL6 | 41.3266 | OKAY |
| TYMP | 1.6518 | OKAY |
| EDIL3 | 1.4631 | OKAY |
| FN1 | 1.2431 | OKAY |
| HGF | 3.2021 | OKAY |
| IFNA1 | 2.157 | OKAY |
| IL10 | 1.6518 | B |
| IL6 | 29.8364 | OKAY |
| IL8 | 8.2477 | OKAY |
| MDK | 1.2605 | OKAY |
| FOXO4 | 1.4429 | OKAY |
| PDGFD | 1.172 | OKAY |
| PF4 | 1.0063 | A |
| PGF | 1.428 | B |
| PRL | 7.1058 | B |
| PTN | 1.8264 | OKAY |
| RUNX1 | 1.0345 | OKAY |
| SERPINF1 | 2.7972 | OKAY |
| TGFB1 | 1.2346 | OKAY |
| TIMP1 | 2.1347 | OKAY |
| TIMP2 | 1.3232 | OKAY |
| VEGFA | 3.8079 | OKAY |
| B2M | 1.1088 | OKAY |
| RPL13A | 1.086 | OKAY |
| GAPDH | 1.1843 | OKAY |

TABLE 19

Angiogenesis-related Analysis - Genes Under expressed in ASC-3D

| Gene Symbol | Fold Regulation | Comments |
|---|---|---|
| AGGF1 | −1.1219 | OKAY |
| AMOT | −1.0288 | OKAY |
| ANGPT2 | −2.5597 | A |
| ANGPTL1 | −1.1696 | OKAY |
| BAI1 | −1.0875 | C |
| CCL15 | −1.0875 | C |
| CD55 | −1.0217 | OKAY |
| CD59 | −1.0324 | OKAY |
| CXCL10 | −7.7061 | A |
| CXCL12 | −2.1675 | OKAY |
| CXCL13 | −1.0875 | C |
| EREG | −1.8803 | OKAY |
| FGF1 | −1.3159 | OKAY |
| FGF2 | −1.1181 | OKAY |
| FIGF | −2.5071 | B |
| FST | −4.8601 | OKAY |
| GRN | −1.2108 | OKAY |
| IFNB1 | −2.16 | B |
| IFNG | −1.0875 | C |
| IL17F | −1.3482 | B |
| KITLG | −3.7738 | OKAY |
| LEP | −1.0875 | C |
| NPPB | −6.0881 | A |
| NPR1 | −1.5812 | OKAY |
| PDGFB | −2.5071 | OKAY |
| PLG | −1.0875 | C |
| PROK1 | −1.522 | B |
| RHOB | −1.0762 | OKAY |
| RNH1 | −1.6033 | OKAY |
| SERPINE1 | −1.271 | OKAY |
| TGFA | −1.6088 | B |
| THBS1 | −1.0396 | OKAY |
| TIMP3 | −4.8433 | B |
| TNF | −3.8397 | A |
| TNNI2 | −1.8545 | A |
| TNNI3 | −1.5812 | A |
| HPRT1 | −1.2666 | OKAY |
| ACTB | −1.1258 | OKAY |
| HGDC | −1.0182 | B |

TABLE 20

Angiogenesis-related Gene Analysis - At Least Two-Fold Change in 3D vs. 2D

| Gene Symbol | Fold Regulation |
|---|---|
| CXCL6 | 41.3266 |
| CSF3 | 34.5114 |
| IL6 | 29.8364 |
| CXCL2 | 10.2603 |
| CXCL3 | 9.0882 |
| IL8 | 8.2477 |
| PRL | 7.1058 |
| CCL2 | 5.6923 |
| VEGFA | 3.8079 |
| CXCL5 | 3.5776 |
| HGF | 3.2021 |
| SERPINF1 | 2.7972 |
| IFNA1 | 2.157 |
| TIMP1 | 2.1347 |
| IFNB1 | −2.16 |
| CXCL12 | −2.1675 |
| FIGF | −2.5071 |
| PDGFB | −2.5071 |
| ANGPT2 | −2.5597 |
| KITLG | −3.7738 |
| TNF | −3.8397 |
| TIMP3 | −4.8433 |
| FST | −4.8601 |

TABLE 20-continued

Angiogenesis-related Gene Analysis - At Least Two-Fold Change in 3D vs. 2D

| Gene Symbol | Fold Regulation |
|---|---|
| NPPB | −6.0881 |
| CXCL10 | −7.7061 |

In the Tables, fold-change is expressed as the normalized expression in the Test Sample (3D Fibracel) divided by the normalized expression in the Control Sample (2D flask). Fold-Regulation represents fold-change results in a biologically meaningful way. Fold-change values greater than one indicate a positive- or an up-regulation, and the fold-regulation is equal to the fold change. Fold-change values less than one indicate a negative or down-regulation, and the fold-regulation is the negative inverse of the fold-change.

Tables 21 to 23 summarize the results for the inflammatory-related panel.

TABLE 21

Inflammatory-related Analysis - Genes Overexpressed in ASC-3D

| Gene Symbol | Fold Regulation | Comments |
|---|---|---|
| ABCF1 | 5.3295 | OKAY |
| C3 | 1.4379 | B |
| C4A | 1.7888 | OKAY |
| C5 | 1.0747 | OKAY |
| CCL1 | 1.2475 | C |
| CCL11 | 9.5071 | B |
| CCL15 | 1.2475 | C |
| CCL16 | 1.1884 | B |
| CCL18 | 1.2475 | C |
| CCL20 | 2.0125 | OKAY |
| CCL23 | 1572.6697 | A |
| CCL7 | 8.1061 | OKAY |
| CCL8 | 8.0222 | B |
| CCR8 | 1.2475 | C |
| CEBPB | 1.2388 | OKAY |
| CRP | 1.2475 | C |
| CXCL1 | 5.348 | OKAY |
| CXCL2 | 10.4396 | OKAY |
| CXCL6 | 31.9778 | OKAY |
| CARD18 | 1.2176 | B |
| IFNA2 | 2.0125 | B |
| IL13 | 1.904 | B |
| IL13RA1 | 1.7219 | OKAY |
| IL17C | 2.1053 | B |
| IL1A | 4.9212 | OKAY |
| IL1B | 2.9465 | OKAY |
| IL1F10 | 1.2134 | B |
| IL36RN | 1.752 | B |
| IL36B | 2.0056 | B |
| IL36G | 2.6009 | B |
| IL1R1 | 1.6403 | OKAY |
| IL1RN | 1.6806 | OKAY |
| IL8 | 10.5487 | OKAY |
| CXCR1 | 1.0636 | B |
| LTB | 1.2475 | C |
| MIF | 1.5199 | OKAY |
| B2M | 1.1439 | OKAY |
| RPL13A | 1.1282 | OKAY |
| GAPDH | 1.0098 | OKAY |
| HGDC | 1.1282 | B |

TABLE 22

Inflammatory-related Analysis - Genes Underexpressed in ASC-3D

| Gene Symbol | Fold Regulation | Comments |
|---|---|---|
| BCL6 | −1.2888 | OKAY |
| CCL17 | −1.5922 | B |
| CCL19 | −1.2449 | B |
| CCL24 | −2.1302 | OKAY |
| CCL26 | −1.7913 | OKAY |
| CCL3 | −1.8545 | OKAY |
| CCL5 | −11.2824 | A |
| CCR1 | −1.1065 | OKAY |
| CCR3 | −1.0614 | B |
| CCR4 | −2.2439 | B |
| CCR5 | −3.0652 | B |
| CCR6 | −1.4804 | B |
| CX3CR1 | −1.6888 | B |
| CXCL11 | −7.215 | B |
| CXCL12 | −1.8934 | OKAY |
| CXCL13 | −1.2579 | B |
| CXCL14 | −2.2673 | A |
| CXCL9 | −1.81 | B |
| IL10RA | −1.4702 | B |
| IL10RB | −1.0913 | OKAY |
| IL36A | −1.46 | B |
| IL22 | −1.2888 | B |
| IL5 | −1.0989 | A |
| IL9R | −3.6706 | B |
| LTA | −1.6313 | B |
| AIMP1 | −1.848 | OKAY |
| SPP1 | −6.1946 | OKAY |
| TNF | −4.598 | A |
| CD40LG | −1.2799 | B |
| TOLLIP | −1.3204 | OKAY |
| XCR1 | −4.2018 | B |
| HPRT1 | −1.1297 | OKAY |
| ACTB | −1.1535 | OKAY |

TABLE 23

Inflammatory-related Gene Analysis - At Least Two-Fold Change in 3D vs. 2D

| Gene Symbol | Fold Regulation |
|---|---|
| CXCL6 | 31.9778 |
| IL8 | 10.5487 |
| CXCL2 | 10.4396 |
| CCL11 | 9.5071 |
| CXCL3 | 9.4742 |
| CCL7 | 8.1061 |
| CCL8 | 8.0222 |
| CCL2 | 5.5751 |
| IL1A | 4.9212 |
| CXCL5 | 3.5529 |
| IL1B | 2.9465 |
| IL36G | 2.6009 |
| IL17C | 2.1053 |
| CCL20 | 2.0125 |
| CCR4 | −2.2439 |
| CXCL14 | −2.2673 |
| IL9R | −3.6706 |
| TNF | −4.598 |
| CXCL10 | −5.173 |
| SPP1 | −6.1946 |
| CXCL11 | −7.215 |
| CCL5 | −11.2824 |

For Tables 18, 19, 21, and 22, in the "Comments" section, an "A" indicates that the gene's average threshold cycle was relatively high (>30 cycles) in either the control or the test sample, and was reasonably low (<30 cycles) in the other sample. These data mean that the gene's expression was relatively low in one sample and reasonably detected in the other sample indicating that the actual fold-change value was at least as large as the calculated and reported fold-change result. This fold-change result may also have greater variation if the p value >0.05; therefore, it is important to have a sufficient number of biological replicates to validate the results for this gene.

A comment of "B" means the gene's average threshold cycle was relatively high (>30), meaning that the relative expression level was low, in both test and control samples, and the p-value for the fold-change was either unavailable or relatively high (p >0.05). This fold-change result may also have greater variations; therefore, it is important to have a sufficient number of biological replicates to validate the results for this gene.

A comment of "C" means the gene's average threshold cycle was either not determined or greater than the defined cut-off value (default 35) in both samples, meaning that its expression was undetected. Thus fold changes for genes with a comment of "C" were considered erroneous and un-interpretable.

A comment of "Okay" indicates there were no issues with the assay.

Fold-change is the normalized expression in the Test Sample divided by the normalized expression in the Control Sample.

Genes in Tables 20 and 23 show at least 2-fold differences, either up- or down-regulation, in ASC-3D versus ASC-2D. Accordingly, each of these genes, subcombinations within Table 20 or Table 23, subcombinations from both Table 20 and Table 23, the genes in Table 20, the genes in Table 23, or all of the genes presented in Table 20 and Table 23 may be used in identifying ASC-3D. Further, the genes presented in any of Tables 18-23 that do not show greater than 2 fold difference in levels in ASC-3D vs ASC-2D may be used to exclude a cell or population of cells as ASC-3D cells if one, a subcombination, or all of those markers show greater than two fold difference relative to both an ASC-3D and ASC-2D control population of cells.

Example 5

Analysis of Gene Expression of Cells Grown on Different 3D Scaffolds 2D 3D Gene Expression Analysis 1. Five batches cultured in 5 scaffolds (including Fibracel) were analyzed for differences between 2D and 3D gene expression patterns.
2. RNA was extracted using RNeasy Mini Kit (QIAGEN, 74104) according to manufacturer instructions with the addition of DNase treatment (QIAGEN, 79254).
3. RNA quality was evaluated using Experion analysis.
4. RNA was reverse transcribed (2000ng) using High Capacity cDNA RT Kit (Applied Biosystems, AB-4374966) according to manufacturer instructions.
5. qPCR was performed using Power SYBR Green PCR Master mix (Applied Biosystems, AB-4367660) in a 20 µl reactions according to manufacturer instructions using PrimeTime qPCR primers (IDT,Israel).
6. Fold-expression was analyzed using the AACT method with GAPDH as normalizing gene.

The analysis was done for three general functional classes of genes—those related to angiogenesis, genes related to inflammation and genes related to extracellular matrix. As indicated by the shared genes between the panels, there is considerable overlap between "angiogenesis-related" and "inflammatory-related" and "extra cellular matrix" genes.

Figure 3:
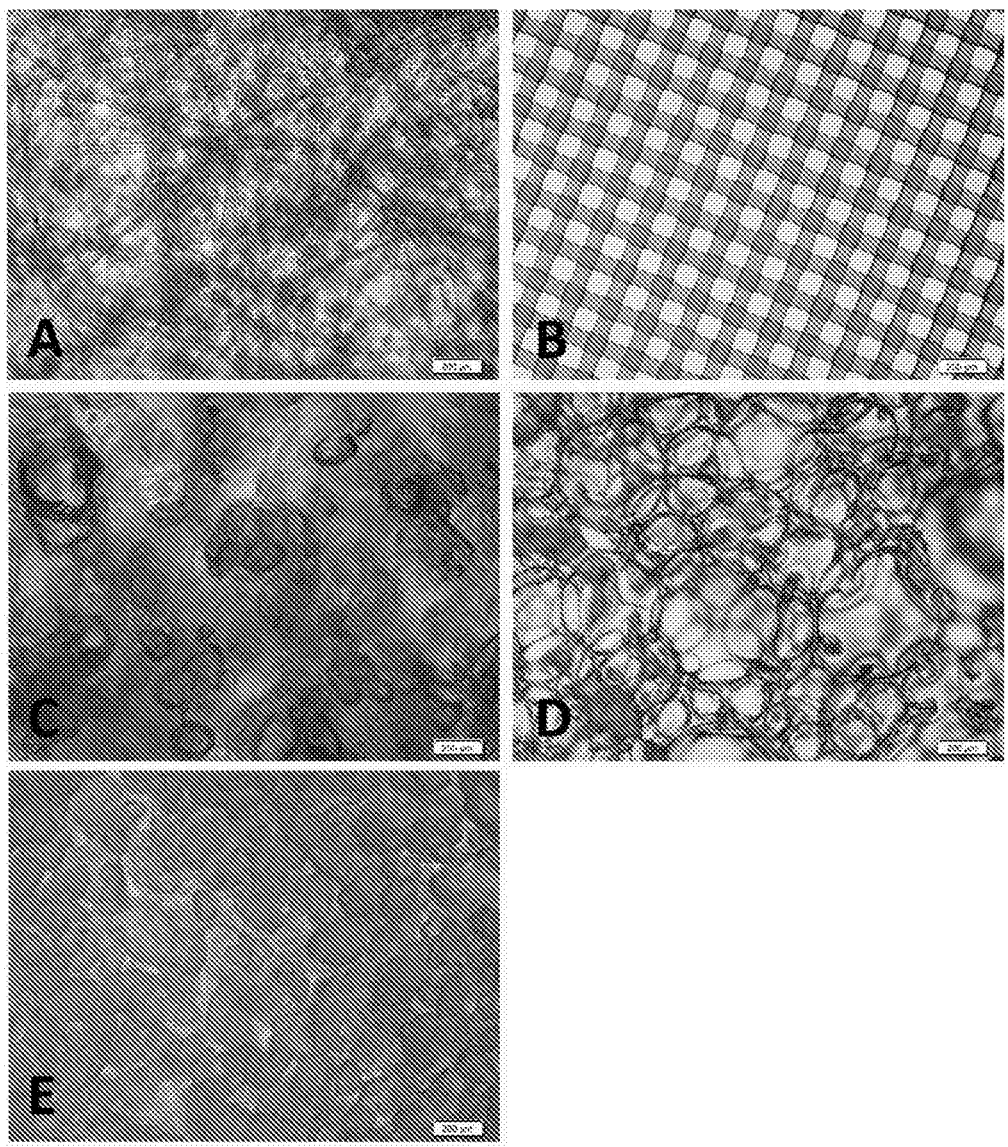
FIG. 3 provides micrographs of various 3D cell culture matrices: 3A, Fibracel (polyester non-woven fibers); 3B, woven polyester fibers; 3C, Spongostan (gelatin sponge); 3D, polyurathane foam; 3E,sintered polyethylene.

The results are shown in Table 24. This Table includes those genes up-regulated in multiple ASC batches and in ASCs cultured in different 3D scaffolds (FIG. 3) as compared with ASCs cultured on a 2D surface. Numbers are fold up-regulation of gene RNA in 3D cultured ASCsys. 2D cultured ASCs. Numbers in the top row represent ASC batches. F=Fibracel, W=woven, G=gelatin based sponge, S=Sintered polyethylene, P=Polyurathane foam. "P-value" represents the statistical significance of the gene regulation fold change between 3D cultured ASCs and 2D ASCs.

TABLE 24

| 3D Fold of 2D | PD110511 F | PD101011 F | PD161111 F | P130611 F | P070911 F | PD060911 W | PD060911 G | PD061210 W |
|---|---|---|---|---|---|---|---|---|
| VEGFA | 4.28 | 3.81 | 4.38 | 5.03 | 5.29 | 6.61 | 4.63 | 5.06 |
| LIF | 19.43 | 8.50 | 3.82 | 18.75 | 13.09 | 3.60 | 5.24 | 33.40 |
| COL7A1 | 6.01 | 6.82 | 12.29 | 7.05 | 2.54 | 8.33 | 13.59 | 11.20 |
| IL6 | 3.95 | 7.38 | 3.12 | 9.24 | 8.09 | 8.02 | 5.21 | 7.25 |
| MMP10 | 14.10 | 13.60 | 90.01 | 44.87 | 4.95 | 59.12 | 44.99 | 31.02 |
| MMP11 | 8.04 | 85.13 | 20.87 | 16.63 | 9.26 | 94.01 | 112.83 | 12.30 |
| FN1 | 3.90 | 3.41 | 5.97 | 4.38 | 3.06 | 7.30 | 10.21 | 4.99 |
| COL15A1 | 37.31 | 17.90 | 32.08 | 6.50 | 7.31 | 148.91 | 158.10 | 11.90 |
| TNC | 10.81 | 6.59 | 16.27 | 4.88 | 4.34 | 9.11 | 9.87 | 6.74 |
| IFNA1 | 5.19 | 3.11 | 7.53 | 4.09 | 3.46 | 5.36 | 8.20 | 5.64 |

| 3D Fold of 2D | PD061210 G | PD061210 S | PD061210 P | PD110511 G | PD110511 W | PD110511 S | PD110511 P | P. Value |
|---|---|---|---|---|---|---|---|---|
| VEGFA | 5.88 | 4.26 | 5.08 | 4.22 | 4.50 | 4.22 | 3.87 | <0.0001 |
| LIF | 58.87 | 19.14 | 33.73 | 65.19 | 21.48 | 74.21 | 98.89 | <0.0001 |
| COL7A1 | 11.75 | 14.13 | 11.78 | 6.86 | 7.77 | 11.42 | 12.32 | <0.0001 |
| IL6 | 16.09 | 6.26 | 2.54 | 20.58 | 6.34 | 13.33 | 3.43 | <0.0001 |
| MMP10 | 70.16 | 72.30 | 159.45 | 35.74 | 32.10 | 35.44 | 176.56 | <0.0001 |
| MMP11 | 35.60 | 27.44 | 28.12 | 31.90 | 28.14 | 37.57 | 86.88 | <0.0001 |
| FN1 | 5.22 | 5.25 | 4.60 | 3.55 | 4.62 | 4.79 | 5.16 | <0.0001 |
| COL15A1 | 15.41 | 25.56 | 10.80 | 8.74 | 13.90 | 19.44 | 11.87 | 0.001 |
| TNC | 9.63 | 7.59 | 4.58 | 48.46 | 60.34 | 67.87 | 34.89 | <0.0001 |
| IFNA1 | 8.28 | 6.31 | 6.73 | 13.19 | 17.02 | 19.81 | 21.92 | <0.0001 |

Example 6

Analysis between scaffolds of VEGFA (Table 25) and IL-6 (Table 26) protein secreted into conditioned media of ASC cultured in 3D scaffolds versus ASC cultured on 2D TCPS.

TABLE 25

| Matrix | Batch PD 110511 Fold change vs. 2D | Batch PD 061210 Fold change vs. 2D |
| --- | --- | --- |
| 2D TCPS | 1 | 1 |
| Gelatin sponge | 10.05 | 13.00 |
| Woven fibers | 58.01 | 8.21 |
| Polyurithane foam | 17.97 | 7.35 |
| Sintered polyethylene | 12.66 | 8.49 |
| Non woven polyester | 32.13 | 18.60 |

TABLE 26

| Matrix | Batch PD 110511 Fold change vs. 2D | Batch PD 061210 Fold change vs. 2D |
| --- | --- | --- |
| 2D TCPS | 1.00 | 1.00 |
| Gelatin sponge | 71.20 | 21.32 |
| Woven fibers | 23.10 | 35.24 |
| Polyurithane foam | 14.89 | 2.30 |
| Sintered polyethylene | 29.09 | 2.97 |
| Non woven polyester | 46.72 | 40.37 |

Example 7

Analysis of differences in proteins secreted into condition medium between 2D TCPS and 3D Fibracel. As shown in FIG. 1 and FIG. 2 in examining several batches, in most instances TIMP-2, IL-8, and TIMP-1 are found in higher concentrations in conditioned medium of ASC cultured in 2D (TCPS) compared to ASC cultured in 3D (Fibracel). Conversely, angiogenin, IL-6, angiopoietin-1 MCP-3 and uPAR are found in higher concentrations in the conditioned medium of ASC cultured in 3D (Fibracel) compared to ASC cultured in 2D (TCPS).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating an autoimmune disease in a subject in need thereof, comprising:
   a. determining whether an ASC was produced by 3D culture, wherein said 3D culture comprises polyester 3D carriers, said method comprising:
      i. measuring in a sample of ASC the expression of 1 or more biomarkers comprising VEGFA, LIF, COL7A1, IL6, MMP10, MMP9, MMP11, FN1, COL15A1, TNC, or IFNA1, wherein said one or more biomarkers comprise VEGFA, and said measuring is performed using gene array or PCR, and
      ii. comparing the measured levels to levels of the same biomarker measured in a sample of ASC produced by 2D culturing ("2D control");
      wherein an increase of at least 2-fold of any 1 or more of VEGFA, LIF, COL7A1, IL6, MMP10, MMP9, MMP11, FN1, COL15A1, TNC, or IFNA1 relative to the 2D control indicates the cell is an ASC produced by 3D culturing comprising polyester 3D carriers; and
   b. administering said ASC to said subject, thereby treating an autoimmune disease.

2. The method of claim 1, wherein expression is measured by gene array.

3. The method of claim 1, wherein each of VEGFA, IL6, and IFNA1 is measured.

4. The method of claim 1, wherein each of VEGFA, LIF, COL7A1, IL6, MMP10, MMP9, MMP11, FN1, COL15A1, TNC, and IFNA1 is measured.

5. The method of claim 1, wherein any subcombination of VEGFA, LIF, COL7A1, IL6, MMP10, MMP9, MMP11, FN1, COL15A1, TNC, or IFNA1 is measured, wherein said subcombination comprises VEGFA.

6. The method of claim 1, wherein VEGFA and one or more of LIF, COL7A1, IL6, MMP10, MMP9, MMP11, FN1, COL15A1, TNC, or IFNA1 is measured.

7. The method of claim 1, wherein VEGFA and two or more of LIF, COL7A1, IL6, MMP10, MMP9, MMP11, FN1, COL15A1, TNC, or IFNA1 is measured.

8. The method of claim 1, wherein VEGFA and three or more of LIF, COL7A1, IL6, MMP10, MMP9, MMP11, FN1, COL15A1, TNC, or IFNA1 is measured.

9. The method of claim 1, wherein VEGFA and four or more of LIF, COL7A1, IL6, MMP10, MMP9, MMP11, FN1, COL15A1, TNC, or IFNA1 is measured.

10. The method of claim 1, wherein VEGFA, IL6, and one or more of LIF, COL7A1, MMP10, MMP9, MMP11, FN1, COL15A1, TNC, or IFNA1 is measured.

11. The method of claim 1, wherein VEGFA, IL6, and two or more of LIF, COL7A1, MMP10, MMP9, MMP11, FN1, COL15A1, TNC, or IFNA1 is measured.

12. The method of claim 1, wherein VEGFA, IL6, and three or more of LIF, COL7A1, MMP10, MMP9, MMP11, FN1, COL15A1, TNC, or IFNA1 is measured.

13. The method of claim 1, wherein VEGFA, IL6, and four or more of LIF, COL7A1, MMP10, MMP9, MMP11, FN1, COL15A1, TNC, or IFNA1 or INFB1 is measured.

14. A method of treating an autoimmune disease in a subject in need thereof, comprising:
   a. determining whether an adherent stromal cell was produced by three dimensional culture, wherein said three dimensional culture comprises polyester three dimensional carriers, said method comprising:
      i. measuring in a culture medium produced from a sample of adherent stromal cells the expression of VEGFA detecting or measuring, wherein said measuring is performed using antibody array or ELISA, and
      ii. comparing the measured levels to levels of the same biomarker measured in a sample of culture medium produced from adherent stromal cells grown in two dimensional culturing ("2D medium control");
      wherein an increase of at least two-fold of VEGFA relative to the 2D medium control indicates the cell is an adherent stromal cell produced by three dimensional culturing comprising polyester three dimensional carriers; and
   b. administering said ASC to said subject, thereby treating an autoimmune disease.

15. The method of claim 14, wherein each of VEGFA and IL6 is measured.

* * * * *